US007834049B2

(12) United States Patent
Wakabayashi et al.

(10) Patent No.: US 7,834,049 B2
(45) Date of Patent: Nov. 16, 2010

(54) INTEGRIN EXPRESSION INHIBITOR

(75) Inventors: Toshiaki Wakabayashi, Ibaraki (JP); Yasuhiro Funahashi, Ibaraki (JP); Naoko Hata, Ibaraki (JP); Taro Semba, Ibaraki (JP); Yuji Yamamoto, Ibaraki (JP); Toru Haneda, Ibaraki (JP); Takashi Owa, Ibaraki (JP); Akihiko Tsuruoka, Ibaraki (JP); Junichi Kamata, Ibaraki (JP); Tadashi Okabe, Ibaraki (JP); Keiko Takahashi, Ibaraki (JP); Kazumasa Nara, Ibaraki (JP); Shinichi Hamaoka, Ibaraki (JP); Norihiro Ueda, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 967 days.

(21) Appl. No.: 11/097,218

(22) Filed: Apr. 4, 2005

(65) Prior Publication Data
US 2005/0176712 A1 Aug. 11, 2005

Related U.S. Application Data

(63) Continuation of application No. 10/181,562, filed as application No. PCT/JP01/00713 on Feb. 1, 2001, now abandoned.

(30) Foreign Application Priority Data

Feb. 3, 2000 (JP) .............................. 2000-26080
Dec. 28, 2000 (JP) ............................ 2000-402084

(51) Int. Cl.
*A61K 31/405* (2006.01)
(52) U.S. Cl. ..................................................... 514/415
(58) Field of Classification Search ................... 514/415
See application file for complete search history.

(56) References Cited

U.S. PATENT DOCUMENTS 5,721,246 A * 2/1998 Yoshino et al. ............. 514/300

5,753,230 A 5/1998 Brooks et al.
(Continued)

FOREIGN PATENT DOCUMENTS

EP 0 673 937 A1 9/1995

(Continued)

OTHER PUBLICATIONS

Owa et al., Journal of Medicinal Chemistry, 1999;42(19):3789-3799.*

(Continued)

*Primary Examiner*—San-ming Hui
(74) *Attorney, Agent, or Firm*—Birch, Stewart, Kolasch & Birch, LLP

(57) ABSTRACT

The present invention provides an integrin expression inhibitor, and an agent for treating arterial sclerosis, psoriasis, cancer, retinal angiogenesis, diabetic retinopathy or inflammatory diseases, an anticoagulant, or a cancer metastasis suppressor on the basis of an integrin inhibitory action. Namely, it provides an integrin expression inhibitor comprising, as an active ingredient, a sulfonamide compound represented by the following formula (I), a pharmacologically acceptable salt thereof or a hydrate of them,

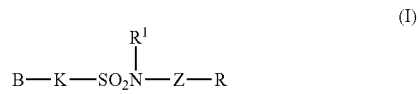

(I)

wherein in the formula, B means a C6-C10 aryl ring or 6- to 10-membered heteroaryl ring which may have a substituent and in which a part of the ring may be saturated; K means a single bond, —CH=CH— or —$(CR^{4b}R^{5b})_m{}^b$— (wherein $R^{4b}$ and $R^{5b}$ are the same as or different from each other and each means hydrogen atom or a C1-C4 alkyl group; and $m^b$ means an integer of 1 or 2); $R^1$ means hydrogen atom or a C1-C6 alkyl group; Z means a single bond or —CO—NH—; and R means a C6-C10 aryl ring or 6- to 10-membered heteroaryl ring which may have a substituent and in which a part of the ring may be saturated, respectively.

4 Claims, 3 Drawing Sheets

U.S. PATENT DOCUMENTS

| | | | |
|---|---|---|---|
| 5,760,028 | A | 6/1998 | Jadhav et al. |
| 5,773,646 | A | 6/1998 | Chandrakumar et al. |
| 5,843,906 | A | 12/1998 | Chandrakumar et al. |

FOREIGN PATENT DOCUMENTS

| | | |
|---|---|---|
| JP | 7-165708 | 6/1995 |
| JP | 8-231505 | 9/1996 |
| WO | WO 93/01182 | 1/1993 |
| WO | WO 95/07276 | 3/1995 |
| WO | WO 96/04016 | 2/1996 |
| WO | WO-97/36858 A1 | 10/1997 |
| WO | WO 97/36859 | 10/1997 |
| WO | WO-97/36860 A1 | 10/1997 |
| WO | WO 97/36861 | 10/1997 |
| WO | WO 97/36862 | 10/1997 |
| WO | WO98/40077 * | 9/1998 |
| WO | WO 98/44797 | 10/1998 |
| WO | WO 98/58902 | 12/1998 |
| WO | WO 99/35163 | 7/1999 |
| WO | WO 99/50249 | 10/1999 |
| WO | WO 99/52493 | 10/1999 |
| WO | WO 00/32575 | 6/2000 |
| WO | WO 00/38786 | 7/2000 |
| WO | WO-00/38786 A2 | 7/2000 |
| WO | WO 00/41469 | 7/2000 |

OTHER PUBLICATIONS

Masao Hayashi et al.; Protein, Nucleic Acid, Enzyme, vol. 44, No. 2, pp. 130-135 (1999) (Abstract).

Donald R. Senger et al.; Proc. Natl. Acad. Sci. USA; vol. 94, pp. 13612-13617 (1997).

Thomas Boehm et al.; Nature, vol. 390, No. 27, pp. 404-407 (1997).

Sanford J. Shattil; Thromb. Haemost., vol. 74, No. 1, pp. 149-155 (1995).

Martin Friedlander et al.; Science, vol. 270, pp. 1500-1502, (1995).

Nariaki Matsuura et al.; Japan Clinic, vol. 53, pp. 1643-1647, (1995).

Ichiro Ota et al.; Clinical Pathology, vol. 45, pp. 528-533, (1997).

Hardman et al., "Goodman & Gilman's The Pharmacological Basks of Therapeutics," $9^{th}$ ed., 1996, pp. 51 and 57-58.

Carter, Stephen K., M.D. et al.; Chemotherapy of Cancer, Second Edition, (1981); A Wiley & Sons, New York, New York; pp. 362-365.

Chittum et al., Benzenesulfonamides of Primary Aminopyridines and Primary Aminoquinolines, 1974, Journal of Chemical and Engineering Data, 19(3), 294-295.

Office Action issued Jun. 11, 2009 in corresponding Canadian Application No. 2,399,001.

* cited by examiner

INTEGRIN EXPRESSION INHIBITOR

CROSS-REFERENCE TO RELATED APPLICATIONS

This application is a Rule 53(b) continuation of U.S. application Ser. No. 10/181,562 filed on Jul. 18, 2002, now abandoned, which is the national phase under 35 U.S.C. §371 of PCT application No. PCT/JP01/00713, which has an international filing date of Feb. 1, 2001, which designated the United States of America.

TECHNICAL FIELD

The present invention relates to an integrin expression inhibitor, specifically, anintegrin α2β1, α3β1, α5β, α6β1, αvβ1, αvβ3 or αvβ5 expression inhibitor. Further it relates to an angiogenesis agent, an anticoagulant, an anticancer agent, a cancer metastasis suppressor, and an agent for treating retinal angiogenesis, diabetic retinopathy, inflammatory diseases, arterial sclerosis, psoriasis and osteoporosis, on the basis of integrin expression inhibitory action.

PRIOR ART

Integrin structurally consists of a heterodimer in which two types of sub-unit, namely, integrin α and integrin β are associated with each other by non-covalent binding. At least 16 types of α chains and 8 types of β chains have been found. A variety of molecular groups differing in ligand specificity are formed by the combination of these α and β chains and 22 types of integrins have been known. Integrin has a function as cell membrane receptor protein for an adhesive molecule of an animal cell, expresses on a cell membrane and participates in the adhesion between a cell and an extracellular matrix (ECM) or between cells. When the cell adhesive molecule is combined with integrin, a signaling system in a cell starts moving and as a result, not only cell adhesion, but also cell evolution, cell proliferation, apoptosis, differentiation, cytoskeleton orientation, cell migration, histogenesis, cancer infiltration and metastasis, wound healing, blood coagulation and the like operate. It has been known that among these integrins, integrin α2β1 of which the adhesive molecules are collagen and laminin participates in platelet aggregation, cancer infiltration and metastasis (HAYASHI Masao & MIYAMOTO Yasunori, PROTEIN, NUCLEIC ACID, ENZYME, Vol. 44, pp 130-135, (1999)) and angiogenesis (Donald R. Senger et al, Proc. Natl. Acad. Sci. USA, 94, 13612-13617, (1997)). It has come to be clarified that among these symptoms, the proliferation of cancer is closely related to angiogenesis. In recent years, it has been demonstrated experimentally that an antiangiogenesis agent can inhibit and further reduce proliferative cancer and no resistant cancer is generated in a transplant cancer model and there is shown a correlation between angiogenesis and exacerbations of many solid cancers such as mammary cancer, prostatic cancer, lung cancer and colonic cancer in clinical examinations (T. Boem et al, Nature, 390 (27) 404-407, (1997)). Also, αvβ1 of which the adhesive molecules are fibronectin and vitronectin participates in the adhesion of a cancer cell to a substrate and αvβ3 of which the adhesive molecules are vitronectin and thrombospongin and αvβ5 of which the adhesive molecule is vitronectin participate in angiogenesis, cancer metastasis and the regeneration of bone (Shattil, S. J., Thromb. Haemost., 74, 149-155, (1995), Friedlander M, et al, Science, 270, 1500-1502, (1995)). Further, it has been known that α3β1 of which the adhesive molecules are fibronectin, collagen, laminin, laminin 5 and the like, α5β1 of which the adhesive molecule is fibronectin and α6β1 of which the adhesive molecules are laminin and laminin 5 participate in cancer infiltration and metastasis (MATSUURA Nariaki et al., JAPAN CLINIC, Vol. 53, pp 1643-1647, (1995), OTA Ichiro et al, CLINICAL PATHOLOGY, Vol. 45, 528-533, (1997)).

WO9950249 discloses the antagonist of integrin αvβ3, however there is no suggestion concerning the expression inhibitory action of integrin αvβ3. In JP-A 7-165708 and JP-A 8-231505, the same sulfonamide compound as that used in the present invention is disclosed; however, there is neither description nor hint concerning integrin expression inhibitory action. WO9301182 discloses anti-tumor agents utilizing a specific tyrosine kinase inhibitive action of a compound having an indole skeleton. These agents are indolylmethylene-2-indolinone compounds, which differ from that of the present invention. WO964016 likewise discloses anti-tumor agents utilizing a specific tyrosine kinase inhibitory action of a compound having an indole skeleton. However, these agents are 2-indolinone-3-methylene derivatives, which differ from that of the present invention.

An antiangiogenesis agent, an anticancer agent, a cancer metastasis suppressor, an anticoagulant agent, and an agent for treating arterial sclerosis, psoriasis, retinal angiogenesis, diabetic retinopathy or inflammatory diseases on the basis of an integrin expression inhibitory action have not been known so far.

The present invention provides an agent for treating a disease against which an integrin expression inhibitory action is effective. Specifically, it is an object of the present invention to provide an antiangiogenic agent, an anticancer agent, a cancer metastasis suppressor, an anticoagulant, and an agent for treating arterial sclerosis, psoriasis, osteoporosis, retinal angiogenesis, diabetic retinopathy or inflammatory diseases, which comprises, as an active ingredient, a compound having an integrin expression inhibitory action. Another object of the present invention is to provide an integrin expression inhibitor comprising a sulfonamide compound.

DISCLOSURE OF THE INVENTION

The present inventors have made earnest studies and as a result, found that a sulfonamide compound having a bicyclic heterocycle has an integrin expression inhibitory action. Thus, they have completed the present invention.

Accordingly, the present invention relates to:
1. 1) an agent for treating arterial sclerosis, psoriasis, cancer, osteoporosis, retinal angiogenesis, diabetic retinopathy or inflammatory diseases, 2) an anticoagulant, 3) a cancer metastasis suppressor or 4) an antiangiogenic agent on the basis of an integrin expression inhibitory action, 2. 1) the agent for treating arterial sclerosis, psoriasis, cancer, osteoporosis, retinal angiogenesis, diabetic retinopathy or inflammatory diseases, 2) an anticoagulant, 3) a cancer metastasis suppressor or 4) an antiangiogenic agent on the basis of integrin expression inhibitory action as described in 1., wherein the integrin is integrin α2, α3, α5, α6, αv, β1, β3, β4, β5, α2β1, β3β1, α5β1, α6β1, αvβ1, αvβ3 or αvβ5, 3. an integrin expression inhibitor comprising, as an active ingredient, a sulfonamide compound represented by the formula (I), a pharmacologically acceptable salt thereof or a hydrate of them:

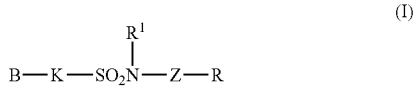

(in the formula, B represents a C6-C10 aryl ring or a 6- to 10-membered heteroaryl ring which may have a substituent and in which a part of the ring may be saturated; K represents a single bond, —CH=CH— or —(CR$^{4b}$R$^{5b}$)$_{m^b}$— (where R$^{4b}$ and R$^{5b}$ are the same as or different from each other and each represents hydrogen atom or a C1-C4 alkyl group; and m$^b$ means an integer of 1 or 2); R$^1$ represents hydrogen atom or a C1-C6 alkyl group; Z represents a single bond or —CO—NH—; and R represents a C6-C10 aryl ring or a 6-to 10-membered heteroaryl ring which may have a substituent and in which a part of the ring may be saturated, respectively), 4. an integrin expression inhibitor comprising, as an active ingredient, the sulfonamide compound as described in 3., a pharmacologically acceptable salt thereof or a hydrate of them, wherein R is indole, quinoline or isoquinoline, 5. an integrin expression inhibitor comprising, as an active ingredient, a sulfonamide compound represented by the formula (I$^a$), a pharmacologically acceptable salt thereof or a hydrate of them:

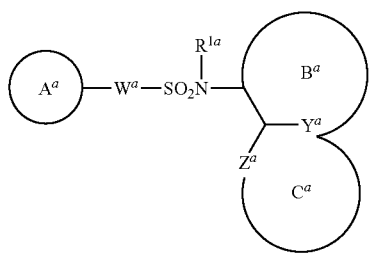

(in the formula, the A$^a$ ring a monocyclic or bicyclic aromatic ring which may have a substituent; the B$^a$ ring represents an optionally substituted 6-membered cyclic unsaturated hydrocarbon or unsaturated 6-membered heterocycle containing one nitrogen atom as a heteroatom; the C$^a$ ring represents an optionally substituted 5-membered heterocycle containing 1 or 2 nitrogen atoms; R$^{1a}$ represents hydrogen atom or a C1-C6 alkyl group;

W$^a$ represents a single bond or —CH=CH—; Y$^a$ represents carbon atom or nitrogen atom; and Z$^a$ represents —N(R$^{2a}$)— (wherein R$^{2a}$ means hydrogen atom or a lower alkyl group) or nitrogen atom, respectively), 6. an integrin expression inhibitor comprising, as an active ingredient, the sulfonamide compound as described in 5., a pharmacologically acceptable salt thereof or a hydrate of them, wherein W$^a$ is a single bond, 7. an integrin expression inhibitor comprising, as an active ingredient, the sulfonamide compound as described in 5., a pharmacologically acceptable salt thereof or a hydrate of them, wherein W$^a$ is a single bond; Z$^a$ is —NH—; and Y$^a$ is carbon atom, 8. the integrin expression inhibitor comprising, as an active ingredient, the sulfonamide compound as described in any of 5., 6. and 7., a pharmacologically acceptable salt thereof or a hydrate of them, wherein the B$^a$ ring is an optionally substituted benzene or pyridine, 9. an integrin expression inhibitor comprising, as an active ingredient, the sulfonamide compound as described in any of 5. to 8., a pharmacologically acceptable salt thereof or a hydrate of them, wherein the C$^a$ ring is an optionally substituted pyrrole, 10. an integrin expression inhibitor comprising, as an active ingredient, the sulfonamide compound as described in 5., a pharmacologically acceptable salt thereof or a hydrate of them, wherein the A$^a$ ring is a benzene or pyridine which may have a substituent; the B$^a$ ring is benzene which may have a substituent; the C$^a$ ring is pyrrole which may have a substituent; W$^a$ is a single bond; and Z$^a$ is —NH—, 11. an integrin expression inhibitor comprising, as an active ingredient, a sulfonamide-containing heterocyclic compound represented by the formula (I$^b$), a pharmacologically acceptable salt thereof or a hydrate of them:

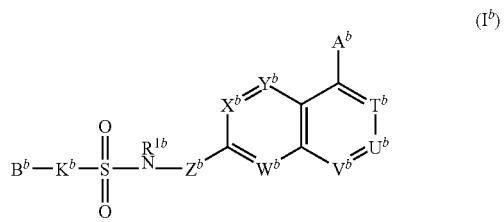

(in the formula, A$^b$ represents hydrogen atom, a halogen atom, hydroxyl group, a C1-C4 alkyl or alkoxy group which may be substituted with a halogen atom, cyano group, —(CO)$_{k^b}$NR$^{2b}$R$^{3b}$ (wherein R$^{2b}$ and R$^{3b}$ are the same as or different from each other and each means hydrogen atom or a C1-C4 alkyl group which may be substituted with a halogen atom; and k$^b$ means 0 or 1), a C2-C4 alkenyl or alkynyl group which may have a substituent, or a phenyl or phenoxy group which may have a substituent selected from the following group A; B$^b$ means an aryl group or monocyclic heteroaryl group which may have a substituent selected from the following group A, or the following formula:

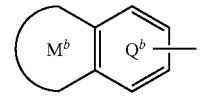

(wherein the ring Q$^b$ means an aromatic ring which may have one or two nitrogen atoms; and the ring M$^b$ means a C5-C12 unsaturated monocycle or heterocycle having a double bond in common with the ring Q$^b$. The ring may have 1 to 4 heteroatoms selected from nitrogen atom, oxygen atom and sulfur atom, the ring Q$^b$ and the ring M$^b$ may jointly have nitrogen atom, and the ring Q$^b$ and the ring M$^b$ may have a substituent selected from the following group A); K$^b$ means a single bond or —(CR$^{4b}$R$^{5b}$)m$^b$— (wherein R$^{4b}$ and R$^{5b}$ are the same as or different from each other and each means hydrogen atom or a C1-C4 alkyl group; and m$^b$ means an integer of 1 or 2); T$^b$, W$^b$, X$^b$ and Y$^b$ are the same as or different from each other and each means =C(D$^b$)- (wherein D$^b$ represents hydrogen atom, a halogen atom, hydroxyl group, a C1-C4 alkyl or alkoxy group which may be substituted with a halogen atom, cyano group, —(CO)$_{n^b}$NR$^{6b}$R$^{7b}$ (wherein R$^{6b}$ and R$^{7b}$ are the same as or different from each other and each means hydrogen atom or a C1-C4 alkyl group which may be substituted with a halogen atom; and n$^b$ means 0 or 1) or a C2-C4 alkenyl or alkynyl group which may have a substituent, respectively) or nitrogen atom; $U^b$ and $V^b$ are the same as or different from each other and each means $=C(D^b)-$ (wherein $D^b$ has the same meaning as above), nitrogen atom, $-CH_2-$, oxygen atom or $-CO-$; $Z^b$ means a single bond or $-CO-NH-$; $R^{1b}$ means hydrogen atom or a C1-C4 alkyl group; and

----- means a single bond or a double bond. Group A: a halogen atom, hydroxyl group, a C1-C4 alkyl or alkoxy group which may be substituted with a halogen atom, cyano group, $-R^{8b}R^{9b}N(NH)_{pu}{}^b-$ (wherein $R^{8b}$ and $R^{9b}$ are the same as or different from each other and each means hydrogen atom or a C1-C4 alkyl group which may be substituted with a halogen atom; and $p^b$ means 0 or 1. Further, $R^{8b}$ and $R^{9b}$ may form a 5-or 6-membered ring together with the nitrogen atom to which they are bound, and the ring may further contain nitrogen atom, oxygen atom or sulfur atom, and also may have a substituent.), an aminosulfonyl group which may be substituted with a mono- or di-C1-C4 alkyl group, a C1-C8 acyl group which may have a substituent, a C1-C4 alkyl-$S(O)_s{}^b$-C1-C4 alkylene group (wherein $s^b$ means an integer of 0, 1 or 2), a phenylsulfonylamino group which may have a C1-C4 alkyl or a substituent, $-(CO)_q{}^bNR^{10b}R^{11b}$ (wherein $R^{10b}$ and $R^{11b}$ are the same as or different from each other and each means hydrogen atom, or a C1-C4 alkyl group which may substituted with an amino group which may be substituted with a halogen atom or a C1-C4 alkyl group; and $q^b$ means 0 or 1), or an aryl group or heteroaryl group which may have a substituent), 12. an integrin expression inhibitor comprising, as an active ingredient, the sulfonamide-containing heterocyclic compound as described in 11., a pharmacologically acceptable salt thereof or a hydrogen of them, wherein $U^b$ and $V^b$ are $=C(D^b)-$ (wherein $D^b$ has the same meaning as above) or nitrogen atom, 13. an integrin expression inhibitor comprising, as an active ingredient, the sulfonamide-containing heterocyclic compound as described in 11. or 12., a pharmacologically acceptable salt thereof or a hydrate of them, wherein $Z^b$ is a single bond, 14. an integrin expression inhibitor comprising, as an active ingredient, a sulfonamide-containing heterocyclic compound as described in any of 11. to 13., a pharmacologically acceptable salt thereof or a hydrate of them, wherein at least one of $T^b$, $U^b$, $V^b$, $W^b$, $X^b$ and $Y^b$ is nitrogen atom, 15. an integrin expression inhibitor comprising, as an active ingredient, the sulfonamide-containing heterocyclic compound as described in any of 11. to 14., a pharmacologically acceptable salt thereof or a hydrate of them, wherein $A^b$ represents a halogen atom, a C1-C4 alkyl group or alkoxy group which may be substituted with a halogen atom, cyano group, $-(CO)_r{}^bNR^{12b}R^{13b}$ (wherein $R^{12b}$ and $R^{13b}$ are the same as or different from each other and each represents hydrogen atom or a C1-C4 alkyl group which may be substituted with a halogen atom; and $r^b$ means 0 or 1) or a C2-C4 alkenyl or alkynyl group which may have a substituent, 16. an integrin expression inhibitor comprising, as an active ingredient, the sulfonamide-containing heterocyclic compound as described in any of 11. to 15., a pharmacologically acceptable salt thereof or a hydrate of them, wherein only one of $T^b$, $U^b$, $V^b$, $W^b$, $X^b$ and $Y^b$ is nitrogen atom, 17. an integrin expression inhibitor comprising, as an active ingredient, the sulfonamide-containing heterocyclic compound as described in any of 11. to 16., a pharmacologically acceptable salt thereof or a hydrate of them, wherein only one of $T^b$, $W^b$ and $Y^b$ is nitrogen atom, 18. an integrin expression inhibitor comprising, as an active ingredient, the sulfonamide compound as described in any of 5. to 17., a pharmacologically acceptable salt thereof or a hydrate of them, wherein the integrin is integrin α2, α3, α5, α6, αv, β1, β3, β4 or β5, 19. an integrin expression inhibitor comprising, as an active ingredient, the sulfonamide compound as described in any of 5. to 17., a pharmacologically acceptable salt thereof or a hydrate of them, wherein the integrin is integrin α2β1, α3β1, α5β1, α6β1, αvβ1, αvβ3 or αvβ5, 20. 1) an agent for treating arterial sclerosis, psoriasis, cancer, retinal angiogenesis, diabetic retinopathy or inflammatory diseases, 2) an anticoagulant, 3) a cancer metastasis suppressor or 4) an antiangiogenic agent on the basis of an integrin expression inhibitory action, which comprises, as an active ingredient, the sulfonamide compound as described in any of 5. to 17., a pharmacologically acceptable salt thereof or a hydrate of them, and 21. 1) an agent for treating arterial sclerosis, psoriasis or osteoporosis or 2) an anticoagulant on the basis of an integrin expression inhibitory action, which comprises, as an active ingredient, the sulfonamide compound as described in any of 5. to 17., a pharmacologically acceptable salt thereof or a hydrate of them.

The present invention provides a method for preventing, treating or improving a disease against which an integrin expression inhibition is effective, by administering a pharmacologically effective dose of the compound represented by any of formulae (I), (Ia) and (Ib), a pharmacologically acceptable salt thereof or a hydrate of them to a patient.

Further, the present invention provides use of the compound represented by any of formulae (I), (Ia) and (Ib), a pharmacologically acceptable salt of the compound or hydrate of them, for producing an agent for preventing, treating or improving a disease against which integrin expression inhibition is effective.

In the present invention, the diseases against which integrin expression inhibition is effective include arterial sclerosis, psoriasis, cancer, osteoporosis, retinal angiogenesis, diabetic retinopathy and inflammatory diseases.

Also, in the present invention, the agent for preventing, treating or improving a disease against which an integrin expression inhibition is effective includes an agent for treating arterial sclerosis, psoriasis, cancer, osteoporosis, retinal angiogenesis, diabetic retinopathy or inflammatory diseases, an anticoagulant agent, a cancer metastasis suppressor and an antiangiogenesis agent.

The present invention will be hereinafter explained in detail.

In B and R, the C6-C10 aryl ring or 6-membered to 10-membered heteroaryl ring which may have a substituent and in which a part of the ring may be saturated means an aromatic hydrocarbon group having 6 to 10 carbon atoms or a 6-membered to 10-membered aromatic heterocycle containing at least one atom among nitrogen atom, oxygen atom and sulfur atom as a heteroatom, and may have one or more substituents on the ring and a part of the ring may be saturated. Specific examples thereof include benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole, benzothiazole, 4,5,6,7-tetrahydroindole, 1,2,3,4-tetrahydroisoquinoline, 2,3-dihydrobenzofuran, indane, tetralone, indoline, isoindoline, chroman and tetralin. The above-mentioned aromatic ring may have 1 to 3 substituents. In the case where plural substituents are present, these substituents may be the same or different. Examples of the substituent may include an amino group which may be substituted with a lower alkyl group or lower cycloalkyl group, a lower alkyl group, a lower alkoxy group, hydroxyl group, nitro group, mercapto group, cyano group, a lower alkylthio group, a halogen group, a group represented by the formula -$a^a$-$b^a$ (wherein $a^a$ means a single bond, —$(CH_2)_k{}^a$—, —O—$(CH_2)_k{}^a$—, —S—$(CH_2)_k{}^a$— or —$N(R^{3a})$—$(CH_2)_k{}^a$— (wherein $k^a$ means an integer of 1 to 5; and $R^{3a}$ means hydrogen atom or a lower alkyl group); and $b^a$ means —$CH_2$-$d^a$ (wherein $d^a$ means an amino group which may be substituted with a lower alkyl group, a halogen atom, hydroxyl group, a lower alkylthio group, cyano group or lower alkoxy group)), a group represented by the formula -$a^a$-$e^a$-$f^a$ (wherein $a^a$ has the same meaning as above; $e^a$ means —S(O)— or —S(O)$_2$—; and $f^a$ means an amino group which may be substituted with a lower alkyl group or lower alkoxy group, a lower alkyl group, trifluoromethyl group, —$(CH_2)_m{}^a$-$b^a$ or —$N(R^{4a})$—$(CH_2)_m{}^a$-$b^a$ (wherein $b^a$ has the same meaning as above; $R^{4a}$ means hydrogen atom or a lower alkyl group; and $m^a$ means an integer from 1 to 5)), a group represented by the formula -$a^a$-$g^a$-$h^a$ (wherein $a^a$ has the same meaning as above; $g^a$ means —C(O)— or —C(S)—; and $h^a$ means an amino group which may be substituted with a lower alkyl group, hydroxyl group, a lower alkyl group, a lower alkoxy group, —$(CH_2)_n{}^a$-$b^a$ or —$N(R^{5a})$—$(CH_2)_n{}^a$-$b^a$ (wherein $b^a$ has the same meaning as above; $R^{5a}$ means hydrogen atom or a lower alkyl group; and na means an integer from 1 to 5)), a group represented by the formula -$a^a$-$N(R^{6a})$-$g^a$-$i^a$ (wherein $a^a$ and $g^a$ have the same meanings as above; $R^{6a}$ means hydrogen atom or a lower alkyl group; $i^a$ means hydrogen atom, a lower alkoxy group or $f^a$ ($f^a$ has the same meaning as above)), a group represented by the formula -$a^a$-$N(R^{7a})$-$e^a$-$f^a$ (wherein $a^a$, $e^a$ and $f^a$ have the same meanings as above; $R^{7a}$ means hydrogen atom or a lower alkyl group), the formula —$(CH_2)_p{}^a$-$j^a$-$(CH_2)_q{}^a$-$b^a$ (wherein $j^a$ means oxygen atom or a sulfur atom; $b^a$ has the same meaning as above; and $p^a$ and $q^a$ are the same as or different from each other and each means an integer from 1 to 5), the formula —$(CH_2)_u{}^a$—$Ar^a$ (wherein $Ar^a$ means a phenyl group or heteroaryl group which may be substituted with a lower alkyl group, lower alkoxy group or halogen atom; and $u^a$ means 0 or an integer from 1 to 5), the formula —CONH—$(CH_2)_u{}^a$—$Ar^a$ (wherein $Ar^a$ and $u^a$ have the same meanings as above) or a group represented by the formula —$SO_2$—$(CH_2)_u{}^a$—$Ar^a$ (wherein $Ar^a$ and $u^a$ have the same meanings as above).

Compounds represented by the formula (I), in which R is indole, quinoline or isoquinoline, are preferable.

In the formula (I$^a$), the "monocyclic or bicyclic aromatic ring which may have a substituent" represented by the $A^a$ ring is an aromatic hydrocarbon or an aromatic heterocycle containing at least one of nitrogen atom, oxygen atom and sulfur atom, wherein 1 to 3 substituents may exist on the ring. Examples of main aromatic rings contained in the $A^a$ ring include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole and benzothiazole. The above-mentioned aromatic ring may have 1 to 3 substituents. When plural substituents are present, these substituents may be the same or different. Examples of the substituent may include an amino group which may be substituted with a lower alkyl group or a lower cycloalkyl group, lower alkyl group, lower alkoxy group, hydroxyl group, nitro group, mercapto group, cyano group, lower alkylthio group, halogen group, a group represented by the formula -$a^a$-$b^a$ (wherein $a^a$ means a single bond, —$(CH_2)_k{}^a$—, —O—$(CH_2)_k{}^a$—, —S—$(CH_2)_k{}^a$— or —$N(R^{3a})$—$(CH_2)_k{}^a$—; $k^a$ means an integer of 1 to 5; $R^{3a}$ means hydrogen atom or a lower alkyl group; and $b^a$ represents —$CH_2$-$d^a$ (where $d^a$ means an amino group which may be substituted with a lower alkyl group, a halogen atom, hydroxyl group, a lower alkylthio group, cyano group or a lower alkoxy group)), a group represented by the formula -$a^a$-$e^a$-$f^a$ (wherein $a^a$ has the same meaning as above; $e^a$ means —S(O)— or —S(O)$_2$—; $f^a$ means an amino group which may be substituted with a lower alkyl group or lower alkoxy group, a lower alkyl group, trifluoromethyl group, —$(CH_2)_m{}^a$-$b^a$ or —$N(R^{4a})$—$(CH_2)_m{}^a$-$b^a$ (wherein $b^a$ has the same meaning as above; $R^{4a}$ means hydrogen atom or a lower alkyl group; and $m^a$ means an integer from 1 to 5)), a group represented by the formula -$a^a$-$g^a$-$h^a$ (wherein $a^a$ has the same meaning as above; $g^a$ means —C(O)— or —C(S)—; $h^a$ means an amino group which may be substituted with a lower alkyl group, hydroxyl group, a lower alkyl group, a lower alkoxy group, —$(CH_2)_n{}^a$-$b^a$ or —$N(R^{5a})$—$(CH_2)_n{}^a$-$b^a$ (wherein $b^a$ has the same meaning as above; $R^{5a}$ means hydrogen atom or a lower alkyl group; and $n^a$ means an integer from 1 to 5)), a group represented by the formula -$a^a$-$N(R^{6a})$-$g^a$-$i^a$ (wherein $a^a$ and $g^a$ have the same meanings as above; $R^{6a}$ means hydrogen atom or a lower alkyl group; and $i^a$ means hydrogen atom, a lower alkoxy group or $f^a$ ($f^a$ has the same meaning as above)), a group represented by the formula -$a^a$-$N(R^{7a})$-$e^a$-$f^a$ (wherein $a^a$, $e^a$ and $f^a$ have the same meanings as above; and $R^{7a}$ means hydrogen atom or a lower alkyl group), the formula —$(CH_2)_p{}^a$-$j^a$-$(CH_2)_q{}^a$-$b^a$ (wherein $j^a$ means oxygen atom or sulfur atom; $b^a$ has the same meaning as above; and $p^a$ and $q^a$ are the same as or different from each other and each means an integer from 1 to 5), the formula —$(CH_2)_u{}^a$—$Ar^a$ (wherein $Ar^a$ means a phenyl group or heteroaryl group which may be substituted with a lower alkyl group, lower alkoxy group or halogen atom; and $u^a$ means 0 or an integer from 1 to 5), the formula —CONH—$(CH_2)_u{}^a$—$Ar^a$ (wherein $Ar^a$ and $u^a$ have the same meanings as above) or a group represented by the formula —$SO_2$—$(CH_2)_u{}^a$—$Ar^a$ (wherein $Ar^a$ and $u^a$ have the same meanings as above).

In the aforementioned examples of the substituent, when the amino group is substituted with two alkyl groups, these alkyl groups may be bound together to form a 5- to 6-membered ring. Further, in the case where the $A^a$ ring is a nitrogen-containing heterocycle having hydroxyl group or mercapto group, the $A^a$ ring may have the form of an oxo group or thioxo group by allowing these groups to form a resonance structure.

The "6-membered cyclic unsaturated hydrocarbon or the unsaturated six-membered heterocycle which contains one nitrogen atom as a heteroatom, which may have a substituent" represented by the $B^a$ ring is a benzene or pyridine a part of which may be hydrogenated and may have one or two substituents on the ring. When two substituents are present, these substituents may be the same or different.

The "five-membered heterocycle which may have a substituent and contains one or two nitrogen atoms" represented by the $C^a$ ring is pyrrole, pyrazole or imidazole a part of which may be hydrogenated and may have one or two substituents on the ring. When two substituents are present, these substituents may be the same or different.

Examples of the substituent which the $B^a$ ring and the $C^a$ ring may have may include a halogen group, cyano group, a lower alkyl group, a lower alkoxy group, hydroxyl group, oxo group, the formula —C(O)-$r^a$ (wherein $r^a$ means hydrogen atom, an amino group which may be substituted with a lower alkyl group, a lower alkyl group, a lower alkoxy group or hydroxyl group), an amino group which may be substituted with a lower alkyl group and trifluoromethyl group.

Examples of the lower alkyl group in the definition of the substituent which $R^{1a}$, $R^{2a}$, and the $A^a$, $B^a$ and $C^a$ rings may have in the above formula ($I^a$) mean a linear or branched alkyl group having 1 to 6 carbon atoms, for example, methyl group, ethyl group, n-propyl group, isopropyl group, n-butyl group, isobutyl group, sec-butyl group, tert-butyl group, n-pentyl group (amyl group), isopentyl group, neopentyl group, tert-pentyl group, 1-methylbutyl group, 2-methylbutyl group, 1,2-dimethylpropyl group, n-hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group. As preferable groups among these groups, methyl group, ethyl group, n-propyl group, isopropyl group, n-butyl group and isobutyl group may be proposed. Among these preferable groups, methyl group, ethyl group, n-propyl group and isopropyl group are most preferable groups.

Examples of the lower cycloalkyl group in the definition of the substituent which the $A^a$ ring may have include a cyclopropyl group, cyclopentyl group and cyclohexyl group.

The lower alkoxy group in the definition of the substituent which the $A^a$ ring, the $B^a$ ring and the $C^a$ ring may have means a lower alkoxy groups derived from the above-mentioned lower alkyl groups such as methoxy group, ethoxy group, n-propoxy group, isopropoxy group, n-butoxy group, isobutoxy group and tert-butoxy group. Among these groups, methoxy group and ethoxy group may be given as most preferable examples. Also, examples of the halogen atom include fluorine atom, chlorine atom and bromine atom.

Among these substituents, particularly preferable examples include 1)
N-(3-cyano-4-methyl-1H-indole-7-yl)-3-cyanobenzenesulfonamide; 2)
N-(3-cyano-4-methyl-1H-indole-7-yl)-6-chloro-3-pyridinesulfonamide; 3)
N-(3-bromo-5-methyl-1H-indole-7-yl)-4-sulfamoylbenzenesulfonamide; 4)
N-(5-bromo-3-chloro-1H-indole-7-yl)-6-amino-3-pyridinesulfonamide; 5)
N-(3-bromo-5-methyl-1H-indole-7-yl)-3-cyanobenzenesulfonamide; 6) N-(4-bromo-1H-indole-7-yl)-4-cyanobenzenesulfonamide; 7)
N-(4-chloro-1H-indole-7-yl)-6-amino-3-pyridinesulfonamide; 8)
N-(3-bromo-4-chloro-1H-indole-7-yl)-6-amino-3-pyridinesulfonamide; 9)
N-(3-bromo-5-methyl-1H-indole-7-yl)-5-cyano-2-thiophenesulfonamide; 10)
N-(4-bromo-3-chloro-1H-indole-7-yl)-2-amino-5-pyrimidinesulfonamide; and 11.)
N-(3-chloro-1H-indole-7-yl)-4-sulfamoylbenzenesulfonamide.

There is the case where the sulfonamide derivative represented by the above formula ($I^a$) forms a salt in combination with an acid or a base. The present invention also involves salts of the compound ($I^a$). Examples of the salt of an acid include inorganic acid salts such as hydrochloride, hydrobromide and sulfate, and salts of organic acids such as acetic acid, lactic acid, succinic acid, fumaric acid, maleic acid, citric acid, benzoic acid, methanesulfonic acid and p-toluenesulfonic acid. Examples of the salt of a base may include inorganic salts such as sodium salts, potassium salts and calcium salts and salts of organic bases such as triethylamine, arginine and lysine.

In the present invention, the "aromatic ring which may have one or two nitrogen atoms" represented by the ring $Q^b$ means an aromatic hydrocarbon or a 6-membered aromatic heterocycle having one or two nitrogen atoms. Examples of primary aromatic rings included in the ring $Q^b$ include benzene, pyridine, pyrimidine, pyrazine and pyridazine. Also, the ring M represented by the term "means a C5-C12 unsaturated monocycle or multi-cycle, which may have 1 to s4 heteroatoms selected from nitrogen atom, oxygen atom and sulfur atom" means a monocycle or a multi-cycle having a double bond together with the ring $Q^b$ and specifically means aromatic hydrocarbons such as benzene and naphthalene, unsaturated hydrocarbons such as cyclopentene, cyclohexene, cycloheptene, cyclooctene, cyclopentadiene, cycloheptadiene and cyclooctadiene, and unsaturated heterocycles such as tetrahydropyridine, pyrrole, furan, thiophene, oxazole, isoxazole, thiazole, isothiazole, pyrazole, imidazole, triazole, pyridine, pyrimidine, pyrazine, pyridazine, triazine, indole, isoindole, quinoline, isoquinoline, indazolizine, naphthyridine, benzofuran, benzopyran, benzothiophene, benzimidazole benzoxazole, benzothiazole, pyrrolopyridine, pyridopyrimidine and imidazopyridine. Also, the term "the ring $Q^b$ possesses one nitrogen atom together with the ring $M^b$" means the case where the nitrogen atom is present at the position where both rings are condensed. Examples of the ring formed in this manner include indazolizine, imidazo[1,2-a]pyridine, imidazo[1,5-a]pyridine and pyrazolo[1,5-a]pyrimidine.

In the present invention, the C1-C4 alkyl group in $R^{1b}$, $R^{4b}$ and $R^{5b}$ or in the "C1-C4 alkyl group which may be substituted with a halogen atom" in $A^b$, $D^b$, $R^{1b}$, $R^{2b}$, $R^{3b}$, $R^{6b}$, $R^{7b}$, $R^{8b}$, $R^{9b}$, $R^{10b}$, $R^{11b}$, $R^{12b}$, $R^{13b}$, $R^{14b}$, $R^{15b}$, $G^{1b}$, $G^{2b}$ and the A group means a linear or branched alkyl group having 1 to 4 carbons atoms. For example, methyl group, ethyl group, n-propyl group, isopropyl group, n-butyl group, isobutyl group, sec-butyl group and tert-butyl group may be proposed. The term "maybe substituted with a halogen atom" means that the alkyl group may be substituted with a halogen atom selected from fluorine atom, chlorine atom, bromine atom and iodine atom. For example, monofluoromethyl group, monochloromethyl group, difluoromethyl group, trifluoromethyl group, 1- or 2-monofluoromethyl group, 1- or 2-monochloroethyl group, 1- or 2-monobromoethyl group, 1,2-difluoroethyl group, 1,2-dichloroethyl group, 1,1,2,2,2-pentafluoroethyl group and 3,3,3-trifluoropropyl group may be proposed. Preferable examples among these groups include monofluoromethyl group, difluoromethyl group, trifluoromethyl group, 1- or 2-monofluoroethyl group, 1,2-difluoroethyl group and 1,1,2,2,2-pentafluoroethyl group.

In the present invention, the C1-C4 alkoxy group in the "C1-C4 alkoxy group which may be substituted with a halogen atom" in $A^a$, $D^b$ and the group A means a linear or branched alkoxy group having 1 to 4 carbon atoms. For example, methoxy group, ethoxy group, n-propyloxy group, isopropyloxy group, n-butyloxy group, isobutyloxy group, sec-butyloxy group and tert-butyloxy group may be proposed. The term "may be substituted with a halogen atom" means that the alkoxy group may be substituted with a halogen atom selected from fluorine atom, chlorine atom, bromine atom and iodine atom. For example, monofluoromethoxy group, difluoromethoxy group, trifluoromethoxy group, 1- or 2-monofluoroethoxy group, 1- or 2-monochloroethoxy group, 1- or 2-monobromoethoxy group, 1,2-difluoroethoxy group, 1, 1,2,2,2-pentafluoroethoxy group and 3,3,3-trifluoropropyloxy group may be proposed. Among these groups, preferable examples include monofluoromethoxy group, difluoromethoxy group, trifluoromethoxy group, 1- or 2-monofluoroethoxy group, 1,2-difluoroethoxy group and 1,1,2,2,2-pentafluoroethoxy group.

In the present invention, the C2-C4 alkenyl or alkynyl group appeared in $A^b$ and $D^b$ means an alkenyl or alkynyl group having 2 to 4 carbon atoms. For example, vinyl group, allyl group, 2- or 3-butenyl group, 1,3-butadienyl group, ethynyl group, 2-propynyl group, 2-methylethynyl group and 2- or 3-butynyl group may be proposed.

In the present invention, the aryl group appeared in Bb and the group A means an aromatic hydrocarbon, and phenyl group and naphthyl group may be exemplified. Also, the heteroaryl group means a monocycle or multi-cycle having one or two or more of nitrogen atom, oxygen atom and sulfur atom. For example, pyrrolyl, imidazolyl group, pyrazolyl group, triazolyl group, furyl group, thienyl group, oxazolyl group, isoxazolyl group, thiazolyl group, isothiazolyl group, thiadiazolyl group, pyridyl group, pyrimidyl group, pyrazyl group, indolyl group, indolizinyl group, benzoimidazolyl group, benzothiazolyl group, benzoxazolyl group, quinolinyl group, isoquinolinyl group, quinazolinyl group and phthalazinyl group may be proposed.

In the present invention, the term "$R^{8b}$ and $R^{9b}$ may form a 5- or 6-membered ring together with the nitrogen atom to which they are bound, and the ring may further contain nitrogen atom, oxygen atom or sulfur atom" in the definition of $R^{8b}$ and $R^{9b}$ means that $R^{8b}$ and $R^{9b}$ form pyrrolidinyl group, piperidinyl group, morpholino group, thiomorpholino group, piperazinyl group etc. together with the nitrogen atom to which they are bound.

In the present invention, the aminosulfonyl group which may be substituted with a mono- or di-C1-C4 alkyl group, C1-C4 alkyl-S(O)$_s^b$-C1-C4-alkylene group, or phenylsulfonylamino group which may have a C1-C4 alkyl group or a substituent and a C1-C4 alkyl group which may be substituted with a C1-C4 alkyl group in the definition of A group means the same alkyl group as above, and examples of the alkylene group may include methylene group, ethylene group, propylene group, butylene group, methylmethylene group, 1- or 2-methylethylene group, 1-, 2- or 3-methylpropylene group and dimethylmethylene group.

Also, the C1-C8 alkanoyl group means, for example, formyl group, acetyl group, propionyl group, butyryl group, isobutyryl group, valeryl group and benzoyl group.

The protective group in the term "an amino group which may have a protective group" appeared in $J^b$ of the present invention may be any group as far as it is known as a protective group in the usual organic synthesis and no particular limitation is imposed on the protective group. For example, benzyloxycarbonyl group, t-butoxycarbonyl group, formyl group, acetyl group, chloroacetyl group, 2,2,2-trichloroethyl group, benzylidene group, benzhydryl group and trityl group may be proposed. Also, the protective group in the carboxy group which may have a protective group and the protective group of the carboxy group in $R^{16b}$ may be any group as far as it is known as a protective group in the usual organic synthesis and no particular limitation is imposed on the protective group. For example, methyl group, ethyl group, propyl group, isopropyl group, t-butyl group, methoxymethyl group, 2,2,2-trichloroethyl group, pivaloyloxymethyl group and benzyl group may be proposed.

In the present invention, the substituent in the term "may have a substituent" means the above-mentioned halogen atom, C1-C4 alkyl group or alkoxy group which may be substituted with a halogen atom, hydroxyl group, hydroxy C1-C4 alkyl group, amino group which may be substituted with a mono- or di-C1-C4 alkyl group, C2-C4 alkenyl or alkynyl group, cyano group, C1-C8 acyl group, aminosulfonyl group which may be substituted with a mono or di C1-C4 alkyl group, carboxy group, C1-C4 alkoxycarbonyl group and carbamoyl group which may be substituted with a mono- or di-C1-C4 alkyl group.

The sulfonamide-containing heterocyclic compound represented by the above formula ($I^b$) occasionally forms a salt in combination with an acid or a base. The present invention also includes salts of the compound ($I^b$) Examples of the salt of an acid include inorganic acid salts such as hydrochloride, hydrobromide and sulfate and salts of organic acids such as acetic acid, lactic acid, succinic acid, fumaric acid, maleic acid, citric acid, benzoic acid, methanesulfonic acid and p-toluenesulfonic acid. Also, as the salt of a base, inorganic salts such as sodium salts, potassium salts and calcium salts and salts of organic bases such as triethylamine, arginine and lysine may be given.

Also, it is needless to say that as well as hydrates of these compounds, optical isomers, if these isomers are present, are included in the present invention. The present invention also includes compounds showing an antiangiogenesis action and produced from the present compound following in vivo metabolism such as oxidation, reduction, hydrolysis and conjugation. Also, the present invention further includes compounds producing the compound of the present invention following in vivo metabolism such as oxidation, reduction and hydrolysis.

The compound ($I^a$) according to the present invention can be produced by various methods. For example, several methods among these methods are specifically disclosed in the publications of JP-A 7-165708 and JP-A 8-231505.

As aforementioned, the compound ($I^a$) of the present invention may be produced using various methods. Among these methods, typical methods are shown as follows.

1) It may be produced by reacting a sulfonic acid represented by the formula ($II^a$):

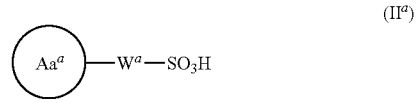

(wherein the $Aa^a$ ring represents a monocyclic or bicyclic aromatic ring which may have a protected or unprotected substituent; and $W^a$ has the same meaning as above) or its reactive derivative with a compound represented by the formula ($III^a$):

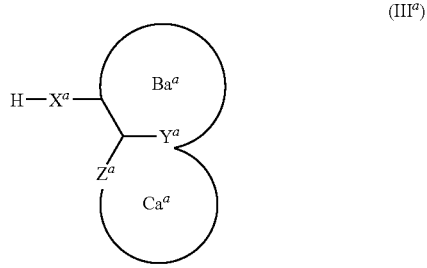

wherein the Ba$^a$ ring represents a 6-membered unsaturated hydrocarbon or unsaturated 6-membered heterocycle which contains on nitrogen atom as a heteroatom, which may have a protected or unprotected substituent; the Ca$^a$ ring a 5-membered ring which may have a protected or unprotected substituent and contains one or two nitrogen atoms; and X$^a$, Y$^a$ and Z$^a$ have the same meanings as above.

Examples of the reactive derivative of the sulfonic acid (II$^a$) may include reactive derivatives usually used frequently such as sulfonyl halides, sulfonic acid anhydrides and N-sulfonylimidazolides. Particularly preferable examples are sulfonyl halides. Although no particular limitation is imposed on the solvent used in the reaction, it is desirable to use a solvent which dissolves raw materials and does not react with these raw materials with ease. For example, pyridine, tetrahydrofuran, dioxane, benzene, ethyl ether, dichloromethane and dimethylformamide, or a mixed solvent using two or more solvents selected from these solvents may be utilized. Also, in the reaction, in the case where a free acid appears with the progress of the reaction as shown in the case of using a sulfonyl halide, the reaction is preferably run in the presence of a proper deoxidizer. Therefore, the use of a basic solvent such as pyridine is particularly preferable. When a neutral solvent is used, a basic substance such as an alkali carbonate and an organic tertiary amine may be added. It is needless to say that usable solvents are not limited to these exemplified solvents. Although the reaction generally proceeds at room temperature, the raw materials may be cooled or heated according to the need. The reaction time is generally 10 minutes to 20 hours but is selected according to the type of raw material and the reaction temperature.

In the case where the amino group or the hydroxyl group is protected in the resulting product, a sulfonamide derivative or sulfonate derivative (I$^a$) having a free hydroxyl group or amino group can be obtained by a usual deprotecting method such as acid treatment, alkali treatment and catalytic reduction, as required.

2) It may be produced by reacting a compound represented by the formula (IV$^a$)

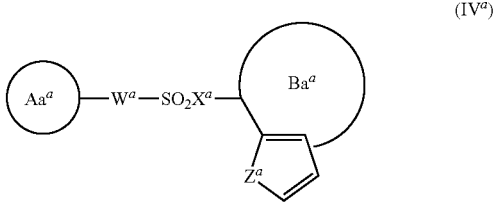

(IV$^a$)

(wherein the Aa$^a$ ring, the Ba$^a$ ring, W$^a$, X$^a$ and Z$^a$ have the same meanings as above) with a halogenating agent. As the halogenating agent, N-chlorosuccinimide, N-bromosuccinimide, 1,3-dibromo-5,5-dimethylhydantoin, N-bromoacetamide, chlorine and bromine may be proposed. Although no particular limitation is imposed on the solvent to be used in the reaction, an alkyl chloride compound such as dichloromethane, chloroform and carbon tetrachloride, or an aromatic chloride such as chlorobenzene and dichlorobenzene is generally used, and a water-soluble solvent such as dimethylformamide, dioxane, pyridine and acetonitrile may be also used. Although the reaction temperature differs depending on the types of halogenating agent and substrate, it is usually run at −50° C. to 100° C.

In the case where the amino group or the hydroxyl group is protected in the resulting product, a sulfonamide derivative or sulfonate derivative (I$^a$) having a free hydroxyl group or amino group can be obtained by a usual deprotecting method such as acid treatment, alkali treatment and catalytic reduction, as required.

3) It may be produced by reacting a compound represented by the formula (V$^a$):

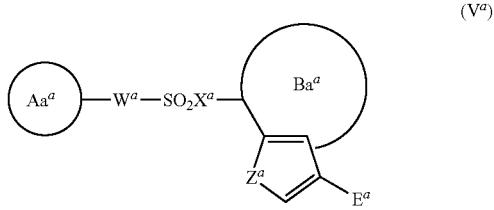

(V$^a$)

(wherein the Aa$^a$ ring, the Ba$^a$ ring, W$^a$, X$^a$ and Z$^a$ have the same meanings as above; and E$^a$ represents a substituent convertible into cyano group by dehydration) with a dehydrating agent. As the substituent convertible into cyano group by dehydration, (hydroxyimino)methyl group and carbamoyl group may be proposed.

Also, it is possible that an oxime or an acid amide is first synthesized from an aldehyde or a carboxylic acid used as a starting material and then reacted with a dehydrating agent without isolating it. As examples of the dehydrating agent, those used in a usual method of synthesizing nitrile, for example, acetic acid anhydride, thionyl chloride, phosphorous oxychloride, selenium dioxide and 1,3-dicyclohexylcarbodiimide may be given. Although no particular limitation is imposed on the solvent to be used in the reaction, those which do not react with these materials with ease is desirable, for example pyridine, ethyl ether, benzene, dimethylformamide, carbon tetrachloride, acetonitrile and tetrahydrofuran, or a mixed solvent of two or more solvents selected from these solvents may be utilized. Although the reaction temperature differs depending on the types of dehydrating agent and substrate, the reaction is usually run at −50° C. to 150° C.

In the case where the amino group or the hydroxyl group is protected in the resulting product, a sulfonamide derivative or sulfonate derivative (I$^a$) having a free hydroxyl group or amino group can be obtained using a usual deprotecting method such as acid treatment, alkali treatment and catalytic reduction, as required.

4) It may be produced by reacting a compound represented by the formula (VI$^a$):

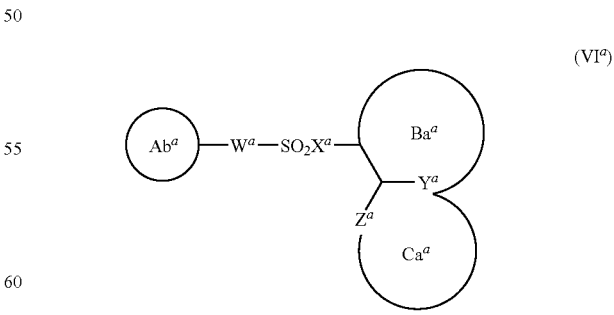

(VI$^a$)

(wherein the Ab$^a$ ring represents a monocyclic or bicyclic aromatic ring which has a substituent convertible into amino group by reduction and may also have a protected or unprotected substituent; and the Ba$^a$ ring, the Ca$^a$ ring, W$^a$, X$^a$, Y$^a$ and $Z^a$ have the same meanings as above) with a reducing agent. As the substituent convertible into amino group by reduction, nitro group, nitroso group, hydroxyamino group and azo group may be exemplified.

A nitro group-reducing method which is commonly examples of the reducing method, catalytic reduction using, as a catalyst, palladium-carbon and platinum oxide and reduction using zinc, iron or tin with an acid may be given. The catalytic reduction may be usually carried out under normal pressure or under pressure in an organic solvent such as methanol, tetrahydrofuran or dimethylformamide.

In the case where the hydroxyl group is protected in the resulting product, a sulfonamide derivative or sulfonate derivative ($I^a$) having a free hydroxyl group can be obtained using a usual deprotecting method such as acid treatment, alkali treatment and catalytic reduction, as required.

5) It may be produced by reacting a compound represented by the formula ($VII^a$)

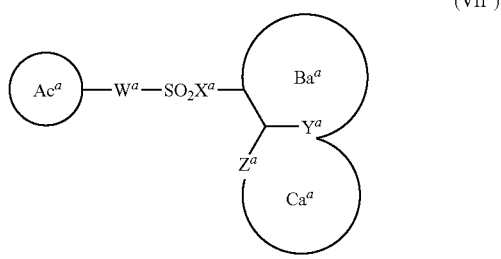

(VII$^a$)

(wherein the $Ac^a$ ring means a monocyclic or bicyclic aromatic ring which has a dissociable group on the ring or in a substituent, and may also have a protected or unprotected substituent; and the $Ba^a$ ring, the $Ca^a$ ring, $W^a$, $X^a$, $Y^a$ and $Z^a$ have the same meanings as above) with a nucleophilic agent. Examples of the leaving group may include a halogen group, methanesulfonyloxy group and p-toluenesulfonyloxy group. Examples of the nucleophilic agent may include amines, alcohols and thiols. In the case of alcohols or thiols, these compounds may have the form of a salt of an alkali metal or the like upon reaction. Although no particular limitation is imposed on the solvent to be used in the reaction, a solvent which dissolves raw materials and does not react with these materials with ease is desirable. For example, tetrahydrofuran, dioxane, dimethylformamide or water may be utilized. Although the reaction temperature differs depending on the type of substrate, the reaction is usually run at –50° C. to 150° C.

In the case where the amino group or the hydroxyl group is protected in the resulting product, a sulfonamide derivative or sulfonate derivative ($I^a$) having a free hydroxyl group or amino group can be obtained by a usual deprotecting method such as acid treatment, alkali treatment and catalytic reduction, as required.

Next, methods for producing the raw material compound ($II^a$) and its reactive derivative and the compound ($III^a$) used in the present invention will be explained.

The raw material compound ($II^a$) and its reactive derivative include known compounds and novel compounds. In the case of these novel compounds, these compounds may be produced by applying a method of synthesizing a known compound which has been already reported or by using a combination of these known methods. For example, a novel sulfonyl chloride may be produced by a method obtained by applying synthetic methods described in Chem. Ber., 90, 841 (1957), J. Med. Chem., 6, 307 (1963), J. Chem. Soc. (c), 1968, 1265, Chem. Lett., 1992, 1483, J. Am. Chem. Soc., 59, 1837 (1937), J. Med. Chem., 23, 1376 (1980), J. Am. Chem. Soc., 70, 375 (1948), J. Am. Chem. Soc., 78, 2171 (1956) etc.

The raw material compound ($III^a$) includes known compounds and novel compounds. In the case where $H—X^a—$ represents an amino group $H_2N—$ in the raw material compound ($III^a$), an $H_2N$ body ($III^a$) can be obtained by reducing the nitro compound by using a nitro group-reducing method which is usually used. Preferable examples of the reducing methods include catalytic reduction using a palladium-carbon catalyst and reduction using a zinc powder-hydrochloric acid. The catalytic reduction may be usually carried out under normal pressure or under pressure in an organic solvent such as methanol, tetrahydrofuran and dimethylformamide.

In the case where $H—X^a—$ means hydroxyl group ($HO—$) in the raw material compound ($III^a$), a HO compound ($III^a$) can be obtained by diazotizing the above amino compound and then hydrolyzing the resulting product.

In the case where the raw material compounds are these novel compounds, these compounds may be produced by applying a method of synthesizing a known compound which has been already reported or by using a combination of these known methods. A novel compound maybe produced by applying the methods described in Can. J. Chem., 42, 1235 (1964), Chem. Abst., 59, 8855f (1963), Tetrahedron Lett., 30, 2129 (1989) etc. through, for example, the following route.

Scheme 1$^a$

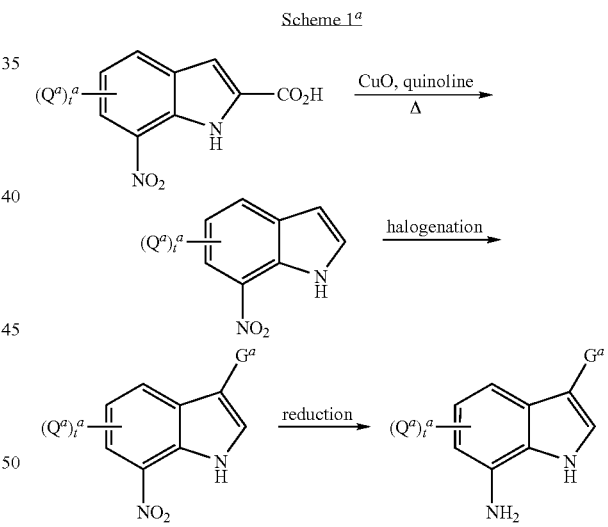

In the formula, $Q^a$s mean the same or different substituents; $G^a$ means a halogen group; and $t^a$ means an integer from 0 to 2.

Scheme 2$^a$

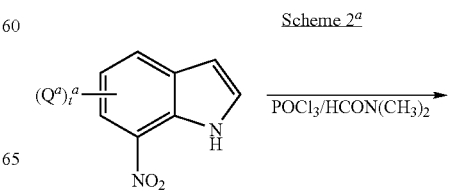

-continued

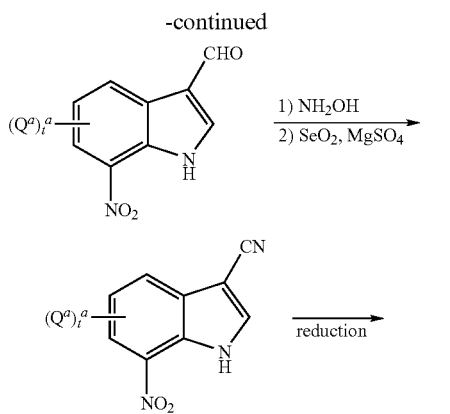

In the formula, $Q^a$ and $t^a$ have the same meanings as above.

Scheme $3^a$

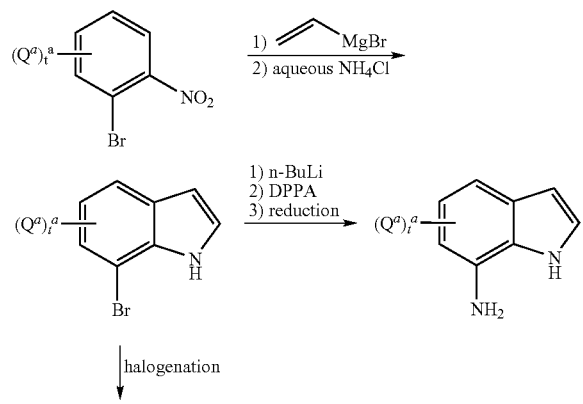

In the formula, $Q^a$, $G^a$ and $t^a$ have the same meanings as above; and DPPA means diphenylphosphorylazide.

Scheme $4^a$

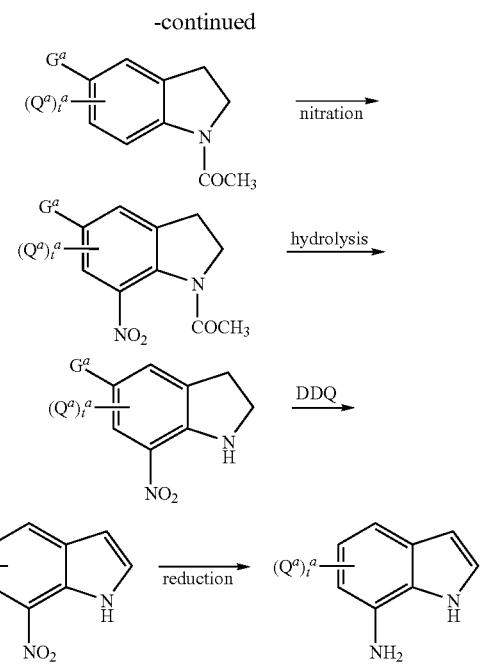

In the formula, $Q^a$, $G^a$ and $t^a$ have the same meanings as above; and DDQ means 2,3-dichloro-5,6-dicyano-1,4-benzoquinone.

Next, the compound ($I^b$) of the present invention may be produced by various methods. Among them, typical methods are as follows.

1) When $Z^b$ is a Single Bond

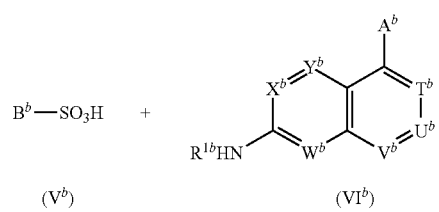

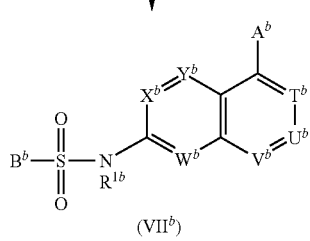

In the formula, $A^b$, $B^b$, $T^b$, $U^b$, $V^b$, $W^b$, $X^b$ and $T^b$ have the same meanings as above. It may be produced by reacting the sulfonic acid represented by the formula ($V^b$) or its reactive derivative with the compound represented by the formula ($VI^b$).

As examples of the reactive derivative of the sulfonic acid ($V^b$), reactive derivatives generally utilized frequently such as sulfonyl halides, sulfonic acid anhydrides and N-sulfonylimidazolides may be proposed. A particularly preferable example is a sulfonyl halide. Although no particular limitation is imposed on the solvent to be used in the reaction, those which dissolve the raw material and do not react with the raw material with ease are desirable. For example, pyridine, tetrahydrofuran, dioxane, benzene, ethyl ether, dichloromethane and dimethylformamide, or a mixed solvent of two or more solvents selected from these may be utilized. Also, in this reaction, in the case where a free acid appears with the progress of the reaction as shown in the case of using a sulfonyl halide, the reaction is preferably run in the presence of a proper deoxidizer. Therefore, the use of a basic solvent such as pyridine is particularly preferable. When a neutral solvent is used, a basic substance such as an alkali carbonate and an organic tertiary amine may be added. It is needless to say that usable solvents are not limited to these exemplified solvents. Although this reaction generally proceeds at room temperature, the raw materials may be cooled or heated according to the need. The reaction time is generally 10 minutes to 20 hours but is optionally selected according to the type of raw material and the reaction temperature.

In the case where the amino group or the hydroxyl group is protected in the resulting product, a sulfonamide derivative ($VII^b$) having a free hydroxyl group or amino group can be obtained using a usual deprotecting method such as acid treatment, alkali treatment and catalytic reduction, as required.

2) When $Z^b$ is —CO—NH—

In the formula, $L^b$ means chlorine atom or bromine atom; $R^{17b}$ represents a C1-C4 alkyl group or benzyl group; and $A^b$, $B^b$, $T^b$, $U^b$, $V^b$, $W^b$, $X^b$ and $T^b$ have the same meanings as above.

It may be produced by reacting a compound represented by the formula ($VIII^b$) isocyanate with a sulfonamide compound represented by the formula ($IX^b$).

The reaction is run in water or a water-miscible non-reactive solvent such as tetrahydrofuran and acetone in the presence of a base such as sodium hydroxide, potassium hydroxide, lithium hydroxide, sodium methoxide and sodium hydride. The reaction is run at a temperature from 0° C. up to 100° C. and preferably about 20 to 30° C.

Another preferable reaction is attained by a method in which an amine represented by the formula ($XI^b$) is reacted with a carbamate represented by the formula ($XII^b$) obtained by reacting a sulfonamide represented by the formula ($IX^b$) with a haloformate represented by the formula ($XIII^b$).

The reaction between the sulfonamide represented by the formula ($IX^b$) with the haloformate represented by the formula ($XIII^b$) is run in a non-reactive solvent such as acetone, tetrahydrofuran and methyl ethyl ketone in the presence of an acid scavenger such as potassium carbonate, sodium carbonate, potassium hydroxide and sodium hydroxide. The reaction is run at a temperature from about 30° C. to a refluxing temperature. Next, the reaction between the carbamate represented by the formula ($XII^b$) and the amine represented by the formula ($XI^b$) is run in an inert and high-boiling point solvent such as dioxane, toluene and diglym under heating at a temperature from about 50° C. to a refluxing temperature.

The amine compound represented by the formula ($VI^b$) or ($XI^b$) as the raw material of the sulfonamide or sulfonylurea-

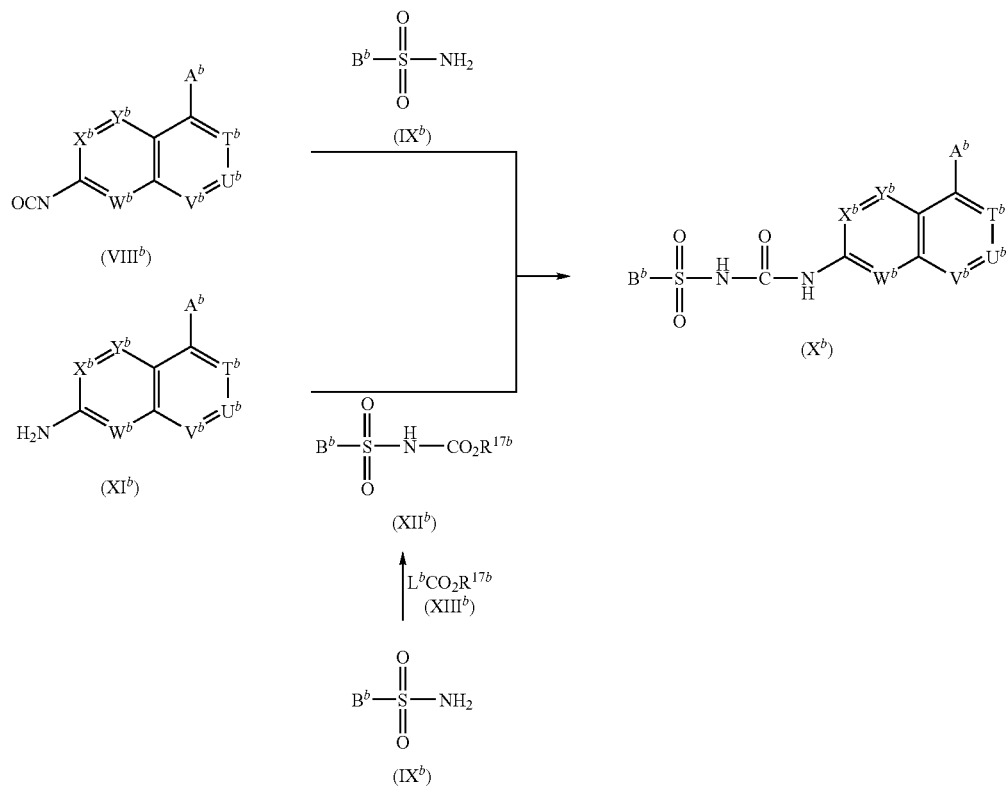

containing heterocyclic compound of the present invention may be produced using a combination of known methods.

For example, quinoline and isoquinoline derivatives may be produced in the following production steps.

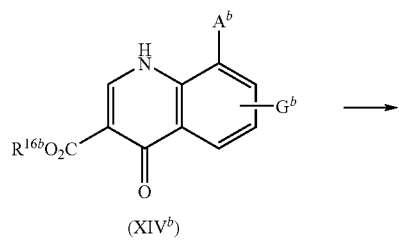

(XIV$^b$)

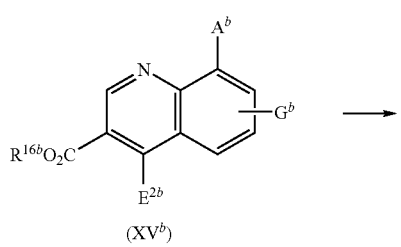

(XV$^b$)

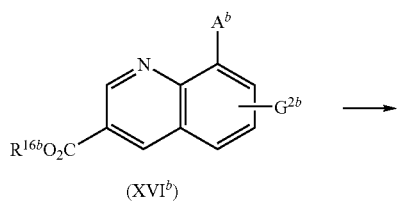

(XVI$^b$)

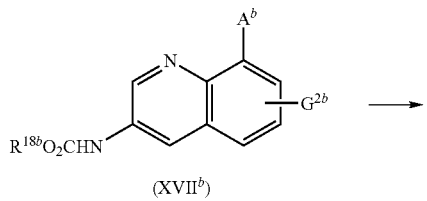

(XVII$^b$)

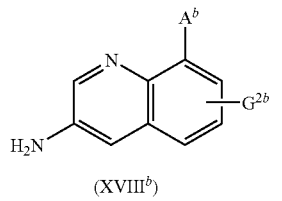

(XVIII$^b$)

In the formula wherein A$^b$, E$^{2b}$, G$^{2b}$ and R$^{16b}$ have the same meanings as above; and R$^{18b}$ means a C1-C4 alkyl group or benzyl group.

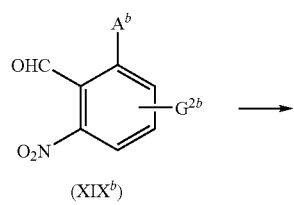

(XIX$^b$)

-continued

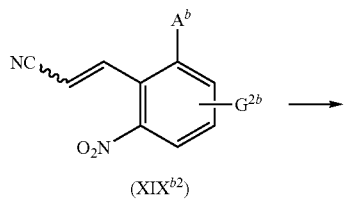

(XIX$^{b2}$)

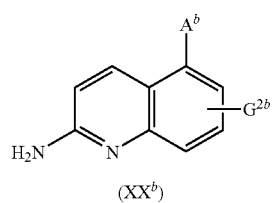

(XX$^b$)

In the formula, A$^b$ and G$^{2b}$ have the same meanings as above.

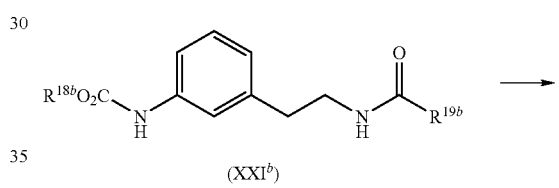

(XXI$^b$)

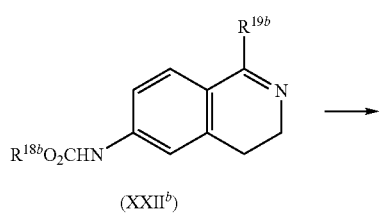

(XXII$^b$)

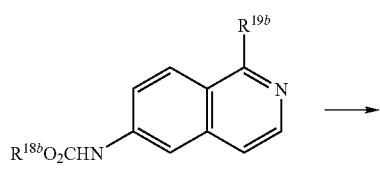

(XXIII$^b$)

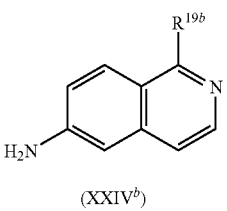

(XXIV$^b$)

In the formula, R$^{18b}$ has the same meaning as above; and R$^{19b}$ means a C1-C4 alkyl group.

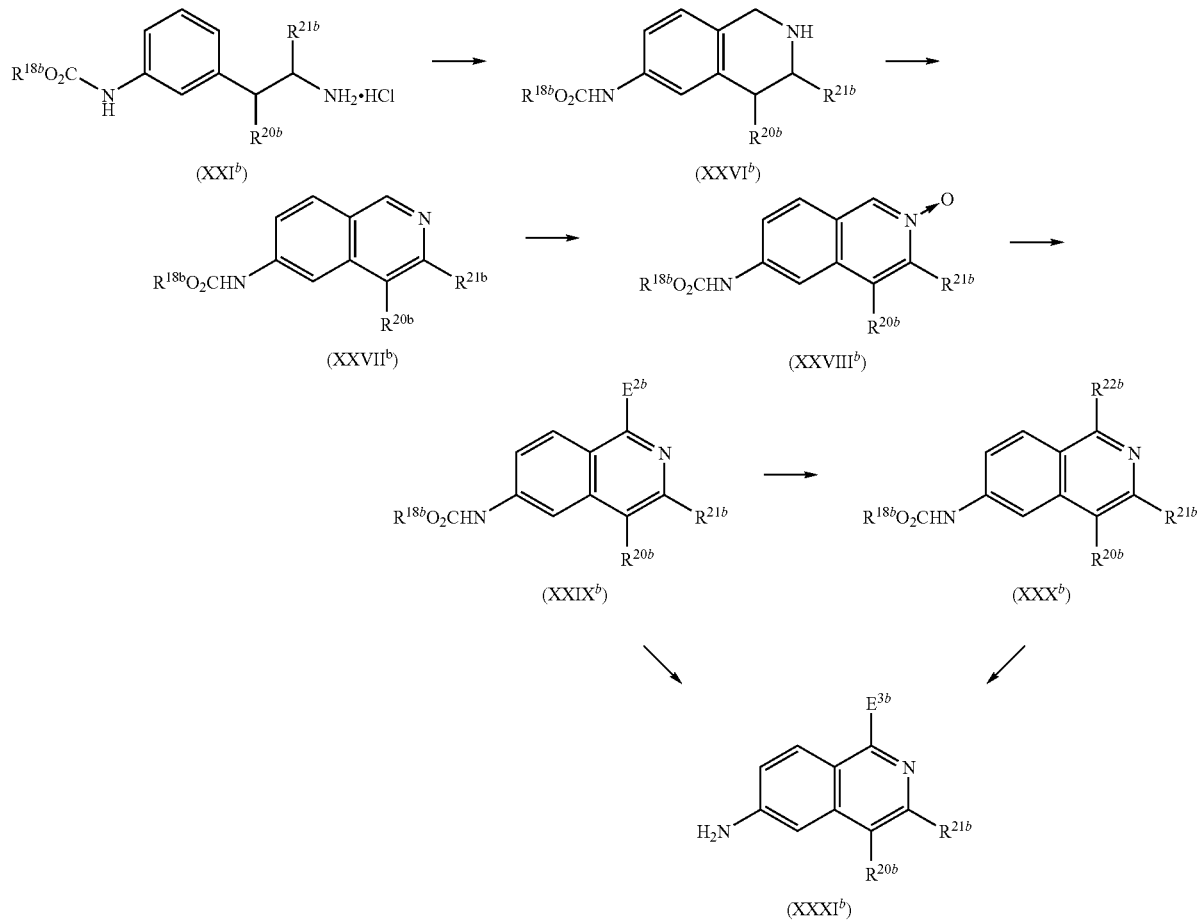

In the formula, $R^{18b}$ and $E^{2b}$ have the same meanings as above; $R^{20b}$ and $R^{21b}$ respectively means hydrogen atom or a C1-C4 alkyl group; $R^{22b}$ represents a C1-C4 alkoxy group, a phenoxy group or phenyl group which may have a substituent, cyano group or an amino group which may be substituted with a mono- or di-C1-C4 alkyl group; and $E^{3b}$ represents hydrogen atom, a halogen atom, a C1-C4 alkoxy group, a phenoxy group or phenyl group which may have a substituent, cyano group or an amino group which may be substituted with a mono- or di-C1-C4 alkyl group.

When the compound of the present invention is used as drugs, it is administered orally or parenterally. The dose of the compound differs depending on the degree of symptoms, the ages, sexes, weights and a difference in sensitivity of patients, the administration method, the time of administration, administration interval, the features of drug preparations, prescription and types of drug preparations, the types of active ingredients etc. and no particular limitation is imposed on the dose. However, the dose is generally 10 to 6000 mg, preferably about 50 to 4000 mg and more preferably 100 to 3000 mg per day for an adult and the drug is generally administered at the defined dose in one to three protons a day.

When preparing oral solid preparations, a filler and further, as required, a binder, a disintegrator, a lubricant, a colorant and a flavoring agent were added to a base drug and then the mixed drugs are made into tablets, coated tablets, granules, fine granules, powders or capsule agents.

As the filler, for example, lactose, cornstarch, saccharose, glucose, sorbitol, crystalline cellulose or silicon dioxide; as the binder, for example, polyvinyl alcohol, ethyl cellulose, methyl cellulose, gum arabic, hydroxypropyl cellulose or hydroxypropylmethyl cellulose; as the lubricant, for example, magnesium stearate, talc or silica; as the colorant, those permitted to be added to drugs; and as the flavor, cocoa powder, menthol, aromatic acid, peppermint oil, borneol, cinnamon powder etc. is used. These tablets and granules may be provided with sugar coating or gelatin coating and in addition, may be properly coated as required.

In the case of preparing injections, a pH regulator, a buffer, a suspending agent, a solubilizer, a stabilizer, an isotonic agent, a preservative etc. are added to a base drug according to the need and the mixture is then made into intravenous injections, subcutaneous injections or intramuscular injections by a usual method. At this time, these injections are occasionally made into freeze-dried products.

Examples of the suspending agent may include methyl cellulose, polysorbate 80, hydroxyethyl cellulose, gum arabic, traganth powder, carboxymethyl cellulose sodium and polyoxyethylene sorbitan monolaurate.

Examples of the solubilizer may include polyoxyethylene hydrogenated castor oil, polysorbate 80, nicotinic acid amide, polyoxyethylene sorbitan monolaurate, macrogol and castor oil fatty acid ethyl ester.

Also, examples of stabilizers may include sodium sulfite and sodium methasulfite; and examples of the preservative may include methyl paraoxybenzoate, ethyl paraoxybenzoate, sorbic acid, phenol, cresol and chlorocresol.

The effect of the compound of the present invention will be shown below by way of examples of pharmacological experiments.

It is to be noted that the compound A in the examples of pharmacological experiments indicates the compound obtained in Synthetic Example 1.

EXAMPLE 1

Integrin Expression Inhibitory Action on a Human Umbilical Venous Endothelial Cells (HUVEC)

Human umbilical venous endothelial cells (HUVEC) of $5 \times 10^5$ in number were seeded in a 75 cm² cell culture bottle and then cultured using an EGM medium (Sanko Junyaku) at 37° C. in a $CO_2$ incubator. Then, after 3 hours, the EGM medium was exchanged for the same medium including compound A, which was then cultured for further 48 hours. Next, the cells were collected and washed with a bovine serum albumin-containing phosphate buffer solution and the above buffer solution containing various anti-human integrin mouse antibodies was added to the cells and the solution containing cells was allowed to stand at 4° C. for 30 minutes. After washed, FITC connective anti-mouse IgG antibody was added to the cells, which was then allowed to stand for 30 minutes and washed again. Next, the cells were fixed and the amount of antibody connected per cell was measured as the amount of FITC by using a flow cytometer.

Figure 1:
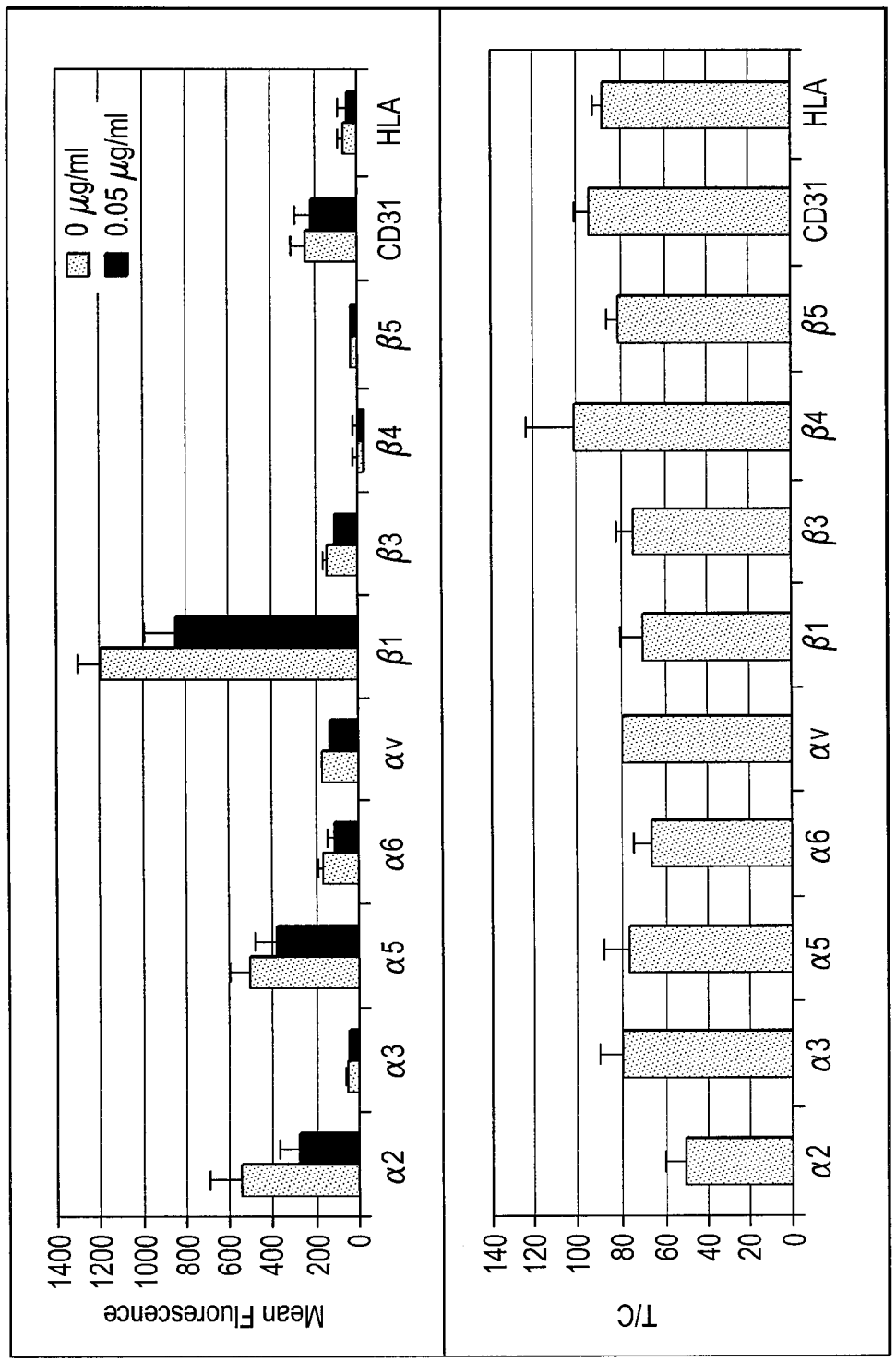
FIG. 1 shows, on the upper side, the results obtained by measuring the quantity of integrin expression after 48 hours when using a compound A (untreated and 0.05 μg/ml) for human umbilical venous endothelial cells and, on the lower side, T/C expressed as % as to the effect of the compound A as compared with the untreated case.

As shown in FIG. 1 described later, the compound A inhibited the expression of integrins α2, α3, α5, α6, αv, β1, β3 and β5 on the surface of the cell in a concentration of 0.05 μg/ml.

EXAMPLE 2

Integrin Expression Inhibitory Action on a Human Colonic Cancer Cell Line (HCT116-C9)

The integrin expression inhibitory action of the compound A on the above cells was examined in the same manner as in Example 1.

Figure 2:
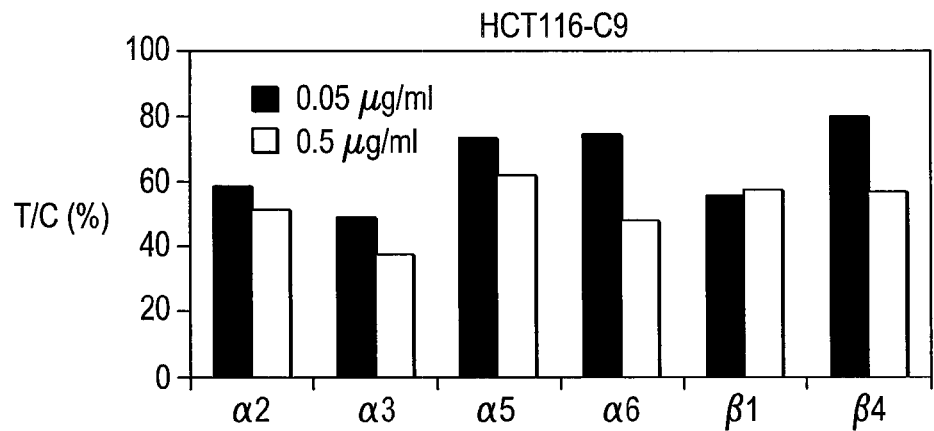
FIG. 2 shows the integrin expression inhibitory action of the compound A (0.05 μg/ml) on a human colonic cancer cell line (HCT116-C9) after 48 hours: the effect of the compounds A as compared with the untreated case is expressed as T/C (%).

As shown in FIG. 2 described later, the compound A inhibited the expression of integrins α2, α3, α5, α6, β1 and β4 in a concentration of 0.05 μg/ml and in a concentration of 0.5 μg/ml.

EXAMPLE 3

Integrin Expression Inhibitory Action on a Human Normal Fibroblast Cell Line (WI38)

The integrin expression inhibitory action of the compound A on the above cells was examined in the same manner as in Example 1.

Figure 3:
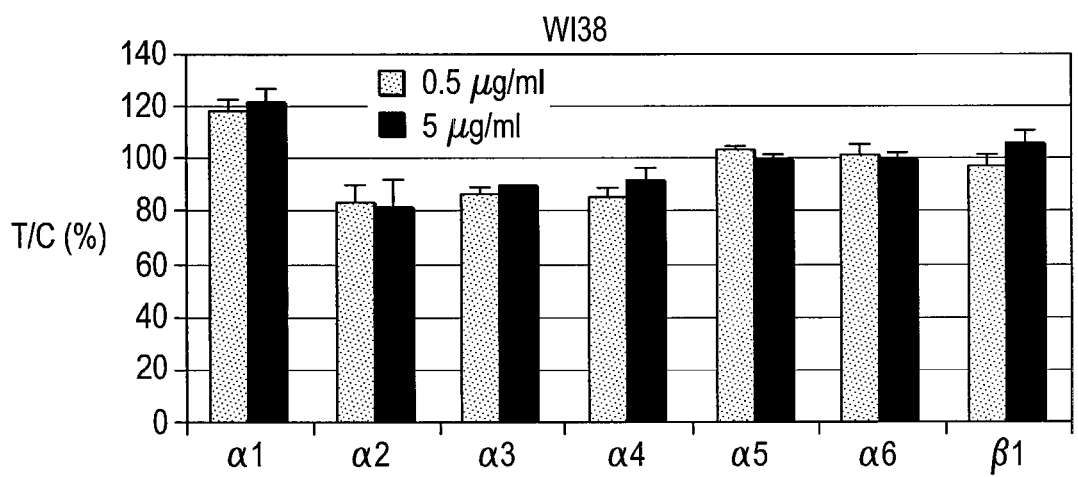
FIG. 3 shows the integrin expression inhibitory action of the compound A with a high concentration (0.5 μg/ml and 5 μg/ml) on a human normal fibroblast cell line (WI38) after 48 hours: the effect of the compounds A as compared with the untreated case is expressed as T/C (%).

As shown in FIG. 3 described later, the compound A having a higher concentration than in Examples 1 and 2 slightly inhibited the expression of integrins α2, α3 and α4, but had no influence on the expression of integrins α1, α5, α6 and β1.

As mentioned above, it is clear that the compound A inhibits the expression of integrin in endothelial cells and cancer cells but exerts almost no inhibitory action or normal fibroblast cells.

EXAMPLE 4

Antiangiogenic Effect-1

The inhibition degree of angiogenesis which was observed when aort$^a$ pieces of rat were incubated in collagen was defined as an antiangiogenic effect. That is, the aorta excised from male rat of Sprague-Dawley strain (10-12 weeks age) was washed with a Hanks' solution so that fat tissues around there were removed minutely. The aort$^a$ was incised to prepare pieces of 2 mm square and they were allowed to stand in a 24-well plate holding the endothelial cells upside. Then, 500 μl of neutralized Type I collagen (Cell Matrix Type I-A; manufactured by Nitta Gelatin) were poured over each well and allowed to stand at room temperature for about 20 minutes in a clean bench to solidify the gel. After confirming that the gel was solidified, 500 μl of MCDB 131 medium (manufactured by Chlorella Kogyo) were added thereto followed by incubating in a $CO_2$ incubator (5% $CO_2$) at 37° C. On the next day, the culture medium was exchanged with 500 μl of MCDB 131 medium containing the test compound and the incubation was continued. After three days, the medium was again exchanged with 500 μl of MCDB 131 medium containing the test compound and, at the stage of the 7th day from the initiation of addition of the test compound, numbers of capillaries formed around the aorta were counted under a microscope. The solution containing the test compound was prepared in a three-fold dilution system where 10 μg/ml was the highest concentration.

Inhibiting rate was calculated from the following formula and 50% inhibiting concentration ($IC_{50}$) for each test compound was determined.

Inhibiting Rate (%)=(C−T)/C×100

C: Numbers of capillaries when no compound was added
T: Numbers of capillaries when a compound was added
The compound according to the present invention showed an $IC_{50}$ value of 0.05 to 3 μg/ml.

EXAMPLE 5

Antiangiogenic Effect-2

0.4 ml of type I collagen was added to a 24-well plate and solidified. Human umbilical venous endothelial cells (HU- VEC) of 8×10⁴ in number were seeded on the collagen and cultured overnight by using endothelial cells culture solution (Gibco BRL) containing 10 ng/ml EGF and 20 ng/ml bFGF. Next, the supernatant was removed and then 0.4 ml of the same collagen was overlaid. A culture solution containing 1.5 ml of the compound A was further added and the cells were cultured for 4 days. Thereafter, the area of the formed tube was measured quantitatively by image analysis.

The IC50 of the compound A was 0.12 µg/ml. It was confirmed that an α2 antibody had the same effect, but this effect was not observed in the case of an a5 antibody.

EXAMPLE 6

Antiangiogenic Effect-3 (In Vivo)

The above activity was evaluated using a method obtained by improving a mouse air capsule method (Sakamoto et al., Cancer Res., 1, 55-57, 1986) in part. Specifically, a millipore ring (Nippon Millipore) was sealed using a 0.22 µm membrane filter (HAWPO, Nippon Millipore) to form a chamber. 1×10⁷ human colic cancer cell strains (WiDr) which were suspended in a phosphoric acid buffer solution were sealed into the chamber. Next, an air capsule was formed on a subcutaneous site of the backside of a C57 Black female mouse of 6 to 8 weeks age and the foregoing chamber was transplanted to the air capsule. The compound A was orally administered after about 6 hours passed after the transplantation was finished and afterwards administered in sequence once a day for 3 days. The erythrocytes of the mouse that was labeled with $^{51}Cr$ was injected from the tail vein 4 days after the chamber was transplanted. After one hour, the skin at the portion which was in contact with the chamber was resected under anesthesia. After the skin was frozen, only the portion which was in contact with the chamber was separated precisely to measure the amount of blood by using a γ counter. Then, a value obtained by subtracting the amount of blood measured in the case of the chamber including no cancer cell from the above amount of blood was determined as the amount of angiogenesis. In the experiment, the control groups consisted of 10 mice per group and the compound-administrated groups consisted of 5 mice per group.

If the results are evaluated by T/C (%): the amount of angiogenesis of the compound-administered groups/the amount of angiogenesis of the vehicle-administered groups× 100, the compound A had such an effect as T/C=53% at a dose of 50 mg/kg.

EXAMPLE 7

Integrin α2 Expression Inhibitory Action on a Human Umbilical Venous Endothelial Cells (HUVEC)

Human umbilical venous endothelial cells (HUVEC) of 5×10⁵ in number were seeded in a 75 cm² cell culture bottle and then cultured using an EGM medium (Sanko Junyaku) at 37° C. in a $CO_2$ incubator. Then, after 3 hours, the EGM medium was exchanged for the same medium including a compound of 0.5 µg/ml, which was then cultured for further 48 hours. Next, the cells were collected and washed with a bovine serum albumin-containing phosphate buffer solution and the above buffer solution containing an anti-human integrin α2 mouse antibody was added thereto and the solution was allowed to stand at 4° C. for 30 minutes. After washed, FITC connective anti-mouse IgG antibody was added to the cells, which was then allowed to stand for 30 minutes and washed again. Next, the cells were fixed and the amount of antibody connected per cell was measured as the amount of FITC by using a flow cytometer. The inhibitory action of each compound is shown by the ratio (%) of the amount of expression to that obtained in the untreated compound. The name of each compound is shown by Synthetic Example number.

Figure 4:
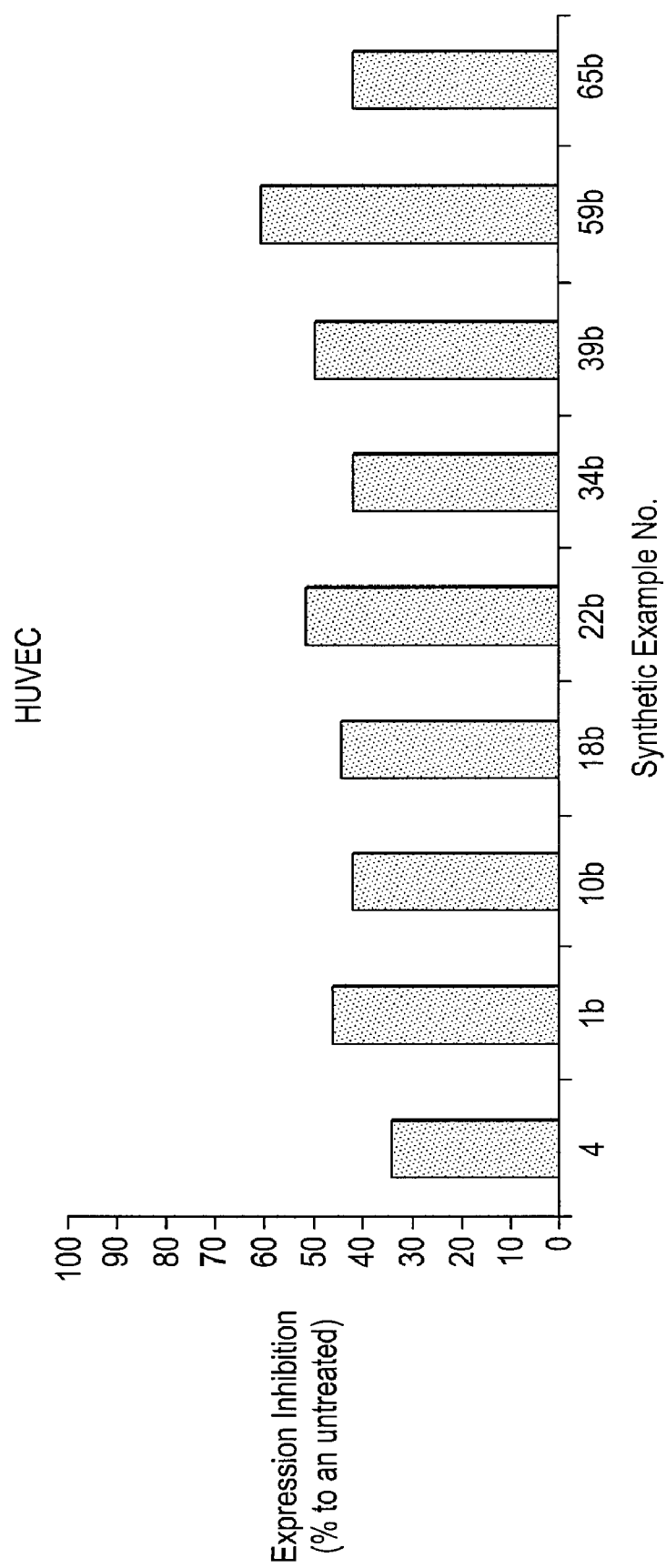
FIG. 4 shows the integrin α2 expression inhibitory action of each compound (0.5 μg/ml) on human umbilical cord endothelial cells (HUVEC) after 48 hours: the rate of the quantity of integrin a2 expressed as compared with the untreated case is expressed as (%). (The name of each compound is shown by Synthetic Example number.)

As shown in FIG. 4 described later, each compound inhibited the expression of integrin α2 on the surface of the cell in a concentration of 0.5 µg/ml.

Compounds according to the present invention are disclosed concretely in JP-A 7-165708 and JP-A 8-231505. Further, Production Examples and Synthetic Examples of typical compounds of the compound of the present invention will be given hereinbelow. It is needless to say that the present invention is not limited only to these Examples.

PRODUCTION EXAMPLE 1

Ethyl Pyruvate
N-(5-methyl-2-nitrophenyl)hydrazone 75.0 g (493 mmol) of 5-methyl-2-nitroaniline was added to a mixed solution of 160 ml of water and 170 ml of concentrated hydrochloric acid and the mixture was stirred. To the mixture was added dropwise 80 ml of an aqueous solution containing 36.0 g (517 mmol) of sodium nitrite at −20° C. The reaction solution was added to a solution obtained by dissolving ethyl 2-methylacetoacetate in 100 ml of ethanol and then adding 200 ml of a 12N aqueous potassium hydroxide thereto, at −20° C. over 30 minutes under stirring. After stirring at the same temperature for 30 minutes, 100 ml of concentrated hydrochloric acid was added thereto. The resulting precipitates were collected by filtration, washed with water and dried under reduced pressure overnight. A mixed solution of diethyl ether and hexane was added thereto and the crystals were collected by filtration, to give 130 g of the title compound.

$^1$H-NMR(DMSO-$d_6$) δ (ppm): 1.29 (3H, t, J=7.2 Hz), 2.16 (3H, s), 2.40 (3H, s), 4.25 (2H, q, J=7.2 Hz), 6.91 (1H, dd, J=8.8, 2.0 Hz), 7.63 (1H, s), 8.07 (1H, d, J=8.8 Hz), 10.69 (1H, s)

PRODUCTION EXAMPLE 2

Ethyl 4-methyl-7-nitro-1H-indole-2-carboxylate

To a xylene suspension (250 ml) of 25.0 g (94.2 mmol) of the compound of Production Example 1 was added 100 g of polyphosphoric acid, followed by heating under reflux for 3 hours. Under ice-cooling, to the reaction mixture were added 80 ml of water and 300 ml of ethyl acetate. The insoluble matters were filtered off and washed with 1.5 l of ethyl acetate, and the filtrate was extracted with ethyl acetate. The organic layer was successively washed with an aqueous saturated sodium bicarbonate, water and brine, dried over magnesium sulfate and concentrated to dryness. To the residue was added a mixed solution of tert-butyl methyl ether and hexane, and the crystals were collected by filtration, to give 11.1 g of the title compound.

$^1$H-NMR(DMSO-$d_6$) δ (ppm): 1.35 (3H, t, J=7.2 Hz), 2.65 (3H, s), 4.38 (2H, q, J=7.2 Hz), 7.16 (1H, d, J=8.4 Hz), 7.51 (1H, s), 8.19 (1H, d, J=8.4 Hz), 11.29 (1H, br s)

PRODUCTION EXAMPLE 3

4-Methyl-7-nitro-1H-indole-2-carboxylic acid 150 ml of a 1 N aqueous sodium hydroxide was added to a tetrahydrofuran solution (150 ml) containing 11.0 g (44.3 mmol) of the compound of Production Example 2, followed by heating under stirring at 80° C. for 30 minutes. The reaction solution was concentrated and 40 ml of 5N hydrochloric acid was added to the residue under ice-cooling to adjust the solution to pH 1. The resulting precipitates were collected by filtration and washed with water. The precipitates were dissolved in 300 ml of tetrahydrofuran, and the mixture was extracted with ethyl acetate. The organic layer was washed with brine, dried over magnesium sulfate and concentrated to dryness, to give 9.60 g of the title compound.

$^1$H-NMR(DMSO-$d_6$) δ (ppm): 2.62 (3H, s), 7.13 (1H, d, J=8.0 Hz), 7.42 (1H, s), 8.15 (1H, d, J=8.0 Hz), 11.00 (1H, br s)

PRODUCTION EXAMPLE 4

4-Methyl-7-nitro-1H-indole 9.58 g (43.5 mmol) of the compound of Production Example 3 was dissolved in 60 ml of 1,3-dimethyl-2-imidazolidinone. To the mixture was added 1.04 g (4.35 mmol) of basic copper carbonate, followed by heating under stirring at 180° C. for 4 hours. 120 ml of ethyl acetate was added to the reaction solution under ice-cooling, the insoluble matters were filtered off, and the filtrate was extracted with ethyl acetate. The organic layer was successively washed with water and brine, dried over magnesium sulfate and concentrated. Then, the residue was purified by silica gel column chromatography, to give 4.87 g of the title compound.

$^1$H-NMR(DMSO-$d_6$) δ (ppm): 2.59 (3H, s), 6.74 (1H, s), 7.03 (1H, d, J=8.4 Hz), 7.48 (1H, s), 8.00 (1H, d, J=8.4 Hz), 11.86 (1H, br s)

PRODUCTION EXAMPLE 5

3-Formyl-4-methyl-7-nitro-1H-indole 1.5 ml (16.1 mmol) of phosphorous oxychloride was added to 12 ml (154 mmol) of dimethylformamide at 0° C. in nitrogen atmosphere, followed by stirring at the same temperature for 20.5 hours. A dimethylformamide solution (20 ml) containing 2.0 g (11.4 mmol) of the compound of Production Example 4 was added thereto at 0° C., followed by heating under stirring at 90° C. for 21 hours. 100 ml of a 1N aqueous sodium hydroxide was added to the reaction solution under ice-cooling, and the mixture was extracted with ethyl acetate. The organic layer was successively washed with water and brine, dried over magnesium sulfate and concentrated to dryness. A mixed solution of tert-butyl methyl ether and hexane was added to the residue, and the crystals were collected by filtration, to give 2.23 g of the title compound.

$^1$H-NMR(DMSO-$d_6$) δ (ppm): 2.90 (3H, s), 7.21 (1H, d, J=8.4 Hz), 8.1 (1H, d, J=8.4 Hz), 8.39 (1H, s), 10.01 (1H, s), 12.71 (1H, br s)

PRODUCTION EXAMPLE 6

3-Cyano-4-methyl-7-nitro-1H-indole 2.21 g (10.8 mmol) of the compound of Production Example 5 was dissolved in 100 ml of dimethylformamide, followed by adding 900 mg (13.0 mmol) of hydroxylamine hydrochloride and 1.05 ml (13.0 mmol) of pyridine. After heating under stirring at 60° C. for 40 minutes, 1,1-carbonyldiimidazole (53.9 mmol) was added to the reaction solution under ice-cooling. After heating under stirring at 60° C. for further 30 minutes, 3.0 ml (21.5 mmol) of triethylamine was added to the reaction solution and the mixture was heated under stirring at the same temperature for further one hour. 50 ml of ice-water was added to the reaction mixture solution under ice-cooling, and the mixture was extracted with ethyl acetate. The organic layer was successively washed with water and brine, dried over magnesium sulfate and concentrated to dryness. A mixed solution of tert-butyl methyl ether and hexane was added to the residue and the crystals were collected by filtration, to give 1.95 g of the title compound.

$^1$H-NMR(DMSO-$d_6$) δ (ppm): 2.78 (3H, s), 7.22 (1H, d, J=8.0 Hz), 8.14 (1H, d, J=8.0 Hz), 8.41 (1H, s), 12.76 (1H, br s)

PRODUCTION EXAMPLE 7

7-Bromo-4-methyl-1H-indole 1 l (1 mol) of a tetrahydrofuran solution containing 1.0 M vinylmagnesium bromide was added to a tetrahydrofuran solution (300 ml) containing 65.0 g (301 mmol) of 2-bromo-5-methylnitrobenzene at −60° C. under stirring for one hour in nitrogen atmosphere. An aqueous saturated ammonium chloride and ethyl acetate were added to the reaction mixture solution, and the insoluble matters were filtered off. The filtrate was dried over magnesium sulfate and concentrated. Then, the residue was purified by silica gel column chromatography, to give 35.5 g of the title compound.

$^1$H-NMR(DMSO-$d_6$) δ (ppm): 2.42 (3H, s), 6.55 (1H, s), 6.73 (1H, d, J=7.6 Hz), 7.16 (1H, d, J=7.6 Hz), 7.35 (1H, s), 11.24 (1H, br s)

PRODUCTION EXAMPLE 8

4-Methyl-1H-indole-7-carboxylic acid 240 ml (384 mmol) of a hexane solution containing 1.6 M butyl lithium was added to a tetrahydrofuran solution (200 ml) containing 35.5 g (169 mmol) of the compound of Production Example 7 at −78° C. under stirring in nitrogen atmosphere. After stirring under ice-cooling for 40 minutes, carbon dioxide was passed through the reaction solution at −50° C. and the mixture was stirred as it was for 15 minutes. Water was added to the reaction mixture solution at the same temperature and the solvent was evaporated. The resulting precipitates were collected by filtration and washed with water. The precipitates was dissolved in 300 ml of tetrahydrofuran, dried over magnesium sulfate and concentrated to dryness, to give 25.9 g of the title compound.

$^1$H-NMR(DMSO-$d_6$) δ (ppm): 2.51 (3H, s), 6.53 (1H, s), 6.88 (1H, d, J=7.6 Hz), 7.31 (1H, s), 7.62 (1H, d, J=7.6 Hz), 10.99 (1H, br s), 12.79 (1H, br s)

PRODUCTION EXAMPLE 9

7-(N-tert-Butoxycarbonyl)amino-4-methyl-1H-indole 7.0 g (40.0 mmol) of the compound of Production Example 8 was suspended in 80 ml of toluene, 22 ml (160 mmol) of triethylamine and 11.2 ml (52 mmol) of diphenylphosphorylazide were added to the mixture in nitrogen atmosphere, and the mixture was stirred at room temperature for 30 minutes. 8 ml (84 mmol) of tert-butanol was added to the reaction solution, followed by heating under stirring at 100° C. for 2.5 hours. Then, the reaction solution was concentrated, and the residue was dissolved in ethyl acetate. The mixture was successively washed with 0.1 N hydrochloric acid, water and brine, dried over magnesium sulfate and concentrated to dryness. A mixed solution of diethyl ether and hexane was added to the residue and the crystals were collected by filtration, to give 7.87 g of the title compound.

$^1$H-NMR(DMSO-d$_6$) δ (ppm): 1.48 (9H, s), 2.38 (3H, s), 6.37-6.44 (1H, m), 6.68 (1H, d, J=8.4 Hz), 7.22-7.31 (2H, m), 8.86 (1H, br s), 10.73 (1H, br s)

PRODUCTION EXAMPLE 10

7-(N-tert-Butoxycarbonyl)amino-3-formyl-4-methyl-1H-indole 40 ml (429 mmol) of phosphorous oxychloride was added to 400 ml (5.2 mol) of dimethylformamide at 0° C. in nitrogen atmosphere, followed by stirring at the same temperature for 25 minutes. 74.0 g (300 mmol) of the compound of Production Example 9 was added thereto at 0° C., followed by stirring at room temperature for 1.5 hours. The reaction mixture was adjusted to pH 8 by adding 250 ml of a 5N aqueous sodium hydroxide thereto under ice-cooling. The organic layer was separated by adding tetrahydrofuran, ethyl acetate and water thereto. It was successively washed with water and brine, and dried over magnesium sulfate. Then, the solvent was evaporated, a mixed solution of diethyl ether and hexane was added to the residue, and the crystals were collected by filtration, to give 53.7 g of the title compound.

$^1$H-NMR(DMSO-d$_6$) δ (ppm): 1.50 (9H, s), 2.71 (3H, s), 6.90 (1H, d, J=7.6 Hz), 7.32-7.41 (1H, m), 8.21 (1H, d, J=1.6 Hz), 8.99 (1H, br s), 9.93 (1H, s), 11.88 (1H, br s)

PRODUCTION EXAMPLE 11

7-(N-tert-Butoxycarbonyl)amino-3-cyano-4-methyl-1H-indole 4.43 g (16.2 mmol) of the compound of Production Example 10 was dissolved in 50 ml of dimethylformamide, followed by adding 1.35 g (19.4 mmol) of hydroxylamine hydrochloride and 1.6 ml (19.8 mmol) of pyridine thereto. After heating under stirring at 60° C. for 45 minutes, 1,1-carbonyldiimidazole (80.8 mmol) was added to the reaction solution under ice-cooling. After heating under stirring at 60° C. for further 30 minutes, 4.5 ml (32.3 mmol) of triethylamine was added to the reaction solution, and the mixture was heated under stirring at the same temperature for further 30 minutes. Water was added to the reaction mixture solution under ice-cooling, and the mixture was extracted with ethyl acetate. The organic layer was successively washed with water and brine, dried over magnesium sulfate and then concentrated to dryness, to give 4.27 of the target compound.

$^1$H-NMR(DMSO-d$_6$) δ (ppm): 1.49 (9H, s), 2.60 (3H, s), 6.89 (1H, d, J=8.0 Hz), 7.34-7.42 (1H, m), 8.20 (1H, d, J=2.8 Hz), 9.04 (1H, br s), 11.80 (1H, br s)

PRODUCTION EXAMPLE 12

7-Amino-3-cyano-4-methyl-1H-indole 12.6 g (62.6 mmol) of the compound of Production Example 6 was dissolved in a mixed solution of 100 ml of tetrahydrofuran and 100 ml of methanol, and the mixture was hydrogenated at an ordinary temperature under 3 atoms in the presence of 430 mg (1.87 mmol) of platinum oxide. The catalyst was filtered off and the filtrate was concentrated to dryness. Then, a mixed solution of tert-butyl methyl ether and hexane was added to the residue and the crystals were collected by filtration, to give 10.7 g of the title compound. 50.5 g (186 mmol) of the compound of Production Example 11 was dissolved in 400 ml of dichloromethane. In nitrogen atmosphere, 210 ml (2.76 mol) of trifluoroacetic acid was added thereto at 0° C., followed by stirring at room temperature for 40 minutes. The reaction mixture was adjusted to pH 7 by adding a 5N aqueous sodium hydroxide thereto. The solvent was removed, and then the residue was extracted with ethylacetate. The organic layer was successively washed with water and brine, dried over magnesium sulfate and concentrated to dryness. A mixed solution of diethyl ether and hexane was added to the residue and the crystals were collected by filtration, to give 24.5 g of the title compound.

$^1$H-NMR(DMSO-d$_6$) δ (ppm): 2.47 (3H, s), 5.07 (2H, s), 6.34 (1H, d, J=7.6 Hz), 6.64 (1H, d, J=7.6 Hz), 8.10 (1H, s), 11.70 (1H, br s)

PRODUCTION EXAMPLE 13

3-Cyanobenzenesulfonyl chloride 25.0 g (212 mmol) of 3-cyanoaniline was added to a mixed solution of 200 ml of water and 250 ml of concentrated hydrochloric acid and the mixture was stirred. An aqueous solution (80 ml) containing 15.5 g (223 mmol) of sodium nitrite was added dropwise into the mixture at −10° C. The reaction solution was added to a sulfur dioxide saturated acetic acid solution (solution prepared by saturating 250 ml of acetic acid with sulfur dioxide and then adding 2.1 g of cuprous chloride thereto) under ice-cooling with stirring. After one hour, the reaction solution was poured into 500 ml of ice-water and extracted with diethyl ether. The extract was successively washed with an aqueous saturated sodium bicarbonate, water and brine, and dried over magnesium sulfate. The solvent was evaporated, and to the residue was added a mixed solution of diethyl ether and hexane. The crystals were collected by filtration, to give 16.0 g of the title compound.

$^1$H-NMR(DMSO-d$_6$) δ (ppm): 7.55 (1H, t, J=8.0 Hz), 7.78 (1H, dd, J=8.0, 1.2 Hz), 7.86-7.92 (2H, m)

PRODUCTION EXAMPLE 14

4-Sulfamoylbenzenesulfonyl chloride 25.0 g (145 mmol) of 4-aminobenzenesulfonamide was added to a mixed solution of 80 ml of water and 50 ml of concentrated hydrochloric acid, followed by stirring. To the mixture was added dropwise an aqueous solution (20 ml) containing 10.5 g (152 mmol) of sodium nitrite at −13° C. to −10° C. over 15 minutes. After 10 minutes, the reaction solution was added to a sulfur dioxide saturated mixture solution (solution prepared by saturating a mixed solution of 150 ml of acetic acid and 12.5 ml of concentrated hydrochloric acid with sulfur dioxide and then adding 3.7 g of cuprous chloride thereto) at −30° C. under stirring. After one hour, 500 ml of ice-water was added to the reaction solution, and the precipitates were collected by filtration. The precipitates were dissolved in a mixed solution of 450 ml of toluene and 150 ml of ethyl acetate. After filtering off the insoluble matters, the filtrate was extracted with ethyl acetate. The organic layer was successively washed with an aqueous saturated sodium bicarbonate and brine, and dried over magnesium sulfate. The solvent was evaporated, and 100 ml of toluene was added to the residue. The crystals were collected by filtration, to give 20.9 g of the title compound.

$^1$H-NMR(DMSO-d$_6$) δ (ppm): 7.65-7.69 (2H, m), 7.71-7.78 (4H, m)

PRODUCTION EXAMPLE 15

5-Bromo-3-chloro-7-nitro-1H-indole 1.4 ml of dimethylformamide and 6.98 g (52.3 mmol) of N-chlorosuccinimide were added to a tetrahydrofuran solution (140 ml) containing 12.00 g (49.8 mmol) of 5-bromo-7-nitro-1H-indole, followed by stirring at room temperature overnight. An aqueous 10% sodium thiosulfate was added thereto, followed by extracting with ethyl acetate. The organic layer was successively washed with water and brine, dried over magnesium sulfate and concentrated to dryness, to give 14.84 g of the title compound.

$^1$H-NMR(DMSO-d$_6$) δ (ppm): 7.79 (1H, s), 8.15 (1H, s), 8.23 (1H, s), 12.32 (1H, br s)

PRODUCTION EXAMPLE 16

7-Amino-5-bromo-3-chloro-1H-indole hydrochloride 70 ml of concentrated hydrochloric acid and 31.97 g (269 mmol) of a tin powder were added to a methanol solution (250 ml) containing 14.84 g (53.9 mmol) of the compound of Production Example 15, and the mixture was stirred at room temperature for 80 minutes. Under ice-cooling, the mixture was adjusted to pH 10 by adding a 5N aqueous sodium hydroxide solution thereto. Then, the resulting precipitates were filtered off and the filtrate was extracted with ethylacetate. The organic layer was successively washed with an aqueous saturated sodium bicarbonate and brine, dried over magnesium sulfate and concentrated. Then, the residue was purified by silica gel column chromatography, to give 14.35 g of 7-amino-5-bromo-3-chloro-1H-indole. The product was dissolved in ethyl acetate, and 17 ml of a 4N aqueous hydrogen chloride-ethylacetate solution was added thereto. The resulting precipitates were collected by filtration and washed with hexane, to give 13.23 g of the title compound.

$^1$H-NMR(DMSO-d$_6$) δ (ppm): 5.11 (3H, br s), 6.64 (1H, s), 6.93 (1H, s), 7.50 (1H, d, J=2.0 Hz), 11.38 (1H, br s)

PRODUCTION EXAMPLE 17

Ethyl pyruvate 2-(4-methyl-2-nitrophenyl)hydrazone 30.00 g (0.197 mol) of 4-methyl-2-nitroaniline was suspended in 110 ml of water, to which was then added 66 ml of concentrated hydrochloric acid. An aqueous solution (35 ml) containing 16.33 g (0.237 mol) of sodium nitrite was added dropwise to the mixture at 10° C. or less and the resulting mixture was stirred under ice-cooling for 40 minutes to prepare a diazonium salt solution.

28.43 g (0.197 mol) of ethyl 2-methylacetoacetate was dissolved in a mixed solution of 150 ml of ethanol and 300 ml of water. Under ice-cooling, an aqueous solution (120 ml) containing 53.36 g (0.808 mol) of potassium hydroxide was added thereto. In succession, the diazonium salt solution which was previously prepared was added dropwise thereinto at the same temperature and the resulting mixture was stirred under ice-cooling for 20 minutes. The mixture was adjusted to pH 1 by adding concentrated hydrochloric acid thereto. The resulting precipitates were collected by filtration, washed with water and dried over phosphorous pentaoxide under reduced pressure, to give 46.42 g of the title compound.

$^1$H-NMR(DMSO-d$_6$) δ (ppm): 1.40 (3H, t, J=7.2 Hz), 2.23 (3H, s), 2.36 (3H, s), 4.35 (2H, q, J=7.2 Hz), 7.44 (1H, dd, J=8.8, 1.6 Hz), 7.93 (1H, d, J=8.8 Hz), 8.00 (1H, s), 10.87 (1H, br s)

PRODUCTION EXAMPLE 18

Ethyl 5-methyl-7-nitro-1H-indole-2-carboxylate 65.33 g of polyphosphoric acid was added to a xylene solution (320 ml) containing 15.92 g (60 mmol) of the compound of Production Example 18, followed by heating under reflux overnight. Water and ethyl acetate were added thereto, and the insoluble matters were filtered off. The organic layer was separated, successively washed with water and brine, dried over magnesium sulfate and concentrated. Then, the residue was purified by silica gel column chromatography, to give 7.32 g of the title compound.

$^1$H-NMR(DMSO-d$_6$) δ (ppm): 1.34 (3H, t, J=7.0 Hz), 2.47 (3H, s), 4.36 (2H, q, J=7.0 Hz), 7.35 (1H, s), 7.99 (1H, s), 8.11 (1H, s), 11.25 (1H, br s)

PRODUCTION EXAMPLE 19

5-Methyl-7-nitro-1H-indole 150 ml of an aqueous 1 N sodium hydroxide solution was added to a tetrahydrofuran solution (80 ml) containing 7.86 g (31.7 mmol) of the compound of Example 19 and the mixture was stirred at room temperature for 3.5 hours. Under ice-cooling, the mixture was adjusted to pH 1 by adding 2N hydrochloric acid and then extracted with ethyl acetate. The organic layer was successively washed with water and brine, dried over magnesium sulfate and concentrated to dryness, to give 7.13 g of 5-methyl-7-nitro-1H-indole-2-carboxylic acid. The product was dissolved in 160 ml of 1,3-dimethyl-2-imidazolidinone, 716 mg (3.24 mmol) of basic copper carbonate was added thereto, and the mixture was stirred at 185° C. for 2 hours. The reaction solution was poured into water, the insoluble matters were filtered off and the filtrate was extracted with ethyl acetate. The organic layer was successively washed with water and brine, dried over magnesium sulfate and concentrated. Then, the residue was purified by silica gel column chromatography, to give 4.50 g of the title compound.

$^1$H-NMR(DMSO-d$_6$) δ (ppm): 2.46 (3H, s), 6.62 (1H, d, J=2.8 Hz), 7.47 (1H, d, J=2.8 Hz), 7.87 (1H, s), 7.92 (1H, s), 11.77 (1H, br s)

PRODUCTION EXAMPLE 20

3-Bromo-5-methyl-7-nitro-1H-indole 0.7 ml of dimethylformamide and 4.78 g of (26.9 mmol) of N-bromosuccinimide were added to a tetrahydrofuran solution (70 ml) containing 4.50 g (25.5 mmol) of the compound of Production Example 20, followed by stirring at room temperature for 70 minutes. An aqueous 10% sodium thiosulfate solution was added thereto, and the mixture was extracted with ethyl acetate. The organic layer was successively washed with water and brine, dried over magnesium sulfate and then concentrated to dryness, to give 6.53 g of the title compound.

$^1$H-NMR(DMSO-d$_6$) δ (ppm): 2.50 (3H, s), 7.67 (1H, s), 7.73 (1H, s), 8.02 (1H, s), 12.10 (1H, br s)

PRODUCTION EXAMPLE 21

7-Amino-3-bromo-5-methyl-1H-indole 6.76 g (26.5 mmol) of the compound of Production Example 20 was suspended in a mixed solution of 150 ml of methanol and 75 ml of water. To the mixture were added 11.34 g (212 mmol) of ammonium chloride and 5.92 g (106 mmol) of an iron powder. After stirring at 80° C. for one hour, the insoluble matters were filtered off and the filtrate was adjusted to pH 8 by adding an aqueous saturated sodium bicarbonate thereto. The mixture was extracted with ethyl acetate, and the organic layer was successively washed with an aqueous saturated bicarbonate, water and brine, dried over magnesium sulfate and concentrated. Then, the residue was purified by silica gel column chromatography, to give 3.30 g of the title compound.

$^1$H-NMR(DMSO-$d_6$) δ (ppm): 2.24 (3H, s), 5.08 (2H, br s), 6.20 (1H, s), 6.41 (1H, s), 7.35 (1H, s), 10.86 (1H, br s)

PRODUCTION EXAMPLE 22

6-Amino-3-pyridinesulfonyl chloride

Under ice-cooling, 10.00 g (0.106 mol) of 2-aminopyridine was added little by little to 123.8 g (1.06 mol) of chlorosulfonic acid. To the mixture was added 50.56 g (0.425 mol) of thionyl chloride. The mixture was heated under reflux for 2.5 hours, and further stirred at 150° C. for 7 hours. The reaction solution was poured into ice-water, neutralized by adding sodium bicarbonate and extracted with ethyl acetate. The organic layer was successively washed with an aqueous saturated sodium bicarbonate, water and brine, dried over magnesium sulfate, and then concentrated to dryness. The residue was suspended in ethyl ether and the insoluble matters were filtered off. The filtrate was concentrated to dryness and the residue was recrystallized from ethyl ether/hexane, to give 6.58 g of the title compound.

PRODUCTION EXAMPLE 23

4,7-Dibromo-1H-indole

The title compound (27.2 g) was obtained from 62.0 (0.224 mol) g of 2,5-dibromonitrobenzene in the same manner as in the Production Example 1 of JP-A 7-165708.

$^1$H-NMR(DMSO-$d_6$) δ (ppm): 6.52 (1H, d, J=3.2 Hz), 7.18 (1H, d, J=8.0 Hz), 7.26 (1H, d, J=8.0 Hz), 7.53 (1H, d, J=3.2 Hz), 11.75 (1H, br s)

PRODUCTION EXAMPLE 24

7-Amino-4-bromo-1H-indole hydrochloride

Into a tetrahydrofuran solution (300 ml) containing 27.2 g (98.9 mmol) of the compound of Production Example 23 was added dropwise a 186 ml (116.3 mmol) of a hexane solution containing 1.6 M n-butyllithium at −78° C. in a nitrogen atmosphere, followed by stirring under ice-cooling for one hour. After cooling again to −78° C., 28 ml (0.13 mmol) of diphenylphosphrylazide was added dropwise thereinto. The mixture was stirred at −78° C. for one hour and in succession, at −40° C. for one hour. A toluene solution (150 g) containing 3.4 M sodium bis(2-methoxyethoxy)aluminum hydride was added thereto at −40° C., followed by stirring at room temperature for one hour. Water (120 ml) was added thereto, the insoluble matters were collected by filtration and the filtrate was extracted with ethyl ether. The organic layer was successively washed with an aqueous saturated sodium bicarbonate and brine, dried over magnesium sulfate and concentrated. Then, the residue was dissolved in ethyl ether, and 50 ml of a 4 N-hydrochloric acid/ethyl acetate solution was added thereto. The resulting precipitates were collected by filtration, to give 14.5 g of the title compound.

$^1$H-NMR(DMSO-$d_6$) δ (ppm): 6.41-6.43 (1H, m), 6.80 (1H, d, J=8.0 Hz), 7.16 (1H, d, J=8.0 Hz), 7.54 (1H, t, J=2.8 Hz), 11.57 (1H, br s)

PRODUCTION EXAMPLE 25

7-Bromo-4-chloro-1H-indole

The title compound was obtained in the same manner as in Production Example 23.

$^1$H-NMR(DMSO-$d_6$) δ (ppm): 6.60-6.61 (1H, m), 7.04 (1H, d, J=8.1 Hz), 7.32 (1H, d, J=8.1 Hz), 7.53 (1H, t, J=2.7 Hz), 11.74 (1H, br s)

PRODUCTION EXAMPLE 26

7-Amino-4-chloro-1H-indole hydrochloride

The title compound was obtained in the same manner as in Production Example 24.

$^1$H-NMR(DMSO-$d_6$) δ (ppm): 6.54-6.55 (1H, m), 7.05 (1H, d, J=8.1 Hz), 7.11 (1H, d, J=8.1 Hz), 7.60 (1H, t, J=2.7 Hz), 11.82 (1H, br s)

PRODUCTION EXAMPLE 27

5-Bromo-2-thiophenecarboxyaldehyde 27.0 ml (43.4 mmol) of a hexane solution containing 1.6 M n-butyllithium was added dropwise into a tetrahydrofuran solution (80 ml) containing 10.0 g (41.3 mmol) of 5-dibromothiophene at −78° C. in a nitrogen atmosphere, followed by stirring for 10 minutes at the same temperature. Then, 3.5 ml (45.5 mmol) of dimethylformamide was added thereto at the same temperature, followed by stirring for 20 minutes. Water was added thereto, and the mixture was extracted with ethyl acetate. The organic layer was successively washed with an aqueous 0.1 N hydrochloric acid solution, water and brine, dried over magnesium sulfate and concentrated to dryness, to give 6.4 g of the title compound.

$^1$H-NMR(DMSO-$d_6$) δ (ppm): 7.49 (1H, d, J=4.0 Hz), 7.87 (1H, d, J=3.9 Hz), 9.81 (1H, s)

PRODUCTION EXAMPLE 28

5-Bromo-2-thiophenecarbonitrile 3.3 g (51.7 mmol) of hydroxylamine hydrochloride and 4.1 g (51.7 mmol) of pyridine were added to a dimethylformamide solution (40 ml) containing 8.2 g (43.1 mmol) of the compound of Production Example 28 and the mixture was stirred at room temperature for 30 minutes. Then, 34.9 g (215.5 mmol) of 1,1'-carbonyldiimidazole was added under ice-cooling and the resulting mixture was stirred at room temperature for one hour. Ice-water was added to the reaction solution, and the mixture was extracted with ethyl acetate. The organic layer was successively washed with an aqueous 0.1 N hydrochloric acid, water and brine, dried over magnesium sulfate and concentrated. Then, the residue was purified by silica gel chromatography, to give 6.7 g of the title compound.

$^1$H-NMR(DMSO-$d_6$) δ (ppm): 7.45 (1H,d, J=4.0 Hz), 7.84 (1H,d, J=4.0 Hz)

PRODUCTION EXAMPLE 29

5-Benzylthio-2-thiophenecarbonitrile 585 mg (13.4 mmol, oily component: 55%) of sodium hydride was suspended in 10 ml of dimethyl sulfoxide, 1.4 g (11.2 mmol) of benzylmercaptan was added thereto, and the mixture was stirred for 10 minutes. Then, 2.1 g (11.2 mmol) of the compound of Production Example 14 was added, followed by stirring at room temperature for one hour. Water was added to the reaction solution, and the mixture was extracted with ethyl acetate. The organic layer was successively washed with water and brine, dried over magnesium sulfate and concentrated. Then, the residue was purified by silica gel chromatography, to give 1.51 g of the title compound.

$^1$H-NMR(DMSO-$d_6$) δ (ppm): 4.26 (2H, s), 7.18 (1H, d, J=4.0 Hz), 7.27-7.30 (5H, m), 7.83 (1H, d, J=4.0 Hz)

PRODUCTION EXAMPLE 30

4-Bromo-1H-indolecarboxylic acid 34 g of the title compound was obtained from 51 g of the compound of Production Example 23 in the same manner as in Production Example 8.

$^1$H-NMR(CDCl$_3$) δ (ppm): 6.51-6.52 (1H, m), 7.35 (1H, d, J=8.0 Hz), 7.48 (1H, t, J=2.8 Hz), 7.66 (1H, d, J=8 Hz), 11.4 (1H, br s), 13.2 (1H, br s)

PRODUCTION EXAMPLE 31

7-(N-tert-Butoxycarbonyl)amino-4-bromo-1H-indole 32 g of the title compound was obtained from 34 g of the compound of Production Example 30 in the same manner as in Production Example 9.

$^1$H-NMR(CDCl$_3$) δ (ppm): 1.51 (9H, s), 6.38-6.39 (1H, m), 7.13 (1H, d, J=8.0 Hz), 7.44-7.46 (2H, m), 9.11 (1H, br s), 11.2 (1H, br s)

PRODUCTION EXAMPLE 32

7-(N-tert-Butoxycarbonyl)amino-4-bromo-3-chloro-1H-indole

N-Chlorosuccinimide was treated in a tetrahydrofuran-dimethylformamide solution containing the compound of Production Example 31, to give the title compound.

$^1$H-NMR(CDCl$_3$) δ (ppm): 1.50 (9H, s), 7.19 (1H, d, J=8.4 Hz), 7.45 (1H, d, J=8.4 Hz), 7.62 (1H, d, J=2.8 Hz), 9.08 (1H, br s), 11.41 (1H, br s)

PRODUCTION EXAMPLE 33

7-Amino-4-bromo-3-chloro-1H-indole hydrochloride 10.87 (31.5 mmol) of the compound of Production Example 32 was dissolved in methanol (120 ml). To the mixture was added concentrated hydrochloric acid (20 ml), followed by stirring at 60° C. for 40 minutes. After the reaction was finished, the solvent was removed, and the mixture was subjected to azeotropic distillation for 3 times using ethanol. The resulting solid was washed with ether, to give 8.5 g of the title compound.

$^1$H-NMR(CDCl$_3$) δ (ppm): 6.67 (1H, d, J=8.0 Hz), 7.13 (1H, d, J=8.0 Hz), 7.65 (1H, d, J=2.8 Hz), 11.74 (1H, br s)

PRODUCTION EXAMPLE 34

2-Amino-5-pyrimidinesulfonyl chloride 21 ml (0.316 mol) of chlorosulfonic acid was cooled in ice-water and 3 g (0.032 mol) of 2-aminopyrimidine was added thereto little by little under stirring. 9.2 ml (0.126 mol) of thionyl chloride was further added thereto, followed by stirring at 150° C. for 70 hours. The reaction solution was returned to room temperature, poured into water and extracted with ethyl acetate. The extract was dried over sodium sulfate and then concentrated to dryness, to give 1.7 g of the title compound.

$^1$H-NMR(CDCl$_3$) δ (ppm): 5.97 (2H, broad), 8.83 (2H, s)

SYNTHETIC EXAMPLE 1

N-(3-Cyano-4-methyl-1H-indole-7-yl)-3-cyanobenzenesulfonamide

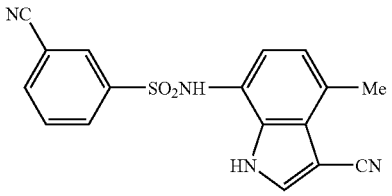

2.00 g (11.7 mmol) of the compound of Production Example 12 was dissolved in 60 ml of tetrahydrofuran, followed by adding 4.0 ml (49.5 mmol) of pyridine and 2.60 g (12.9 mmol) of the compound of Production Example 13 thereto. After stirring at room temperature for 16 hours, the mixture was adjusted to pH 1 to 2 by adding 2 N hydrochloric acid and extracted with ethyl acetate. The organic layer was successively washed with water and brine, dried over magnesium sulfate and concentrated. Then, the residue was purified by silica gel chromatography, to give 3.90 g of the title compound. (The compound hereinafter is referred to as Compound A.)

Melting point: 220-221° C. (recrystallized from ethanol/n-hexane)

$^1$H-NMR(DMSO-$d_6$) δ (ppm): 2.55 (3H, s), 6.50 (1H, d, J=8.0 Hz), 6.77 (1H, d, J=8.0 Hz), 7.71 (1H, t, J=8.0 Hz), 7.90 (1H, d, J=8.0 Hz), 8.05-8.13 (2H, m), 8.16 (1H, s), 10.11 (1H, br s), 12.01 (1H, br s)

SYNTHETIC EXAMPLE 2

N-(3-Cyano-4-methyl-1H-indole-7-yl)-6-chloro-3-pyridinesulfonamide

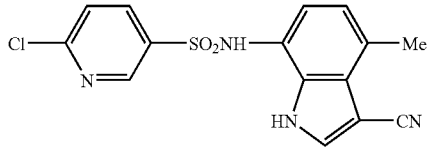

700 mg (4.09 mmol) of the compound of Production Example 12 was dissolved in 20 ml of tetrahydrofuran, followed by adding 1.3 ml (16.1 mmol) of pyridine and 950 mg (4.48 mmol) of 6-chloro-3-pyridinesulfonyl chloride thereto. After stirring at room temperature for 2 hours, the reaction solution was adjusted to pH 1 to 2 by adding 1 N hydrochloric acid and extracted with ethyl acetate. The organic layer was successively washed with water and brine, dried over magnesium sulfate and concentrated. Then, the residue was purified by silica gel column chromatography, to give 1.16 g of the title compound.

Melting point: 262 to 263° C. (recrystallized from ethanol/n-hexane).

$^1$H-NMR(DMSO-$d_6$) δ (ppm): 2.57 (3H, s), 6.55 (1H, d, J=7.6 Hz), 6.82 (1H, d, J=7.6 Hz), 7.69 (1H, d, J=8.4 Hz), 8.01 (1H, dd, J=8.4, 2.4 Hz), 8.17 (1H, d, J=2.8 Hz), 8.60 (1H, d, J=2.4 Hz), 10.21 (1H, br s), 12.03 (1H, br s)

SYNTHETIC EXAMPLE 3

N-(3-Bromo-5-methyl-1H-indole-7-yl)-4-sulfamoyl-benzenesulfonamide

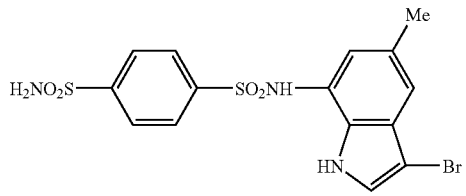

200 mg (0.89 mmol) of the compound of Production Example 22 was dissolved in 6 ml of tetrahydrofuran, followed by adding 0.3 ml (3.71 mmol) of pyridine and 300 mg (1.17 mmol) of the compound of Production Example 14 thereto. After stirring at room temperature for 48 hours, the mixture was adjusted to pH 1 to 2 by adding 1 N hydrochloric acid and extracted with ethyl acetate. The organic layer was successively washed with water and brine, dried over magnesium sulfate and concentrated. Then, a mixed solution of diethyl ether and hexane was added to the residue and the resulting crystals were collected by filtration, to give 387 mg of the title compound.

Melting point: 196-197° C. (recrystallized from ethanol/n-hexane)

$^1$H-NMR(DMSO-$d_6$) δ (ppm): 2.24 (3H, s), 6.60 (1H, s), 6.98 (1H, s), 7.44 (1H, s), 7.55 (2H, br s), 7.85-7.95 (4H, m), 10.13 (1H, br s), 11.01 (1H, br s)

SYNTHETIC EXAMPLE 4

N-(5-Bromo-3-chloro-1H-indole-7-yl)-6-amino-3-pyridinesulfonamide

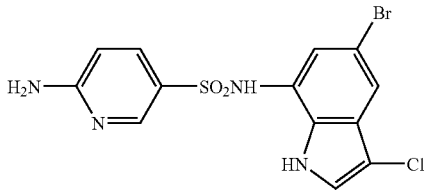

1.00 g (3.55 mmol) of the compound of Production Example 16 was suspended in 25 ml of tetrahydrofuran, followed by adding 0.86 ml (10.6 mmol) of pyridine and 718 mg (3.73 mmol) of the compound of Production Example 8 thereto under ice-cooling. After stirring at room temperature for 3 hours, water was added thereto and the mixture was extracted with ethyl acetate. The organic layer was successively washed with water and brine, dried over magnesium sulfate and concentrated. Then, the residue was purified by silica gel column chromatography, to give 1.27 g of the title compound.

Melting point: started coloring from a temperature close to 237° C. and decomposed at 240 to 242° C. (recrystallized from ethanol-water)

$^1$H-NMR(DMSO-$d_6$) δ (ppm): 6.37 (1H, d, J=8.8 Hz), 6.94 (2H, br s), 6.97 (1H, s), 7.36 (1H, s), 7.54-7.57 (2H, m), 8.16 (1H, d, J=2.8 Hz), 9.94 (1H, br s), 11.17 (1H, br s)

Hydrochloride $^1$H-NMR(DMSO-$d_6$) δ (ppm): 6.59 (1H, d, J=9.2 Hz), 7.00 (1H, s), 7.40 (1H, s), 7.56 (1H, d, J=2.4 Hz), 7.70 (1H, dd, J=9.2, 2.0 Hz), 8.20 (1H, d, J=2.0 Hz), 10.20 (1H, br s), 11.37 (1H, br s)

SYNTHETIC EXAMPLE 5

N-(3-Bromo-5-methyl-1H-indole-7-yl)-3-cyanobenzenesulfonamide

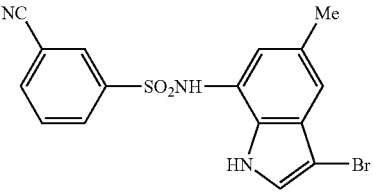

Under ice-cooling, 0.19 ml (2.35 mmol) of pyridine and 280 mg (1.39 mmol) of 3-cyanobenzenesulfonyl chloride were added to a tetrahydrofuran solution (6 ml) containing 260 mg (1.16 mmol) of the compound of Production Example 22, followed by stirring at room temperature overnight. Then, 0.2 N hydrochloric acid was added thereto and the mixture was extracted with ethyl acetate. The organic layer was successively washed with water and brine, dried over magnesium sulfate and concentrated. Then, the residue was purified by silica gel column chromatography, to give 360 mg of the title compound.

Melting point: started decomposing gradually from a temperature close to 148° C. and decomposed rapidly at 163 to 164° C. (recrystallized from ethanol/n-hexane).

¹H-NMR(DMSO-d₆) δ (ppm): 2.25 (3H, s), 6.54 (1H, s), 7.01 (1H, s), 7.42 (1H, d, J=2.8 Hz), 7.71 (1H, t, J=7.6 Hz), 7.93 (1H, d, J=7.6 Hz), 8.07-8.11 (2H, m), 10.09 (1H, br s), 11.04 (1H, br s)

SYNTHETIC EXAMPLE 6

N-(4-Bromo-1H-indole-7-yl)-4-cyanobenzene-sulfonamide

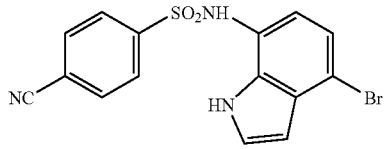

700 mg (2.8 mmol) of the compound of Production Example 25 and 685 mg (3.4 mmol) of 4-cyanobenzenesulfonyl chloride were processed in the same manner as in Synthetic Example 1, to give 686 mg of the title compound.

Melting point: 214 to 216° C.

¹H-NMR(DMSO-d₆) δ (ppm): 6.35 (1H, d, J=2.6 Hz), 6.53 (1H, d, J=8.0 Hz), 7.04 (1H, d, J=8.0 Hz), 7.41 (1H, t, J=2.8 Hz), 7.85 (2H, d, J=8.0 Hz), 8.00 (2H, d, J=8.0 Hz), 10.24 (1H, br s), 11.19 (1H, br s)

SYNTHETIC EXAMPLE 7

N-(4-Chloro-1H-indole-7-yl)-6-amino-3-pyridine-sulfonamide

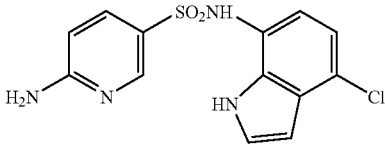

1330 mg (6.4 mmol) of the compound of Production Example 23 and 1000 mg (4.9 mmol) of the compound of Production Example 12 were processed in the same manner as in Synthetic Example 1, to give 961 mg of the title compound.

Melting point: 204 to 206° C.

¹H-NMR(DMSO-d₆) δ (ppm): 6.38 (1H, d, J=9.0 Hz), 6.43 (1H, t, J=2.2 Hz), 6.77 (1H, d, J=7.7 Hz), 6.86 (2H, br s), 7.42 (1H, t, J=2.6 Hz), 7.56 (1H, dd, J=2.6, 9.0 Hz), 8.14 (1H, d, J=2.6 Hz), 9.70 (1H, br s), 11.07 (1H, br s)

SYNTHETIC EXAMPLE 8

N-(3-Bromo-4-chloro-1H-indole-7-yl)-6-amino-3-pyridinesulfonamide and a hydrochloride

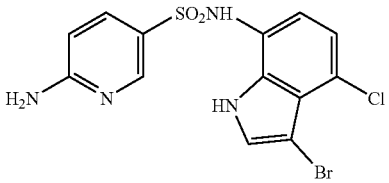

1 ml of dimethylformamide and 359 mg (2.0 mmol) of N-bromosuccinimide were added to a tetrahydrofuran solution (10 ml) containing 650 mg (2.0 mmol) of the compound of Synthetic Example 7, followed by stirring at room temperature overnight. Then, an aqueous 0.2 N hydrochloric acid was added thereto, and the mixture was extracted with ethyl acetate. The organic layer was successively washed with an aqueous sodium thiosulfate, water and brine, dried over magnesium sulfate and concentrated. Then, the residue was purified by silica gel column chromatography, to give 662 mg of the title compound.

¹H-NMR(DMSO-d₆) δ (ppm): 6.38 (1H, d, J=8.8 Hz), 6.76 (1H, d, J=8.4 Hz), 6.88 (2H, br s), 6.97 (1H, d, =8.4 Hz), 7.52-7.56 (2H, m) 8.12 (1H, d, J=2.4 Hz), 9.68 (1H, br s), 11.44 (1H, br s)

The resulting title compound (660 mg) was dissolved in 3 ml of acetone, followed by adding 0.62 ml of a 4 N-hydrochloric acid/ethyl acetate solution thereto. The resulting precipitates were collected by filtration, to give 590 mg of a hydrochloride.

Melting point: started decomposing gradually from a temperature close to 267° C.

¹H-NMR(DMSO-d₆) δ (ppm): 6.65 (1H, d, J=9.2 Hz), 6.78 (1H, d, J=8.1 Hz), 6.98 (1H, d, J=8.2 Hz), 7.57 (1H, d, =2.6 Hz), 7.73 (1H, dd, J=2.0, 9.0 Hz), 8.15 (1H, d, J=2.4 Hz), 10.00 (1H, br s), 11.67 (1H, br s)

SYNTHETIC EXAMPLE 9

N-(3-Bromo-5-methyl-1H-indole-7-yl)-5-cyano-2-thiophenesulfonamide

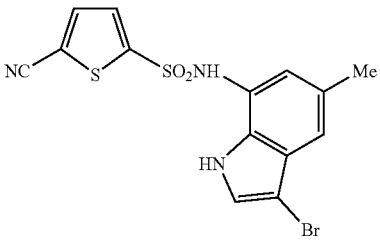

Under ice-cooling, chlorine gas was introduced into a concentrated hydrochloric solution (15 ml) containing 1.3 g (5.6 mmol) of the compound of Production Example 30. After stirring for 30 minutes, the reaction solution was added to ice-water and extracted with ethyl acetate. The organic layer was successively washed with water and brine, dried over magnesium sulfate and concentrated. The residue was added to a pyridine solution (6 ml) containing 1.2 g (5.35 mmol) of the compound of Production Example 22, followed by stirring at room temperature overnight. Water was added thereto, and the mixture was extracted with ethyl acetate. The organic layer was successively washed with an aqueous 1 N hydrochloric acid, water and brine, dried over magnesium sulfate and concentrated. Then, the residue was purified by silica gel chromatography, to give 1227 mg of the title compound.

Melting point: 166 to 169° C. (decomposed)

¹H-NMR(DMSO-d₆) δ (ppm): 2.30 (3H, s), 6.65 (1H, s), 7.07 (1H, s), 7.44 (1H, s), 7.54 (1H, d, J=4.0 Hz), 7.94 (1H, d, J=4.0 Hz), 10.47 (1H, br s), 11.04 (1H, br s)

SYNTHETIC EXAMPLE 10

N-(4-Bromo-3-chloro-1H-indole-7-yl)-2-amino-5-pyrimidinesulfonamide

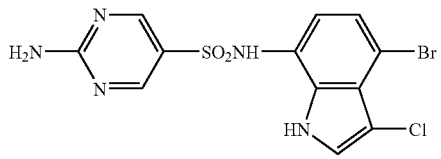

513 mg (2.65 mmol) of the compound of Production Example 35 was added to 5 ml of a pyridine solution containing 712 mg (2.52 mmol) of the compound of Production Example 34, followed by stirring for 15 hours. Water was added to the reaction solution, and extracted with a mixed solution of ethyl acetate and tetrahydrofuran (10:1). The organic layer was dried over magnesium sulfate and then concentrated. The residue was purified by silica gel column chromatography, to give 950 mg of the title compound.

Melting point: 285 to 289° C.

$^1$H-NMR(DMSO-$d_6$) δ (ppm): 6.75 (1H, d, J=8.0 Hz), 7.19 (1H, d, J=8.0 Hz), 7.59 (1H, d, J=3.0 Hz), 7.65 (2H, s), 8.37 (2H, s), 9.82 (1H, s), 11.43 (1H, s)

SYNTHETIC EXAMPLE 11

N-(3-Chloro-1H-indole-7-yl)-4-sulfamoylbenzenesulfonamide

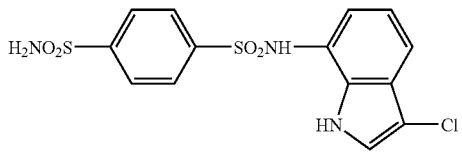

767 mg (3.0 mmol) of 4-sulfamoylbenzenesulfonyl chloride was reacted with 264 mg (2.0 mmol) of 7-amino-1H-indole and treated, to give 445 mg of N-(1H-indole-7-yl)-4-sulfanoylbenzenesulfonamide. The resulting compound was chlorinated using N-chlorosuccinimide in dichloromethane, to give 349 mg of the title compound.

Melting point: started coloring partially in a black color from a temperature close to 220° C. and decomposed gradually from a temperature close to 240° C. (recrystallized from ethanol-n-hexane).

$^1$H-NMR(DMSO-$d_6$) δ (ppm): 6.75 (1H, d, J=7.6 Hz), 6.96 (1H, dd, J=8.0, 7.6 Hz), 7.29 (1H, d, J=7.6 Hz), 7.50 (1H, d, J=2.8 Hz), 7.58 (2H, s), 7.90-7.98 (4H, m), 10.23 (1H, s), 11.07-11.17 (1H, m)

PRODUCTION EXAMPLE 1a

7-Bromo-1H-indole 100 ml (100 mmol) of a tetrahydrofuran solution containing 1.0 M vinylmagnesium bromide was added to a tetrahydrofuran solution (250 ml) containing 5.05 g (25 mmol) of 2-bromonitrobenzene at −40° C. in nitrogen atmosphere, followed by stirring as it was for 40 minutes. The reaction mixture was poured into 500 ml of an aqueous saturated ammonium chloride, and the mixture was extracted with ethyl ether. The extract was dried over magnesium sulfate and concentrated. Then, the residue was purified by silica gel column chromatography, to give 2.89 g of the title compound.

$^1$H-NMR(DMSO-$d_6$) δ (ppm): 6.56 (1H, dd, J=2.9, 1.8 Hz), 6.94 (1H, t, J=7.8 Hz), 7.30 (1H, d, J=7.8 Hz), 7.40 (1H, t, J=2.9 Hz), 7.56 (1H, d, J=7.8 Hz), 11.16-11.46 (1H, br m)

PRODUCTION EXAMPLE 2a

7-Amino-1H-indole 16.5 ml (41.3 mmol) of a hexane solution containing 2.5 M n-butyllithium was added dropwise to a tetrahydrofuran solution (50 ml) containing 2.70 g (13.8 mmol) of Production Example 1a at −70° C. in nitrogen atmosphere, and the mixture was stirred at −70° C. for 15 minutes and then at −20 to −10° C. for 30 minutes. After cooling to −70° C. again, 3.9 ml (18 mmol) of diphenylphosphorylazide was added dropwise thereinto. The mixture was stirred at −70° C. for one hour and then at −40° C. for one hour. After adding 22.3 ml (75.8 mmol) of a toluene solution containing 3.4 M sodium bis(2-methoxyethoxy)aluminum hydride thereto at −40° C., the mixture was stirred at −30 to −20° C. for 30 minutes and then at room temperature for 30 minutes. A phosphoric acid buffer solution having a pH of 7.0 was added thereto, the insoluble matters were collected by filtration and the filtrate was extracted with ethyl ether. The organic layer was successively washed with an aqueous saturated sodium bicarbonate and brine, dried over magnesium sulfate and concentrated. Then, the residue was purified by silica gel column chromatography, to give 1.29 g of the title compound.

$^1$H-NMR(DMSO-$d_6$) δ (ppm): 5.01 (2H, br s), 6.25-6.33 (2H, m), 6.70 (1H, dd, J=7.9, 7.3 Hz), 6.78 (1H, dd, J=7.9, 0.7 Hz), 7.23 (1H, t, J=2.7 Hz), 10.48-10.72 (1H, br m)

The following raw material compounds were synthesized from 2-bromonitrobenzene derivatives in the same manner as in Production Examples 1a and 2a.

7-amino-4-methoxy-1H-indole
7-amino-4-bromo-1H-indole

PRODUCTION EXAMPLE 3a

7-Bromo-3-chloro-4-methyl-1H-indole 4.0 g (30.0 mmol) of N-chlorosuccinimide was added to an acetonitrile solution (250 ml) containing 5.8 g (27.6 mmol) of 7-bromo-4-methyl-1H-indole synthesized from 2-bromo-5-methylnitrobenzene in the same manner as in Production Example 1a, followed by stirring at room temperature overnight. 50 ml of a 1N aqueous sodium hydroxide was added thereto, and the mixture was extracted with ethyl acetate. The organic layer was washed with water, dried over magnesium sulfate and concentrated. Then, the residue was purified by silica gel column chromatography, to give 6.7 g of the title compound.

$^1$H-NMR(CDCl$_3$) δ (ppm): 2.74 (3H, s), 6.75-7.26 (3H, m), 8.23 (1H, brs)

PRODUCTION EXAMPLE 4a

7-Amino-3-chloro-4-methyl-1H-indole 2.6 g of the title compound was obtained from 6.37 g (26.1 mmol) of the compound of Production Example 3a in the same manner as in Production Example 2a.

¹H-NMR(CDCl₃) δ (ppm): 2.70 (3H, s), 6.39-7.14 (3H, m), 8.15 (1H, br s)

PRODUCTION EXAMPLE 5a

4-Sulfamoylbenzenesulfonyl chloride 6.4 g (37.2 mmol) of 4-aminobenzenesulfonamide was added to a mixed solution of 12.5 ml of water and 6.3 ml of concentrated hydrochloric acid, followed by stirring. An aqueous saturated solution containing 2.56 g (37.1 mmol) of sodium nitrite was added drop wise there into at 0° C. or less. The reaction solution was added to an acetic acid solution saturated with sulfur dioxide (solution obtained by saturating 35 ml of acetic acid with sulfur dioxide and then adding 1.5 g of cupric chloride dihydrate thereto) under ice-cooling with stirring. After 10 minutes, the reaction solution was poured into ice-water, and the precipitates were collected by filtration and washed with water. The precipitates were dissolved in tetrahydrofuran, dried over magnesium sulfate and then concentrated to dryness, to give 3.5 g of the title compound.

PRODUCTION EXAMPLE 6a 4-(Sulfamoylmethyl)benzenesulfonyl chloride 5.0 g (23.1 mmol) of 4-nitrophenylmethanesulfonamide was suspended in 90% acetic acid, which was then hydrogenated at normal temperature under normal pressure in the presence of palladium-carbon. After filtering off the catalyst, the filtrate was concentrated to dryness, to give 4.3 g of 4-aminophenylmethanesulfonamide. The obtained compound was added to a mixed solution of 40 ml of water and 4.1 ml of concentrated hydrochloric acid, followed by stirring. An aqueous saturated solution containing 1.63 g (23.6 mmol) of sodium nitrite was added dropwise there into at 0° C. or less. The reaction solution was added to an acetic acid solution saturated with sulfur dioxide (solution obtained by saturating 30 ml of acetic acid with sulfur dioxide and then adding 0.97 g of cupric chloride.dihydrate thereto) under ice-cooling with stirring. After stirring at room temperature for 40 minutes, the reaction solution was poured into ice-water and the mixture was saturated with sodium chloride. The mixture was extracted with ethyl acetate, and the extract was dried over magnesium sulfate and then concentrated to dryness, to give 1.7 g of the title compound.

¹H-NMR(DMSO-d₆) δ (ppm): 4.26 (2H, s), 7.32 (2H, d, J=8.4 Hz), 7.59 (2H, d, J=8.4 Hz)

The following compounds were synthesized in the same manner as in Production Example 5a or 6a.
4-(N-methylsulfamoyl)benzenesulfonyl chloride
4-(N-ethylsulfamoyl)benzenesulfonyl chloride
4-(N-methoxysulfamoyl)benzenesulfonyl chloride
4-[(methanesulfonamide)methyl]benzenesulfonyl chloride
4-(N-methylmethanesulfonamide)benzenesulfonyl chloride
4-(1-pyrrolidinylsulfonyl)benzenesulfonyl chloride
4-(1-pyrrolidinylcarbonyl)benzenesulfonyl chloride
3-cyanobenzenesulfonyl chloride
4-(methylsulfonyl)benzenesulfonyl chloride
4-[(N-methylmethanesulfonamide)methyl]benzenesulfonyl chloride PRODUCTION EXAMPLE 7a 3-Cyano-7-nitro-1H-indole 10.15 g (53.4 mmol) of 3-formyl-7-nitro-1H-indole was dissolved in 150 ml of dimethylformamide, and 3.93 g (56.0 mmol) of hydroxylamine hydrochloride and 4.5 ml (55.6 mmol) of pyridine were added thereto. After heating under stirring at 70 to 80° C. for 2 hours, 6.3 g (56.8 mmol) of selenium dioxide and about 5 g of magnesium sulfate were added thereto. After heating at 70 to 80° C. for further 2.5 hours, the insoluble matters were filtered off and the filtrate was concentrated. Water was added thereto, and the resulting crystals were collected by filteration and successively washed with water and ethyl ether. The crystals were dissolved in a mixed solution of tetrahydrofuran and acetone, and the insoluble matters were filtered off. After concentrating the filtrate, ethyl acetate was added to the residue and the crystals were collected by filtration, to give 8.61 g of the title compound.

¹H-NMR(DMSO-d₆) δ (ppm): 7.48 (1H,t,J=8.1 Hz), 8.17 (1H, d, J=8.1 Hz), 8.27 (1H,d, J=8.1 Hz), 8.47 (1H, s), 12.70-13.00 (1H, br)

PRODUCTION EXAMPLE 8a

7-Amino-3-cyano-1H-indole 2.80 g (15.0 mmol) of the compound of Production Example 7a was suspended in 100 ml of methanol and hydrogenated under normal pressure at normal temperature in the presence of palladium-carbon. After filtering off the catalyst, the reaction mixture was concentrated to dryness, to give 2.31 g of the title compound.

¹H-NMR(DMSO-d₆) δ (ppm): 5.32, 5.34 (2H, s+s), 6.47 (1H, d, J=7.5 Hz), 6.81 (1H, d, J=7.9 Hz), 6.94 (1H, dd, J=7.9, 7.5 Hz), 8.13 (1H, s), 11.55-11.90 (1H, br), PRODUCTION EXAMPLE 9a 7-Amino-3,4-dichloro-1H-indole 7-Bromo-4-chloro-1H-indole obtained from 2-bromo-5-chloronitrobenzene in the same manner as in Production Example 1a was first chlorinated in the same manner as in Production Example 3a, and then the bromo group was converted into an amino group, to give the title compound.

¹H-NMR(DMSO-d₆) δ (ppm): 5.26 (2H, s), 6.29 (1H, d, J=8.1 Hz), 6.74 (1H, d, J=8.1 Hz), 7.45-7.51 (1H, m), 11.08-11.27 (1H, m)

7-Amino-4-tert-butyldimethylsilyloxy-3-chloro-1H-indole was synthesized in the same manner.

PRODUCTION EXAMPLE 10a

7-Amino-3-chloro-1H-indole 1.076 g (6.64 mmol) of 7-nitro-1H-indole was dissolved in 30 ml of acetonitrile, and 920 mg (6.89 mmol) of N-chlorosuccinimide was added thereto. After stirring at room temperature for 36 hours, an aqueous saturated sodium bicarbonate was added thereto. The precipitates were collected by filtration and washed with water, to give 1.2 g of 3-chloro-7-nitro-1H-indole. 863 mg (4.39 mmol) of the powder was suspended in 10 ml of ethanol, and 4.95 g (21.9 mmol) of stannous chloride.dihydrate and 100 μl of concentrated hydrochloric acid were added thereto. After heating under reflux for 30 minutes, an aqueous saturated sodium bicarbonate was added thereto and the insoluble matters were filtered off. After extracting by adding ethyl acetate thereto, the extract was dried over magnesium sulfate and concentrated. The residue was purified by silica gel column chromatography, to give 490 mg of the title compound.

The title compound was also obtained by hydrogenating 3-chloro-7-nitro-1H-indole at normal temperature under normal pressure in the presence of a platinum-carbon catalyst.

$^1$H-NMR(DMSO-d$_6$) δ (ppm): 5.14 (2H, s), 6.36 (1H, dd, J=7.5, 1.0 Hz), 6.68 (1H, dd, J=7.9, 0.73 Hz), 6.81 (1H, dd, J=7.9, 7.5 Hz), 7.39 (1H, d, J=2.7 Hz), 10.85 (1H, br s)

PRODUCTION EXAMPLE 11a 4-(2-Sulfamoylethyl)benzenesulfonyl chloride 1.3 g (7.3 mmol) of 2-phenylethanesulfonamide was added to 2.4 g (36.5 mmol) of chlorosulfonic acid under ice-cooling over 20 minutes, followed by stirring at room temperature for further 90 minutes. The reaction mixture solution was poured into ice-water, and then extracted with ethyl acetate. The extract was successively washed with an aqueous saturated sodium bicarbonate and brine, and dried over magnesium sulfate. The solvent was evaporated, to give 1.6 g of the title compound.

$^1$H-NMR(DMSO-d$_6$) δ (ppm): 2.97-3.02 (2H, m), 3.21-3.26 (2H, m), 7.21 (2H, d, J=8.4 Hz), 7.53 (2H, d, J=8.4 Hz)

The following raw material compounds were synthesized in the same manner.

4-[2-(methylsulfonyl)ethyl]benzenesulfonyl chloride
4-[2-(N-methylmethanesulfonamide)ethyl]benzenesulfonyl chloride
4-[2-(methanesulfonamido)ethyl]benzenesulfonyl chloride
4-(N-methylacetamido)benzenesulfonyl chloride PRODUCTION EXAMPLE 12a 5-Bromo-7-nitro-1H-indole 5.05 g (17.7 mmol) of 1-acetyl-5-bromo-7-nitroindoline was dissolved into a mixed solution of 6 ml of ethanol and 40 ml of 6 N hydrochloric acid, followed by heating under reflux for 3 hours. After neutralizing by adding sodium carbonate thereto, the mixture was extracted with ethyl acetate. The extract was washed with water, dried over magnesium sulfate and concentrated. Then, the residue was purified by silica gel column chromatography, to give 4.13 g of 5-bromo-7-nitroindoline. 301 mg (1.24 mmol) of this compound was added to 10 ml of toluene, and then 580 mg (2.55 mmol) of 2,3-dichloro-5,6-dicyano-1,4-benzoquinone was added thereto. After heating under reflux for 3.5 hours while stirring, the insoluble matters were filtered off and the filtrate was concentrated. The residue was purified by silica gel column chromatography, to give 252 mg of the title compound.

PRODUCTION EXAMPLE 13a

5-Bromo-3-formyl-7-nitro-1H-indole 210 mg (1.4 mmol) of phosphorous oxychloride was added to 1.0 g (14 mmol) of dimethylformamide at 0° C. in nitrogen atmosphere, followed by stirring for 30 minutes. 240 mg (1.0 mmol) of the compound of Production Example 12a was added thereto at 0° C., and the mixture was stirred at 0° C. for 20 minutes and then at 100° C. for 30 minutes. The reaction mixture was ice-cooled and then poured into ice-water. The mixture was stirred for 30 minutes, while it was kept at pH 7 to 8 by adding a 1N aqueous sodium hydroxide. The resulting precipitates were collected by filtration, washed with water and then purified by silica gel column chromatography, to give 239 mg of the title compound.

$^1$H-NMR(DMSO-d$_6$) δ (ppm): 8.31 (1H, d, J=1.8 Hz), 8.55 (1H, s), 8.65 (1H, d, J=1.8 Hz), 10.05 (1H, s), 12.89 (1H, br s)

PRODUCTION EXAMPLE 14a

7-Amino-5-bromo-3-cyano-1H-indole 214 mg (0.8 mmol) of 5-bromo-3-cyano-7-nitro-1H-indole obtained from the compound of Production Example 13a in the same manner as in Production Example 7a was dissolved in a mixed solution of 10 ml of methanol and 10 ml of tetrahydrofuran. The mixture was hydrogenated at 3.0 kg/cm$^2$ in the presence of platinum oxide, then the catalyst was filtered off and the filtrate was concentrated to dryness, to give 189 mg of the title compound.

$^1$H-NMR(DMSO-d$_6$) δ (ppm): 5.68-5.71 (2H, m), 6.60 (1H, d, J=2.0 Hz), 6.91 (1H, d, J=2.0 Hz), 8.16 (1H, s)

PRODUCTION EXAMPLE 15a

3-Acetyl-7-amino-1H-indole 11 ml (11 mmol) of a hexane solution containing 1.0 M dimethylaluminum chloride was added to a dichloromethane solution (50 ml) containing 1.2 g (7.5 mmol) of 7-nitro-1H-indole at 0° C. in nitrogen atmosphere. Then, 2.1 ml (29.5 mmol) of acetyl chloride was added thereto at 0° C., followed by stirring at room temperature for 4 hours. An aqueous saturated ammonium chloride was added to the reaction system and the resulting precipitates were collected by filtration. These precipitates were washed sufficiently with hot ethanol. The washing solution was combined with the filtrate and the combined solution was concentrated. Water was added to the residue, and the mixture was extracted with ethyl acetate. The extract was washed with brine, and dried over magnesium sulfate. The solvent was evaporated, and the residue was purified by silica gel column chromatography, to give 3-acetyl-7-nitro-1H-indole. The product was dissolved in 100 ml of methanol and hydrogenated at normal temperature under normal pressure in the presence of palladium-carbon. After filtering off the catalyst, the filtrate was concentrated to dryness, to give 790 mg of the title compound.

SYNTHETIC EXAMPLE 1a

N-(1H-Indole-7-yl)-4-nitrobenzenesulfonamide 1.50 g (11.3 mmol) of the compound of Production Example 2a was dissolved in 40 ml of pyridine, followed by adding 2.57 g (11.6 mmol) of 4-nitrobenzenesulfonyl chloride thereto at room temperature under stirring. After stirring at room temperature overnight, the solvent was evaporated, and to the residue were added ethyl acetate and 0.2 N hydrochloric acid. The organic layer was separated, washed with water, dried over magnesium sulfate. Then, the solvent was evaporated, and the residue was purified by silica gel column chromatography, to give 3.50 g of the title compound.

$^1$H-NMR(DMSO-d$_6$) δ (ppm): 6.42 (1H, dd, J=2.8, 2.0 Hz), 6.66 (1H, d, J=7.6 Hz), 6.83 (1H, dd, J=8.0, 7.6 Hz), 7.31 (1H, dd, J=3.2, 2.8 Hz), 7.36 (1H, d, J=8.0 Hz), 7.94-8.02 (2H, m), 8.30-8.38 (2H, m), 10.23 (1H, s), 10.74-10.87 (1H, m)

SYNTHETIC EXAMPLE 2a

N-(3-Chloro-1H-indole-7-yl)-4-nitrobenzenesulfonamide 8.98 g (28.3 mmol) of the compound of Synthetic Example 1a was dissolved in a mixed solution of 280 ml of dichloromethane and 7 ml of dimethylformamide, followed by adding 4.16 g (31.2 mmol) of N-chlorosuccinimide under stirring in a nitrogen atmosphere. After stirring at room temperature for 1.5 hours, 50 ml of water was added thereto and the mixture was concentrated until the amount of the mixture became about 80 ml. The organic layer was separated by adding ethyl acetate and 0.2 N hydrochloric acid thereto, successively washed with aqueous saturated sodium bicarbonate and brine, and dried over magnesium sulfate. Then, the solvent was evaporated, and the residue was purified by silica gel column chromatography, to give 7.98 g of the title compound.

Melting point: 199.5 to 200.5° C. (recrystallized from chloroform)

$^1$H-NMR(DMSO-$d_6$) δ (ppm): 6.72 (1H, d, J=7.6 Hz), 6.96 (1H, dd, J=8.0, 7.6 Hz), 7.31 (1H, d, J=8.0 Hz), 7.47-7.53 (1H, m), 7.92-8.02 (2H, m), 8.30-8.41 (2H, m), 10.33 (1H, s), 11.07-11.22 (1H, m)

SYNTHETIC EXAMPLE 3a

4-Amino-N-(3-chloro-1H-indole-7-yl)benzenesulfonamide 7.98 g (22.7 mmol) of the compound of Synthetic Example 2a was dissolved in 220 ml of methanol, followed by heating under reflux with stirring. 10 ml of concentrated hydrochloric acid and 7.40 g of a zinc powder were added thereto three times at intervals of 10 minutes, followed by refluxing for further 10 minutes. After cooling, the reaction mixture was neutralized by adding significantly excess sodium bicarbonate and the insoluble matters were filtered off. After concentrating the filtrate, the residue was dissolved in ethyl acetate. The mixture was successively washed with an aqueous saturated sodium bicarbonate, a 2N aqueous sodium carbonate solution and brine, dried over magnesium sulfate, and then the solvent was evaporated. The residue was purified by silica gel column chromatography, to give 7.21 g of the title compound.

Melting point: 174.5 to 176° C. (recrystallized from ethanol-n-hexane)

$^1$H-NMR(DMSO-$d_6$) δ (ppm): 5.97 (2H, br s), 6.48 (2H, d, J=8.8 Hz), 6.88 (1H, d, J=7.6 Hz), 6.95 (1H, dd, J=8.0, 7.6 Hz), 7.19 (1H, d, J=8.0 Hz), 7.36 (2H, d, J=8.8 Hz), 7.46 (1H, d, J=2.4 Hz), 9.56 (1H, s), 10.86-10.98 (1H, m)

SYNTHETIC EXAMPLE 4a

N-(3-Chloro-1H-indole-7-yl)-4-(methanesulfonamide)benzenesulfonamide 68 mg (0.211 mmol) of the compound of Synthetic Example 3a was dissolved in 1 ml of pyridine, followed by adding 15 µl (0.194 mmol) of methanesulfonyl chloride. After stirring at room temperature overnight, an aqueous sodium bicarbonate was added thereto, and the mixture was extracted with ethyl acetate. The organic layer was successively washed with dilute hydrochloric acid and water, dried over magnesium sulfate, and concentrated. Then, the residue was purified by silica gel thin layer chromatography, to give 76 mg of the title compound.

Melting point: 213.5 to 214° C. (decomposed) (recrystallized from ethanol/n-hexane)

$^1$H-NMR(DMSO-$d_6$) δ (ppm): 3.08 (3H, s), 6.83 (1H,d, J=7.5 Hz), 6.96 (1H, dd, J=7.9, 7.7 Hz), 7.23 (2H,d, J=8.8 Hz), 7.24 (1H,d, J=7.5 Hz), 7.47 (1H,d, J=2.7 Hz), 7.68 (2H,d, J=8.8 Hz), 9.92 (1H, br s), 10.38 (1H, br s), 10.99 (1H, br s)

SYNTHETIC EXAMPLE 5a

4-Bromomethyl-N-(1H-indole-7-yl)benzenesulfonamide

4-Bromomethylbenzenesulfonyl chloride and the compound of Production Example 2a were reacted in tetrahydrofuran at room temperature in the presence of an equivalent mol of pyridine and treated in the same manner as in Synthetic Example 1am, to give the title compound.

$^1$H-NMR(DMSO-$d_6$) δ (ppm): 4.70 (2H, s), 6.40 (1H, dd, J=3.1, 1.1 Hz), 6.71 (1H, ddd, J=7.4, 3.2, 0.92 Hz), 6.81 (1H, ddd, J=8.1, 7.4, 0.92 Hz), 7.29-7.32 (2H, m), 7.57 (2H, d, J=8.2 Hz), 7.73 (2H, d, J=8.4 Hz), 9.96 (1H, br s), 10.75 (1H, br s)

SYNTHETIC EXAMPLE 6a

N-(1,3-Dihydro-2H-indole-2-one-7-yl)-4-methylbenzenesulfonamide

The title compound was obtained in the same manner as in Synthetic Example 1a.

Melting point: started decomposing gradually from a temperature close to 246° C. and decomposed rapidly at 267 to 269° C. (recrystallized from dioxane).

SYNTHETIC EXAMPLE 7a

3-Chloro-N-(3-chloro-1H-indole-7-yl)benzenesulfonamide 2.18 g (7.11 mmol) of 3-chloro-N-(1H-indole-7-yl)benzenesulfonamide synthesized in the same manner as in Synthetic Example 1a was chlorinated in the same manner as in Example 2a, to give 1.86 g of the title compound.

Melting point: 180 to 181° C. (recrystallized from dichloromethane/diisopropyl ether)

$^1$H-NMR(DMSO-$d_6$) δ (ppm): 6.73 (1H, d, J=7.6 Hz), 6.97 (1H, dd, J=8.0, 7.6 Hz), 7.30 (1H, d, J=8.0 Hz), 7.45-7.51 (1H, m), 7.51-7.76 (4H, m), 10.09 (1H, s), 11.02-11.18 (1H, m)

SYNTHETIC EXAMPLE 8a

4-Amino-N-(3,4-dichloro-1H-indole-7-yl)benzenesulfonamide 2.03 g of the title compound was obtained from 2.43 g (6.29 mmol) of N-(3,4-dichloro-1H-indole-7-yl)-4-nitrobenzenesulfonamide synthesized in the same manner as in Synthetic Example 1a in the same manner as in Example 3a.

Melting point: 205 to 206.5° C. (decomposed) (recrystallized from ethanol/n-hexane)

$^1$H-NMR(DMSO-$d_6$) δ (ppm): 6.00 (2H, s), 6.50 (2H, d, J=8.4 Hz), 6.77 (1H, d, J=8.0 Hz), 6.94 (1H, d, J=8.0 Hz), 7.35 (2H, d, J=8.4 Hz), 7.51-7.58 (1H, m), 9.57 (1H, s), 11.20-11.38 (1H, m)

SYNTHETIC EXAMPLE 9a

4-[N-(1H-Indole-7-yl)sulfamoyl]benzoic acid

The title compound was obtained in the same manner as in Synthetic Example 1a.

$^1$H-NMR(DMSO-$d_6$) δ (ppm): 6.40 (1H, dd, J=2.9, 1.9 Hz), 6.67 (1H, d, J=7.5 Hz), 6.82 (1H, dd, J=7.9, 7.5 Hz), 7.31 (1H, dd, J=2.9, 2.7 Hz), 7.33 (1H, d, J=7.9 Hz), 7.81-7.88 (2H, m), 7.99-8.07 (2H, m), 10.07 (1H, s), 10.73-10.83 (1H, m), 13.30-13.58 (1H, br)

SYNTHETIC EXAMPLE 10a

N-(3-Chloro-1H-indole-7-yl)-4-cyanobenzene-sulfonamide 76 mg of the title compound was obtained in the same manner as in Example 2a, from 100 mg of 4-cyano-N-(1H-indole-7-yl)benzenesulfonamide synthesized in the same manner as in Synthetic Example 1a.

Melting point: 210 to 211° C. (recrystallized from ethyl acetate/n-hexane)

$^1$H-NMR(DMSO-$d_6$) δ (ppm): 6.71 (1H, dd, J=7.6, 0.8 Hz), 6.96 (1H, dd, J=8.0, 7.6 Hz), 7.30 (1H, d, J=8.0 Hz), 7.48 (1H, dd, J=2.4, 0.8 Hz), 7.82-7.90 (2H, m), 7.97-8.05 (2H, m), 10.25 (1H, s), 11.04-11.15 (1H, m)

SYNTHETIC EXAMPLE 11a

3-Chloro-N-(3-chloro-4-hydroxy-1H-indole-7-yl)benzenesulfonamide 52 mg of the title compound was obtained in the same manner as in Example 2a, from 100 mg of 3-chloro-N-(4-methoxy-1H-indole-7-yl)benzenesulfonamide synthesized in the same manner as in Synthetic Example 1a.

$^1$H-NMR(DMSO-$d_6$) δ (ppm): 3.79 (3H, s), 6.37 (1H,d, J=8.4 Hz), 6.45 (1H,d, J=8.4 Hz), 7.24-7.31 (1H, m), 7.48-7.77 (4H, m), 9.76 (1H, s), 11.06-11.17 (1H, m)

SYNTHETIC EXAMPLE 12a

3-Chloro-N-(3-chloro-4-hydroxy-1H-indole-7-yl)benzenesulfonamide 220 mg (0.47 mmol) of N-(4-tert-butyldimethylsilyloxy-3-chloro-1H-indole-7-yl)-3-chlorobenzenesulfonamide synthesized in the same manner as in Synthetic Example 1a was added to a mixed solution (2 ml) of an aqueous 40% hydrogen fluoride solution/acetonitrile (1:10). After stirred at room temperature overnight, water was added thereto and the mixture was extracted with ethyl acetate. The extract was dried over magnesium sulfate and concentrated. Then, the residue was purified by silica gel column chromatography, to give 141 mg of the title compound.

$^1$H-NMR(DMSO-$d_6$) δ (ppm): 6.15 (1H, dd, J=8.2, 1.5 Hz), 6.26 (1H,d, J=8.2 Hz), 7.12 (1H, s), 7.47-7.64 (4H, m), 9.54 (1H, s), 10.85 (1H, s)

SYNTHETIC EXAMPLE 13a

N-(1H-Indazole-7-yl)-4-methoxybenzenesulfonamide

The title compound was obtained in the same manner as in Synthetic Example 1a.

Melting point: 155 to 156° C. (recrystallized from ethyl acetate-n-hexane)

$^1$H-NMR(DMSO-$d_6$) δ (ppm): 3.77 (3H, s), 6.91-6.99 (2H, m), 6.98-7.07 (2H, m), 7.45-7.53 (1H, m), 7.64-7.74 (2H, m), 8.01-8.07 (1H, m), 9.97 (1H, s), 12.61-12.72 (1H, m)

SYNTHETIC EXAMPLE 14a

6-Chloro-N-(3-chloro-1H-indole-7-yl)-3-pyridine-sulfonamide

The title compound was obtained by chlorinating 6-chloro-N-(1H-indole-7-yl)-3-pyridinesulfonamide obtained by reacting 6-chloro-3-pyridinesulfonyl chloride and the compound of Production Example 2a in the same manner as in Example 1a.

$^1$H-NMR(DMSO-$d_6$) δ (ppm): 6.73 (1H, d, J=7.7 Hz), 6.97 (1H, dd, J=7.9, 7.7 Hz), 7.30 (1H, d, J=7.9 Hz), 7.46 (1H, d, J=2.6 Hz), 7.67 (1H, d, J=8.4 Hz), 8.03 (1H, dd, J=8.4, 2.6 Hz), 8.62 (1H, d, J=2.6 Hz), 10.18-10.34 (1H, br), 11.06-11.17 (1H, m)

SYNTHETIC EXAMPLE 15a

N-(3-Chloro-1H-indole-7-yl)-4-(methylthiomethyl)benzenesulfonamide 1.97 g (5.37 mmol) of the compound of Synthetic Example 5a was dissolved in 10 ml of tetrahydrofuran. To the mixture were added 10 ml (39.4 mmol) of an aqueous 15% sodium methylthiolate solution and a catalytic amount of methyltrioctylammonium chloride at room temperature, followed by stirring over night. 20 ml of water was added thereto, and the mixture was extracted with ethyl acetate. The organic layer was washed with water, dried over magnesium sulfate and concentrated. Then, the residue was purified by silica gel column chromatography, to give 1.51 g of N-(1H-indole-7-yl)-4-(methylthiomethyl)benzenesulfonamide. The product was chlorinated in the same manner as in Example 2a, to give 839 mg of the title compound.

$^1$H-NMR(DMSO-$d_6$) δ (ppm): 1.87 (3H, s), 3.70 (2H, s), 6.77 (1H, dd, J=7.6, 2.1 Hz), 6.94 (1H, dd, J=7.9, 7.7 Hz), 7.24 (1H, d, J=7.9 Hz), 7.42 (2H, d, J=8.2 Hz), 7.47 (1H, d, J=2.6 Hz), 7.67 (2H, d, J=8.4 Hz), 9.96 (1H, br s), 11.01 (1H, br s)

SYNTHETIC EXAMPLE 16a

3-Chloro-N-(3-formyl-1H-indole-7-yl)benzene-sulfonamide 1.3 ml (13.9 mmol) of phosphorous oxychloride was added dropwise to 14.5 ml of dimethylformamide at 10° C. or less under stirring in nitrogen atmosphere. After stirring at about 5° C. for 30 minutes, 2.50 g (8.15 mmol) of 3-chloro-N-(1H-indole-7-yl)benzenesulfonamide synthesized in the same manner as in Example 1 was added thereto in three portions. After stirring at about 5° C. for further 30 minutes, 200 ml of cooled water was added thereto. The reaction mixture was adjusted to pH about 14 by adding a 1N aqueous sodium hydroxide and then to pH about 2 by adding 1N hydrochloric acid, and then extracted by adding ethyl acetate thereto. The organic layer was washed with brine, dried over magnesium sulfate and concentrated. The residue was purified by silica gel column chromatography, to give 1.45 g of the title compound.

$^1$H-NMR(DMSO-$d_6$) δ (ppm): 6.70 (1H, dd, J=7.6, 0.8 Hz), 7.06 (1H, dd, J=8.0, 7.6 Hz), 7.51-7.75 (4H, m), 7.93 (1H,d, J=8.0 Hz), 8.22-8.28 (1H, m), 9.93 (1H, s), 10.17 (1H, s), 11.86-11.98 (1H, m)

SYNTHETIC EXAMPLE 17a

3-Chloro-N-(3-cyano-1H-indole-7-yl)benzene-sulfonamide 274 mg (3.94 mmol) of hydroxylamine hydrochloride and 0.32 ml (3.96 mmol) of pyridine were added to a dimethylformamide solution (18 ml) containing 1.20 g (3.58 mmol) of the compound of Synthetic Example 16a at 70 to 80° C. under stirring. After stirring for 2.5 hours as it was, 437 mg (3.94 mmol) of selenium dioxide and about 100 mg of magnesium sulfate powder were added thereto. After stirring at the same temperature for further 2 hours, the solvent was evaporated. To the residue was added ethyl acetate, and the insoluble matters were collected by filtration. The filtrate was successively washed with 0.1 N hydrochloric acid and brine, dried over magnesium sulfate and the solvent was evaporated. The residue was purified by silica gel column chromatography, to give 678 mg of the title compound.

Melting point: 204.5 to 205° C. (recrystallized from ethyl acetate/n-hexane)

$^1$H-NMR(DMSO-$d_6$) δ (ppm): 6.71 (1H, d, J=7.6 Hz), 7.08 (1H, dd, J=8.0, 7.6 Hz), 7.47 (1H, d, J=8.0 Hz), 7.50-7.76 (4H, m), 8.17-8.25 (1H, m), 10.21 (1H, s), 11.92-12.09 (1H, m)

SYNTHETIC EXAMPLE 18a

6-Chloro-N-(3-cyano-1H-indole-7-yl)-3-pyridine-sulfonamide

The title compound was obtained in the same manner as in Synthetic Example 1a.

$^1$H-NMR(DMSO-$d_6$) δ (ppm): 6.77 (1H, d, J=7.9 Hz), 7.12 (1H, t, J=7.9 Hz), 7.50 (1H, d, J=7.9 Hz), 7.72 (1H, d, J=8.4 Hz), 8.06 (1H, dd, J=8.4, 2.6 Hz), 8.23 (1H, d, J=2.6 Hz), 8.65 (1H, d, J=2.6 Hz), 10.34-10.48 (1H, br), 11.98-12.12 (1H, m)

SYNTHETIC EXAMPLE 19a

N-(3-Chloro-1H-indole-7-yl)-4-sulfamoylbenzene-sulfonamide 767 mg (3.0 mmol) of the compound of Production Example 5a and 264 mg (2.0 mmol) of the compound of production Example 2a were reacted and treated in the same manner as in Example 1a, to give 445 mg of N-(1H-indole-7-yl)-4-sulfamoylbenzenesulfonamide. The product was chlorinated in the same manner as in Example 2a, to give 349 mg of the title compound.

Melting point: started coloring partially in a black color from a temperature close to 220° C. and decomposed gradually from a temperature close to 240° C. (recrystallized from ethanol/n-hexane).

$^1$H-NMR(DMSO-$d_6$) δ (ppm): 6.75 (1H, d, J=7.6 Hz), 6.96 (1H, dd, J=8.0, 7.6 Hz), 7.29 (1H, d, J=7.6 Hz), 7.50 (1H, d, J=2.8 Hz), 7.58 (2H, s), 7.90-7.98 (4H, m), 10.23 (1H, s), 11.07-11.17 (1H, m)

SYNTHETIC EXAMPLE 20a

3-Chloro-N-(8-imidazo[1,2-a]pyridinyl)benzene-sulfonamide hydrochloride 1.97 g (18 mmol) of 2,3-diaminopyridine was dissolved in a mixed solution of tetrahydrofuran and water, and a tetrahydrofuran solution containing 1.90 g (9.0 mmol) of 3-chlorobenzenesulfonyl chloride was added thereto. After stirring at room temperature overnight, the mixture was concentrated, and water and dichloromethane were added to the residue. The organic layer was separated, and the wall of the reactor was rubbed. The resulting crystals were collected by filtration, to give 1.41 g of N-(2-amino-3-pyridiny)-3-chlorobenzenesulfonamide. 530 mg (1.87 mmol) of the crystals was dissolved in methanol and 367 mg (1.87 mmol) of an aqueous 40% chloroacetoaldehyde solution was added thereto. After heating under reflux for 4 hours, the mixture was concentrated to dryness. A small amount of methanol was added to the residue and the crystals were collected by filtration, to give 373 mg of the title compound.

Melting point: gradually decomposed from a temperature close to 210° C. (recrystallized from ethanol)

SYNTHETIC EXAMPLE 21a

N-(3,4-Dichloro-1H-indole-7-yl)-4-sulfamoylbenze-nesulfonamide 429 mg (1.68 mmol) of the compound of Production Example 5a and 250 mg (1.24 mmol) of the compound of Production Example 9a were reacted and treated in the same manner as in Example 1a, to give 200 mg of the title compound.

Melting point: started coloring from a temperature close to 282° C. and gradually decomposed (recrystallized from ethanol/ethyl ether).

$^1$H-NMR(DMSO-$d_6$) δ (ppm): 6.62 (1H, d, J=8.1 Hz), 6.95 (1H, d, J=8.1 Hz), 7.53-7.62 (3H, m), 7.87-7.99 (4H, m), 10.17-10.33 (1H, br), 11.44-11.56 (1H, m)

SYNTHETIC EXAMPLE 22a

N-(3-Chloro-1H-indole-7-yl)-4-(methylthio)benze-nesulfonamide

The title compound was obtained in the same manner as in Synthetic Examples 1a and 2a.

$^1$H-NMR(DMSO-$d_6$) δ (ppm): 2.48 (3H, s), 6.82 (1H, dd, J=7.9, 1.5 Hz), 6.96 (1H, dd, J=8.1, 7.5 Hz), 7.25 (1H, dd, J=7.9, 0.92 Hz), 7.33 (2H, d, J=8.8 Hz), 7.49 (1H, d, J=2.7 Hz), 7.62 (2H, d, J=8.6 Hz), 9.96 (1H, br s), 11.02 (1H, br s)

SYNTHETIC EXAMPLE 23a

N-(3-Chloro-1H-indole-7-yl)-4-(methylsulfonyl)benzenesulfonamide 54.2 mg (0.154 mmol) of the compound of Synthetic Example 22a was dissolved in a mixed solution of 2 ml of methanol and 1.2 ml of water, to which were then added 30 mg of ammonium molybdate tetrahydrate and 0.6 ml of aqueous 30% hydrogen peroxide at room temperature. After stirring overnight, water was added thereto and the mixture was extracted with ethyl acetate. The extract was washed with water, dried over magnesium sulfate and concentrated. Then, the residue was purified by silica gel column chromatography, to give 29.4 mg of the title compound.

Melting point: started coloring from a temperature close to 250° C. and decomposed at 264 to 266° C. (recrystallized from ethanol/n-hexane)

$^1$H-NMR(DMSO-$d_6$) δ (ppm): 3.28 (3H, s), 6.75 (1H, d, J=7.7 Hz), 6.97 (1H, dd, J=7.9, 7.7 Hz), 7.30 (1H, d, J=8.1 Hz), 7.50 (1H, d, J=2.7 Hz), 7.97 (2H, d, J=8.2 Hz), 8.09 (2H, d, J=8.4 Hz), 10.29 (1H, br s), 11.12 (1H, br s)

SYNTHETIC EXAMPLE 24a

N-(3-Chloro-1H-indole-7-yl)-4-(methylsulfinyl)benzenesulfonamide 19.9 mg (0.056 mmol) of the compound of Synthetic Example 22a was dissolved in 2 ml of dichloromethane, followed by adding 10 mg (0.058 mmol) of m-chloroperbenzoate under stirring under ice-cooling. After one hour, an aqueous saturated sodium bicarbonate was added thereto, and the mixture was extracted with ethyl acetate. The extract was washed with water, dried over magnesium sulfate and concentrated. Then, the residue was purified by silica gel thin layer chromatography, to give 14.4 mg of the title compound.
$^1$H-NMR(DMSO-d$_6$) δ (ppm): 2.76 (3H, s), 6.78 (1H, dd, J=7.5, 1.1 Hz), 6.96 (1H, dt, Jd=0.55 Hz, Jt=7.8 Hz), 7.28 (1H, dd, J=7.6, 0.82 Hz), 7.48 (1H, d, J=2.7 Hz), 7.82 (2H, d, J=8.6 Hz), 7.89 (2H, d, J=8.8 Hz), 10.15 (1H, br s), 11.06 (1H, br s)

SYNTHETIC EXAMPLE 25a

3-Chloro-N-(3-chloro-1H-pyrrolo[3,2-c]pyridine-7-yl)benzenesulfonamide

The title compound was obtained in the same manner as in Synthetic Examples 1a and 2a.
$^1$H-NMR(DMSO-d$_6$) δ (ppm): 7.41-7.65 (2H, m), 7.65-7.77 (2H, m), 7.74-7.86 (2H, m), 8.40-8.62 (1H, br m), 12.38-12.58 (1H, br), 13.56-13.74 (1H, br)

SYNTHETIC EXAMPLE 26a

4-Acetamide-N-(3-chloro-4-methyl-1H-indole-7-yl)benzenesulfonamide

The title compound was obtained in the same manner as in Synthetic Example 1a.
Melting point: decomposed gradually from a temperature close to 225° C. (recrystallized from ethanol/n-hexane)
$^1$H-NMR(DMSO-d$_6$) δ (ppm): 2.03 (3H, s), 2.56 (3H, s), 6.54-6.60 (2H, m), 7.33 (1H, d, J=2.6 Hz), 7.60 (2H, d, J=9.0 Hz), 7.64 (2H, d, J=9.0 Hz), 9.63 (1H, br s), 10.24 (1H, br s), 10.92 (1H, br s)

SYNTHETIC EXAMPLE 27a

4-Amino-N-(3-chloro-4-methyl-1H-indole-7-yl)benzenesulfonamide 3.75 g (9.9 mmol) of the compound of Synthetic Example 26a was dissolved in 25 ml of an aqueous 2 N sodium hydroxide, followed by stirring at 100° C. for 2 hours. After returning to room temperature, the mixture was adjusted to pH 6 by adding acetic acid. The resulting precipitates were collected by filtration and purified by silica gel column chromatography, to give 1.1 g of the title compound.
Melting point: decomposed gradually from a temperature close to 230° C. (recrystallized from ethanol/n-hexane)
$^1$H-NMR(DMSO-d$_6$) δ (ppm): 2.56 (3H, s), 5.93 (2H, br s), 6.46 (2H, d, J=8.8 Hz), 6.59 (1H, d, J=7.8 Hz), 6.64 (1H, d, J=7.8 Hz), 7.31 (2H, d, J=8.8 Hz), 7.36 (1H, d, J=2.9 Hz), 9.34 (1H, br s), 10.88 (1H, br s)

SYNTHETIC EXAMPLE 28a

4-Cyano-N-(3-cyano-1H-indole-7-yl)benzenesulfonamide

The title compound was obtained in the same manner as in Synthetic Example 1a.
Melting point: 250.5 to 252° C. (recrystallized from ethyl acetate/n-hexane)
$^1$H-NMR(DMSO-d$_6$) δ (ppm): 6.67 (1H, d, J=7.7 Hz), 7.05 (1H, t, J=7.9 Hz), 7.44 (1H, d, J=7.7 Hz), 7.78-7.87 (2H, m), 7.97-8.05 (2H, m), 8.16-8.23 (1H, m), 10.28-10.43 (1H, br), 11.92-12.09 (1H, m)

SYNTHETIC EXAMPLE 29a

4-Carbamoyl-N-(3-chloro-1H-indole-7-yl)benzenesulfonamide

To a solution of 1.0 g (3.01 mmol) of the compound of Synthetic Example 10a added to 4.8 ml of ethanol 2.4 ml were added a 30% aqueous hydrogen peroxide and 360 μl of an aqueous 6 N sodium hydroxide were respectively added in three portions under stirring. (reaction temperature: about 50° C.). After stirring at 50° C. for further 30 minutes, the reaction mixture was acidified by adding dilute hydrochloric acid and then extracted with ethyl acetate. The organic layer was collected by fractionation, washed with water, dried over magnesium sulfate and concentrated. The residue was purified by silica gel column chromatography, to give 600 mg of the title compound.
Melting point: started coloring and decomposing from a temperature close to 248° C. and rapidly decomposed at 252.5 to 253.5° C. (recrystallized from ethanol/n-hexane)
$^1$H-NMR(DMSO-d$_6$) δ (ppm): 6.76 (1H, d, J=7.5 Hz), 6.95 (1H, dd, J=8.1, 7.5 Hz), 7.27 (1H, d, J=8.1 Hz), 7.49 (1H, d, J=2.6 Hz), 7.59 (1H, br s), 7.76-7.83 (2H, m), 7.91-7.98 (2H, m), 8.12 (1H, br s), 10.10 (1H, s), 11.01-11.12 (1H, m)

SYNTHETIC EXAMPLE 30a

N-(4-Bromo-1H-indole-7-yl)-4-nitrobenzenesulfonamide

The title compound was obtained in the same manner as in Synthetic Example 1a.
$^1$H-NMR(DMSO-d$_6$) δ (ppm): 6.35-6.41 (1H, m), 6.56 (1H, d, J=8.4 Hz), 7.06 (1H, dd, J=8.4, 0.8 Hz), 7.41-7.48 (1H, m), 7.92-8.02 (2H, m), 8.30-8.41 (2H, m), 10.34 (1H, s), 11.18-11.32 (1H, m)

SYNTHETIC EXAMPLE 31a

N-(3-Chloro-4-cyano-1H-indole-7-yl)-4-nitrobenzenesulfonamide 200 mg (0.505 mmol) of the compound of Synthetic Example 30a was dissolved in 0.8 ml of N-methylpyrrolidone, followed by adding 83 mg (0.91 mmol) of cuprous cyanide. After stirring at 180 to 190° C. for 3 hours, 40 ml of ice-water was added thereto. The insoluble matters were collected by filtration, washed with water, and extracted with hot ethanol and hot chloroform. The extract was concentrated and the residue was purified by silica gel thin layer chromatography, to give 65 mg of N-(4-cyano-1H-indole-7-yl)-4-nitrobenzenesulfonamide. This product was chlorinated in the same manner as in Example 2, to give 42 mg of the title compound.
$^1$H-NMR(DMSO-d$_6$) δ (ppm): 6.98 (1H, d, J=8.0 Hz), 7.51 (1H, d, J=8.0 Hz) 7.79 (1H, d, J=2.8 Hz), 7.99-8.08 (2H, m), 8.31-8.40 (2H, m), 10.75-10.95 (1H, br), 11.62-11.73 (1H, m)

SYNTHETIC EXAMPLE 32a

4-Amino-N-(3-chloro-4-cyano-1H-indole-7-yl)benzenesulfonamide

The title compound was obtained from the compound of Synthetic Example 31a in the same manner as in synthetic Example 3a. Melting point: started decomposing from a temperature close to 232° C. and rapidly decomposed at 249.5 to 255° C. (recrystallized from ethanol-n-hexane)
$^1$H-NMR(DMSO-d$_6$) δ (ppm): 6.09 (2H, s), 6.52 (2H, d, J=8.8 Hz), 7.10 (1H, d, J=8.4 Hz), 7.46 (2H, d, J=8.8 Hz), 7.50 (1H, d, J=8.4 Hz), 7.72-7.79 (1H, m), 10.20 (1H, s), 11.40-11.59 (1H, m)

SYNTHETIC EXAMPLE 33a

6-Amino-N-(3-chloro-1H-indole-7-yl)-3-pyridine-sulfonamide 2.48 g (7.25 mmol) of the compound of Synthetic Example 14a and 679 mg (5.07 mmol) of lithium iodide were added to 25 ml of ethanol. 10 ml of liquid ammonia was added thereto, and the mixture was heated at 120° C. for 26 hours in a sealed tube and then concentrated. The residue was dissolved in ethyl acetate, and the mixture was successively washed with an aqueous saturated sodium bicarbonate and water, dried over magnesium sulfate and concentrated. Then, the residue was purified by silica gel column chromatography, to give 982 mg of the title compound.

Melting point: 206 to 207° C. (recrystallized from ethyl-n-hexane)
$^1$H-NMR(DMSO-$d_6$) δ (ppm): 6.37 (1H, d, J=8.8 Hz), 6.83-6.94 (1H, m), 6.88 (2H, br s), 6.99 (1H, dd, J=7.9, 7.7 Hz), 7.25 (1H, dd, J=7.9, 0.7 Hz), 7.48 (1H, d, J=2.7 Hz), 7.56 (1H, dd, J=8.8, 2.4 Hz), 8.14 (1H, d, J=2.4 Hz), 9.70 (1H, s), 10.92-11.03 (1H, m)

SYNTHETIC EXAMPLE 34a

N-(3-Chloro-1H-indole-7-yl)-4-(methylsulfinylmethyl)benzenesulfonamide

The title compound was obtained by oxidizing the compound of Synthetic Example 15a in the same manner as in Example 24a.
$^1$H-NMR(DMSO-$d_6$) δ (ppm): 2.41 (3H, s), 3.98 (1H, d, J=12.6 Hz), 4.18 (1H, d, J=12.8 Hz), 6.77 (1H, d, J=7.5 Hz), 6.94 (1H, dd, J=7.9, 7.7 Hz), 7.25 (1H, d, J=7.9 Hz), 7.43 (2H, d, J=8.1 Hz), 7.47 (1H, d, J=2.8 Hz), 7.73 (2H, d, J=8.1 Hz), 10.01 (1H, br s), 11.03 (1H, br s)

SYNTHETIC EXAMPLE 35a

N-(3-Chloro-1H-indole-7-yl)-4-(2-sulfamoylethyl)benzenesulfonamide 865 mg (3.05 mmol) of the compound of Production Example 11a was reacted with 376 mg (2.84 mmol) of the compound of Production Example 2a and treated in the same manner as in Example 1a. The resulting 957 mg of N-(1H-indole-7-yl)-4-(2-sulfamoylethyl)benzenesulfonamide was chlorinated in the same manner as in Example 2a, to give 980 mg of the title compound.

Melting point: 217 to 219° C. (decomposed) (recrystallized from ethanol-n-hexane)
$^1$H-NMR(DMSO-$d_6$) δ (ppm): 3.01-3.06 (2H, m), 3.23-3.28 (2H, m), 6.81 (1H, dd, J=7.5, 0.37 Hz), 6.88 (2H, br s), 6.95 (1H, dd, J=8.1, 7.5 Hz), 7.24 (1H, dd, J=7.8, 0.37 Hz), 7.42 (2H, d, J=8.4 Hz), 7.49 (1H, d, J=2.6 Hz), 7.68 (2H, d, J=8.2 Hz), 9.99 (1H, br s), 11.02 (1H, br s)

SYNTHETIC EXAMPLE 36a

N-(3-Chloro-1H-indole-7-yl)-4-[2-(methylsulfonyl)ethyl]benzenesulfonamide

The title compound was obtained in the same manner as in Synthetic Examples 1a and 2a.

Melting point: started coloring from a temperature close to 180° C. and decomposed at 201 to 203° C. (recrystallized from ethanol-n-hexane)
$^1$H-NMR(DMSO-$d_6$) δ (ppm): 2.92 (3H, s), 3.01-3.07 (2H, m), 3.40-3.46 (2H, m), 6.81 (1H, d, J=7.9 Hz), 6.94 (1H, dd, J=7.9, 7.7 Hz), 7.24 (1H, d, J=7.7 Hz), 7.45 (2H, d, J=8.2 Hz), 7.49 (1H, d, J=2.7 Hz), 7.68 (2H, d, J=8.2 Hz), 9.99 (1H, br s), 11.03 (1H, br s)

SYNTHETIC 37a

6-Amino-N-(3-cyano-1H-indole-7-yl)-3-pyridine-sulfonamide

The compound of Synthetic Example 18a was aminated in the same manner as in Example 33a, to give the title compound.

Melting point: 300° C. or more (recrystallized from ethanol-n-hexane)
$^1$H-NMR(DMSO-$d_6$) δ (ppm): 6.39 (1H, d, J=9.0 Hz), 6.88 (1H, d, J=7.7 Hz), 6.89 (2H, s), 7.11 (1H, dd, J=7.9, 7.7 Hz), 7.41 (1H, dd, J=7.9, 0.7 Hz), 7.55 (1H, dd, J=9.0, 2.6 Hz), 8.12 (1H, d, J=2.6 Hz), 8.19 (1H, s), 9.72-9.90 (1H, br), 11.78-11.92 (1H, m)

SYNTHETIC EXAMPLE 38a

4-Acetamido-3-chloro-N-(3-chloro-1H-indole-7-yl)benzenesulfonamide

The title compound was obtained in the same manner as in Synthetic Examples 1a and 2a.
$^1$H-NMR(DMSO-$d_6$) δ (ppm): 2.14 (3H, s), 6.77 (1H, d, J=7.7 Hz), 6.98 (1H, dd, J=7.9, 7.7 Hz), 7.29 (1H, d, J=7.9 Hz), 7.50 (1H, d, J=2.7 Hz), 7.64 (1H, dd, J=8.6, 2.2 Hz), 7.75 (1H, d, J=2.2 Hz), 8.04 (1H, d, J=8.6 Hz), 9.69 (1H, br s), 10.04 (1H, br s), 11.11 (1H, br s)

SYNTHETIC EXAMPLE 39a

N-(3-cyano-1H-indole-7-yl)-8-quinolinesulfonamide

The title compound was obtained in the same manner as in Synthetic Example 1a.
$^1$H-NMR(DMSO-$d_6$) δ (ppm): 6.68 (1H, d, J=7.3 Hz), 6.89 (1H, dd, J=7.9, 7.7 Hz), 7.25 (1H, d, J=8.1 Hz), 7.69-7.74 (2H, m), 8.21 (1H, d, J=2.9 Hz), 8.30 (1H, dd, J=8.2, 1.3 Hz), 8.35 (1H, dd, J=7.4, 1.4 Hz), 8.54 (1H, dd, J=8.3, 1.7 Hz), 9.15 (1H, dd, J=4.3, 1.7 Hz), 10.04 (1H, br s), 12.14 (1H, br s)

SYNTHETIC EXAMPLE 40a

5-Chloro-N-(3-cyano-1H-indole-7-yl)-2-thiophenesulfonamide

The title compound was obtained in the same manner as in Synthetic Example 1a.
$^1$H-NMR(DMSO-$d_6$) δ (ppm): 6.88 (1H, ddd, J=7.7, 2.2, 0.73 Hz), 7.16 (1H, dd, J=7.9, 7.7 Hz), 7.20 (1H, d, J=4.0 Hz), 7.36 (1H, d, J=4.2 Hz), 7.51 (1H, d, J=8.1 Hz), 8.23 (1H, d, J=3.1 Hz), 10.42 (1H, br s), 12.01 (1H, br s)

SYNTHETIC EXAMPLE 41a

N-(3-Chloro-1H-indole-7-yl)-4-(methoxycarbonylamino)benzenesulfonamide 170 mg (1.8 mmol) of methyl chloroformate was added to a pyridine solution (1 ml) containing 38 mg (0.18 mmol) of the compound of Synthetic Example 3a, followed by stirring at room temperature overnight. The reaction mixture was concentrated and the residue was purified by silica gel column chromatography, to give 20 mg of the title compound.

$^1$H-NMR(DMSO-d$_6$) δ (ppm): 3.65 (3H, s), 6.80 (1H, d, J=7.7 Hz), 6.93 (1H, t, J=7.9 Hz), 7.21 (1H, dd, J=7.7, 0.37 Hz), 7.45 (1H, d, J=2.7 Hz), 7.51 (2H, d, J=9.0 Hz), 7.63 (2H, d, J=8.8 Hz), 9.85 (1H, br s), 10.07 (1H, s), 10.97 (1H, br s)

SYNTHETIC EXAMPLE 42a

4-Acetyl-N-(3-cyano-1H-indole-7-yl)benzene-sulfonamide

The title compound was obtained in the same manner as in Synthetic Example 1a.

$^1$H-NMR(DMSO-d$_6$) δ (ppm): 2.60 (3H, s), 6.74 (1H, d, J=7.7 Hz), 7.05 (1H, dd, J=7.9, 7.7 Hz), 7.42 (1H, d, J=7.9 Hz), 7.81-7.88 (2H, m), 8.03-8.10 (2H, m), 8.21 (1H, s), 10.18-10.50 (1H, br), 11.92-12.07 (1H, m)

SYNTHETIC EXAMPLE 43a

N-(3-Chloro-1H-indole-7-yl)-4-(N-methoxysulfa-moyl)benzenesulfonamide

The title compound was obtained in the same manner as in Synthetic Examples 1a and 2a.

$^1$H-NMR(DMSO-d$_6$) δ (ppm): 3.65 (3H, s), 6.73 (1H, d, J=7.6 Hz), 6.96 (1H, dd, J=8.0, 7.6 Hz), 7.30 (1H, d, J=8.0 Hz), 7.50 (1H, d, J=2.4 Hz), 7.98 (4H, s), 10.29 (1H, br s), 10.76 (1H, br s), 11.12 (1H, br s)

SYNTHETIC EXAMPLE 44a

N-(3-Cyano-1H-indole-7-yl)-β-styrenesulfonamide

The title compound was obtained in the same manner as in Synthetic Example 1a.

$^1$H-NMR(DMSO-d$_6$) δ (ppm): 7.14-7.20 (2H, m), 7.32 (2H, s), 7.35-7.47 (4H, m), 7.60-7.68 (2H, m), 8.23 (1H, s), 9.70-10.03 (1H, br), 11.85-12.12 (1H, br)

SYNTHETIC EXAMPLE 45a

3-Chloro-N-(3-cyano-1H-indole-7-yl)-2-methylben-zenesulfonamide

The title compound was obtained in the same manner as in Synthetic Example 1a.

$^1$H-NMR(DMSO-d$_6$) δ (ppm): 2.61 (3H, s), 6.69 (1H,d, J=7.7 Hz), 7.04 (1H,t,J=7.9 Hz), 7.36 (1H, dd, J=8.1, 7.9 Hz), 7.42 (1H, d, J=7.9 Hz), 7.73 (1H, dd, J=8.1, 1.1 Hz), 7.77 (1H, dd, J=8.0, 0.82 Hz), 8.25 (1H, d, J=3.1 Hz), 10.37 (1H, s), 11.99 (1H, br s)

SYNTHETIC EXAMPLE 46a

N-(3-Chloro-1H-indole-7-yl)-6-isopropylamino-3-pyridinesulfonamide 400 mg (1.17 mmol) of the compound of Synthetic Example 14a and 0.80 ml (9.39 mmol) of isopropylamine were added to 5 ml of dioxane, followed by heating at 100° C. for 7.5 hours in a sealed tube. After concentrating, the mixture was dissolved in ethyl acetate, which was then successively washed with aqueous dilute citric acid, an aqueous saturated sodium bicarbonate and water. The mixture was dried over magnesium sulfate, and then concentrated. The residue was purified by silica gel thin layer chromatography, to give 235 mg of the title compound.

Melting point: started coloring from the temperature close to 210° C. and decomposed at 213 to 215° C. (recrystallized from ethyl acetate/n-hexane).

$^1$H-NMR(DMSO-d$_6$) δ (ppm): 1.09 (6H, d, J=6.6 Hz), 3.90-4.08 (1H, m), 6.39 (1H, d, J=9.0 Hz), 6.90-7.05 (2H, m), 7.24 (1H, d, J=7.9 Hz), 7.33 (1H, d, J=7.7 Hz), 7.48 (1H, d, J=2.4 Hz), 7.54 (1H, dd, J=9.0, 2.6 Hz), 8.22 (1H, d, J=2.6 Hz), 9.65-9.84 (1H, br), 10.88-11.04 (1H, m)

SYNTHETIC EXAMPLE 47a

N-(3-Chloro-1H-indole-7-yl)-6-[[2-(dimethylamino)ethyl]amino]-3-pyridinesulfonamide The title compound was obtained from the compound of Synthetic Example 14a and N,N-dimethylethylenediamine in the same manner as in Synthetic Example 46a.

$^1$H-NMR(DMSO-d$_6$) δ (ppm): 2.14 (6H, s), 2.35 (2H, t, J=6.6 Hz), 3.24-3.44 (2H, m), 6.48 (1H, d, J=9.0 Hz), 6.92 (1H, d, J=7.7 Hz), 6.99 (1H, dd, J=7.9, 7.7 Hz), 7.22 (1H, d, J=7.9 Hz), 7.27-7.39 (1H, m), 7.47 (1H, d, J=2.4 Hz), 7.54 (1H, dd, J=9.0, 2.6 Hz), 8.21 (1H, d, J=2.6 Hz), 10.91-11.03 (1H, m)

SYNTHETIC EXAMPLE 48a

N-(3-Cyano-1H-indole-7-yl)-2-furansulfonamide

The title compound was obtained in the same manner as in Synthetic Example 1a.

$^1$H-NMR(DMSO-d$_6$) δ (ppm): 6.62 (1H, ddd, J=3.7, 1.8, 0.37 Hz), 6.78 (1H, d, J=7.5 Hz), 7.04 (1H, d, J=3.5 Hz), 7.12 (1H, t, J=7.9 Hz), 7.49 (1H, d, J=8.1 Hz), 7.99-8.00 (1H, m), 8.23 (1H, d, J=3.1 Hz), 10.49 (1H, br s), 12.04 (1H, br s)

SYNTHETIC EXAMPLE 49a

N-(3-Chloro-1H-indole-7-yl)-4-[(dimethylaminosul-fonyl)amino]benzenesulfonamide

The title compound was obtained from the compound of Synthetic Example 3a and dimethylsulfamoyl chloride in the same manner as in Synthetic Example 1a.

$^1$H-NMR(DMSO-d$_6$) δ (ppm): 2.66 (6H, s), 6.81 (1H, dd, J=7.7, 0.92 Hz), 6.95 (1H, dd, J=7.9, 7.7 Hz), 7.20 (2H, d, J=8.8 Hz), 7.23 (1H, d, J=8.1 Hz), 7.47 (1H, d, J=2.7 Hz), 7.64 (2H, d, J=8.8 Hz), 10.98 (1H, br s)

SYNTHETIC EXAMPLE 50a

N-(3-Methyl-1H-indole-7-yl)-4-(methylsulfonyl)benzenesulfonamide 580 mg (15.3 mmol) of sodium borohydride and 150 mg of 10% palladium-carbon were added to a 2-propanol suspension (25 ml) containing 300 mg (1.58 mmol) of 3-formyl-7-nitro-1H-indole, followed by refluxing for 6 hours. After water was added to the reaction system, the catalyst was filtered off. The filtrate was extracted with ethyl acetate, and the extract was washed with brine and then dried over magnesium sulfate. The solvent was evaporated, and the residue was dissolved in 5 ml of pyridine. The mixture was reacted and treated with 170 mg (0.67 mmol) of 4-(methylsulfonyl)benzenesulfonyl chloride in the same manner as in Example 1a, to give 149 mg of the title compound.

$^1$H-NMR(DMSO-d$_6$) δ (ppm): 2.18 (3H, s), 3.24 (3H, s), 6.69 (1H, d, J=7.7 Hz), 6.81 (1H, t, J=7.7 Hz), 7.06 (1H, br s), 7.25 (1H, d, J=7.8 Hz), 7.95 (2H, d, J=8.8 Hz), 8.04 (2H, d, J=8.2 Hz), 10.14 (1H, br s), 10.40 (1H, br s)

SYNTHETIC EXAMPLE 51a

3-Cyano-N-(3-cyano-1H-indol-7-yl)benzenesulfonamide

The title compound was obtained in the same manner as in Synthetic Example 1a.

$^1$H-NMR(DMSO-d$_6$) δ (ppm): 6.71 (1H, d, J=7.2 Hz), 7.09 (1H, dd, J=8.0, 7.6 Hz), 7.49 (1H, d, J=8.0 Hz), 7.74 (1H, dd, J=8.0, 7.6 Hz), 7.94 (1H, d, J=8.0 Hz), 8.11-8.14 (2H, m), 8.23 (1H, d, J=2.8 Hz), 10.30 (1H, br s), 12.05 (1H, br s)

SYNTHETIC EXAMPLE 52a

N-(3-Chloro-1H-indol-7-yl)-4-(N-methylmethanesusulfonamide)benzenesulfonamide

The title compound was obtained in the same manner as in Synthetic Examples 1a and 2a.

Melting point: 199 to 201° C. (decomposed) (recrystallized from ethanol-n-hexane)

$^1$H-NMR(DMSO-d$_6$) δ (ppm): 2.98 (3H, s), 3.24 (3H, s), 6.83 (1H, dd, J=7.7, 0.37 Hz), 6.96 (1H, dd, J=7.9, 7.7 Hz), 7.26 (1H, dd, J=7.9, 0.55 Hz), 7.48 (1H, d, J=2.7 Hz), 7.50-7.54 (2H, m), 7.72-7.76 (2H, m), 10.04 (1H, br s), 11.02 (1H, br s)

SYNTHETIC EXAMPLE 53a

N-(3-Chloro-1H-indol-7-yl)-4-[(methanesulfonamide)methyl]benzenesulfonamide

The title compound was obtained in the same manner as in Synthetic Examples 1a and 2a.

Melting point: started coloring from the temperature close to 180° C. and decomposed at 189 to 191° C. (recrystallized from ethanol-n-hexane)

$^1$H-NMR(DMSO-d$_6$) δ (ppm): 2.81 (3H, s), 4.19 (2H, d, J=6.0 Hz), 6.79 (1H, d, J=7.7 Hz), 6.94 (1H, dd, J=7.9, 7.7 Hz), 7.24 (1H, d, J=7.9 Hz), 7.47 (2H, d, J=8.8 Hz), 7.47-7.49 (1H, m), 7.64 (1H, t, J=6.4 Hz), 7.72 (2H, d, J=8.4 Hz), 10.00 (1H, s), 11.03 (1H, br s)

SYNTHETIC EXAMPLE 54a

N-(3-Chloro-1H-indol-7-yl)-4-(1-pyrrolidinylsulfonyl)benzenesulfonamide

The title compound was obtained from 4-(1-pyrrolidinylsulfonyl)benzenesulfonyl chloride and the compound of Production Example 10a in the same manner as in Synthetic Example 1a.

$^1$H-NMR(DMSO-d$_6$) δ (ppm): 1.55-1.59 (4H, m), 3.07-3.11 (4H, m), 6.71 (1H, d, J=7.6 Hz), 6.95 (1H, ddd, J=8.2, 7.4, 1.2 Hz), 7.30 (1H, d, J=8.0 Hz), 7.46 (1H, d, J=2.4 Hz), 7.89 (2H, d, J=8.8 Hz), 7.92 (2H, d, J=8.4 Hz), 10.18 (1H, br s), 11.03 (1H, br s)

SYNTHETIC EXAMPLE 55a

N-(3-Cyano-1H-indol-7-yl)-1-methyl-4-imidazolesulfonamide

The title compound was obtained in the same manner as in Synthetic Example 1a.

$^1$H-NMR(DMSO-d$_6$) δ (ppm): 3.61 (3H, s), 7.00 (1H, dd, J=7.7, 0.92 Hz), 7.07 (1H, dd, J=7.9, 7.7 Hz), 7.35 (1H, d, J=7.9 Hz), 7.75-7.76 (2H, m), 8.19 (1H, d, J=3.1 Hz), 10.03 (1H, br s), 11.92 (1H, br s)

SYNTHETIC EXAMPLE 56a

N-(3-Chloro-1H-indol-7-yl)-6-[(2-hydroxyethyl)amino]-3-pyridinesulfonamide

The title compound was obtained from the compound of Synthetic Example 14a and 2-aminoethanol in the same manner as in Synthetic Example 46a.

$^1$H-NMR(DMSO-d$_6$) δ (ppm): 3.24-3.40 (2H, m), 3.42-3.52 (2H, m), 4.66-4.77 (1H, m), 6.48 (1H, d, J=9.3 Hz), 6.92 (1H, d, J=7.7 Hz), 7.00 (1H, t, J=7.7 Hz), 7.24 (1H, d, J=7.7 Hz), 7.40-7.62 (2H, m), 7.48 (1H, d, J=2.2 Hz), 8.22 (1H, d, J=2.6 Hz), 9.63-9.90 (1H, br), 10.90-11.07 (1H, m)

SYNTHETIC EXAMPLE 57a

N-(3-Chloro-1H-indol-7-yl)-6-mercapto-3-pyridinesulfonamide 340 mg (0.99 mmol) of the compound of Synthetic Example 14a and 151 mg (1.98 mmol) of thiourea were added to 5 ml of ethanol, followed by heating under reflux for 2 hours. After concentrating, 1.6 ml of water and 57 mg of sodium carbonate were added to the residue and the resulting mixture was stirred at room temperature for 10 minutes. 85 mg of sodium hydroxide was added thereto and the mixture was further stirred for 10 minutes, followed by filtering off the insoluble matters. The filtrate was acidified with hydrochloric acid, and the resulting precipitates were collected by filtration, washed with water, then dissolved in tetrahydrofuran and dried over magnesium sulfate. After concentrating, the residue was purified by silica gel thin layer chromatography, to give 121 mg of the title compound.

$^1$H-NMR(DMSO-d$_6$) δ (ppm): 6.84 (1H, d, J=7.6 Hz), 7.03 (1H, t, J=7.6 Hz), 7.28 (1H, d, J=9.2 Hz), 7.31 (1H, d, J=7.6 Hz), 7.44 (1H, dd, J=9.2, 2.4 Hz), 7.48 (1H, d, J=2.6 Hz), 7.68 (1H, d, J=2.4 Hz), 9.58-9.80 (1H, br), 11.08-11.19 (1H, m)

SYNTHETIC EXAMPLE 58a 7-(4-Chlorobenzenesulfonamide)-1H-indole-2-carboxylic acid The title compound was obtained in the same manner as in Synthetic Example 1a.

$^1$H-NMR(DMSO-d$_6$) δ (ppm): 6.65 (1H, d, J=7.6 Hz), 6.87 (1H, dd, J=8.0, 7.6 Hz), 7.00 (1H, s), 7.26 (1H, d, J=8.0 Hz), 7.56-7.65 (2H, m), 7.68-7.77 (2H, m), 9.62-10.00 (1H, br), 11.40-11.74 (1H, br)

SYNTHETIC EXAMPLE 59a

N-(3-Chloro-1H-indol-7-yl)-6-cyclopropylamino-3-pyridinesulfonamide

The title compound was obtained in the same manner as in Synthetic Example 46a.

Melting point: started coloring from a temperature close to 228° C. and decomposed at 233.5 to 235° C. (recrystallized from ethyl acetate-n-hexane)

$^1$H-NMR(DMSO-d$_6$) δ (ppm): 0.36-0.46 (2H, m), 0.63-0.75 (2H, m), 2.44-2.64 (1H, m), 6.45-6.64 (1H, m), 6.93 (1H,d, J=7.7 Hz), 7.00 (1H, dd, J=7.9, 7.7 Hz), 7.24 (1H, d, J=7.9 Hz), 7.49 (1H, d, J=2.7 Hz), 7.57-7.73 (2H, m), 8.25 (1H, d, J=2.6 Hz), 9.68-9.90 (1H, br), 10.92-11.04 (1H, m)

SYNTHETIC EXAMPLE 60a

N-(3-Cyano-1H-indol-7-yl)-5-methyl-3-pyridine-sulfonamide

The title compound was obtained in the same manner as in Synthetic Example 1a.

Melting point: gradually decomposed at a temperature close to 288° C. (recrystallized from ethanol-n-hexane)

$^1$H-NMR(DMSO-d$_6$) δ (ppm): 2.33 (3H, s), 6.75 (1H, d, J=7.7 Hz), 7.09 (1H, dd, J=7.9, 7.7 Hz), 7.48 (1H, d, J=7.9 Hz), 7.87-7.91 (1H, m), 8.22 (1H, d, J=3.1 Hz), 8.58-8.67 (2H, m), 10.28 (1H, br s), 11.95-12.08 (1H, m)

SYNTHETIC EXAMPLE 61a

N-(3-Chloro-1H-indol-7-yl)-4-(N-methylsulfamoyl)benzenesulfonamide

The title compound was obtained in the same manner as in Synthetic Examples 1a and 2a.

$^1$H-NMR(DMSO-d$_6$) δ (ppm): 2.39 (3H, d, J=5.2 Hz), 6.71 (1H, dd, J=7.8, 2.0 Hz), 6.96 (1H, dd, J=8.0, 7.6 Hz), 7.30 (1H, d, J=8.0 Hz), 7.48 (1H, d, J=2.8 Hz), 7.68 (1H, q, J=4.9 Hz), 7.87-7.93 (4H, m), 10.20 (1H, br s), 11.08 (1H, br s)

SYNTHETIC EXAMPLE 62a

N-(3-Chloro-1H-indol-7-yl)-4-[2-(methanesulfona-mide)ethyl]benzenesulfonamide

The title compound was obtained in the same manner as in Synthetic Examples 1a and 2a.

$^1$H-NMR(DMSO-d$_6$) δ (ppm): 2.73-2.81 (5H, m), 3.13-3.19 (2H, m), 6.82 (1H, d, J=7.7 Hz), 6.95 (1H, dd, J=8.1, 7.7 Hz), 7.09 (1H, t, J=5.9 Hz), 7.24 (1H, d, J=8.1 Hz), 7.39 (2H, d, J=8.2 Hz), 7.48 (1H, d, J=2.7 Hz), 7.68 (2H, d, J=8.4 Hz), 9.97 (1H, br s), 11.02 (1H, br s)

SYNTHETIC EXAMPLE 63a

N-(3-Chloro-1H-indol-7-yl)-4-(sulfamoylmethyl)benzenesulfonamide 389 mg (1.44 mmol) of the compound of Production Example 6a was reacted with 159 mg (1.2 mmol) of the compound of Production Example 2a and the reaction product was treated in the same manner as in Example 1a, to give 233 mg of N-(1H-indol-7-yl)-4-(sulfamoylmethyl)benzenesulfonamide.

The compound was chlorinated in the same manner as in Example 2a, to give 160 mg of the title compound.

Melting point: 237 to 238.5° C. (decomposed) (recrystallized from ethanol/n-hexane)

$^1$H-NMR(DMSO-d$_6$) δ (ppm): 4.33 (2H, s), 6.84 (1H, dd, J=7.7, 0.73 Hz), 6.93 (2H, s), 6.92-6.97 (1H, m), 7.24 (1H, dd, J=7.9, 0.37 Hz), 7.48 (1H, d, J=2.7 Hz), 7.48-7.52 (2H, m), 7.75-7.79 (2H, m), 10.08 (1H, br s), 11.04 (1H, br s)

SYNTHETIC EXAMPLE 64a

N-(3-Chloro-1H-indol-7-yl)-4-thiocarbamoylbenzene-sulfonamide 400 mg (1.21 mmol) of the compound of Synthetic Example 10a was dissolved in 10 ml of dimethylformamide, to which was then added 0.5 ml of triethylamine. Hydrogen sulfide was made to pass through the mixture at a bath temperature of 60 to 70° C. for 45 minutes. After concentrating, the residue was dissolved in ethyl acetate, successively washed with dilute hydrochloric acid, an aqueous saturated sodium bicarbonate and water, and dried over magnesium sulfate. After evaporating the solvent, the residue was purified by silica gel column chromatography, to give 355 mg of the title compound.

Melting point: 223 to 225° C. (decomposed) (recrystallized from ethanol/n-hexane)

$^1$H-NMR(DMSO-d$_6$) δ (ppm): 6.81 (1H, d, J=7.7 Hz), 6.96 (1H, dd, J=7.9, 7.7 Hz), 7.27 (1H,d, J=7.9 Hz), 7.50 (1H,d, J=2.7 Hz), 7.73-7.80 (2H, m), 7.86-7.93 (2H, m), 9.58-9.73 (1H, br m), 10.02-10.18 (1H, br m), 10.15 (1H, s), 11.03-11.12 (1H, m)

SYNTHETIC EXAMPLE 65a

5-Bromo-N-(3-cyano-1H-indol-7-yl)-2-pyridine-sulfonamide

The title compound was obtained in the same manner as in Synthetic Example 1a.

Melting point: 245.5 to 246.5° C. (decomposed) (recrystallized from ethyl acetate/n-hexane)

$^1$H-NMR(DMSO-d$_6$) δ (ppm): 6.82 (1H, d, J=7.7 Hz), 7.07 (1H, dd, J=7.9, 7.7 Hz), 7.44 (1H, d, J=7.9 Hz), 7.80 (1H, d, J=8.2 Hz), 8.23 (1H, d, J=2.2 Hz), 8.29 (1H, dd, J=8.2, 2.2 Hz), 8.92 (1H, d, J=2.2 Hz), 10.42-10.67 (1H, br), 11.93-12.08 (1H, m)

SYNTHETIC EXAMPLE 66a

N-(3-Cyano-1H-indol-7-yl)-2-naphthalenesulfona-mide

The title compound was obtained in the same manner as in Synthetic Example 1a.

$^1$H-NMR(DMSO-d$_6$) δ (ppm): 6.74 (1H, dd, J=7.6, 2.8 Hz), 7.00 (1H, dd, J=7.9, 7.7 Hz), 7.39 (1H, dd, J=8.0, 0.46 Hz), 7.61-7.72 (2H, m), 7.80 (1H, dd, J=8.6, 1.8 Hz), 8.01 (1H, d, J=8.1 Hz), 8.08 (1H, s), 8.10 (1H, s), 8.21 (1H, d, J=2.9 Hz), 8.34 (1H, d, J=1.6 Hz), 10.23 (1H, br s), 12.01 (1H, br s)

SYNTHETIC EXAMPLE 67a

N-(3-Acetyl-1H-indol-7-yl)-3-chlorobenzene-sulfonamide

The title compound was obtained in the same manner as in Synthetic Example 1a.

$^1$H-NMR(DMSO-d$_6$) δ (ppm): 2.44 (3H, s), 6.65 (1H, d, J=7.5 Hz), 7.01 (1H, dd, J=7.9, 7.7 Hz), 7.53-7.63 (2H, m), 7.69-7.73 (2H, m), 8.01 (1H, dd, J=8.1, 0.73 Hz), 8.26 (1H, d, J=2.9 Hz), 10.10 (1H, s), 11.75 (1H, br s)

SYNTHETIC EXAMPLE 68a

4-Amino-N-(5-bromo-3-cyano-1H-indole-7-yl)benzenesulfonamide

The title compound was obtained by hydrogenating N-(5-bromo-3-cyano-1H-indole-7-yl)-4-nitrobenzenesulfonamide, obtained from 4-nitrobenzenesulfonyl chloride and the compound of Production Example 14a in the same manner as in Example 1a, at normal temperature under normal pressure in the presence of platinum oxide.
$^1$H-NMR(DMSO-$d_6$) δ (ppm): 6.07 (2H, br s), 6.52 (2H, d, J=8.4 Hz), 6.97-6.99 (1H, m), 7.36 (2H, dd, J=8.7, 1.6 Hz), 7.51 (1H, br s), 8.25 (1H, s), 9.93 (1H, d, J=5.5 Hz), 11.97 (1H, br s)

SYNTHETIC EXAMPLE 69a

N-(3-Chloro-1H-indole-7-yl)-4-(N-ethylsulfamoyl)benzenesulfonamide

The title compound was obtained in the same manner as in Synthetic Examples 1a and 2a.
Melting point: 213.5 to 215° C. (recrystallized from ethanol/n-hexane)
$^1$H-NMR(DMSO-$d_6$) δ (ppm): 0.90 (3H, t, J=7.2 Hz), 2.76 (2H, dq, Jd=5.8 Hz, Jq=7.2 Hz), 6.70 (1H, d, J=7.4 Hz), 6.95 (1H, dd, J=8.0, 7.6 Hz), 7.29 (1H, d, J=8.0 Hz), 7.47 (1H, d, J=2.8 Hz), 7.78 (1H, t, J=5.6 Hz), 7.90 (4H, s), 10.18 (1H, br s), 11.06 (1H, br s)

SYNTHETIC EXAMPLE 70a

N-(3-Chloro-1H-indole-7-yl)-4-(ethanesulfonamide)benzenesulfonamide

The title compound was obtained in the same manner as in Synthetic Example 4a.
Melting point: 214 to 215° C. (decomposed) (recrystallized from ethanol/n-hexane)
$^1$H-NMR(DMSO-$d_6$) δ (ppm): 1.14 (3H, t, J=7.3 Hz), 3.16 (2H, q, J=7.3 Hz), 6.82 (1H, d, J=7.5 Hz), 6.96 (1H, dd, J=7.9, 7.7 Hz), 7.23 (2H, d, J=8.8 Hz), 7.24 (1H, d, J=7.5 Hz), 7.47 (1H, d, J=2.6 Hz), 7.66 (2H, d, J=8.8 Hz), 9.90 (1H, br s), 10.37 (1H, br s), 10.96 (1H, br s)

SYNTHETIC EXAMPLE 71a

N-(3-Chloro-1H-indole-7-yl)-6-[(2-cyanoethyl)amino]-3-pyridinesulfonamide

The title compound was obtained in the same manner as in Synthetic Example 46a.
$^1$H-NMR(DMSO-$d_6$) δ (ppm): 2.72 (2H, t, J=6.4 Hz), 3.46-3.55 (2H, m), 6.53 (1H, d, J=9.0 Hz), 6.90 (1H, d, J=7.7 Hz), 6.99 (1H, dd, J=7.9, 7.7 Hz), 7.25 (1H, d, J=7.9 Hz), 7.48 (1H, d, J=2.6 Hz), 7.61 (1H, dd, J=9.0, 2.4 Hz), 7.78-7.87 (1H, m), 8.25 (1H, d, J=2.4 Hz), 9.70-9.95 (1H, br), 10.92-11.04 (1H, m)

SYNTHETIC EXAMPLE 72a

N-(3-Chloro-1H-indole-7-yl)-4-(N-methylcarbamoyl)benzenesulfonamide 533 mg (1.68 mmol) of the compound of Synthetic Example 9a was dissolved in a mixed solution of 5 ml of dimethylformamide and 2.5 ml of dimethyl sulfoxide, to which were then added 171 mg (2.53 mmol) of methylamine hydrochloride and 705 µl (5.06 mmol) of triethylamine. 436 µl (2.02 mmol) of diphenylphosphrylazide was added thereto, followed by stirring at room temperature overnight. Then, the mixture was concentrated and extracted with ethyl acetate. The extract was successively washed with dilute hydrochloric acid, an aqueous saturated sodium bicarbonate and water, and dried over magnesium sulfate. After concentrating, the residue was purified by silica gel column chromatography, to give 465 mg of N-(1H-indole-7-yl)-4-(N-methylcarbamoyl)benzenesulfonamide. The obtained compound was chlorinated in the same manner as in Synthetic Example 2a, to give 413 mg of the title compound.
Melting point: 252 to 253° C. (decomposed) (recrystallized from ethanol/n-hexane)
$^1$H-NMR(DMSO-$d_6$) δ (ppm): 2.76 (3H, d, J=4.6 Hz), 6.74 (1H, d, J=7.7 Hz), 6.94 (1H, dd, J=7.9, 7.7 Hz), 7.27 (1H, d, J=7.9 Hz), 7.49 (1H, d, J=2.7 Hz), 7.76-7.83 (2H, m), 7.87-7.94 (2H, m), 8.61 (1H, q, J=4.6 Hz), 10.10 (1H, s), 11.03-11.13 (1H, m)

SYNTHETIC EXAMPLE 73a

N-(3-chloro-1H-indole-7-yl)-4-(methylsulfonylmethyl)benzenesulfonamide 510 mg of the compound of Synthetic Example 34a was oxidized using aqueous 30% hydrogen peroxide in the same manner as in Example 23a, to give 307 mg of the title compound.
Melting point: started coloring from a temperature close to 225° C. and decomposed gradually from a temperature close to 235° C. (recrystallized from ethanol/n-hexane)
$^1$H-NMR(DMSO-$d_6$) δ (ppm): 2.88 (3H, s), 4.57 (2H, s), 6.77 (1H, d, J=7.6 Hz), 6.94 (1H, dd, J=7.9, 7.7 Hz), 7.25 (1H, d, J=8.0 Hz), 7.47 (1H, d, J=2.7 Hz), 7.51-7.56 (2H, m), 7.73-7.78 (2H, m), 10.05 (1H, br s), 11.04 (1H, br s)

SYNTHETIC EXAMPLE 74a

N-(3-Chloro-1H-indole-7-yl)-4-(N,N-dimethylsulfamoyl)benzenesulfonamide

The title compound was obtained in the same manner as in Synthetic Examples 1a and 2a.
$^1$H-NMR(DMSO-$d_6$) δ (ppm): 2.57 (6H, s), 6.71 (1H, dd, J=7.4, 0.6 Hz), 6.97 (1H, dd, J=8.0, 7.6 Hz), 7.31 (1H, d, J=8.0 Hz), 7.47 (1H, d, J=2.8 Hz), 7.86 (2H, d, J=8.4 Hz), 7.91 (2H, d, J=8.4 Hz), 10.19 (1H, br s), 11.04 (1H, br s)

SYNTHETIC EXAMPLE 75a

N-(3-Chloro-1H-indole-7-yl)-4-(1-pyrrolidinylcarbonyl)benzenesulfonamide

The title compound was obtained in the same manner as in Synthetic Example 1a.
$^1$H-NMR(DMSO-$D_6$)$_6$ (ppm): 1.79 (2H, dt, Jd=12.8 Hz, Jt=6.4 Hz), 1.85 (2H, dt, Jd=13.6 Hz, Jt=6.8 Hz), 3.22 (2H, t, J=6.4 Hz), 3.44 (2H, t, J=6.8 Hz), 6.78 (1H, d, J=7.2 Hz), 6.96 (1H, dd, J=8.0, 7.2 Hz), 7.28 (1H, d, J=8.0 Hz), 7.47 (1H, d, J=2.4 Hz), 7.60 (2H, d, J=8.0 Hz), 7.74 (2H, d, J=8.4 Hz), 10.06 (1H, br s), 11.01 (1H, br s)

SYNTHETIC EXAMPLE 76a

3-Chloro-N-(3-chloro-1H-indole-7-yl)-N-methylbenzenesulfonamide 120 mg (0.352 mmol) of the compound of Synthetic Example 7a was dissolved in 10 ml of dimethylformamide, to which was then added 19.2 mg (0.479 mmol) of sodium hydride (60%). After stirring at room temperature for 30 minutes, 30 μl (0.482 mmol) of methyl iodide was added thereto. After two hours, water was added thereto, followed by extracting with ethyl acetate. The organic layer was washed with water and dried over magnesium sulfate. After concentrating, the residue was purified by silica gel thin layer chromatography, to give 87 mg of the title compound.

$^1$H-NMR(DMSO-$d_6$) δ (ppm): 3.26 (3H, s), 6.51 (1H, dd, J=7.6, 0.64 Hz), 7.00 (1H, dd, J=7.9, 7.7 Hz), 7.47 (1H,d, J=8.1 Hz), 7.53 (1H,d, J=2.7 Hz), 7.54-7.59 (2H, m), 7.65 (1H,t,J=7.9 Hz), 7.84 (1H, ddd, J=8.1, 2.1, 1.1 Hz), 11.62 (1H, br s)

SYNTHETIC EXAMPLE 77a

N-(3,4-Dichloro-1H-indole-7-yl)-4-(sulfamoylmethyl)benzenesulfonamide

The title compound was obtained in the same manner as in Synthetic Example 1a.

Melting point: decomposed gradually from a temperature close to 297° C. (recrystallized from ethanol/n-hexane)

$^1$H-NMR(DMSO-$d_6$) δ (ppm): 4.34 (2H, s), 6.72 (1H, d, J=8.1 Hz), 6.93 (2H, s), 6.94 (1H, d, J=8.1 Hz), 7.51 (2H, d, J=8.1 Hz), 7.57 (1H, dd, J=2.7, 0.55 Hz), 7.75 (2H, d, J=8.2 Hz), 10.10 (1H, br s), 11.44 (1H, br s)

SYNTHETIC EXAMPLE 78a

N-(3-Cyano-1H-indole-7-yl)-4-[2-(methylsulfonyl)ethyl]benzenesulfonamide

The title compound was obtained in the same manner as in Synthetic Example 1a.

$^1$H-NMR(DMSO-$d_6$) δ (ppm): 2.94 (3H, s), 3.03-3.08 (2H, m), 3.42-3.47 (2H, m), 6.77 (1H, dd, J=7.7, 0.37 Hz), 7.05 (1H, t, J=7.9 Hz), 7.41 (1H, d, J=8.1 Hz), 7.46 (2H, d, J=8.2 Hz), 7.66 (2H, d, J=8.2 Hz), 8.20 (1H, s), 10.09 (1H, br s), 11.92 (1H, br s)

SYNTHETIC EXAMPLE 79a

N-(3-Chloro-1H-indole-7-yl)-4-(N-methylacetamido)benzenesulfonamide

The title compound was obtained in the same manner as in Synthetic Examples 1a and 2a.

$^1$H-NMR(DMSO-$d_6$) δ (ppm): 1.84 (3H, br s), 3.16 (3H, s), 6.81 (1H, d, J=7.7 Hz), 6.96 (1H, dd, J=8.0, 7.6 Hz), 7.27 (1H, d, J=7.9 Hz), 7.45-7.49 (2H, m), 7.47 (1H, d, J=2.7 Hz), 7.70-7.75 (2H, m), 10.02 (1H, br s), 11.01 (1H, br s)

SYNTHETIC EXAMPLE 80a

N-(3-Chloro-1H-indole-7-yl)-6-hydroxy-3-pyridinesulfonamide

Under ice-cooling, into a solution of the compound of Example 33a (100 mg, 0.31 mmol) dissolved in 2 ml of glacial acetic acid was added dropwise 1 ml of an aqueous solution containing 32 mg (0.46 mmol) of sodium nitrite. After stirring for one hour, the mixture was adjusted to about pH 8 by adding an aqueous sodium bicarbonate and further stirred for 10 minutes. The reaction mixture was extracted with ethyl acetate, and the extract was washed with water, dried over magnesium sulfate and concentrated. Then, the residue was purified by silica gel thin layer chromatography, to give 54 mg of the title compound.

Melting point: 244-245° C. (decomposed) (recrystallized from ethyl acetate/n-hexane)

$^1$H-NMR(DMSO-$d_6$) δ (ppm): 6.39 (1H, d, J=9.5 Hz), 6.88 (1H, d, J=7.7 Hz), 7.04 (1H, dd, J=7.9, 7.7 Hz), 7.32 (1H, d, J=7.9 Hz), 7.50 (1H, d, J=2.7 Hz), 7.58 (1H, dd, J=9.5, 3.1 Hz), 7.64 (1H, d, J=3.1 Hz), 9.76-9.94 (1H, br), 11.01-11.13 (1H, m), 11.98-12.15 (1H, br)

SYNTHETIC EXAMPLE 81a

N-(3-Chloro-1H-indole-7-yl)-4-[2-(N-methylmethanesulfonamido)ethyl]benzenesulfonamide The title compound was obtained in the same manner as in Synthetic Examples 1a and 2a.

$^1$H-NMR(DMSO-$d_6$) δ (ppm): 2.69 (3H, s), 2.76 (3H, s), 2.86 (2H, t, J=7.5 Hz), 3.26 (2H, t, J=7.5 Hz), 6.78 (1H, dd, J=7.4, 0.55 Hz), 6.94 (1H, t, J=7.7 Hz), 7.24 (1H, dd, J=7.7, 0.37 Hz), 7.39 (2H, d, J=8.2 Hz), 7.48 (1H, d, J=2.6 Hz), 7.66 (2H, d, J=8.2 Hz), 9.94 (1H, br s), 11.02 (1H, br s)

SYNTHETIC EXAMPLE 82a

N-(3-Chloro-1H-indole-7-yl)-4-(trifluoromethanesulfonamido)benzenesulfonamide

128 μl (0.76 mmol) of trifluoromethanesulfonic acid anhydride was added to a pyridine solution (5 ml) containing 62 mg (0.19 mmol) of the compound of Synthetic Example 3a at 0° C., followed by stirring as it was overnight. The reaction solution was evaporated. A phosphoric acid buffer solution having a pH of 7 was added thereto, followed by extracting with ethyl acetate. Then, the extract was washed with brine and dried over magnesium sulfate. The solvent was evaporated and the residue was purified by silica gel column chromatography, to give 20 mg of the title compound.

$^1$H-NMR(DMSO-$d_6$) δ (ppm): 6.79 (1H, d, J=7.7 Hz), 6.94 (1H, dd, J=7.9, 7.7 Hz), 7.16 (2H, d, J=8.6 Hz), 7.23 (1H, d, J=7.9 Hz), 7.46 (1H, d, J=2.7 Hz), 7.58 (2H, d, J=8.1 Hz), 9.84 (1H, br s), 10.98 (1H, br s)

SYNTHETIC EXAMPLE 83a

N-(3-Chloro-1H-indole-7-yl)-4-[(N-methylmethanesulfonamido)methyl]benzenesulfonamide The title compound was obtained in the same manner as in Synthetic examples 1a and 2a.

Melting point: 200.5 to 202° C. (recrystallized from ethanol)

$^1$H-NMR(DMSO-$d_6$) δ (ppm): 2.63 (3H, s), 2.94 (3H, s), 4.27 (2H, s), 6.80 (1H,d, J=7.3 Hz), 6.95 (1H, dd, J=8.1, 7.5

Hz), 7.25 (1H, d, J=7.9 Hz), 7.45 (2H, d, J=8.2 Hz), 7.47 (1H, d, J=2.7 Hz), 7.74 (2H, d, J=8.2 Hz), 10.00 (1H, s), 11.00 (1H, br s)

SYNTHETIC EXAMPLE 84a

3-Chloro-N-(3-chloro-1H-pyrrolo[2,3-c]pyridine-7-yl)benzenesulfonamide

To 84 ml of aqueous concentrated ammonia were added 600 mg (3.05 mmol) of 7-bromo-1H-pyrrolo[2,3-c]pyridine synthesized from 2-bromo-3-nitropyridine in the same manner as in Production Example 1a, 194 mg of a copper powder and 603 mg of cuprous chloride. The mixture was heated in a sealed tube at 120° C. for 15 hours and then treated, to give 170 mg of 7-amino-1H-pyrrolo[2,3-c]pyridine. The resulting product was reacted and treated in the same manner as in Examples 1a and 2a, to give 57 mg of the title compound.

$^1$H-NMR(DMSO-$d_6$) δ (ppm): 6.93 (1H, d, J=6.6 Hz), 7.45 (1H, dd, J=6.6, 5.8 Hz), 7.53 (1H, dd, J=8.0, 7.6 Hz), 7.61 (1H, d, J=7.6 Hz), 7.73 (1H, d, J=2.8 Hz), 7.85 (1H, d, J=8.0 Hz), 7.96 (1H, d, J=1.2 Hz), 11.90-12.10 (1H, m), 12.72 (1H, br s)

SYNTHETIC EXAMPLE 85a

N-(3-Chloro-1H-indole-7-yl)-4-[3-(1-imidazolyl)propyl]benzenesulfonamide

To 4-(3-bromopropyl)-N-(3-chloro-1H-indole-7-yl)benzenesulfonamide (213 mg, 0.5 mmol) were added 170 mg (2.5 mmol) of imidazole and 6 ml of dimethylformamide, followed by heating at 80° C. for 3 hours in a nitrogen atmosphere. Then, the reaction mixture was poured into water and extracted with chloroform. The extract was dried over magnesium sulfate and concentrated. Then, the residue was purified by silica gel column chromatography, to give 160 mg of the title compound.

Melting point: 86 to 90° C.

$^1$H-NMR(DMSO-$d_6$) δ (ppm): 1.95-2.04 (2H, m), 2.55 (2H, t, J=7.9 Hz), 3.92 (2H, t, J=7.1 Hz), 6.81 (1H, dd, J=7.7, 0.9 Hz), 6.88 (1H, t, J=1.1 Hz), 6.94 (1H, dd, J=7.9, 7.7 Hz), 7.16 (1H, t, J=1.2 Hz), 7.23 (1H, d, J=7.7 Hz), 7.32 (2H, d, J=8.4 Hz), 7.47 (1H,d, J=2.7 Hz), 7.60 (1H, br s), 7.65 (2H,d, J=8.4 Hz), 9.91-10.01 (1H, m), 10.98-11.02 (1H, m)

SYNTHETIC EXAMPLE 86a

N-(3-Chloro-1H-indole-7-yl)-4-[N-[2-(2-pyridinyl)ethyl]carbamoyl]benzenesulfonamide 2.82 g (12.8 mmol) of 4-(chlorosulfonyl)benzoic acid and 1.42 g (8.54 mmol) of 7-amino-3-chloro-1H-indole were reacted with each other in pyridine at room temperature under stirring overnight, to give 2.33 g of 4-[N-(3-chloro-1H-indole-7-yl)sulfamoyl]benzoic acid. To 303 mg (0.86 mmol) of the product were successively added 260 μl of dimethylformamide, 204 μl (0.95 mmol) of diphenylphosphorylazide, 132 μl (0.95 mmol) of triethylamine and 113 μl (0.94 mmol) of 2-(2-aminoethyl)pyridine, followed by stirring at room temperature overnight. After concentrating, ethyl acetate and an aqueous saturated sodium bicarbonate were added thereto. The organic layer was separated and washed with brine. After evaporating the solvent, the residue was purified by silica gel column chromatography, to give 175 mg of the title compound.

Melting point: 220.5 to 222° C.

$^1$H-NMR(DMSO-$d_6$) δ (ppm): 2.95-2.99 (2H, m), 3.56-3.62 (2H, m), 6.75 (1H,d, J=7.5 Hz), 6.94 (1H, dd, J=7.9, 7.7 Hz), 7.19-7.28 (3H, m), 7.48 (1H, d, J=2.8 Hz), 7.69 (1H, dt, Jd=1.8 Hz, Jt=7.7 Hz), 7.79 (2H, d, J=8.6 Hz), 7.88 (2H, d, J=8.6 Hz), 8.48-8.51 (1H, m), 8.75 (1H, t, J=5.2 Hz), 10.09-10.12 (1H, m), 11.06-11.09 (1H, m)

SYNTHETIC EXAMPLE 87a

4-Amidino-N-(3-chloro-1H-indole-7-yl)benzenesulfonamide 3.3 ml (3.3 mmol) of a hexane solution containing 1.0 M trimethylaluminum and 10 ml of toluene were added to 162 mg (3.0 mmol) of ammonium chloride. After the generation of gas was ceased, the mixture was evaporated until the amount of the solution became about 3 ml. While stirring, 97 mg (0.30 mmol) of the compound of Production Example 4a was added thereto and the mixture was heated at 80° C. for 4 hours. After cooling, a concentrated ammonia was added thereto, the insoluble matters were filtered off and the filtrate was concentrated. Ethyl acetate was added thereto, the insoluble matters were filtered off and the filtrate was concentrated. The residue was purified by silica gel column chromatography, to give 35 mg of the title compound.

$^1$H-NMR(DMSO-$d_6$) δ (ppm): 6.93 (1H, dd, J=7.7, 1.5 Hz), 6.96 (1H, dd, J=7.7, 7.5 Hz), 7.24 (1H, dd, J=7.5, 1.3 Hz), 7.50 (1H, d, J=2.7 Hz), 7.90 (2H, d, J=8.6 Hz), 8.01 (2H, d, J=8.6 Hz), 9.16-9.62 (2H, br), 10.40-10.75 (1H, br), 11.50 (1H, s)

SYNTHETIC EXAMPLE 88a

N-(3-Chloro-1H-indole-7-yl)-4-[N-[2-(1-imidazolyl)ethyl]sulfamoyl]benzenesulfonamide 557 mg (1.13 mmol) of 4-[N-(2-bromoethyl)sulfamoyl]-N-(3-chloro-1H-indole-7-yl)benzenesulfonamide and 820 mg (12.0 mmol) of imidazole were added to 10 ml of dimethylformamide and the mixture was stirred at 80° C. for 2 days. After concentrating, the residue was dissolved in ethyl acetate. The mixture was washed with water, dried over sodium sulfate and concentrated. The residue was purified by silica gel column chromatography, to give 324 mg of the title compound.

Melting point: started coloring gradually from a temperature close to 200° C. and decomposed at 218 to 221° C. (recrystallized from ethanol/n-hexane)

$^1$H-NMR(DMSO-$d_6$) δ (ppm): 3.05 (2H, ddd, J=6.2, 6.0, 5.9 Hz), 3.96 (2H, dd, J=6.0, 5.9 Hz), 6.69-6.72 (1H, m), 6.84 (1H, br s), 6.92 (1H, dd, J=7.9, 7.7 Hz), 7.08 (1H, br s), 7.26 (1H, d, J=7.5 Hz), 7.44 (1H, d, J=2.7 Hz), 7.55 (1H, br s), 7.82-7.88 (4H, m), 8.06 (1H, t, J=5.9 Hz), 10.18-10.36 (1H, br), 11.09 (1H, d, J=2.4 Hz)

SYNTHETIC EXAMPLE 89a 3-(5-Bromonicotinamido)-N-(3-cyano-1H-indole-7-yl)benzenesulfonamide 785 mg (3.54 mmol) of 3-nitrobenzenesulfonyl chloride was reacted with 506 mg (3.22 mmol) of the compound of Production Example 3a in the same manner as in Production Example 4a and treated, to give 950 mg of N-(3-cyano-1H-indole-7-yl)-3-nitrobenzenesulfonamide. The product was reduced using zinc powder/concentrated hydrochloric acid in 30 ml of methanol according to a conventional method, to give 459 mg of 3-amino-N-(3-cyano-1H-indole-7-yl)benzenesulfonamide. 109 mg (0.35 mmol) of the product was dissolved in 2 ml of pyridine and 179 mg (0.70 mmol) of 5-bromonicotinoyl chloride hydrochloride was added thereto. After stirring at room temperature overnight, the mixture was concentrated. An aqueous diluted citric acid was added to the residue. The resulting precipitates were collected by filtration, and successively washed with water, an aqueous diluted sodium bicarbonate, water and ether. The precipitates were dissolved in tetrahydrofuran, and the mixture was dried over magnesium sulfate and concentrated. Crystals precipitated by adding ether and n-hexane were collected by filtration, to give 108 mg of the title compound.

$^1$H-NMR(DMSO-$d_6$) δ (ppm): 6.81 (1H, dd, J=7.7, 0.7 Hz), 7.07 (1H, t, J=7.9 Hz), 7.42 (1H, dd, J=7.9, 0.7 Hz), 7.47-7.51 (1H, m), 7.55 (1H, t, J=7.9 Hz), 7.93-7.97 (1H, m), 8.21-8.23 (1H, m), 8.31 (1H, t, J=1.8 Hz), 8.55 (1H, dd, J=2.4, 2.0 Hz), 8.93 (1H, d, J=2.4 Hz), 9.06 (1H, d, J=2.0 Hz), 10.23-10.25 (1H, m), 10.75 (1H, br s), 11.94-11.96 (1H, m)

SYNTHETIC EXAMPLE 90a

N-(3-Chloro-1H-indole-7-yl)-4-[N-(2-thiazolyl)sulfamoyl]benzenesulfonamide 5.2 g (20.4 mmol) of sulfathiazole was added to a mixed solution of 14 ml of water and 3.4 ml of concentrated hydrochloric acid and the mixture was stirred. To the mixture was added dropwise an aqueous saturated solution of 2.1 g (30.4 mmol) of sodium nitrite at 0° C. or less. Then, 5 ml of acetic acid was added thereto, followed by stirring at 5° C. for about 10 minutes. An acetic acid solution saturated with sulfur dioxide (solution prepared by saturating 18 ml of acetic acid with sulfur dioxide and then adding 830 mg of cupric chloride.dihydrate thereto) was added dropwise to the reaction solution at 0° C. under stirring. After 5 minutes, the reaction solution was poured into ice-water. The precipitates were collected by filtration, washed with water and dried, to give 2.9 g of 4-chlorosulfonyl-N-(2-thiazolyl)benzenesulfonamide. 570 mg (1.68 mmol) of the product was reacted with 200 mg (1.2 mmol) of the compound of Production Example 1a in the same manner as in Production Example 4a and treated, to give 456 mg of the title compound.

$^1$H-NMR(DMSO-$d_6$) δ (ppm): 6.68 (1H, dd, J=7.5, 0.73 Hz), 6.87 (1H, d, J=4.6 Hz), 6.93 (1H, dd, J=8.1, 7.5 Hz), 7.26-7.30 (1H, m), 7.28 (1H, d, J=4.6 Hz), 7.46 (1H, d, J=2.7 Hz), 7.82-7.88 (2H, m), 7.88-7.94 (2H, m), 10.10-10.26 (1H, br), 11.04-11.10 (1H, m), 12.83-13.01 (1H, br)

SYNTHETIC EXAMPLE 91a

5-Chloro-N-(3-chloro-1H-indole-7-yl)-4-(5-methyl-3-pyridinesulfonamido)-2-thiophenesulfonamide 645 mg (2.46 mmol) of 5-chloro-4-nitro-2-thiophenesulfonyl chloride was reacted with 410 mg (2.46 mmol) of the compound of Production Example 1a in the same manner as in Production Example 4a and treated, to give 194 mg of 5-chloro-N-(3-chloro-1H-indole-7-yl)-4-nitro-2-thiophenesulfonamide. The product was reduced using zinc powder/concentrated hydrochloric acid in 10 ml of methanol according to a conventional method, to give 75 mg of 4-amino-5-chloro-N-(3-chloro-1H-indole-7-yl)-2-thiophenesulfonamide. 72 mg (0.20 mmol) of the product was dissolved in 2 ml of tetrahydrofuran, and 18 µl of pyridine and 38 mg (0.2 mmol) of 5-methyl-3-pyridinesulfonyl chloride were added thereto. After stirring at room temperature overnight, the organic layer was separated by adding ethyl acetate and 1N hydrochloric acid thereto. It was successively washed with water, an aqueous sodium bicarbonate and water, dried over magnesium sulfate and concentrated. Then, the residue was purified by silica gel column chromatography, to give 82 mg of the title compound.

$^1$H-NMR(DMSO-$d_6$) δ (ppm): 2.33 (3H, s), 6.76 (1H, d, J=7.7 Hz), 7.03 (1H, dd, J=7.9, 7.7 Hz), 7.35 (1H, s), 7.38 (1H, d, J=7.9 Hz), 7.51 (1H, d, J=2.7 Hz), 7.80 (1H, dd, J=2.0, 1.5 Hz), 8.60 (1H, dd, J=2.0, 0.4 Hz), 8.71 (1H, dd, J=1.5, 0.4 Hz), 10.35-10.40 (1H, m), 10.73-10.80 (1H, br), 11.16-11.19 (1H, m)

PRODUCTION EXAMPLE 1b

2-Amino-5-bromoquinoline

2-Bromo-6-nitrobenzaldehyde (30.4 g), magnesium oxide (75 g) and dimethyl sulfoxide (11.3 ml) were sufficiently stirred for one minute. Then, to the mixture was added diethyl (cyanomethyl)phosphonate (25.8 ml) and the mixture was stirred for further 2 hours. The stirring was stopped and the reaction mixture was allowed to stand overnight. Thereafter, ethylacetate was added thereto and the resulting mixture was stirred, followed by filtering. The filtrate was concentrated and the residue was purified by silica gel column chromatography (ethyl acetate), to give 32 g of 3-(2-bromo-6-nitrophenyl)-2-propenenitrile (E isomer:Z isomer=3:1).

$^1$H-NMR(CDCl$_3$) δ (ppm): 5.63 (d, J=16.5 Hz,E-isomer1H), 5.81 (d, J=10.8 Hz,Z-isomer 1H), 7.42-7.52 (m,E-isomer 1H,Z-isomer 2H), 7.56 (d, J=16.5 Hz,E-isomer 1H), 7.90-8.16 (m,E-isomer 2H, Z-isomer 2H).

Next, ethanol (250 ml), tin (60 g) and distilled water (150 ml) were added to 32 g of 3-(2-bromo-6-nitrophenyl)-2-propenenitrile (E isomer:Z isomer=3:1), followed by heating under stirring at 90° C. To the mixture was added dropwise concentrated hydrochloric acid (256 ml), followed by stirring at the same temperature for 3 hours. After returning to room temperature, the liquid layer was decanted and cooled to 0° C. The resulting solid was collected by filtration. An aqueous ammonia was added thereto, and the mixture was extracted by ethyl acetate. The extract was concentrated and the residue was purified by silica gel column chromatography (ethyl acetate), to give 5.0 g of the title compound.

$^1$H-NMR(CDCl$_3$) δ (ppm): 4.88 (2H, bs), 6.79 (1H, d, J=9.3 Hz), 7.39 (1H, t, J=8.9 Hz), 7.51 (1H, d, J=8.9 Hz), 7.61 (1H, d, J=8.9 Hz), 8.27 (1H, d, J=9.3 Hz).

PRODUCTION EXAMPLE 2b

2-Amino-5-chloroquinoline

The title compound was obtained from 2-chloro-6-nitrobenzaldehyde in the same manner as in Production Example 1b.

$^1$H-NMR(CDCl$_3$) δ (ppm): 5.25 (2H,bs), 6.80 (1H, d, J=9.7 Hz), 7.32 (1H, dd, J=7.5 Hz,1.5 Hz), 7.46 (1H, t, J=7.5 Hz), 7.57 (1H, m), 8.30 (1H, d, J=9.7 Hz, 1.0 Hz).

PRODUCTION EXAMPLE 3b

3-Carbethoxy-4-hydroxy-8-bromoquinoline

A mixture of 50 g (0.291 mol) of 2-bromoaniline and 63 g (0.291 mol) of diethylethoxymethylene malonate was heated at 100° C. under reduced pressure for 3 hours and further at 200° C. for 12 hours. After the reaction was completed, the reaction mixture solid was washed with ethyl acetate and the crystals were collected by filtration and dried, to give 50 g of the title compound.

$^1$H-NMR(DMSO-d$_6$) δ (ppm): 1.26 (3H, t, J=7.2 Hz), 4.21 (2H, q, J=7.2 Hz), 7.34 (1H, t, J=7.6 Hz), 8.03 (1H, dd, J=1.6 Hz, 7.6 Hz), 8.15 (1H, dd, J=1.6 Hz, 7.6 Hz), 8.43 (1H, s), 11.56 (1H, s).

PRODUCTION EXAMPLE 4b

3-Carbethoxy-8-bromoquinoline

A mixture of 2.5 g (8.4 mmol) of 3-carbethoxy-4-hydroxy-8-bromoquinoline and 10 ml of phosphorous oxychloride was heated under reflux for one hour. After the reaction was completed, phosphorous oxychloride was removed and the residue was purified by NH silica gel, to give 2.6 g of a chloro-compound. Next, 500 mg (1.6 mmol) of the chloro-compound was dissolved in 20 ml of dioxane, 1 g of zinc powder and 3 ml of acetic acid were added thereto, followed by heating at 65° C. for 30 minutes. Ethyl acetate was added to the reaction solution, and the mixture was filtered through Celite. The filtrate was washed with brine, dried over magnesium sulfate and concentrated. To the residue was added 1 ml of acetic acid, and the mixture was allowed to stand for 12 hours and then acetic acid was removed. The residue was subjected to silica gel column chromatography, and eluted with the solvent (ethyl acetate/n-hexane=1/7), to give obtaining 180 mg of the title compound.

$^1$H-NMR(CDCl$_3$) δ (ppm): 1.47 (3H, t, J=7.2 Hz), 4.50 (2H, q, J=7.2 Hz), 7.50 (1H, t, J=7.6 Hz), 7.93 (1H, dd, J=1.2 Hz, 7.6 Hz), 8.18 (1H, dd, J=1.2 Hz, 7.6 Hz), 8.85 (1H, d, J=2 Hz), 9.57 (1H, d, J=2 Hz).

PRODUCTION EXAMPLE 5b

3-Amino-8-bromoquinoline 500 mg (1.8 mmol) of 3-carbethoxy-8-bromoquinoline was added to an aqueous ethanol (10 ml)/1 N NaOH solution (10 ml) and the mixture was stirred at room temperature for 3 hours. Ethanol was removed and the residue was neutralized with 1N HCl. The resulting solid was collected by filtration, washed with water and dried, to give 450 mg of a carboxylic acid. Next, 450 mg (1.8 mmol) of the carboxylic acid was added to 25 ml of tert-butanol. Further, to the mixture were added 0.58 ml (2.7 mmol) of DPPA and 0.37 ml (2.7 mmol) of triethylamine, followed by heating under reflux for 12 hours. The reaction solution was concentrated, and the residue was subjected to silica gel chromatography and eluted with the solvent (ethyl acetate-n-hexane=1-4), to give 352 mg of an amide compound. Next, 350 mg (1.1 mmol) of the amide compound was added to a mixed solution of 4 ml of methanol/2 ml of conc. HCl, and the mixture was stirred at room temperature for one hour. The reaction solution was basified with an aqueous ammonia and extracted with ethyl acetate. The organic layer was washed with brine, dried over magnesium sulfate and then concentrated, to give 240 mg of the title compound.

$^1$H-NMR(DMSO-d$_6$) δ (ppm): 5.88 (2H, s), 7.13 (1H, d, J=2.8 Hz), 7.24 (1H, dd, J=7.6 Hz, 8.4 Hz), 7.59-7.65 (2H, m), 8.49 (1H, d, J=2.8 Hz).

PRODUCTION EXAMPLE 6b

3-Amino-8-iodoquinoline

The title compound was obtained from 2-iodoaniline in the same manner as in Production Examples (3b-5b).

$^1$H-NMR(DMSO-d$_6$) δ (ppm): 5.85 (2H, s), 7.07 (1H, d, J=2.8 Hz), 7.10 (1H, t, J=7.6 Hz), 7.62 (1H, dd, J=1.2 Hz, 7.6 Hz), 7.90 (1H, dd, J=1.2 Hz, 7.6 Hz), 8.45 (1H, d, J=2.8 Hz).

PRODUCTION EXAMPLE 7b

3-Amino-8-cyanoquinoline

The title compound was obtained from 2-cyanoaniline in the same manner as in Production Examples (3b-5b).

$^1$H-NMR(DMSO-d$_6$) δ (ppm): 6.03 (2H, br s), 7.22 (1H, d, J=2.8 Hz), 7.48 (1H, dd, J=7.2 Hz, 8.4 Hz), 7.84 (1H, dd, J=1.2 Hz, 8.4 Hz), 7.94 (1H, dd, J=1.2 Hz, 8.4 Hz), 8.57 (1H, d, J=2.8 Hz).

PRODUCTION EXAMPLE 8b

3-Amino-8-(methylsulfonyl)quinoline

The title compound was obtained in the same manner as in Production Examples (3b-5b).

$^1$H-NMR(CDCl$_3$) δ (ppm): 6.00 (2H, s), 7.26 (1H, d, J=2.4 Hz), 7.53 (1H, t, J=7.2 Hz), 7.91 (1H, dd, J=1.6 Hz, 7.2 Hz), 7.96 (1H, dd, J=1.2 Hz, 8.4 Hz), 8.58 (1H, d, J=2.8 Hz).

PRODUCTION EXAMPLE 9b

3-Amino-8-chloroquinoline

The title compound was obtained in the same manner as in Production Examples (3b-5b).

$^1$H-NMR(DMSO-d$_6$) δ (ppm): 5.90 (2H, s), 7.17 (1H, d, J=2.8 Hz), 7.33 (1H, t, J=7.6 Hz), 7.46 (1H, d, J=7.6 Hz), 7.58 (1H, d, J=7.6 Hz), 8.52 (1H, d, J=2.8 Hz).

PRODUCTION EXAMPLE 10b

3-Amino-8-trifluoromethylquinoline

The title compound was obtained in the same manner as in Production Examples (3b-5b).

$^1$H-NMR(DMSO-d$_6$) δ (ppm): 5.94 (2H, s), 7.23 (1H, d, J=2.8 Hz), 7.48 (1H, t, J=7.6 Hz), 7.69 (1H, d, J=7.6 Hz), 7.91 (1H, d, J=7.6 Hz), 8.55 (1H, d, J=2.8 Hz).

PRODUCTION EXAMPLE 11b

Ethyl-8-chloro-4-vinylquinoline-3-carboxylate

Tributylvinyltin (2.8 ml) and tetrakistriphenylphosphine-palladium (171 mg) were added to a toluene solution (20 ml) containing 2.0 g (7.4 mmol) of ethyl-4,8-dichloroquinoline-3-carboxylate obtained in the same manner as in Production Example 4b, followed by stirring for 2 hours under heating under reflux. The reaction solution was filtered through Celite and the filtrate was concentrated. Then, the residue was purified by silica gel chromatography, to give 1.92 g of the title compound.

$^1$H-NMR(DMSO-d$_6$) δ (ppm): 1.36 (3H, t, J=7.6 Hz), 4.37 (2H, d, J=7.6 Hz), 5.52 (1H, d, J=18.0 Hz), 5.58 (1H, d, J=16.4 Hz), 7.40 (1H, dd, J=16.4, 18.0 Hz), 7.70 (1H, t, J=8.0 Hz), 8.11 (1H, d, J=8.0 Hz), 8.25 (1H, d, J=8.0 Hz), 9.24 (1H, s).

PRODUCTION EXAMPLE 12b

3-Amino-8-chloro-4-vinylquinoline

The title compound was obtained from ethyl-4-vinyl-8-chloroquinoline-3-carboxylate in the same manner as in Production Example 5b.
$^1$H-NMR(DMSO-$d_6$) δ (ppm): 5.69 (1H, dd, J=1.6, 18.0 Hz), 5.81 (2H, s), 5.84 (1H, dd, J=1.6, 11.6 Hz), 6.91 (1H, dd, J=11.6, 18.0 Hz), 7.38 (1H, t, J=8.0 Hz), 7.52 (1H, dd, J=1.2, 8.0 Hz), 7.85 (1H, dd, J=1.2, 8.0 Hz), 8.60 (1H, s).

PRODUCTION EXAMPLE 13b

Ethyl-7-amino-2-chloroquinoline-4-carboxylate 43 g (231 mmol) of diethyl oxaloacetate was added to 25 g (231 mmol) of methaphenylenediamine and the mixture was stirred at 160° C. for one hour. After cooling as it was, the crystals were washed with methanol. Phosphorous oxychloride (3.6 ml) was added to a chloroform solution (30 ml) containing 3.0 g (13 mmol) of the crystals, followed by heating under reflux for one hour. After cooling as it was, the mixture was poured into ice-water and basified with a 1 N aqueous sodium hydroxide. Then, crystals were collected by filtration and washed with tetrahydrofuran, and the filtrate was evaporated, to give 4.85 g of the title compound.
$^1$H-NMR(DMSO-$d_6$) δ (ppm): 1.31-1.42 (3H, m), 4.34-4.46 (2H, m), 6.92 (1H, d, J=2.4 Hz), 7.12 (1H, dd, J=2.4, 9.2 Hz), 7.40 (1H, s), 8.21 (1H, d, J=9.2 Hz).

PRODUCTION EXAMPLE 14b

2-Benzylthio-4-methoxypyridazine 843 mg (21 mmol, 55% oily) of sodium hydride was suspended in dimethyl sulfoxide (30 ml). Under ice-cooling, 2.0 ml (16.7 mmol) of benzylmercaptan was added thereto, followed by stirring for 10 minutes. To the reaction mixture was added 2.5 g (17.6 mmol) of 4-methoxy-2-chloropyridazine, followed by stirring at room temperature overnight. To the reaction mixture was added an aqueous saturated ammonium chloride, followed by extracting with ethyl acetate. The organic layer was washed with brine, dried over magnesium sulfate and concentrated. Then, the residue was purified by silica gel chromatography, to give 1.63 g of the title compound.
$^1$H-NMR(DMSO-$d_6$) δ (ppm): 3.98 (3H, s), 4.48 (2H, s), 7.12 (1H, d, J=8.8 Hz), 7.22-7.26 (1H, m), 7.29-7.37 (2H, m), 7.41-7.44 (2H, m), 7.57 (1H, d, J=8.8 Hz).

PRODUCTION EXAMPLE 15b

2-Benzylthio-4-carboxyamidopyridine

Thionyl chloride (120 ml) was added to 25 g (159 mmol) of 2-chloroisonicotinic acid, and the mixture was stirred while heating under reflux for 3 hours. After cooling as it was, the mixture was evaporated, to give the residue. A tetrahydrofuran solution (200 ml) containing the reside was poured into a mixed solution of an aqueous ammonium (200 ml) and a tetrahydrofuran (200 ml) under ice-cooling. After stirring under ice-cooling for 15 minutes, the mixture was evaporated. Crystals were collected by filtration and washed with water, to give 22.6 g of white crystals. 4.2 ml (36 mmol) of benzylthiomercaptan and 10 g (77 mmol) of potassium carbonate were added to a dimethylformamide solution containing 5.13 g (32 mmol) of the white crystals, and the mixture was stirred while heating under reflux for 3 hours. Water was added to the reaction solution, and the mixture was extracted with ethyl acetate. The organic layer was washed with brine, dried over magnesium sulfate and evaporated. Then, the residue was purified by silica gel chromatography, and the resulting crystals were washed with hexane, to give 6.3 g of the title compound.
$^1$H-NMR(DMSO-$d_6$) δ (ppm): 4.46 (2H, s), 7.22-7.33 (3H, m), 7.41 (2H, d, J=7.2 Hz), 7.49 (1H, dd, J=1.6, 5.2 Hz), 7.67 (1H, s), 7.73 (1H, s), 8.21 (1H, s), 8.58 (1H, d, J=5.2 Hz).

PRODUCTION EXAMPLE 16b

7-Amino-2-chloro-4-methylquinoline 32 ml (251 mmol) of ethyl acetoacetate was added to 27 g (251 mmol) of methaphenylenediamine and the mixture was stirred at 200° C. for one hour. After cooling as it was, crystals were washed with hexane. 15 ml of phosphorous oxychloride was added to 9.5 g (54 mmol) of the crystals, followed by heating under reflux for 2 hours. After cooling as it was, the reaction mixture was poured into ice-water and basified with an aqueous saturated ammonium. The resulting crystals were collected by filtration and washed with water. The crystals were washed with methanol and the filtrate was evaporated, to give 4.85 g of the title compound.
$^1$H-NMR(DMSO-$d_6$) δ (ppm): 3.18 (3H, s), 5.95 (2H, s), 6.82 (1H, d, J=2.4 Hz), 6.98 (1H, s), 7.01 (1H, dd, J=2.4, 8.8 Hz), 7.76 (1H, d, J=8.8 Hz).

PRODUCTION EXAMPLE 17b 3,4-Dihydroisoquinoline

N-Bromosuccinimide (39.2 g) was added to a methylene chloride solution (300 ml) containing 26.67 g (0.2 mol) of 1,2,3,4-tetrahydroisoquinoline under ice-cooling over 20 minutes. After stirring for 40 minutes, an aqueous 30% sodium hydroxide solution (130 ml) was added to the reaction solution. The organic layer was washed with water and then extracted with a 10% aqueous hydrochloric acid (200 ml). The aqueous layer was washed with methylene chloride, basified with an aqueous ammonia, and then extracted with methylene chloride. The extract was dried over magnesium sulfate and then evaporated. The resulting residue was distilled (about 16 mmHg, 120° C.), to give 21.5 g of the title compound as an oil.
$^1$H-NMR(DMSO-$d_6$) δ (ppm): 2.66 (2H, t, J=8 Hz), 3.62 (2H, td, J=2 Hz, 8 Hz), 7.19-7.21 (1H, m), 7.29-7.33 (1H, m), 7.35-7.40 (1H, m), 8.31 (1H, t, J=2 Hz).

PRODUCTION EXAMPLE 18b

7-Nitroisoquinoline 15 g of potassium nitrite was added to a concentrated sulfuric acid (70 ml) solution containing 18 g (0.14 mol) of 3,4-dihydroisoquinoline was added thereto at −15° C. over 20 minutes. After stirring at room temperature for one hour, the mixture was heated at 60° C. for 40 minutes. The reaction solution was poured into ice-water and basified with an aqueous ammonia. The mixture was extracted with ethyl acetate, and the organic layer was washed with brine and dried over magnesium sulfate. After concentrating, decaline (100 ml), nitrobenzene (100 ml) and 2 g of Pd-Black were added to the residue, and the mixture was heated at 200° C. overnight in nitrogen stream. The reaction solution was washed with ethyl acetate and then extracted with 2N hydrochloric acid. The aqueous layer was washed with ethyl acetate and then an aqueous sodium hydroxide was added thereto. The resulting precipitates were collected by filtration and washed with water, to give 14.4 g of the title compound.

$^1$H-NMR(CDCl$_3$) δ (ppm): 7.79 (1H, d, J=5.6 Hz), 8.00 (1H, d, J=9.2 Hz), 8.48 (1H, dd, J=2.4 Hz, 9.2 Hz), 8.75 (1H, d, J=5.6 Hz), 8.96 (1H, d, J=2 Hz), 9.48 (1H, s).

PRODUCTION EXAMPLE 19b

4-Bromo-7-nitroisoquinoline 1.2 ml of aqueous HBr and 3 ml of bromine were added to 1.6 g (9.19 mmol) of 7-nitroquinoline and the mixture was heated at 180° C. for 5.5 hours. The reaction solution was extracted with ethylacetate. The extract was successively washed with an aqueous sodium hydroxide, an aqueous sodium thiosulfate and brine, dried over magnesium sulfate and concentrated. Then, the resulting residue was purified by silica gel column chromatography (eluted with hexane-hexane:ethyl acetate=4:1), to give 500 mg of the title compound.

$^1$H-NMR(CDCl$_3$) δ (ppm): 8.36 (1H, d, J=9.2 Hz), 8.58 (1H, d, J=2.4 Hz, 9.2 Hz), 8.93 (1H, s), 8.96 (1H, d, J=3.2 Hz), 9.38 (1H, s).

PRODUCTION EXAMPLE 20b

7-Amino-4-bromoisoquinoline 66 mg (0.26 mmol) of 7-nitro-4-bromoisoquinoline was dissolved in 1 ml of ethanol, 2 ml of tetrahydrofuran and 1 ml of water. To the mixture were added 70 mg of an iron powder and 140 mg of ammonium chloride, followed by heating at 50° C. for 3 hours. A 1N aqueous sodium hydroxide was added to the reaction solution, and the mixture was extracted with chloroform. The organic layer was dried over magnesium sulfate and concentrated. The resulting residue was crystallized from isopropyl ether, to give 33 mg of the title compound.

$^1$H-NMR(DMSO-d$_6$) δ (ppm): 5.98 (2H, s), 6.97 (1H, d, J=2.4 Hz), 7.31 (1H, dd, J=2.4 Hz, 8.8 Hz), 8.28 (1H, s), 8.89 (1H, s).

PRODUCTION EXAMPLE 21b 6-(4-Toluenesulfonylamino)isoquinoline

6-Aminoisoquinoline (3.348 g, Synthesis, 733 (1975)) was dissolved in pyridine (30 ml). To the mixture was added 4-toluenesulfonyl chloride (5.13 g), followed by stirring at room temperature overnight. Water was added thereto, and the mixture was extracted with ethyl acetate. The extract was washed with brine and dried over anhydrous magnesium sulfate. The solvent was evaporated and the residue was recrystallized from ethanol, to give the title compound (5.958 g, 85%) as pale yellow crystals.

$^1$H-NMR (DMSO-d$_6$) δ (ppm): 2.28 (3H, s), 7.32 (2H, d, J=8.2 Hz), 7.40 (1H, dd, J=1.6, 9.2 Hz), 7.55 (1H, br s), 7.67 (1H, d, J=5.6 Hz), 7.74 (2H, d, J=8.2 Hz), 7.97 (1H, d, J=9.2 Hz), 8.36 (1H, d, J=5.6 Hz), 9.10 (1H, s)

PRODUCTION EXAMPLE 22b

1-Chloro-6-(4-toluenesulfonylamino)isoquinoline 6-(4-Toluenesulfonylamino) isoquinoline (3.0 g, Production Example 21b) was dissolved in chloroform (100 ml). Under ice-cooling, m-chloroperbenzoic acid (2.57 g) was added thereto, followed by stirring at room temperature overnight. The solvent was evaporated, and the resulting crystals were washed with diethyl ether, collected by filtration and dried, to give pale yellow crystals. The crystals were suspended in chloroform (83 ml) and phosphorous oxychloride (19 ml) was added thereto, followed by heating under reflux for 5 hours. After cooling, the solvent was evaporated. The residue was basified by adding an aqueous saturated sodium bicarbonate in an ice bath, and then the mixture was extracted with ethyl acetate. The extract was washed with brine and dried over anhydrous magnesium sulfate, and the solvent was evaporated. The residue was purified by silica gel column, to give crude crystals of the title compound (1.630 g, 49.40%). The crystals were recrystallized from ethanol, to give the title compound as colorless crystals.

$^1$H-NMR (DMSO-d$_6$) δ (ppm): 2.29 (3H, s), 7.34 (2H, d, J=8.0 Hz), 7.52 (1H, dd, J=2.0, 9.0 Hz), 7.65 (1H, d, J=2.0 Hz), 7.76 (1H, d, J=5.6 Hz), 7.77 (2H, d, J=8.0 Hz), 8.14 (1H, d, J=9.0 Hz), 8.16 (1H, d, J=5.6 Hz).

PRODUCTION EXAMPLE 23b

6-Amino-1-chloroisoquinoline

1-Chloro-6-(4-toluenesulfonylamino) isoquinoline (3.323 g, Production Example 22b) was dissolved in sulfuric acid (30 ml), followed by stirring at room temperature overnight. The reaction solution was poured into ice, and basified by adding an aqueous sodium hydroxide solution and then potassium carbonate thereto, followed by extracting with ethyl acetate. The extract was washed with brine and dried over anhydrous magnesium sulfate. The solvent was evaporated, to give the title compound (1.37 g, 76.81%) as yellowish brown crystals.

$^1$H-NMR (DMSO-d$_6$) δ (ppm): 6.23 (2H, br s), 6.76 (1H, s), 7.09 (1H, d, J=9.6 Hz), 7.37 (1H, d, J=6.4 Hz), 7.89 (1H, d, J=9.6 Hz), 7.90 (1H, d, J=6.4 Hz).

PRODUCTION EXAMPLE 24b

2-Chloro-1,6-naphthyridine 1,6-Naphthyridine-2-one (1.0 g, J. Org. Chem. 4744 (1990)) was dissolved in phosphorous oxychloride (19 ml), followed by heating under reflux at 120° C. for 2 hours. After cooling, the solvent was evaporated, and the residue was basified with water and potassium carbonate. Then, the mixture was extracted with ethyl acetate, and the extract was washed with brine and dried over anhydrous magnesium sulfate. The solvent was evaporated, to give the title compound (0.658 g, 58.45%) as orange crystals.

$^1$H-NMR (CDCl$_3$) δ (ppm): 7.55 (1H, d, J=8.8 Hz), 7.86 (1H, d, J=6.0 Hz), 8.28 (1H, d, J=8.8 Hz), 8.80 (1H, d, J=6.0 Hz), 9.29 (1H, s).

PRODUCTION EXAMPLE 25b

2-Amino-1,6-naphthyridine

2-Chloro-1,6-naphthyridine (0.628 g, Production Example 22b) and an aqueous ammonia (40 ml) were heated at 130° C.

for 11 hours in a sealed tube. After cooling, the mixture was extracted with ethyl acetate, and the extract was washed with brine and dried over anhydrous magnesium sulfate. The solvent was evaporated and the residue was purified by silica gel column, to give the title compound (0.497 g, 89.73%) as pale yellow crystals.

$^1$H-NMR(DMSO-d$_6$) δ (ppm): 6.81 (1H, d, J=8.8 Hz), 7.24 (1H, d, J=5.8 Hz), 7.97 (1H, d, J=8.8 Hz), 8.34 (1H, d, J=5.8 Hz), 8.80 (1H, s).

PRODUCTION EXAMPLE 26b

N-(3-Nitrophenethyl)phthalimide

3-Nitrophenethyl alcohol (15 g) was dissolved in tetrahydrofuran (225 ml). After adding triphenylphosphine (26 g) and phthalimide (13.9 g) thereto, the mixture was ice-cooled and diethylazodicarboxylate (15.5 ml) was added dropwise thereinto. After stirring at room temperature for one hour, the resulting crystals were collected by filtration, washed with diethyl ether and dried, to give N-(3-nitrophenethyl)phthalimide as colorless crystals.

$^1$H-NMR(CDCl$_3$) δ (ppm): 3.12 (2H, t, J=7.4 Hz), 3.98 (2H, t, J=7.4 Hz), 7.47 (1H, dd, J=8.0, 8.0 Hz), 7.60 (1H, d, J=8.0 Hz), 7.72 (2H, m), 7.83 (2H, m), 8.09 (1H, d, J=8.0 Hz), 8.12 (1H, s).

PRODUCTION EXAMPLE 27b

3-Nitrophenethylamine

N-(3-Nitrophenethyl)phthalimide obtained in Production Example 26b was suspended in ethanol (150 ml). To the mixture was added hydrazine (5.7 ml), followed by heating under reflux for one hour. The reaction solution was once dissolved completely, but crystals again precipitated. The crystals were filtered off and washed with cooled ethanol. Then, the solvent was evaporated, to give the title compound (5.559 g, 99%) as a yellow oil.

$^1$H-NMR (CDCl$_3$) δ (ppm): 2.87 (2H, t, J=6.8 Hz), 3.04 (2H, t, J=6.8 Hz), 7.48 (1H, dd, J=7.6, 8.4 Hz), 7.55 (1H, ddd, J=1.2, 1.6, 7.6 Hz), 8.08 (2H, m).

PRODUCTION EXAMPLE 28b

N-Acetyl-N-(3-nitrophenethyl)amine

3-Nitrophenethylamine (5.559 g, Production Example 25b) was dissolved in pyridine (33 ml), and acetyl chloride (2.5 ml) was added dropwise thereinto under ice-cooling. After stirring at room temperature for 0.5 hr, the mixture was ice-cooled again. Water was added thereto, and the mixture was extracted with ethyl acetate. The extract was washed with brine and dried over anhydrous magnesium sulfate. The solvent was evaporated, to give the title compound (6.323 g, 91%) as a yellow oil.

$^1$H-NMR (CDCl$_3$) δ (ppm): 1.97 (3H, s), 2.95 (2H, t, J=7.0 Hz), 3.55 (2H, dt, J=6.0, 7.0 Hz), 5.60 (1H, br s), 7.49 (1H, dd, J=7.2, 8.0 Hz), 7.55 (1H, d, J=7.2 Hz), 8.07 (1H, s), 8.12 (1H, d, J=8.0 Hz).

PRODUCTION EXAMPLE 29b

N-Acetyl-N-(3-aminophenethyl)amine

N-Acetyl-N-(3-nitrophenethyl)amine (2.1 g, Production Example 28b) was dissolved in ethanol (40 ml). To the mixture were added an iron powder (2.25 g), ammonium acetate (4.3 g) and water (20 ml), followed by heating under reflux for 1.5 hours. Solid was filtered off and washed with ethanol, and then the filtrate was partially evaporated. The residue was extracted with ethyl acetate, washed with brine and dried over anhydrous magnesium sulfate. The solvent was evaporated, to give the title compound (1.723 g, 96%) as a yellow oil.

$^1$H-NMR (CDCl$_3$) δ (ppm): 1.94 (3H, s), 2.72 (2H, t, J=6.8 Hz), 3.50 (2H, dt, J=6.0, 6.8 Hz), 6.53 (1H, s), 6.57 (1H, d, J=8.0 Hz), 6.59 (1H, d, J=7.2 Hz), 7.10 (1H, dd, J=7.2, 8.0 Hz).

PRODUCTION EXAMPLE 30b

N-Acetyl-N-(3-ethoxycarbonylaminophenethyl)amine

N-Acetyl-N-(3-aminophenethyl)amine (1.7 g, Production Example 29b) was dissolved in pyridine (5 ml). Under ice-cooling, ethyl chloroformate (1.4 ml) was added dropwise thereinto, followed by stirring at room temperature for one hour. Then, the mixture was ice-cooled again and water was added thereto. The mixture was extracted with ethyl acetate, and the extract was washed with brine and dried over anhydrous magnesium sulfate. The solvent was evaporated, to give the title compound (2.358 g, 97%) as a yellow oil.

$^1$H-NMR (CDCl$_3$) δ (ppm): 1.29 (3H, t, J=7.2 Hz), 1.93 (3H, s), 2.76 (2H, t, J=7.0 Hz), 3.47 (2H, dt, J=6.0, 7.0 Hz), 4.20 (2H, q, J=7.2 Hz), 5.57 (1H, br s), 6.86 (1H, d, J=7.2 Hz), 7.21 (1H, dd, J=7.2, 8.0 Hz), 7.28 (1H, d, J=8.0 Hz), 7.29 (1H, s)

PRODUCTION EXAMPLE 31b

6-Ethoxycarbonylamino-1-methyl-3,4-dihydroisoquinoline

Using N-acetyl-N-(3-ethoxycarbonylaminophenethyl) amine (1.0 g, Production Example 30b), a cyclization reaction was run according to the method described in Heterocycles 31 (2), 341 (1990). After the reaction was completed, the reaction solution was poured into ice and basified with potassium carbonate. Then, the solution was extracted with ethyl acetate, and the extract was washed with brine and dried over anhydrous magnesium sulfate. The solvent was evaporated, to give the title compound as a brown oil.

$^1$H-NMR(CDCl$_3$) δ (ppm): 1.19 (3H, t, J=7.2 Hz), 2.23 (3H, s), 2.60 (2H, t, J=7.4 Hz), 3.55 (2H, t, J=7.4 Hz), 4.13 (2H, q, J=7.2 Hz), 7.31 (1H, d, J=6.8 Hz), 7.32 (1H, s), 7.34 (1H, d, J=6.8 Hz).

PRODUCTION EXAMPLE 32b

6-Ethoxycarbonylamino-1-methylisoquinoline p-Cymene (100 ml) and palladium carbon (0.9 g) were added to 6-ethoxycarbonylamino-1-methyl-3,4-dihydroisoquinoline, followed by heating under stirring at 195° C. for one hour in a nitrogen atmosphere. The catalyst was filtered off and washed with ethanol, and then the filtrate was partially evaporated. After extracting with 1N hydrochloric acid, the extract was basified with potassium carbonate and then extracted with ethyl acetate. The extract was washed with brine and dried over anhydrous magnesium sulfate anhydride. The solvent was evaporated, to give the title compound (0.629 g, 69%, 2 steps) as pale yellow crystals.

$^1$H-NMR(CDCl$_3$) δ (ppm): 1.30 (3H, t, J=7.2 Hz), 2.89 (3H, s), 4.26 (2H, q, J=7.2 Hz), 7.40 (1H, d, J=5.8 Hz), 7.56

(1H, dd, J=1.6, 8.8 Hz), 7.99 (1H, d, J=8.8 Hz), 8.05 (1H, d, J=1.6 Hz), 8.30 (1H, d, J=5.6 Hz), 8.37 (1H, s).

PRODUCTION EXAMPLE 33b

6-Amino-1-methylisoquinoline

6-Ethoxycarbonylamino-1-methylisoquinoline (0.629 g, Production Example 32b) was dissolved in ethanol (20 ml), to which was then added an aqueous 8 N sodium hydroxide solution (6.8 ml), followed by heating under reflux for 1.5 hours. After cooling as it was to room temperature, an aqueous saturated ammonium chloride was added thereto and the mixture was extracted with ethyl acetate. The extract was washed with brine and dried over anhydrous magnesium sulfate. The solvent was evaporated, to give the title compound (0.311 g, 72%) as pale yellow crystals.
$^1$H-NMR(CDCl$_3$) δ (ppm): 2.81 (3H, s), 4.24 (2H, br s), 6.60 (1H, d, J=2.0 Hz), 6.91 (1H, ddd, J=1.6, 2.0, 8.8 Hz), 7.18 (1H, d, J=5.6 Hz), 7.84 (1H, d, J=8.8 Hz), 8.16 (1H, dd, J=1.6, 5.6 Hz).

PRODUCTION EXAMPLE 34b

N-t-Butoxycarbonyl-3-nitrophenethylamine

3-Nitrophenethylamine (4.559 g, Production Example 27b) was dissolved in tetrahydrofuran (130 ml), to which were then added triethylamine (8.4 ml) and di-t-butyl dicarbonate (6.6 g), followed by stirring at room temperature for 2 hours. After evaporating the solvent, brine was added thereto and the mixture was then extracted with ethyl acetate. The extract was washed with brine and dried over anhydrous magnesium sulfate. The solvent was evaporated, to give the title compound (8.789 g, including impurities) as a yellow oil. It was used in the next reaction without being further purified.
$^1$H-NMR(CDCl$_3$) δ (ppm): 1.53 (9H, s), 2.92 (2H, t, J=7.6 Hz), 3.42 (2H, dt, J=6.4, 6.8 Hz), 4.58 (1H, br s), 7.48 (1H, dd, J=7.2, 8.0 Hz), 7.54 (1H, d, J=8.0 Hz), 8.07 (1H, s), 8.10 (1H, d, J=7.2 Hz)

PRODUCTION EXAMPLE 35b 3-(2-t-Butoxycarbonylaminoethyl)-aniline

The title compound (5.521 g, 76%) was obtained as a yellow oil by using N-t-butoxycarbonyl-3-nitrophenethylamine (8.789 g, including impurities, Production Example 34b) in the same manner as in Production Example 170b.
$^1$H-NMR(CDCl$_3$) δ (ppm): 1.44 (9H, s), 2.70 (2H, t, J=7.4 Hz), 3.36 (2H, br q), 4.54 (1H, br s), 6.54 (1H, s), 6.57 (1H, d, J=8.0 Hz), 6.60 (1H, d, J=7.2 Hz), 8.10 (1H, dd, J=7.2, 8.0 Hz).

PRODUCTION EXAMPLE 36b 3-(2-Butoxycarbonylaminoethyl)ethoxycarbonylaminobenzene

The title compound (0.320 g) was obtained as a yellow oil by using 3-(2-t-butoxycarbonylaminoethyl)aniline (5.521 g, Production Example 35b) in the same manner as in Production Example 29b. It was used in the next reaction without being further purified.
$^1$H-NMR(CDCl$_3$) δ (ppm): 1.31 (3H, t, J=7.2 Hz), 1.43 (9H, s), 2.77 (2H, t, J=7.4 Hz), 3.67 (2H, brq), 4.22 (2H, q, J=7.4 Hz), 4.55 (1H, br s), 6.52 (1H, br s), 6.89 (1H, m), 7.24 (1H, m).

PRODUCTION EXAMPLE 37b

3-Ethoxycarbonylaminophenethylamine hydrochloride 3-(2-t-Butoxycarbonylaminoethyl)-ethoxycarbonylaminobenzene (14.96 g, Production Example 36b) was dissolved in ethanol (15 ml), to which was then added hydrochloric acid (15 ml) under ice-cooling, followed by stirring at room temperature for 20 minutes. Hydrochloric acid (12 ml) and ethanol (15 ml) were added thereto, followed by stirring at room temperature for 20 minutes. Then, hydrochloric acid (20 ml) and ethanol (30 ml) were further added thereto, followed by stirring at room temperature for 30 minutes. After evaporating (subjecting azeotropic distillation together with toluene) the solvent, the title compound (11.99 g) was obtained as pale yellow crystals.
$^1$H-NMR(DMSO-d$_6$) δ (ppm): 1.22 (3H, t, J=7.2 Hz), 2.82 (2H, m), 2.95 (2H, m), 4.10 (2H, q, J=7.2 Hz), 6.86 (1H, d, J=7.6 Hz), 7.20 (1H, dd, J=7.6, 8.4 Hz), 7.31 (1H, d, J=8.4 Hz), 7.36 (1H, s), 8.05 (2H, br s), 9.61 (1H, s).

PRODUCTION EXAMPLE 38b

6-Aminoethyl-1,2,3,4-tetrahydroisoquinoline

The title compound (4.226 g, including impurities) was obtained as a yellow oil by using 3-ethoxycarbonylaminophenethylamine hydrochloride (4.7 g) obtained in Production Example 39b according to the method described in Chem. Pharm. Bull. 42 (8), 1676 (1994).
$^1$H-NMR(CDCl$_3$) δ (ppm): 1.29 (3H, t, J=7.2 Hz), 2.68 (1H, br s), 2.83 (3H, m), 3.73 (2H, m), 4.20 (2H, q, J=7.2 Hz), 6.77 (1H, s), 6.94 (1H, d, J=8.4 Hz), 7.07 (1H, d, J=8.4 Hz), 7.18 (1H, br s).

PRODUCTION EXAMPLE 39b

6-Ethoxycarbonylaminoisoquinoline p-Cymene (100 ml) and palladium carbon (0.9 g) were added to 6-aminoethyl-1,2,3,4-tetrahydroisoquinoline (10 g, Production Example 38b), followed by heating under stirring at 195° C. for one hour in a nitrogen atmosphere. The catalyst was filtered off, and the reaction mixture was washed with ethanol. Then, the filtrate was evaporated, and the resulting crystals were washed with diethyl ether and dried. The solvent was evaporated, to give the title compound (6.51 g, 66%) as pale yellow crystals.
$^1$H-NMR(CDCl$_3$) δ (ppm): 1.36 (3H, t, J=7.2 Hz), 3.74 (1H, m), 4.29 (2H, q, J=7.2 Hz), 6.70 (1H, d, J=2.0 Hz), 7.46 (1H, dd, J=2.0, 8.8 Hz), 7.58 (1H, d, J=6.0 Hz), 7.90 (1H, d, J=8.8 Hz), 8.04 (1H, br s), 8.46 (1H, d, J=6.0 Hz), 9.13 (1H, s).

PRODUCTION EXAMPLE 40b

6-Ethoxycarbonylaminoisoquinoline-N-oxide

The title compound (293 mg) was obtained as pale yellow crystals by using 6-ethoxycarbonylaminoisoquinoline (250 mg, Production Example 39b) in the same manner as in Production Example 22b.
$^1$H-NMR(DMSO-d$_6$) δ (ppm): 1.25 (3H, t, J=7.2 Hz), 4.26 (2H, q, J=7.2 Hz), 7.61 (1H, dd, J=2.0, 8.8 Hz), 7 79 (1H, d, J=8.8 Hz), 7.81 (1H, d, J=7.2 Hz), 8.04 (1H, dd, J=2.0, 7.2 Hz), 8.79 (1H, s), 8.46 (1H, d, J=6.0 Hz), 9.13 (1H, s).

PRODUCTION EXAMPLE 41b

1-Chloro-6-ethoxycarbonylaminoisoquinoline

The title compound (173 mg, 60%, 2 steps) was obtained as pale yellow crystals by using 6-ethoxycarbonylaminoisoquinoline-N-oxide (250 mg) in the same manner as in Production Example 22b.

$^1$H-NMR(CDCl$_3$) δ (ppm): 1.34 (3H, t, J=7.2 Hz), 4.29 (2H, q, J=7.2 Hz), 7.36 (1H, br s), 7.50 (1H, d, J=5.6 Hz), 7.52 (1H, dd, J=2.4, 9.2 Hz), 8.11 (1H, m), 8.19 (1H, d, J=5.6 Hz), 8.22 (1H, d, J=9.2 Hz).

PRODUCTION EXAMPLE 42b

1-Methoxy-6-methoxycarbonylaminoisoquinoline

1-Chloro-6-ethoxycarbonylaminoisoquinoline (2.27 g, Production Example 41b) was dissolved in dimethyl sulfoxide (45 ml), to which was then added a 28% sodium methoxide solution (8.7 ml), followed by heating under stirring at 110° C. for 1.5 hours. After cooling as it was to room temperature, an aqueous saturated ammonium chloride was added thereto and the mixture was extracted with ethyl acetate. The extract was washed with brine and dried over anhydrous magnesium sulfate. The solvent was evaporated, to give the title compound (1.75 g, 84%) as a brown oil.

$^1$H-NMR(CDCl$_3$) δ (ppm): 3.74 (3H, s), 4.03 (3H, s), 7.05 (1H, d, J=5.8 Hz), 7.41 (1H, dd, J=2.0, 9.2 Hz), 7.86 (1H, d, J=5.8 Hz), 7.90 (1H, br s), 8.06 (1H, d, J=9.2 Hz), 8.08 (1H, br s).

PRODUCTION EXAMPLE 43b

6-Amino-1-methoxyisoquinoline

The title compound (1.04 g, 99%) was obtained as pale brow crystals by using 1-methoxy-6-methoxycarbonylaminoisoquinoline (1.75 g, Production Example 42b) and also methanol as the solvent in the same manner as in Production Example 41b.

$^1$H-NMR(CDCl$_3$) δ (ppm): 4.07 (3H, s), 4.07 (2H, br s), 6.78 (1H, d, J=2.2 Hz), 6.88 (1H, dd, J=2.2, 8.8 Hz), 6.95 (1H, d, J=6.0 Hz), 7.84 (1H, d, J=6.0 Hz), 8.03 (1H, d, J=8.8 Hz).

PRODUCTION EXAMPLE 44b

N-Propinyl-(3-nitrophenethyl)amine

The title compound (3.070 g, 77%, including impurities) was obtained as a yellow oil by using 3-nitrophenethylamine (3.0 g, Production Example 27b) and propionyl chloride (2.5 ml) in the same manner as in Production Example 28b.

$^1$H-NMR(CDCl$_3$) δ (ppm): 1.14 (3H, t, J=7.6 Hz), 2.19 (2H, q, J=7.6 Hz), 2.96 (2H, t, J=6.8 Hz), 3.56 (2H, dt, J=6.4, 6.8 Hz), 7.49 (1H, dd, J=7.6, 8.0 Hz), 7.55 (1H, d, J=7.6 Hz), 8.07 (1H, s), 8.10 (1H, d, J=8.0 Hz).

PRODUCTION EXAMPLE 45b

N-Propinyl-(3-aminophenethyl)amine

N-Propinyl-(3-nitrophenethyl)amine (3.070 g, Production Example 44b) was used to run a reaction in the same manner as in Production Example 29b. The resulting residue was purified by silica gel column, to give the title compound (0.857 g, 32%) as a pale yellow oil.

$^1$H-NMR(CDCl$_3$) δ (ppm): 1.12 (3H, t, J=7.6 Hz), 2.19 (2H, q, J=7.6 Hz), 2.71 (2H, t, J=6.8 Hz), 3.49 (2H, dt, J=6.0, 6.8 Hz), 5.56 (1H, br s), 6.52 (1H, s), 6.56 (1H, d, J=7.6 Hz), 6.56 (1H, d, J=7.6 Hz), 7.09 (1H, dd, J=7.6, 7.6 Hz).

PRODUCTION EXAMPLE 46b

N-Propinyl-(3-ethoxycarbonylaminophenethyl)amine

N-Propinyl-(3-aminophenethyl)amine (0.857 g, Production Example 44b) was used to run a reaction in the same manner as in Production Example 30b. The resulting residue was purified by silica gel column, to give the title compound (0.747 g, 61%) as a pale yellow oil.

$^1$H-NMR(CDCl$_3$) δ (ppm): 1.12 (3H, t, J=7.6 Hz), 1.30 (3H, t, J=7.0 Hz), 2.16 (2H, q, J=7.6 Hz), 2.78 (2H, t, J=6.8 Hz), 3.50 (2H, dt, J=6.0, 6.8 Hz), 4.21 (2H, q, J=7.0 Hz), 6.67 (1H, br s), 6.87 (1H, d, J=6.8 Hz), 7.00 (1H, br s), 7.22 (1H, dd, J=6.8, 8.4 Hz), 7.26 (1H, d, J=8.4 Hz), 7.28 (1H, s)

PRODUCTION EXAMPLE 47b

6-Ethoxycarbonylamino-1-ethylisoquinoline

6-Ethoxycarbonylamino-1-ethyl-3,4-dihydroisoquinoline was obtained as brown crystals by using N-propynyl-(3-ethoxycarbonylaminophenethyl)amine (0.747 g, Production Example 46b) in the same manner as in Production Examples 31b-32b, and then the title compound (0.516 g, 75%, 2 steps) was obtained as a yellow oil.

The data of the intermediate and the title compound are as follows.

6-Ethoxycarbonylamino-1-ethyl-3,4-dihydroisoquinoline $^1$H-NMR(CDCl$_3$) δ (ppm): 1.21 (3H, t, J=7.6 Hz), 1.30 (3H, t, J=7.0 Hz), 2.66 (2H, t, J=7.4 Hz), 2.74 (2H, q, J=7.6 Hz), 3.64 (2H, t, J=7.4 Hz), 4.23 (2H, q, J=7.0 Hz), 7.32 (1H, d, J=8.4 Hz), 7.37 (1H, s), 7.43 (1H, d, J=8.4 Hz), 7.79 (1H, s).

6-Ethoxycarbonylamino-1-ethylisoquinoline $^1$H-NMR(CDCl$_3$) δ (ppm): 1.32 (3H, t, J=7.0 Hz), 1.41 (3H, t, J=7.6 Hz), 3.27 (2H, q, J=7.6 Hz), 4.27 (2H, q, J=7.0 Hz), 7.40 (1H, d, J=6.0 Hz), 7.52 (1H, dd, J=2.0, 8.8 Hz), 7.89 (1H, s), 8.02 (1H, d, J=2.0 Hz), 8.25 (1H, d, J=8.8 Hz), 8.34 (1H, J=6.0 Hz).

PRODUCTION EXAMPLE 48b

6-Amino-1-ethylisoquinoline

The title compound (0.320 g, 88%) was obtained as pale yellow crystals by using 6-ethoxycarbonylamino-1-ethylisoquinoline (0.516 g, Production Example 47b) in the same manner as in Production Example 33b.

$^1$H-NMR(CDCl$_3$) δ (ppm): 1.31 (3H, t, J=7.2 Hz), 3.21 (2H, q, J=7.2 Hz), 4.20 (2H, br s), 6.82 (1H, d, J=2.4 Hz), 6.95 (1H, dd, J=2.4, 8.8 Hz), 7.21 (1H, d, J=6.0 Hz), 7.94 (1H, d, J=8.8 Hz), 8.24 (1H, d, J=6.0 Hz)

PRODUCTION EXAMPLE 49b

1-Methoxy-4-(3-nitrophenyl)propane-1-ene

Methoxymethylphosphonium chloride (31.1 g) was suspended in tetrahydrofuran (200 ml), to which was then added potassium t-butoxide (10.2 g) under ice-cooling. When the reaction solution was changed to red in color, a solution obtained by dissolving 3-nitroacetophenone (10 g) in tetrahydrofuran (100 ml) was added thereto little by little by using a pipette. After stirring at room temperature for 2.5 hours, an aqueous saturated ammonium chloride was added thereto under ice-cooling. The mixture was extracted with ethyl acetate, and the extract was washed with brine and dried over magnesium sulfate anhydride. The solvent was evaporated, and the resulting residue was purified by silica gel column, to give the title compound (8.010 g) as a yellow oil.

PRODUCTION EXAMPLE 50b 2-(3-Nitrophenyl)propanal

2 N hydrochloric acid (150 ml) was added to 1-methoxy-4-(3-nitrophenyl)propane-1-ene (8.010 g), followed by heating under stirring at 80° C. for 4 hours. Then, hydrochloric acid (5 ml) was added thereto, followed by heating under reflux for 2.5 hours. After cooling, the mixture was neutralized by an aqueous sodium hydroxide solution and extracted with ethyl acetate. The extract was washed with brine and dried over anhydrous magnesium sulfate. The solvent was evaporated, to give the title compound (7.531 g) as a yellow oil.

PRODUCTION EXAMPLE 51b 2-(3-Nitrophenyl)propane-1-ol 2-(3-Nitrophenyl)propanal (7.531 g) was dissolved in ethanol (100 ml), to which was then added sodium borohydride (1.9 g) under ice-cooling, followed by stirring at room temperature for one hour. Brine was added thereto, followed by extracting with ethyl acetate. The extract was washed with brine and dried over anhydrous magnesium sulfate. A residue obtained by evaporating the solvent was purified by silica gel column, to give the title compound (6.275 g, 57.19% in 3 steps) as a brown oil.
$^1$H-NMR(CDCl$_3$) δ (ppm): 1.34 (3H, d, J=6.8 Hz), 1.51 (1H, br s), 3.09 (1H, tq, J=6.8, 6.8 Hz), 3.78 (2H, d, J=6.8 Hz), 7.50 (1H, dd, J=7.6, 8.4 Hz), 7.60 (1H, ddd, J=1.2,1.6,7.6 Hz), 8.10 (1H, ddd, J=1.2,2.4,8.4 Hz), 8.13 (1H, dd, J=1.6, 2.4 Hz).

PRODUCTION EXAMPLE 52b 2-(3-Nitrophenyl)propylamine

The title compound was obtained as a yellow oil by using 2-(3-nitrophenyl)propane-1-ol (1.908 g, Production Example 51b) in the same manner as in Production Examples 26b-27b.

PRODUCTION EXAMPLE 53b 1-t-Butoxycarbonylamino-2-(3-nitrophenyl)propane

The reaction was conducted using 2-(3-nitrophenyl)propylamine obtained in Production Example 52b in the same manner as in Production Example 35b. The resulting residue was purified by silica gel column, to give the title compound (2.626 g) as a yellow oil.
$^1$H-NMR(CDCl$_3$) δ (ppm): 1.31 (3H, d, J=6.8 Hz), 1.40 (9H, s), 3.10 (1H, m), 3.26 (1H, m), 3.38 (1H, m), 7.49 (1H, dd, J=7.6, 8.4 Hz), 7.56 (1H, d, J=7.6 Hz), 8.08 (1H, s), 8.10 (1H, d, J=8.4 Hz).

PRODUCTION EXAMPLE 54b 2-(3-Aminophenyl)-1-t-butoxycarbonylaminopropane

The title compound was obtained as a yellow oil by using the obtained 1-t-butoxycarbonylamino-2-(3-nitrophenyl) propane (2.626 g) in the same manner as in Production Examples 29b.

PRODUCTION EXAMPLE 55b 1-t-Butoxycarbonylamino-2-(3-ethoxycarbonylaminophenyl)propane The reaction was conducted using the obtained 2-(3-aminophenyl)-1-t-butoxycarbonylaminopropane in the same manner as in Production Example 30b. The resulting residue was purified by silica gel column, to give the title compound (2.960 g, 77.56% in 3 steps) as a brown oil.
$^1$H-NMR(CDCl$_3$) δ (ppm): 1.25 (3H, d, J=7.6 Hz), 1.31 (3H, t, J=7.2 Hz), 1.41(9H, s), 2.90 (1H, m), 3.18 (1H, ddd, J=4.2,7.6, 9.2 Hz), 3.39 (1H, m), 4.42 (2H, q, J=7.6 Hz), 4.45 (1H, br s), δ 87 (1H, br s), 6.94 (1H, m), 7.22 (3H, m).

PRODUCTION EXAMPLE 56b

6-Ethoxycarbonylamino-4-methyl-1,2,3,4-tetrahydroisoquinoline

The title compound (2.967 g, crude) was obtained as a yellow solid by using 1-t-butoxycarbonylamino-2-(3-ethoxycarbonylaminophenyl)propane (2.960 g, Production Example 55b) in the same method as in Production Examples 38b-39b.

PRODUCTION EXAMPLE 57b

6-Ethoxycarbonylamino-4-methylisoquinoline

The title compound (2.061 g, crude) was obtained as pale yellow crystals by using the obtained 6-ethoxycarbonylamino-4-methyl-1,2,3,4-tetrahydroisoquinoline (2.967 g, crude) in the same manner as in Production Example 40b.
$^1$H-NMR(CDCl$_3$) δ (ppm): 1.36 (3H, t, J=7.2 Hz), 2.59 (3H, s), 4.30 (2H, q, J=7.2 Hz), 7.12 (1H, d, J=2.0 Hz), 7.49 (1H, dd, J=2.0, 8.8 Hz), 7.91 (1H, d, J=8.8 Hz), 8.12 (1H, s), 8.32 (1H, s), 9.00 (1H, s).

PRODUCTION EXAMPLE 58b

6-Amino-4-methylisoquinoline

The reaction was conducted using the obtained 6-ethoxycarbonylamino-4-methylisoquinoline (2.061 g, crude) in the same manner as in Production Example 30b. The resulting crystals were washed with diethyl ether and dried, to give the title compound (0.403 g, 27.75% in 4 steps) as pale yellow crystals.
$^1$H-NMR(CDCl$_3$) δ (ppm): 2.48 (3H, s), 4.18 (2H, br s), 6.95 (1H, d, J=2.0 Hz), 7.00 (1H, dd, J=2.0, 8.8 Hz), 7.76 (1H, d, J=8.8 Hz), 8.19 (1H, s), 8.86 (1H, s).

PRODUCTION EXAMPLE 59b 2-(3-Nitrophenyl)butane-1-ol

The title compound (5.456 g, 50.08% in 3 steps) was obtained as a yellow oil by using 3-nitropropiophenone (10 g) in the same method as in Production Examples 52b-55b.

¹H-NMR(CDCl₃) δ (ppm): 0.86 (3H, t, J=7.4 Hz), 1.63 (1H, m), 1.85 (1H, m), 3.24 (1H, m), 3.83 (2H, m), 7.50 (1H, dd, J=7.2, 8.0 Hz), 7.57 (1H, d, J=8.0 Hz), 8.10 (1H, s), 8.13 (1H, d, J=7.2 Hz).

PRODUCTION EXAMPLE 60b 2-(3-Nitrophenyl)butylamine

The title compound (5.247 g) was obtained as a yellow oil by using 2-(3-nitrophenyl)butane-1-ol (5.456 g, Production Example 59b) in the same manner as in Production Examples 26b-27b.

PRODUCTION EXAMPLE 61b 1-t-Butoxycarbonylamino-2-(3-nitrophenyl)butane

Successively, the reaction was conducted using the obtained 2-(3-nitrophenyl)butylamine (5.247 g) in the same manner as in Production Example 27b. The resulting residue was purified by silica gel column, to give the title compound (7.679 g) as a pale yellow oil.
¹H-NMR(CDCl₃) δ (ppm): 0.83 (3H, t, J=7.4 Hz), 1.39 (9H, s), 1.63 (1H, m), 1.79 (1H, m), 2.84 (1H, m), 3.21 (1H, m), 3.52 (1H, m), 4.42 (1H, br s), 7.49 (1H, d, J=7.6 Hz), 7.52 (1H, dd, J=6.8, 7.6 Hz), 8.04 (1H, s), 8.10 (1H, d, J=6.8 Hz)

PRODUCTION EXAMPLE 62b 2-(3-Aminophenyl)-1-t-butoxycarbonylaminobutane

The title compound (6.311 g, 85.40% in 4 steps) was obtained as a yellow oil by using 1-t-butoxycarbonylamino-2-(3-nitrophenyl)butane (7.679 g) in the same method as in Production Example 29b.

PRODUCTION EXAMPLE 63b 1-t-Butoxycarbonylamino-2-(3-ethoxycarbonylaminophenyl)butane The title compound (8.230 g, crude) was obtained as an orange solid by using the obtained compound in the same method as in Production Example 30b.
¹H-NMR(CDCl₃) δ (ppm): 0.81 (3H, t, J=7.4 Hz), 1.31 (3H, t, J=7.2 Hz), 1.40 (9H, s), 1.55 (1H, m), 1.68 (1H, m), 2.63 (1H, m), 3.14 (1H, ddd, J=4.8, 8.8, 13.6 Hz), 3.52 (1H, m), 4.22 (2H, q, J=7.2 Hz), 4.38 (1H, br s), δ 63 (1H, br s), 6.87 (1H, m), 7.23 (3H, m).

PRODUCTION EXAMPLE 64b

6-Ethoxycarbonylamino-4-ethyl-1,2,3,4-tetrahydroisoquinoline

The title compound was obtained as a brown oil by using 1-t-butoxycarbonylamino-2-(3-ethoxycarbonylaminophenyl)butan e (8.230 g, crude, Production Example 63b) in the same method as in Production Examples 38b-39b.

PRODUCTION EXAMPLE 65b

6-Ethoxycarbonylamino-4-ethylisoquinoline

A reaction was run using the obtained 6-ethoxycarbonylamino-4-ethyl-1,2,3,4-tetrahydroisoquinoline (3.0 g) in the same manner as in Production Example 40b. The resulting crude crystals were washed with ethanol/diethyl ether and dried, to give the title compound as orange crystals.
¹H-NMR (DMSO-d₆) δ (ppm): 1.27 (3H, t, J=7.2 Hz), 1.28 (3H, t, J=7.2 Hz), 2.91 (2H, q, J=7.2 Hz), 4.18 (2H, q, J=7.2 Hz), 7.64 (1H, d, J=8.8 Hz), 8.00 (1H, d, J=8.8 Hz), 8.25 (1H, s), 8.27 (1H, s), 8.98 (1H, s), 10.12 (1H, s)

PRODUCTION EXAMPLE 66b

6-Amino-4-ethylisoquinoline

The reaction was conducted using 6-ethoxycarbonylamino-4-ethylisoquinoline in the same manner as in Production Example 30b. The resulting residue was purified by NH-silica gel column, and the resulting crude crystals were washed with diethyl ether and dried, to give the title compound (0.637 g) as orange crystals.
¹H-NMR(CDCl₃) δ (ppm): 1.35 (3H, t, J=7.6 Hz), 2.92 (2H, q, J=7.6 Hz), 4.17 (2H, br s), 6.99 (1H, d, J=8.4 Hz), 7.00 (1H, s), 7.77 (1H, d, J=8.4 Hz), 8.21 (1H, s), 8.86 (1H, s).

PRODUCTION EXAMPLE 67b

Diethyl methyl-(3-nitrobenzyl)malonate

Sodium (0.7 g) was dissolved in ethanol (45 ml), to which were then added diethylmethyl malonate (5.26 ml) and 3-nitrobenzyl chloride (5 g), followed by heating under reflux for 2 hours. The mixture was ice-cooled and an aqueous ammonium chloride was added thereto, followed by extracting with ethyl acetate. The extract was washed with brine and dried over anhydrous magnesium sulfate. The solvent was evaporated, to give the title compound (9.724 g) as a pale yellow oil.
¹H-NMR(CDCl₃) δ (ppm): 1.27 (6H, t, J=7.2 Hz), 1.37 (3H, s), 3.32 (2H, s), 4.21 (4H, q, J=7.2 Hz), 7.44 (1H, d, J=7.6 Hz), 7.48 (1H, dd, J=7.6, 7.6 Hz), 8.03 (1H, s), 8.11 (1H, d, J=7.6 Hz).

PRODUCTION EXAMPLE 68b Ethyl 1-methyl-2-(3-nitrophenyl)propionate

The obtained diethyl methyl-(3-nitrobenzyl)malonate (9.724 g) was dissolved in dimethyl sulfoxide (30 ml), to which were then added water (0.54 ml) and lithiumchloride (2.54 g), followed by stirring under heating at 190° C. for 3.5 hours. After cooling as it was, water was added thereto, followed by extracting with ethyl acetate. The extract was washed with brine and dried over anhydrous magnesium sulfate. The solvent was evaporated, to give the title compound (5.071 g, 73.35% in 2 steps) as a brown oil.
¹H-NMR(CDCl₃) δ (ppm): 1.20 (3H, t, J=7.2 Hz), 1.21 (3H, d, J=7.2 Hz), 2.79 (2H, m), 3.10 (1H, m), 4.10 (2H, q, J=7.2 Hz), 7.45 (1H, dd, J=7.6, 8.0 Hz), 7.52 (1H, d, J=7.6 Hz), 8.06 (1H, s), 8.08 (1H, d, J=8.0 Hz)

PRODUCTION EXAMPLE 69b

1-Methyl-2-(3-nitrophenyl)propionic acid

Ethyl 1-methyl-2-(3-nitrophenyl)propionate (5.071 g, Production Example 68b) was dissolved in ethanol (50 ml), to which was then added an aqueous 5 N sodium hydroxide solution (43 ml), followed by heating under reflux for 2.5 hours. After cooling as it was, diethyl ether and water were added thereto, and the aqueous layer was separated. The organic layer was extracted with aqueous saturated sodium bicarbonate. The aqueous layers were combined, acidified by adding dilute hydrochloric acid, and then extracted with diethyl ether. The extract was washed with brine and dried over anhydrous magnesium sulfate. The solvent was evaporated, and the resulting residue was purified by silica gel column, to give the title compound (2.918 g, 65.27%) as a red oil.

$^1$H-NMR(CDCl$_3$) δ (ppm): 1.24 (3H, d, J=6.0 Hz), 2.83 (2H, s), 3.16 (1H, m), 7.47 (1H, dd, J=7.2, 8.0 Hz), 7.54 (1H, d, J=7.2 Hz), 8.08 (1H, s), 8.10 (1H, d, J=8.0 Hz). PRODUCTION EXAMPLE 70b N-Boc-1-methyl-2-(3-nitrophenyl)ethylamine 1-Methyl-2-(3-nitrophenyl)propionic acid (2.918 g, Production Example 69b) was dissolved in t-butanol (36 ml), to which were then added triethylamine (4.09 ml) and diphenylphosphorylazide, followed by heating under reflux for 2.5 hours. After cooling as it was, the solvent was evaporated. An aqueous saturated sodium bicarbonate was added thereto, followed by extracting with ethylacetate. The extract was washed with brine and dried over anhydrous magnesium sulfate. The solvent was evaporated, and the resulting residue was purified by silica gel column, to give the title compound (2.117 g, 54.14%) as yellow crystals.

$^1$H-NMR(CDCl$_3$) δ (ppm): 1.13 (3H, d, J=6.8 Hz), 2.82 (1H, m), 2.92 (1H, m), 3.94 (1H, br s), 7.47 (1H, dd, J=7.2, 8.0 Hz), 7.54 (1H, d, J=7.2 Hz), 8.05 (1H, s), 8.09 (1H, d, J=8.0 Hz).

PRODUCTION EXAMPLE 71b

N-Boc-2-(3-aminophenyl)-1-methylethylamine

A reaction was conducted using N-Boc-1-methyl-2-(3-nitrophenyl)ethylamine (2.117 g, Production Example 70b) in the same manner as in Production Example 29b. After extracting, the resulting residue was purified by silica gel column, to give the title compound (0.976 g, 51.63%) as a yellow oil.

PRODUCTION EXAMPLE 72b

N-Boc-1-methyl-2-(3-ethoxycarbonylaminophenyl) ethylamine

The title compound (1.173 g, crude) was obtained as a yellow oil by using N-Boc-2-(3-aminophenyl)-1-methylethylamine (0.976 g) in the same method as in Production Example 30b. It was used in the next reaction without carrying out a further purification.

$^1$H-NMR(CDCl$_3$) δ (ppm): 1.09 (3H, d, J=6.4 Hz), 1.31 (3H, t, J=7.2 Hz), 1.43 (9H, s), 2.62 (1H, dd, J=6.8 Hz, 13.2 Hz), 2.82 (1H, m), 3.88 (1H, m), 4.22 (2H, q, J=7.2 Hz), 4.38 (1H, m), 6.56 (1H, m), 6.89 (1H, d, J=6.8 Hz), 7.18 (1H, s), 7.22 (1H, dd, J=6.8, 8.0 Hz), 7.23 (1H, d, J=8.0 Hz)

PRODUCTION EXAMPLE 73b 2-(3-Ethoxycarbonylaminophenyl)-1-methylethylamine hydrochloride N-Boc-1-methyl-2-(3-ethoxycarbonylaminophenyl)ethylamine (1.173 g, crude) was dissolved in ethanol (5.0 ml), to which was then added hydrochloric acid (5 ml), followed by stirring at room temperature for 1.5 hours. Then, hydrochloric acid (2.5 ml) was further added thereto, followed by stirring at room temperature for 2 hours. The solvent was evaporated, to give the title compound (1.148 g, crude) as a yellow oil. It was used in the next reaction without carrying out a further purification.

$^1$H-NMR(DMSO-d$_6$) δ (ppm): 1.03 (3H, d, J=6.8 Hz), 1.22 (3H, t, J=7.2 Hz), 2.55 (1H, m), 2.95 (1H, m), 3.32 (1H, m), 4.10 (2H, q, J=7.2 Hz), 6.84 (1H, d, J=7.2 Hz), 7.21 (1H, dd, J=7.2, 7.2 Hz), 7.29 (1H, d, J=7.2 Hz), 7.35 (1H, s), 8.00 (1H, br s), 9.60 (1H, s).

PRODUCTION EXAMPLE 74b

6-Ethoxycarbonylamino-3-methyl-1,2,3,4-tetrahydroisoquinoline

The reaction was conducted using 2-(3-ethoxycarbonylaminophenyl)-1-methylethylamine hydrochloride (1.148 g, Production Example 73b) according to the method of Chem. Pharm. Bull. 42 (8), 1676 (1994). The product was purified by NH-silica gel column, to give the title compound (0.441 g).

$^1$H-NMR(CDCl$_3$) δ (ppm): 1.24 (3H, d, J=6.4 Hz), 1.30 (3H, t, J=7.2 Hz), 2.48 (1H, dd, J=10.0 Hz, 16.4 Hz), 2.75 (1H, dd, J=3.6 Hz, 16.4 Hz), 3.01 (1H, m), 4.03 (2H, brq), 4.21 (2H, q, J=7.2 Hz), 6.66 (1H, s), 6.95 (1H, d, J=8.4 Hz), 7.09 (1H, d, J=8.4 Hz), 7.14 (1H, s).

PRODUCTION EXAMPLE 75b

6-Ethoxycarbonylamino-3-methylisoquinoline

The title compound (0.356 g) was obtained using the obtained 6-ethoxycarbonylamino-3-methyl-1,2,3,4-tetrahydroisoquinoline (0.441 g) in the same method as in Production Example 39b.

$^1$H-NMR(CDCl$_3$) δ (ppm): 1.34 (3H, t, J=7.2 Hz), 2.67 (3H, s), 4.28 (2H, q, J=7.2 Hz), 7.08 (1H, br s), 7.39 (1H, dd, J=2.0, 8.8 Hz), 7.40 (1H, s), 7.85 (1H, d, J=8.8 Hz), 7.94 (1H, br s), 9.05 (1H, s).

PRODUCTION EXAMPLE 76b

6-Amino-3-methylisoquinoline

Crude crystals (0.182 g) obtained using the obtained 6-ethoxycarbonylamino-3-methylisoquinoline (0.356 g) in the same method as in Production Example 33b were washed with diethyl ether and dried, to give the title compound (93 g) as pale yellow crystals.

$^1$H-NMR(CDCl$_3$) δ (ppm): 2.63 (3H, s), 4.14 (2H, br s), 6.77 (1H, d, J=2.0 Hz), 6.93 (1H, dd, J=2.0, 8.8 Hz), 7.18 (1H, s), 7.72 (1H, d, J=8.8 Hz), 8.9

SYNTHETIC EXAMPLE 1b

N-(8-Bromoquinoline-3-yl)-3-pyridinesulfonamide

3-Amino-8-bromoquinoline (300 mg, Production Example 5b) was dissolved in pyridine (5 ml), to which was then added 3-pyridinesulfonyl chloride (254 mg), followed by stirring at room temperature for 30 minutes. After the reaction was completed, the reaction solution was poured into brine and extracted with ethyl acetate. The organic layer was dried over magnesium sulfate and then concentrated. The resulting crude crystals were washed with ethyl acetate and IPA, to give the title compound (270 mg).

$^1$H-NMR(DMSO-d$_6$) δ (ppm): 7.47 (1H, t, J=8.0 Hz), 7.52-7.60 (1H, m), 7.99-8.03 (2H, m), 8.10 (1H, d, J=2.4 Hz), 8.18-8.22 (1H, m), 8.71 (1H, d, J=2.4 Hz), 8.78 (1H, dd, J=1.6 Hz, 4.8 Hz), 8.98 (1H, d, J=2.4 Hz), 11.23 (1H, br s)

SYNTHETIC EXAMPLE 2b

N-(5-Bromoquinoline-2-yl)-5-methyl-3-pyridine-sulfonamide

The title compound was obtained from 2-amino-5-bromoquinoline (Production Example 1b) and 5-methyl-3-pyridinesulfonyl chloride in the same manner as in Synthetic Example 1b.
$^1$H-NMR(DMSO-$d_6$) δ (ppm): 2.37 (3H, s), 7.58-7.72 (4H, m), 8.11 (1H, br s), 8.37 (1H, d, J=9.6 Hz), 8.59 (1H, d, J=1.2 Hz), 8.86 (1H, br s).

SYNTHETIC EXAMPLE 3b

6-Amino-N-(8-bromoquinoline-3-yl)-3-pyridine-sulfonamide

The title compound was obtained from 3-amino-8-bromoquinoline (Production Example 5b) and 6-amino-3-pyridinesulfonyl chloride in the same manner as in Synthetic Example 1b.
$^1$H-NMR(DMSO-$d_6$) δ (ppm): 6.40 (1H, d, J=8.8 Hz), 6.93 (2H, br s), 7.44 (1H, t, J=8.0 Hz), 7.65 (1H, dd, J=2.4 Hz, 8.8 Hz), 7.96-7.99 (2H, m), 8.01 (1H, d, J=2.4 Hz), 8.31 (1H, d, J=2.4 Hz), 8.70 (1H, d, J=2.4 Hz), 10.73 (1H, br s).

SYNTHETIC EXAMPLE 4b

N-(8-Bromoquinoline-3-yl)-4-cyanobenzenesulfonamide

The title compound was obtained from 3-amino-8-bromoquinoline (Production Example 5b) and 4-cyanobenzenesulfonyl chloride in the same manner as in Synthetic Example 1b.
$^1$H-NMR(DMSO-$d_6$) δ (ppm): 7.46 (1H, t, J=8.0 Hz), 7.96-8.07(7H, m), 8.70 (1H, d, J=2.4 Hz), 11.27 (1H, br s).

SYNTHETIC EXAMPLE 5b

6-Chloro-N-(8-bromoquinoline-3-yl)-3-pyridine-sulfonamide

The title compound was obtained from 3-amino-8-bromoquinoline (Production Example 5b) and 6-chloro-3-pyridinesulfonyl chloride in the same manner as in Synthetic Example 1b.
$^1$H-NMR(DMSO-$d_6$) δ (ppm): 7.47 (1H,t,J=8.0 Hz), 7.71 (1H, d, J=8.4 Hz), 7.99-8.03 (2H, m), 8.10 (1H, d, J=2.4 Hz), 8.20 (1H, dd, J=8.4 Hz), 8.71 (1H, d, J=2.4 Hz), 8.83 (1H, d, J=2.4 Hz), 10.73 (1H, br s).

SYNTHETIC EXAMPLE 6b

N-(8-Bromoquinoline-3-yl)-4-(N-ethylsulfamoyl)benzenesulfonamide

The title compound was obtained from 3-amino-8-bromoquinoline (Production Example 5b) and 4-(N-ethylsulfamoyl)benzenesulfonyl chloride in the same manner as in Synthetic Example 1b.
$^1$H-NMR(DMSO-$d_6$) δ (ppm): 0.82 (3H, t, J=7.2 Hz), 2.69-2.76 (2H, m), 7.45 (1H, t, J=8.4 Hz), 7.75 (1H, t, J=5.6 Hz), 7.90-8.04(7H, m), 8.70 (1H, d, J=2.8 Hz), 11.18 (1H, br s).

SYNTHETIC EXAMPLE 7b

N-(8-Bromoquinoline-3-yl)-5-cyano-2-pyridine-sulfonamide

The title compound was obtained from 3-amino-8-bromoquinoline (Production Example 5b) and 5-cyano-3-pyridinesulfonyl chloride in the same manner as in Synthetic Example 1b.
$^1$H-NMR(DMSO-$d_6$) δ (ppm): 7.46 (1H, t, J=8.0 Hz), 7.95 (1H, d, J=8.0 Hz), 8.01 (1H, d, J=8.0 Hz), 8.11 (1H, d, J=2.4 Hz), 8.21 (1H, d, J=8.4 Hz), 8.57 (1H, dd, J=2.0 Hz, 8.4 Hz), 8.79 (1H, d, J=2.4 Hz), 9.14 (1H, d, J=2.0 Hz), 11.49 (1H, br s).

SYNTHETIC EXAMPLE 8b

N-(8-Cyanoquinoline-3-yl)-3-pyridinesulfonamide

The title compound was obtained from 3-amino-8-cyanoquinoline (Production Example 7b) and 3-pyridinesulfonyl chloride in the same manner as in Synthetic Example 1b.
$^1$H-NMR(DMSO-$d_6$) δ (ppm): 7.59 (1H, dd, J=4.8 Hz, 8.0 Hz), 7.70 (1H, t, J=8.0 Hz), 8.21-8.25 (3H, m), 8.33 (1H, d, J=8.0 Hz), 8.77-8.79 (2H, m), 9.01 (1H, d, J=2.8 Hz), 11.34 (1H, br s).

SYNTHETIC EXAMPLE 9b

N-(8-Cyanoquinoline-3-yl)-4-cyanobenzenesulfonamide

The title compound was obtained from 3-amino-8-cyanoquinoline (Production Example 7b) and 4-cyanobenzenesulfonyl chloride in the same manner as in Synthetic Example 1b.
$^1$H-NMR(DMSO-$d_6$) δ (ppm): 7.71 (1H, t, J=8.0 Hz), 7.96-8.07 (4H, m), 8.18 (1H, d, J=2.8 Hz), 8.24 (1H, d, J=8.0 Hz), 8.31 (1H, d, J=8.0 Hz), 8.78 (1H, d, J=2.8 Hz), 11.37 (1H, br s).

SYNTHETIC EXAMPLE 10b

N-(5-Bromoquinoline-2-yl)-3-pyridinesulfonamide

The title compound was obtained from 2-amino-5-bromoquinoline (Production Example 1b) and 3-pyridinesulfonyl chloride in the same manner as in Synthetic Example 1b.
$^1$H-NMR(DMSO-$d_6$) δ (ppm): 7.57-7.61 (3H, m), 7.70-7.72 (2H, m), 8.28 (1H, br), 8.38 (1H, d, J=9.6 Hz), 8.75 (1H, dd, J=1.2 Hz, 4.8 Hz), 9.07 (1H, br).

SYNTHETIC EXAMPLE 11b

N-(8-Bromoquinoline-3-yl)-5-indanesulfonamide

The title compound was obtained from 3-amino-8-bromoquinoline (Production Example 5b) and 5-indanesulfonyl chloride in the same manner as in Synthetic Example 1b.
$^1$H-NMR(DMSO-$d_6$) δ (ppm): 1.92-2.01 (2H, m), 2.81-2.86 (4H, m), 7.34 (1H, d, J=8.0 Hz), 7.44 (1H, t, J=8.0 Hz), 7.60 (1H, dd, J=1.6 Hz, 8.0 Hz), 7.70 (1H, d, J=1.6 Hz), 7.95 (1H, d, J=8.0 Hz), 7.97 (1H, d, J=8.0 Hz), 8.03 (1H, d, J=2.4 Hz), 8.71 (1H, d, J=2.4 Hz), 10.93 (1H, br s).

SYNTHETIC EXAMPLE 12b

N-(8-Iodoquinoline-3-yl)-N*-acetyl-5-indoline-sulfonamide

The title compound was obtained from 3-amino-8-iodoquinoline (Production Example 6b) and N-acetyl-6-indolinesulfonyl chloride in the same manner as in Synthetic Example 1b.

$^1$H-NMR(DMSO-$d_6$) δ (ppm): 2.11 (3H, s), 3.11 (2H, t, J=8.4 Hz), 4.06 (2H, t, J=8.4 Hz), 7.28 (1H,t,J=8.0 Hz), 7.65-7.68 (2H, m), 7.93-7.96 (2H, m), 8.05 (1H, d, J=9.2 Hz), 8.22 (1H, dd, J=1.2 Hz, 7.6 Hz), 8.64 (1H, d, J=2.4 Hz), 10.87 (1H, br s).

SYNTHETIC EXAMPLE 13b

N-(8-Bromoquinoline-3-yl)-3-quinolinesulfonamide

The title compound was obtained from 3-amino-8-bromoquinoline (Production Example 5b) and 3-quinolinesulfonyl chloride in the same manner as in Synthetic Example 1b.

$^1$H-NMR(DMSO-$d_6$) δ (ppm): 7.38 (1H, t, J=8.0 Hz), 7.70-7.74 (1H, m), 7.90-8.00 (3H, m), 8.07 (1H, d, J=8.0 Hz), 8.13 (1H, d, J=2.4 Hz), 8.19 (1H, dd, J=0.8 Hz, 8.4 Hz), 8.75 (1H, d, J=2.4 Hz), 9.00-9.01 (1H, m), 9.19 (1H, d, J=2.4 Hz), 11.31 (1H, br s).

SYNTHETIC EXAMPLE 14b

N-(8-Bromoquinoline-3-yl)-N*-acetyl-1,2,3,4-tetrahydroquinoline-6-sulfonamide

The title compound was obtained from 3-amino-8-bromoquinoline (Production Example 5b) and N-acetyl-1, 2,3,4-tetrahydroquinoline-6-sulfonyl chloride in the same manner as in Synthetic Example 1b.

$^1$H-NMR(CDCl$_3$) δ (ppm): 1.86-2.01 (2H, m), 2.77 (2H,t, J=6.4 Hz), 3.65-3.76 (2H, m),

SYNTHETIC EXAMPLE 15b

N-(8-Iodoquinoline-3-yl)-4-isoquinolinesulfonamide

The title compound was obtained from 3-amino-8-iodoquinoline (Production Example 6b) and 4-isoquinolinesulfonyl chloride in the same manner as in Synthetic Example 1b.

$^1$H-NMR(DMSO-$d_6$) δ (ppm): 7.26 (1H, t, J=8.0 Hz), 7.82-7.86 (1H, m), 7.93-7.95 (1H, m), 7.98 (1H, d, J=2.4 Hz), 8.02-8.06 (1H, m), 8.19 (1H, dd, J=1.2 Hz, 7.6 Hz), 8.27 (1H, d, J=8.4 Hz), 8.59 (1H, d, J=2.4 Hz), 8.67 (1H, d, J=8.4 Hz), 9.12 (1H, s), 9.52 (1H, s), 11.57 (1H, br s).

SYNTHETIC EXAMPLE 16b

4-Cyano-N-(8-iodoquinoline-3-yl)-benzenesulfonamide

The title compound was obtained from 3-amino-8-iodoquinoline (Production Example 6b) and 4-cyanobenzenesulfonyl chloride in the same manner as in Synthetic Example 1b.

$^1$H-NMR(DMSO-$d_6$) δ (ppm): 7.31 (1H, t, J=8.0 Hz), 7.96-8.04 (6H, m), 8.26 (1H, dd, J=1.2 Hz, 7.2 Hz), 8.65 (1H, d, J=2.8 Hz), 11.24 (1H, br s).

SYNTHETIC EXAMPLE 17b

N-(8-Iodoquinoline-3-yl)-3-pyridinesulfonamide

The title compound was obtained from 3-amino-8-iodoquinoline (Production Example 6b) and 3-pyridinesulfonyl chloride in the same manner as in Synthetic Example 1b.

$^1$H-NMR(DMSO-$d_6$) δ (ppm): 7.31 (1H, t, J=8.0 Hz), 7.57-7.60 (1H, m), 7.99 (1H, d, J=1.2 Hz, 8.4 Hz), 8.04 (1H, d, J=2.8 Hz), 8.18-8.21 (1H, m), 8.26 (1H, dd, 1.2 Hz, 7.2 Hz), 8.66 (1H, d, J=2.8 Hz), 8.77 (1H, dd, J=1.6 Hz, 4.8 Hz), 8.98 (1H, d, J=2.8 Hz), 11.20 (1H, br s).

SYNTHETIC EXAMPLE 18b

N-(5-Bromoquinoline-2-yl)-4-cyanobenzenesulfonamide

The title compound was obtained from 2-amino-5-bromoquinoline (Production Example 1b) and 4-cyanobenzenesulfonyl chloride in the same manner as in Synthetic Example 1b.

$^1$H-NMR(DMSO-$d_6$) δ (ppm): 7.57-7.73 (4H, m), 8.00-8.08 (4H, m), 8.38 (1H, d, J=8.8 Hz).

SYNTHETIC EXAMPLE 19b

N-(8-Bromoquinoline-3-yl)-6-ethyl-3-pyridinesulfonamide

Pyridine (0.5 ml) and a methylenechloride (0.5 ml) solution containing 6-ethyl-3-pyridinesulfonyl chloride (30 ml) were added to 3-amino-8-bromoquinoline (18 mg, Production Example 5b) at 0° C. After stirring at room temperature for 30 minutes, water was added thereto and the mixture was extracted with ethyl acetate. The extract was purified by preparative TLC (hexane-ethyl acetate=1:1), to give the title compound (20 mg).

$^1$H-NMR(CDCl$_3$) δ (ppm): 1.25 (3H, t, J=7.5 Hz), 2.70 (2H, q, J=7.50 Hz), 7.34-7.98 (5H, m), 8.19 (1H, d, J=3.3 Hz), 8.54 (1H, s), 8.83 (1H, d, J=3.3 Hz).

SYNTHETIC EXAMPLE 20b

4-Chloro-N-(5-chloroquinoline-2-yl)-benzenesulfonamide

Pyridine (1 ml) and 4-chlorobenzenesulfonyl chloride (255 mg) were added to 2-amino-5-chloroquinoline (119 mg, Production Example 2b) at room temperature, followed by stirring at room temperature for 3 days. Then, water was added thereto, followed by extracting with ethyl acetate. The ethyl acetate layer was dried over sodium sulfate and concentrated. Then, the resulting solid was washed with methanol, to give the title compound (20 mg).

$^1$H-NMR(CDCl$_3$) δ (ppm): 6.96 (1H, d, J=9.7 Hz), 7.34 (1H, d, J=8.4 Hz), 7.42-7.48 (3H, m), 7.54 (1H,t,J=8.4 Hz), 7.94 (2H, d, J=6.3 Hz), 8.29 (1H, d, J=9.7 Hz)

SYNTHETIC EXAMPLE 21b

N-(8-Chloroquinoline-3-yl)-6-ethyl-3-pyridinesulfonamide

The title compound was obtained from 3-amino-8-chloroquinoline (Production Example 9b) and 6-ethyl-3-pyridinesulfonyl chloride in the same manner as in Synthetic Example 1b.

¹H-NMR(CDCl₃) δ (ppm): 1.28 (3H, t, J=8.3 Hz), 2.86 (2H, q, J=8.3 Hz), 7.24 (1H, d, J=8.0 Hz), 7.49 (1H, t, J=8.0 Hz) 7.73 (1H, d, J=8.0 Hz), 7.78 (1H, d, J=8.0 Hz), 7.95 (1H, dd, J=8.0 Hz, 2.1 Hz), 8.18 (1H, d, J=2.5 Hz), 8.67 (1H, d, J=2.5 Hz), 8.93 (1H, d, J=2.1 Hz).

SYNTHETIC EXAMPLE 22b

N-(5-Chloroquinoline-2-yl)-6-ethyl-3-pyridine-sulfonamide

The title compound was obtained from 2-amino-5-chloroquinoline (Production Example 2b) and 6-ethyl-3-pyridinesulfonyl chloride in the same manner as in Synthetic Example 1b.

¹H-NMR(CDCl₃) δ (ppm): 1.32 (3H, t, J=8.3 Hz), 2.89 (2H, q, J=8.3 Hz), 6.97 (1H, d, J=9.4 Hz), 7.29 (1H, d, J=8.0 Hz), 7.35 (1H, d, J=8.0 Hz), 7.44 (1H, d, J=8.0 Hz), 7.56 (1H, t, J=8.0 Hz), 8.18 (1H, dd, J=8.0 Hz, 2.6 Hz), 8.30 (1H, d, J=9.4 Hz), 9.10 (1H, d, J=2.6 Hz).

SYNTHETIC EXAMPLE 23b

N-(8-Chloroquinoline-3-yl)-benzenesulfonamide

The title compound was obtained from 3-amino-8-chloroquinoline (Production Example 9b) and benzenesulfonyl chloride in the same manner as in Synthetic Example 1b.

¹H-NMR(DMSO-d₆) δ (ppm): 7.30-7.48 (6H, m), 7.84 (2H, d, J=7.4 Hz), 8.11 (1H, d, J=3.1 Hz), 8.66 (1H, d, J=3.1 Hz).

SYNTHETIC EXAMPLE 24b

4-Cyano-N-(5-chloroquinoline-2-yl)-benzenesulfonamide

The title compound was obtained from 3-amino-8-bromoquinoline (Production Example 2b) and 4-cyanobenzenesulfonyl chloride in the same manner as in Synthetic Example 1b.

¹H-NMR(CDCl₃) δ (ppm): 6.96 (1H, d, J=9.5 Hz), 7.35 (1H, d, J=8.7 Hz), 7.45 (1H, d, J=8.7 Hz), 7.57 (1H, t J=8.7 Hz), 7.78 (2H, d, J=8.9 Hz), 8.10 (2H, d, J=8.9 Hz), 8.33 (1H, d, J=9.5 Hz).

SYNTHETIC EXAMPLE 25b

N-(5-Chloroquinoline-2-yl)-4-methylbenzenesulfonamide

The title compound was obtained from 2-amino-5-chloroquinoline (Production Example 2b) and 4-toluenesulfonyl chloride in the same manner as in Synthetic Example 1b.

¹H-NMR(CDCl₃) δ (ppm): 2.41 (3H, s), 6.98 (1H, d, J=9.3 Hz), 7.28 (2H, d, J=8.2 Hz), 7.35 (1H, d, J=7.9 Hz), 7.41 (1H, d, J=7.9 Hz), 7.53 (1H, t, J=7.9 Hz), 7.88 (2H, d, J=8.2 Hz), 8.26 (1H, d, J=9.3 Hz).

SYNTHETIC EXAMPLE 26b

N-(5-Chloroquinoline-2-yl)-4-sulfamoylbenzenesulfonamide

The title compound was obtained from 2-amino-5-chloroquinoline (Production Example 2b) and 4-sulfamoylbenzenesulfonyl chloride in the same manner as in Synthetic Example 1b.

¹H-NMR(CDCl₃) δ (ppm): 7.42-7.49 (3H, m,), 7.58 (1H, t,J=8.0 Hz), 8.00-8.12 (4H, m,) 8.39 (1H, d, J=9.3 Hz).

SYNTHETIC EXAMPLE 27b

N-(5-Bromoquinoline-2-yl)-4-(N-ethylsulfamoyl)benzenesulfonamide

The title compound was obtained from 2-amino-5-chloroquinoline (Production Example 2b) and 4-(N-ethylsulfamoyl) benzenesulfonyl chloride in the same manner as in Synthetic Example 1b.

¹H-NMR(CDCl₃) δ (ppm): 1.14 (3H,t,J=7.5 Hz), 3.01-3.09 (2H, m), 7.08 (1H, d, J=9.5 Hz), 7.42 (1H, dd, J=7.6 Hz,1.3 Hz), 7.49 (1H,t,J=7.6 Hz), 7.65 (1H, dd, J=7.6 Hz,1.3 Hz), 7.96 (2H, d, J=8.7 Hz), 8.10 (2H, d, J=8.7 Hz), 8.31 (1H, d, J=9.5 Hz).

SYNTHETIC EXAMPLE 28b

3-Cyano-N-(8-chloroquinoline-3-yl)benzenesulfonamide

The title compound was obtained from 3-amino-8-chloroquinoline (Production Example 9b) and 3-cyanobenzenesulfonyl chloride in the same manner as in Synthetic Example 1b.

¹H-NMR(CDCl₃) δ (ppm): 7.52 (1H, t, J=7.9 Hz), 7.59 (1H, t, J=7.9 Hz), 7.72-7.86 (3H, m), 8.00 (1H, d, J=7.9 Hz), 8.13 (1H, d, J=3.2 Hz), 8.16 (1H, s), 8.64 (1H, d, J=3.2 Hz).

SYNTHETIC EXAMPLE 29b

N-(8-Chloroquinoline-3-yl)-3-methylbenzenesulfonamide

The title compound was obtained from 3-amino-8-chloroquinoline (Production Example 9b) and 3-toluenesulfonyl chloride in the same manner as in Synthetic Example 1b.

¹H-NMR(CDCl₃) δ (ppm): 2.35 (3H, s), 7.16-7.79 (7H, m), 8.09 (1H, d, J=2.7 Hz), 8.65 (1H, d, J=2.7 Hz).

SYNTHETIC EXAMPLE 30b

N-(8-Chloroquinoline-3-yl)-3-sulfamoylbenzenesulfonamide

The title compound was obtained from 3-amino-8-chloroquinoline (Production Example 9b) and 3-sulfamoylbenzenesulfonyl chloride in the same manner as in Synthetic Example 1b.

¹H-NMR(CDCl₃) δ (ppm): 7.46 (1H, t, J=7.6 Hz), 7.53 (1H, t, J=7.6 Hz), 7.58-7.78 (2H, m), 8.00 (1H, d, J=7.6 Hz), 8.04 (1H, d, J=7.6 Hz), 8.14 (1H, d, J=2.8 Hz), 8.47 (1H, s), 8.59 (1H, d, J=2.8 Hz).

SYNTHETIC EXAMPLE 31b

N-(8-Methylquinoline-3-yl)-3-pyridinesulfonamide 562 mg of white crystals were obtained using 1.02 g (5.2 mmol, Production Example 16b) of 7-amino-2-chloro-4-methylquinoline and 0.9 g (5.2 mmol) of 3-pyridinesulfonyl chloride in the same manner as in Synthetic Example 1b. Methanol (4 ml), tetrahydrofuran (4 ml) and 10% palladium carbon (5 mg) were added to 102 mg (0.29 mmol) of the white crystals, followed by stirring for 6 hours in a hydrogen atmosphere. The reaction solution was filtered through Celite, and then evaporated. The residue was washed with ethyl acetate, to give 65 mg of the title compound.
$^1$H-NMR(DMSO-d$_6$) δ (ppm): 2.82 (3H, s), 7.64-7.66 (2H, m), 7.73 (1H, d, J=5.2 Hz), 8.03 (1H, s), 8.30-8.35 (2H, m), 8.82 (1H, dd, J=1.2, 4.8 Hz), 9.00 (1H, d, J=5.2 Hz), 9.11 (1H, d, J=2.0 Hz)

SYNTHETIC EXAMPLE 32b

N-(8-Methylquinoline-3-yl)-4-cyanobenzenesulfonamide 358 mg of white crystals were obtained using 305 mg (1.58 mmol, Production Example 16b) of 7-amino-2-chloro-4-methylquinoline and 0.48 g (2.4 mmol) of 4-cyanobenzenesulfonyl chloride in the same manner as in Synthetic Example 1b. Acetic acid (6 ml), water (2 ml) and zinc (122 mg) were added to 140 mg (0.38 mmol) of the white crystals, followed by stirring at 60° C. for 15 minutes. After the reaction solution was filtered through Celite, an aqueous saturated sodium bicarbonate solution was added, followed by extracting with ethyl acetate. The organic layer was washed with brine, dried over magnesium sulfate and concentrated. Then, the residue was purified by silica gel chromatography, to give 82 mg of the title compound.
$^1$H-NMR(DMSO-d$_6$) δ (ppm): 2.60 (3H, s), 7.26 (1H, dd, J=1.2, 4.4 Hz), 7.41 (1H, dd, J=2.4, 8.8 Hz), 7.64 (1H, d, J=2.4 Hz), 7.97-8.06 (1H, m), 7.98 (2H, d, J=8.4 Hz), 8.04 (2H, d, J=8.4 Hz), 8.66 (1H, d, J=4.4 Hz), 11.06 (1H, s).

SYNTHETIC EXAMPLE 33b

N-(6-Chloro-8-cyanoquinoline-3-yl)-3-pyridinesulfonamide 764 mg of white crystals were obtained using 3.0 mg (13 mmol, Production Example 13b) of ethyl-7-amino-2-chloroquinoline-4-carboxylate and 2.3 g (13 mmol) of 3-pyridinesulfonyl chloride in the same manner as in Synthetic Example 1b. An aqueous 1 N sodium hydroxide solution (0.5 ml) was added to an ethanol solution (6 ml) of 108 mg (0.28 mmol) of the white crystals, followed by stirring overnight. An aqueous 1 N hydrochloric acid solution was added to the reaction solution, followed by extracting with ethyl acetate twice. The organic layer was washed with brine, dried over magnesium sulfate and concentrated, to give the residue. Under ice-cooling, oxalyl chloride (0.04 ml) and one droplet of dimethylformamide were added to a tetrahydrofuran solution (10 ml) containing the residue, followed by stirring at room temperature for 30 minutes. After 30 minutes, an aqueous saturated ammonium solution (5 ml) was added thereto, followed by stirring for further 10 minutes. Brine was added to the reaction solution, followed by extracting with ethyl acetate. The organic layer was dried over magnesium sulfate and concentrated, to give the residue. Under ice-cooling, pyridine (0.06 ml) and trifluoroacetic acid anhydride (0.05 ml) were added to a tetrahydrofuran solution (6 ml) containing the residue, followed by stirring at room temperature for 30 minutes. Brine was added to the reaction solution, followed by extracting with ethyl acetate. The organic layer was dried over magnesium sulfate and concentrated. The residue was purified by silica gel chromatography, to give 37 mg of the title compound.
$^1$H-NMR(DMSO-d$_6$) δ (ppm): 7.62-7.66 (1H, m), 7.68-7.72 (2H, m), 8.08 (1H, d, J=8.8 Hz), 8.23 (1H, s), 8.26-8.29 (1H, m), 8.81 (1H, dd, J=1.6, 4.8 Hz), 9.04 (1H, d, J=2.4 Hz).

SYNTHETIC EXAMPLE 34b

N-(8-Chloroquinoline-3-yl)-4-cyanobenzenesulfonamide 58 mg of the title compound was obtained using 38 mg (0.21 mmol) of 3-amino-8-chloroquinoline (0.21 mmol, Production Example 9b) and 43 mg (0.21 mmol) of 4-cyanobenzenesulfonyl chloride in the same manner as in Synthetic Example 1b.
$^1$H-NMR(DMSO-d$_6$) δ (ppm): 7.55 (1H, t, J=7.6 Hz), 7.84 (1H, d, J=7.6 Hz), 7.95 (1H, t, J=7.6 Hz), 7.99 (2H, d, J=8.8 Hz), 8.04 (2H, d, J=8.8 Hz), 8.09 (1H, d, J=2.8 Hz), 8.73 (1H, d, J=2.8 Hz), 11.39 (1H, s).

SYNTHETIC EXAMPLE 35b

N-(8-Chloroquinoline-3-yl)-4-(N-ethylsulfamoyl)benzenesulfonamide 36 mg of the title compound was obtained using 36 mg (0.19 mmol, Production Example 9b) of 3-amino-8-chloroquinoline and 52 mg (0.19 mmol) of 4-(N-ethylsulfamoyl)benzenesulfonyl chloride in the same manner as in Synthetic Example 1b.
$^1$H-NMR(DMSO-d$_6$) δ (ppm): 0.84 (3H, t, J=7.2 Hz), 2.78-2.71 (2H, m), 7.54 (1H, t, J=7.6 Hz), 7.77 (1H, t, J=6.0 Hz), 7.83 (1H,t, J=7.6 Hz), 7.92-7.95 (1H, m), 7.93 (2H, d, J=8.8 Hz), 8.03 (2H, d, J=8.8 Hz), 8.07 (1H, d, J=2.4 Hz), 8.73 (1H, d, J=2.4 Hz), 11.20 (1H, s).

SYNTHETIC EXAMPLE 36b

N-(8-Chloroquinoline-3-yl)-3-pyridinesulfonamide 29 mg of the title compound was obtained using 33 mg (0.19 mmol, Production Example 9b) of 3-amino-8-chloroquinoline and 33 mg (0.19 mmol) of 3-pyridinesulfonyl chloride in the same manner as in Synthetic Example 1b.
$^1$H-NMR(DMSO-d$_6$) δ (ppm): 7.54 (1H,t,J=7.6 Hz), 7.60 (1H, dd, J=4.8, 7.6 Hz), 7.81 (1H ,d, J=7.6 Hz), 7.94 (1H, d, J=7.6 Hz), 8.09 (1H, d, J=2.8 Hz), 8.19-8.26 (1H, m), 8.72 (1H, d, J=2.8 Hz), 8.77 (1H, d, J=1.6, 4.8 Hz), 9.00 (1H, d, J=2.8 Hz), 11.46 (1H, s).

SYNTHETIC EXAMPLE 37b

N-(8-Chloroquinoline-3-yl)-5-ethylsulfamoyl-2-pyridinesulfonamide 10 mg of the title compound was obtained using 30 mg (0.17 mmol, Production Example 9b) of 3-amino-8-chloroquinoline and 95 mg (0.34 mmol) of 5-ethylsulfamoyl-2-chlorosulfonylpyridine in the same manner as in Synthetic Example 1b.
$^1$H-NMR(DMSO-d$_6$) δ (ppm): 0.88 (3H, t, J=7.6 Hz), 2.79-2.86 (2H, m), 7.55 (1H, t, J=7.6 Hz), 7.85 (1H, t, J=7.6 Hz), 7.94 (1H, d, J=7.6 Hz), 8.00 (1H, t, J=6.4 Hz), 8.16 (1H, d, J=2.8 Hz), 8.27 (1H, d, J=8.0 Hz), 8.41 (1H, d, J=2.4, 8.0 Hz), 8.84 (1H, d, J=2.8 Hz), 9.04 (1H, d, J=2.4 Hz), 11.47 (1H, s)

SYNTHETIC EXAMPLE 38b

N-(8-Trifluoromethylquinoline-3-yl)-4-cyanobenzenesulfonamide 59 mg of the title compound was obtained using 35 mg (0.17 mmol, Production Example 10b) of 3-amino-8-trifluoromethylquinoline and 37 mg (0.18 mmol) of 4-cyanobenzenesulfonyl chloride in the same manner as in Synthetic Example 1b.
$^1$H-NMR(DMSO-$d_6$) δ (ppm): 7.71 (1H, t, J=7.6 Hz), 8.03-8.09 (5H, m), 8.19 (1H, d, J=2.4 Hz), 8.30 (1H, d, J=7.6 Hz), 8.78 (1H, d, J=2.4 Hz), 11.72 (1H, s).

SYNTHETIC EXAMPLE 39b

N-(8-Trifluoromethylquinoline-3-yl)-4-(N-ethylsulfamoyl)benzenesulfonamide 60 mg of the title compound was obtained using 35 mg (0.17 mmol, Production Example 10b) of 3-amino-8-trifluoromethylquinoline and 56 mg (0.20 mmol) of 4-(N-ethylsulfamoyl)benzenesulfonyl chloride in the same manner as in Synthetic Example 1b.
$^1$H-NMR(DMSO-$d_6$) δ (ppm): 0.83 (3H, t, J=7.2 Hz), 2.71-2.78 (2H, m), 7.69 (1H, t, J=8.0 Hz), 7.76 (1H, t, J=5.6 Hz), 7.93 (1H, d, J=8.8 Hz), 8.04-8.07 (3H, m), 8.13 (1H, d, J=2.8 Hz), 8.25 (1H, d, J=8.0 Hz), 8.75 (1H, d, J=2.8 Hz), 11.28 (1H, s).

SYNTHETIC EXAMPLE 40b

N-(8-Trifluoromethylquinoline-3-yl)-3-pyridine-sulfonamide 71 mg of the title compound was obtained using 45 mg (0.21 mmol, Production Example 10b) of 3-amino-8-trifluoromethylquinoline and 45 mg (0.25 mmol) of 3-pyridinesulfonyl chloride in the same manner as in Synthetic Example 1b.
$^1$H-NMR(DMSO-$d_6$) δ (ppm): 7.59-7.63 (1H, m), 7.70 (1H, t, J=7.6 Hz), 8.06 (1H, d, J=7.6 Hz), 8.20 (1H, d, J=2.8 Hz), 8.23-8.24 (1H, m), 8.30 (1H, d, J=7.6 Hz), 8.76 (1H, d, J=2.8 Hz), 8.79 (1H, dd, J=1.6, 4.8 Hz), 9.03 (1H, d, J=2.0 Hz), 11.64 (1H, s).

SYNTHETIC EXAMPLE 41b

N-(8-Chloroquinoline-3-yl)-1,2,3,4-tetrahydro-6-naphthalene-sulfonamide 46 mg of the title compound was obtained using 33 mg (0.19 mmol, Production Example 9b) of 3-amino-8-chloroquinoline and 73 mg (0.22 mmol) of 6-chlorosulfonyl-1,2,3,4-tetrahydronaphthalene in the same manner as in Synthetic Example 1b.
$^1$H-NMR(DMSO-$d_6$) δ (ppm): 1.68 (4H, br), 2.71 (4H, br), 7.20 (1H, t, J=8.4 Hz), 7.52 (1H, t, J=7.6 Hz), 7.53 (1H, dd, J=2.0, 8.4 Hz), 7.58 (1H, d, J=2.0 Hz), 7.80 (1H, d, J=7.6 Hz), 7.93 (1H, d, J=7.6 Hz), 8.06 (1H, d, J=2.4 Hz), 8.73 (1H, d, J=2.4 Hz), 10.94 (1H, s).

SYNTHETIC EXAMPLE 42b

N-(8-Chloroquinoline-3-yl)-2,3-dihydro-5-benzofuransulfonamide 57 mg of the title compound was obtained using 30 mg (0.17 mmol, Production Example 9b) of 3-amino-8-chloroquinoline and 44 mg (0.20 mmol) of 5-chlorosulfonyl-2,3-dihydrobenzofuran in the same manner as in Synthetic Example 1b.
$^1$H-NMR(DMSO-$d_6$) δ (ppm): 3.19 (2H, t, J=8.8 Hz),4.58 (2H, t, J=8.8 Hz), 6.86 (1H, d, J=8.8 Hz), 7.23 (1H, t, J=7.6 Hz), 7.62 (1H, dd, J=1.6, 8.8 Hz), 7.72 (1H, d, J=1.6 Hz), 7.80 (1H, d, J=7.6 Hz), 7.92 (1H, d, J=7.6 Hz), 8.03 (1H, d, J=2.4 Hz), 8.73 (1H, d, J=2.4 Hz), 10.85 (1H, s).

SYNTHETIC EXAMPLE 43b

N-(8-Chloro-4-vinylquinoline-3-yl)-4-cyanobenzenesulfonamide 15 mg of the title compound was obtained using 30 mg (0.15 mmol, Production Example 12b) of 3-amino-4-vinyl-8-chloroquinoline and 36 mg (0.18 mmol) of 4-cyanobenzenesulfonyl chloride in the same manner as in Synthetic Example 1b.
$^1$H-NMR(DMSO-$d_6$)δ (ppm): 5.29 (1H, d, J=17.6 Hz), 5.59 (1H, d, J=11.6 Hz), 6.75 (1H, dd, J=11.6, 17.6 Hz), 7.59 (1H, t, J=8.0 Hz), 7.80 (2H, dd, J=8.8 Hz), 7.96 (1H, d, J=8.0 Hz), 8.00-8.04 (3H, m), 8.74 (1H, s), 10.58 (1H, s).

SYNTHETIC EXAMPLE 44b

N-(8-Trifluoromethylquinoline-3-yl)-5-(N-acethylindoline)sulfonamide 186 mg of the title compound was obtained using 109 mg (0.51 mmol, Production Example 10b) of 3-amino-8-trifluoromethylquinoline and 200 mg (0.77 mmol) of 5-chlorosulfonyl-N-acetylindoline in the same manner as in Synthetic Example 1b.
$^1$H-NMR(DMSO-$d_6$) δ (ppm): 2.13 (3H, s), 3.14 (2H, t, J=8.0 Hz), 4.09 (2H, t, J=8.8 Hz), 7.67 (1H, t, J=8.4 Hz), 7.69-7.73 (2H, m), 8.01 (1H, d, J=7.2 Hz), 8.07-8.09 (2H, m), 8.24 (1H, d, J=8.4 Hz), 8.73 (1H, d, J=2.8 Hz), 10.98 (1H, s)

SYNTHETIC EXAMPLE 45b

N-(8-Bromoquinoline-3-yl)-2-methylthio-5-pyridinesulfonamide 197 mg (0.556 mmol) of white crystals were obtained using 100 mg (0.56 mmol, Production Example 5b) of 3-amino-8-bromoquinoline and 142 mg (0.67 mmol) of 2-chloro-5-pyridinesulfonyl chloride in the same manner as in Synthetic Example 1b. Dimethylformamide (1 ml), pyridine (1 ml) and 111 mg (1.6 mmol) of sodium thiomethoxide were added to 60 mg (0.17 mmol) of the crystals, followed by stirring at room temperature for 3 hours. Brine was added to the reaction solution, followed by extracting with ethyl acetate. The organic layer was dried over magnesium sulfate and concentrated, to give the residue. The residue was purified by silica gel chromatography, to give 62 mg of the title compound.
$^1$H-NMR(DMSO-$d_6$) δ (ppm): 3.33 (3H, s), 7.47 (1H, d, J=8.8 Hz), 7.55 (1H, t, J=8.0 Hz), 7.84 (1H, d, J=6.8 Hz), 7.97 (1H, d, J=8.8 Hz), 7.98 (1H, d, J=8.8 Hz), 8.13 (1H, d, J=2.0 Hz), 8.74 (1H, d, J=2.4 Hz), 8.82 (1H, d, J=2.0 Hz), 11.16 (1H, s).

SYNTHETIC EXAMPLE 46b

N-(8-Bromoquinoline-3-yl)-4-(2-methylsulfonylethyl)benzenesulfonamide 55 mg of the title compound was obtained using 30 mg (0.13 mmol, Production Example 5b) of 3-amino-8-bromoquinoline and 57 mg (0.20 mmol) of 4-(2-methylsulfonylethyl)benzenesulfonyl chloride in the same manner as in Synthetic Example 1b.

¹H-NMR(DMSO-d₆) δ (ppm): 2.92 (3H, s), 3.00-3.05 (2H, m), 3.37-3.44 (2H, m), 7.46 (1H, t, J=7.6 Hz), 7.48 (2H, d, J=8.0 Hz), 7.80 (2H, d, J=8.0 Hz), 7.96 (1H, d, J=7.6 Hz), 7.99 (1H, d, J=7.6 Hz), 8.04 (1H, d, J=2.4 Hz), 8.71 (1H, d, J=2.4 Hz), 11.02 (1H, s)

SYNTHETIC EXAMPLE 47b

N-(8-Bromoquinoline-3-yl)-4-oxa-7-benzothiochromansulfonamide 99 mg of the title compound was obtained using 51 mg (0.23 mmol, Production Example 5b) of 3-amino-8-bromoquinoline and 86 mg (0.34 mmol) of 7-chlorosulfonyl-4-oxabenzothiochroman in the same manner as in Synthetic Example 1b.

¹H-NMR(DMSO-d₆) δ (ppm): 3.18 (2H, t, J=8.4 Hz), 4.39 (2H, t, J=8.4 Hz), 6.92 (1H, d, J=8.8 Hz), 7.42 (1H, dd, J=2.4, 8.8 Hz), 7.46 (1H, t, J=7.6 Hz), 7.59 (1H, d, J=2.4 Hz), 7.99 (1H, d, J=7.6 Hz), 8.02 (1H, d, J=7.6 Hz), 8.05 (1H, br), 8.71 (1H, d, J=2.4 Hz), 10.92 (1H, s).

SYNTHETIC EXAMPLE 48b

N-(8-Bromoquinoline-3-yl)-4-(2-acetamidoethyl)benzenesulfonamide 56 mg of the title compound was obtained using 30 mg (0.13 mmol, Production Example 5b) of 3-amino-8-bromoquinoline and 201 mg (0.77 mmol) of N-(4-chlorosulfonylphenethylethyl)acetamide in the same manner as in Synthetic Example 1b.

¹H-NMR(DMSO-d₆) δ (ppm): 2.71 (2H, t, J=7.2 Hz), 3.25-3.20 (2H, m), 7.37 (2H, d, J=8.4 Hz), 7.46 (1H, t, J=8.0 Hz), 7.78 (2H, d, J=8.4 Hz), 7.86 (1H, br), 7.97 (1H, d, J=8.0 Hz), 8.00 (1H, d, J=8.0 Hz), 8.04 (1H, d, J=2.8 Hz), 8.72 (1H, d, J=2.8 Hz), 10.99 (1H, s).

SYNTHETIC EXAMPLE 49b

N-(8-Bromoquinoline-3-yl)-1,2,3,4-tetrahydro-N-acetyl-7-isoquinolinesulfonamide 180 mg of white crystals were obtained using 145 mg (0.65 mmol, Production Example 5b) of 3-amino-8-bromoquinoline and 277 mg (0.85 mmol) of 1,2,3,4-tetrahydro-2-(trifluoroacetyl)isoquinoline-7-sulfonyl chloride in the same manner as in Synthetic Example 1b. Ethanol (20 ml) and an aqueous 1 N sodium hydroxide solution (0.5 ml) were added to the crystals, followed by stirring at room temperature for 30 minutes. An aqueous 1 N hydrochloric acid solution (0.4 ml) was added to the reaction solution, followed by extracting with ethyl acetate. The organic layer was washed with brine, dried over magnesium sulfate and concentrated, to give the residue. Pyridine (0.5 ml) and acetic acid anhydride (0.014 ml) were added to the residue, followed by stirring at room temperature for one hour. Brine was added thereto, followed by extracting with ethyl acetate. The organic layer was dried over magnesium sulfate and concentrated. Then, the residue was purified by silica gel chromatography, to give 113 mg of the title compound.

¹H-NMR(DMSO-d₆) δ (ppm): 1.19-1.28 (2H, m), 2.05 (3H, s), 2.97 (1H, t, J=6.4 Hz), 3.03 (1H, t, J=6.4 Hz), 3.75 (1H, t, J=6.4 Hz), 4.73 (1H, s), 7.37 (1H, t, J=8.8 Hz), 7.53-7.58 (1H, m), 7.75-7.87 (2H, m), 7.91 (1H, d, J=8.0 Hz), 8.19-8.27 (2H, m), 8.76-8.78 (1H, m).

SYNTHETIC EXAMPLE 50b

N-(8-Bromoquinoline-3-yl)-1,1-dioxido-6-benzothiochromansulfonamide

White crystals were obtained using 71 mg (0.32 mmol, Production Example 5b) of 3-amino-8-bromoquinoline and 119 mg (0.48 mmol) of 6-chlorosulfonylbenzothiochroman. Under ice-cooling, chloroform (10 ml) and methachloroperbenzoic acid (145 mg) were added to the crystals under ice-cooling, followed by stirring at room temperature for one hour. An aqueous saturated sodium thiosulfate solution was added thereto, followed by extracting with ethyl acetate. The organic layer was washed with brine and dried over magnesium sulfate. After concentrating, the residue was purified by silica gel chromatography, to give 113 mg of the title compound.

¹H-NMR(DMSO-d₆) δ (ppm): 2.26-2.29 (2H, m), 3.05 (2H, t, J=6.0 Hz), 3.53-3.56 (2H, m), 7.48 (1H, t, J=7.6 Hz), 7.86-7.90 (2H, m), 7.96-8.04 (3H, m), 8.10 (1H, d, J=2.4 Hz), 8.75 (1H, d, J=2.4 Hz), 11.24 (1H, s).

SYNTHETIC EXAMPLE 51b

N-(8-Bromoquinoline-3-yl)-4-(3-methylsulfonylpropyl)benzenesulfonamide 62 mg of the title compound was obtained using 33 mg (0.14 mmol, Production Example 5b) of 3-amino-8-bromoquinoline and 66 mg (0.22 mmol) of 4-(3-methylsulfonylpropyl)benzenesulfonyl chloride in the same manner as in Synthetic Example 1b.

¹H-NMR(DMSO-d₆) δ (ppm): 1.90-1.98 (2H, m), 2.72 (2H, t, J=8.0 Hz), 2.93 (3H, s), 3.06 (2H, t, J=8.0 Hz), 7.42 (2H, d, J=8.0 Hz), 7.46 (1H, t, J=7.6 Hz), 7.97 (2H, d, J=7.6 Hz), 8.00 (1H, d, J=7.6 Hz), 8.05 (1H, d, J=2.4 Hz), 8.72 (1H, d, J=2.4 Hz), 11.01 (1H, s).

SYNTHETIC EXAMPLE 52b

N-(8-Bromoquinoline-3-yl)-4-fluorobenzenesulfonamide 50 mg of the title compound was obtained using 33 mg (0.14 mmol, Production Example 5b) of 3-amino-8-bromoquinoline and 39 mg (0.20 mmol) of 4-fluorobenzenesulfonyl chloride in the same manner as in Synthetic Example 1b.

¹H-NMR(DMSO-d₆) δ (ppm): 7.40 (1H, t, J=8.8 Hz), 7.47 (1H, t, J=7.6 Hz), 7.89-7.93 (2H, m), 9.78 (1H, dd, J=0.9, 7.6 Hz), 8.01 (1H, dd, J=0.9, 7.6 Hz), 8.06 (1H, d, J=2.4 Hz), 8.71 (1H, d, J=2.4 Hz), 11.06 (1H, s).

SYNTHETIC EXAMPLE 53b

N-(8-Bromoquinoline-3-yl)-4-methoxy-2-pyridazinesulfonamide

Under ice-cooling, chlorine gas was brown into a concentrated hydrochloric acid solution (8 ml) containing 0.86 g (3.7 mmol, Production Example 14b) of 2-benzylthio-5-methoxypyridazine for one hour, followed by stirring. Then, ice-water was added to the reaction solution, followed by extracting with ethyl acetate. The organic layer was successively washed with water and brine, dried over magnesium sulfate and concentrated, to give 700 mg (2.1 mmol) of the residue. 93 mg of the title compound was obtained using 180 mg (0.54 mmol)

of the residue and 60 mg (0.27 mmol, Production Example 5b) of 3-amino-8-bromoquinoline in the same manner as in Synthetic Example 1b.

$^1$H-NMR(DMSO-d$_6$) δ (ppm): 4.07 (3H, s), 7.44 (1H, d, J=9.2 Hz), 7.47 (1H, t, J=7.6 Hz), 7.96 (1H, t, J=7.6 Hz), 8.02 (1H, t, J=7.6 Hz), 8.13 (1H, d, J=2.4 Hz), 8.17 (1H, d, J=9.2 Hz), 8.82 (1H, d, J=2.4 Hz), 11.54 (1H, s).

SYNTHETIC EXAMPLE 54b

N-(8-Bromoquinoline-3-yl)-benzenesulfonamide 49 mg of the title compound was obtained using 30 mg (0.13 mmol, Production Example 5b) of 3-amino-8-bromoquinoline and 35 mg (0.20 mmol) of benzenesulfonyl chloride in the same manner as in Synthetic Example 1b.

$^1$H-NMR(DMSO-d$_6$) δ (ppm): 7.45 (1H, d, J=7.6 Hz), 7.53-7.63 (3H, m), 7.84-7.86 (2H, m), 7.96 (1H, dd, J=1.2, 7.6 Hz), 7.99 (1H, dd, J=1.2, 7.6 Hz), 8.04 (1H, d, J=2.8 Hz), 8.71 (1H, d, J=2.8 Hz), 11.02 (1H, s).

SYNTHETIC EXAMPLE 55b

N-(8-Bromoquinoline-3-yl)-4-carboxyamido-2-pyridinesulfonamide

Chlorine gas was brown into a concentrated hydrochloric acid solution (16 ml) containing 1.1 g (4.3 mmol, Production Example 15b) of 2-benzylthio-4-carboxyamidopyridine for one hour under ice-cooling, followed by stirring. Then, the reaction solution was added to ice-water, followed by extracting with ethyl acetate. The organic layer was successively washed with water and brine, dried over magnesium sulfate and concentrated.

37 mg of the title compound was obtained using 140 mg (0.40 mmol) of the residue and 45 mg (0.20 mmol) of 3-amino-8-bromoquinoline in the same manner as in Synthetic Example 1b.

$^1$H-NMR(DMSO-d$_6$) δ (ppm): 7.46 (1H, d, J=8.0 Hz), 7.94-7.96 (2H, m), 8.00-8.02 (2H, m), 8.12 (1H, d, J=2.4 Hz), 8.44 (1H, br), 8.49 (1H, br), 8.83-8.85 (2H, m), 11.35 (1H, s)

SYNTHETIC EXAMPLE 56b

N-(8-Bromoquinoline-3-yl)-3-methoxybenzenesulfonamide 70 mg of the title compound was obtained using 40 mg (0.18 mmol, Production Example 5b) of 3-amino-8-bromoquinoline and 56 mg (0.27 mmol) of 3-methoxybenzenesulfonyl chloride in the same manner as in Synthetic Example 1b.

$^1$H-NMR(DMSO-d$_6$) δ (ppm): 3.76 (3H, s), 7.17 (1H, dd, J=2.8, 8.0 Hz), 7.34-7.40 (2H, m), 7.45 (1H, t, J=7.6 Hz), 7.46 (1H, t, J=7.6 Hz), 7.99 (2H, t, J=7.6 Hz), 8.07 (1H, d, J=2.4 Hz), 8.72 (2H, m), 11.35 (1H, d, J=2.4 Hz)

SYNTHETIC EXAMPLE 57b

N-(8-Bromoquinoline-3-yl)-3-hydroxybenzenesulfonamide 73 mg of the title compound was obtained using 45 mg (0.20 mmol, Production Example 5b) of 3-amino-8-bromoquinoline and 117 mg (0.61 mmol) of 3-hydroxybenzenesulfonyl chloride in the same manner as in Synthetic Example 1b.

$^1$H-NMR(DMSO-d$_6$) δ (ppm): 6.97 (1H, d, J=8.0 Hz), 7.18 (1H, br), 7.25 (1H, d, J=8.0 Hz), 7.34 (1H, t, J=8.0 Hz), 7.47 (1H, t, J=8.0 Hz), 7.97 (1H, d, J=8.0 Hz), 8.01 (1H, d, J=8.0 Hz), 8.04 (1H, d, J=2.4 Hz), 8.73 (1H, d, J=2.4 Hz), 10.15 (1H, s), 10.96 (1H, s).

SYNTHETIC EXAMPLE 58b

N-(4-Bromoquinoline-7-yl)-4-chlorobenzenesulfonamide 20 mg (0.09 mmol, Production Example 20b) of 7-amino-4-bromoisoquinoline was dissolved in 1.5 ml of pyridine, to which was then added 23 mg of 4-chlorobenzenesulfonyl chloride, followed by stirring at room temperature overnight. Water was added to the reaction solution, and the mixture was extracted with ethyl acetate. The extract was dried over magnesium sulfate and concentrated. Then, the resulting residue was purified by silica gel thin layer chromatography, to give 13 mg of the title compound.

Melting point: gradually decomposed from 229° C.

$^1$H-NMR(DMSO-d$_6$) δ (ppm): 7.59-7.61 (2H, m), 7.66 (1H, dd, J=2 Hz, 9.2 Hz), 7.82-7.84 (3H, m), 7.99 (1H, d, J=9.2 Hz), 8.60 (1H, s).

SYNTHETIC EXAMPLE 59b

N-(4-Bromoisoquinoline-7-yl)-6-chloro-3-pyridinesulfonamide

The title compound was obtained using 7-amino-4-isoquinoline (Production Example 20b) and 6-chloro-3-pyridinesulfonyl chloride in the same manner as in Synthetic Example 57b.

$^1$H-NMR(DMSO-d$_6$) δ (ppm): 7.66 (1H, dd, J=2.4 Hz, 9.2 Hz), 7.70 (1H, d, J=8.4 Hz), 7.89 (1H, d, J=2.4 Hz), 8.02 (1H, d, J=9.2 Hz), 8.20 (1H, dd, J=2.4 Hz, 8.4 Hz), 8.64 (1H, s), 8.84 (1H, d, J=2.4 Hz), 9.26 (1H, s).

SYNTHETIC EXAMPLE 60b 2-(4-Chlorobenzenesulfonylamino)-1,6-naphthyridine

2-Amino-1,6-naphthyridine (200 mg, Production Example 25b) was dissolved in dichloromethane (6.0 ml), to which were then added triethylamine (0.20 ml) and 4-chlorobenzenesulfonyl chloride (0.31 g), followed by stirring at 40° C. for 1.5 hours. An aqueous saturated sodium bicarbonate was added thereto, followed by extracting with ethyl acetate. The extract was washed with brine and dried over anhydrous magnesium sulfate. The solvent was evaporated and the residue was purified by silica gel column, to give the title compound (84 mg, 21.44%) as pale yellow crystals.

$^1$H-NMR(CDCl$_3$) δ (ppm): 7.10 (1H, d, J=9.2 Hz), 7.37 (1H, d, J=5.4 Hz), 7.46 (2H, d, J=8.8 Hz), 7.93 (2H, d, J=8.8 Hz), 8.94 (1H, d, J=9.2 Hz), 8.66 (1H, d, J=5.4 Hz), 8.92 (1H, br s).

SYNTHETIC EXAMPLE 61b

1-Chloro-6-(4-cyanobenzenesulfonylamino)isoquinoline

The title compound was obtained using 6-amino-1-chloroisoquinoline (Production Example 23b) and 4-cyanobenzenesulfonyl chloride in the same method as in Synthetic Example 1b.

¹H-NMR(DMSO-d₆) δ (ppm): 7.52 (1H, dd, J=2.0, 8.8 Hz), 7.68 (1H, d, J=2.0 Hz), 7.79 (1H, d, J=5.6 Hz), 8.03 (4H, m), 8.18 (1H, d, J=5.6 Hz), 8.21 (1H, d, J=8.8 Hz), 11.36 (1H, s).

SYNTHETIC EXAMPLE 62b

1-Chloro-6-(4-chlorobenzenesulfonylamino)isoquinoline

The title compound was obtained using 6-amino-1-chloro-isoquinoline (Production Example 23b) and 4-chlorobenzenesulfonyl chloride in the same method as in Synthetic Example 1b.
¹H-NMR(CDCl₃) δ (ppm): 7.33 (1H, br s), 7.39 (1H, dd, J=2.0, 8.8 Hz), 7.44 (2H, d, J=8.8 Hz), 7.50 (1H, d, J=5.6 Hz), 7.58 (1H, d, J=2.0 Hz), 7.81 (2H, d, J=8.8 Hz), 8.24 (1H, d, J=5.6 Hz), 8.25 (1H, d, J=8.8 Hz)
FAB-MS: 353.

SYNTHETIC EXAMPLE 63b

1-Chloro-6-(4-pyrrolidine-1-ylsulfonyl)benzenesulfonylamino)isoquinoline

The target compound was obtained using 6-amino-1-chloro-isoquinoline (Production Example 23b) and 4-(pyrrolidine-1-ylsulfonyl)benzenesulfonyl chloride in the same method as in Synthetic Example 1b.
¹H-NMR(CDCl₃) δ (ppm): 1.71 (4H, m), 3.20 (4H, t, J=7.0 Hz), 7.46 (1H, d, J=5.4 Hz), 7.49 (1H, dd, J=2.0, 9.2 Hz), 7.61 (1H, d, J=2.0 Hz), 7.87 (2H, d, J=8.8 Hz), 8.02 (2H, d, J=8.8 Hz), 8.19 (1H, d, J=9.2 Hz), 8.20 (1H, d, J=5.4 Hz), 9.72 (1H, s).

SYNTHETIC EXAMPLE 64b

1-Chloro-6-(4-(N-ethylsulfamoyl)benzenesulfonylamino)isoquinoline

The title compound was obtained using 6-amino-1-chloro-isoquinoline (Production Example 23b) and 4-(N-ethylsulfamoyl)benzenesulfonyl chloride in the same method as in Synthetic Example 1b.
¹H-NMR(DMSO-d₆) δ (ppm): 0.81 (3H, t, J=7.2 Hz), 2.73 (2H, m), 7.53 (1H, d, J=9.2 Hz), 7.67 (1H, s), 7.75 (1H, d, J=6.0 Hz), 7.78 (1H, d, J=6.0 Hz), 7.92 (2H, d, J=8.0 Hz).

SYNTHETIC EXAMPLE 65b

1-Methoxy-6-(pyridine-3-ylsulfonylamino)isoquinoline

The title compound was obtained using 6-amino-1-methoxyisoquinoline (Production Example 43b) and 3-pyridinesulfonyl chloride in the same method as in Synthetic Example 1b.
¹H-NMR(DMSO-d₆) δ (ppm): 4.09 (3H, s), 7.09 (1H, d, J=6.0 Hz), 7.25 (1H, dd, J=2.0, 8.8 Hz), 7.37 (1H, d, J=8.0, 8.8 Hz), 7.48 (1H, d, J=2.0 Hz), 7.96 (1H, d, J=6.0 Hz), 8.07 (1H, ddd, J=1.6, 2.0, 8.0 Hz), 8.14 (1H, d, J=8.8 Hz), 8.74 (1H, dd, J=1.6, 8.8 Hz), 9.08 (1H, d, J=2.0 Hz)
ESI-MS: 316.0.

SYNTHETIC EXAMPLE 66b 6-(4-Cyanobenzenesulfonylamino)-1-methoxyisoquinoline

The title compound was obtained using 6-amino-1-methoxyisoquinoline (Production Example 43b) and 4-cyanobenzenesulfonyl chloride in the same method as in Synthetic Example 1b.
¹H-NMR(DMSO-d₆) δ (ppm): 3.97 (3H, s), 7.25 (1H, d, J=5.6 Hz), 7.32 (1H, d, J=8.8 Hz), 7.51 (1H, s), 7.90 (1H, d, J=5.6 Hz), 7.97 (2H, d, J=7.6 Hz), 8.01 (2H, d, J=7.6 Hz), 8.03 (1H, d, J=8.8 Hz).

SYNTHETIC EXAMPLE 67b 6-(4-Carbamoylbenzenesulfonylamino)-1-methoxyisoquinoline The title compound was obtained using 6-(4-cyanobenzenesulfonylamino)-1-methoxyisoquinoline (Production Example 65b) according to the method described in Synthesis, 949 (1989).
¹H-NMR(DMSO-d₆) δ (ppm): 3.96 (3H, s), 7.24 (1H, d, J=6.4 Hz), 7.33 (1H, d, J=9.2 Hz), 7.51 (1H, s), 7.55 (1H, br s), 7.88 (1H, d, J=6.4 Hz), 7.89 (2H, d, J=8.0 Hz), 7.93 (2H, d, J=8.0 Hz), 8.01 (1H, d, J=9.2 Hz), 8.06 (1H, br s), 10.95 (1H, s)
FAB-MS: 358.

SYNTHETIC EXAMPLE 68b 6-(4-(N-Ethylsulfamoyl)benzenesulfonylamino)-1-methoxyisoquinoline The title compound was obtained using 6-amino-1-methoxyisoquinoline (Production Example 43b) and 4-(N-ethylsulfamoyl)benzenesulfonyl chloride in the same method as in Synthetic Example 1b.
¹H-NMR(DMSO-d₆) δ (ppm): 0.81 (3H, t, J=6.8 Hz), 2.71 (2H, m), 3.96 (3H, s), 7.23 (1H, d, J=6.4 Hz), 7.32 (1H, d, J=8.8 Hz), 7.48 (1H, s), 7.73 (1H, br s), 7.89 (2H, d, J=8.0 Hz), 7.90 (1H, d, J=6.4 Hz), 8.01 (3H, m), 11.03 (1H, br s)
ESI MS: 422.0.

SYNTHETIC EXAMPLE 69b 6-(2-Aminopyridine-5-ylsulfonylamino)-1-methoxyisoquinoline The title compound was obtained using 6-amino-1-methoxyisoquinoline (Production Example 43b) and 6-amino-3-pyridinesulfonyl chloride in the same method as in Synthetic Example 1b.
¹H-NMR(DMSO-d₆) δ (ppm): 3.96 (3H, s), 6.39 (1H, d, J=8.8 Hz), 6.89 (2H, s), 7.25 (1H, d, J=4.2 Hz), 7.32 (1H, d, J=9.2 Hz), 7.47 (1H, s), 7.64 (1H, d, J=9.2 Hz), 7.89 (1H, d, J=4.2 Hz), 8.01 (1H, d, J=8.8 Hz), 8.31 (1H, s), 10.95 (1H, s).
ESI MS: 331.0.

SYNTHETIC EXAMPLE 70b

1-Methoxy-6-(4-methylbenzenesulfonylamino)isoquinoline

The title compound was obtained using 6-amino-1-methoxyisoquinoline (Production Example 43b) and 4-toluenesulfonyl chloride in the same method as in Synthetic Example 1b.
¹H-NMR(DMSO-d₆) δ (ppm): 2.28 (3H, s), 3.96 (3H, s), 7.22 (1H, d, J=6.0 Hz), 7.32 (3H, m), 7.48 (1H, s), 7.71 (2H, d, J=8.4 Hz), 7.88 (1H, d, J=6.0 Hz), 8.00 (1H, d, J=9.2 Hz), 10.79 (1H, s).
ESI MS: 329.0.

SYNTHETIC EXAMPLE 71b

6-(4-Acetylaminobenzenesulfonylamino)-1-methoxyisoquinoline

The title compound was obtained using 6-amino-1-methoxyisoquinoline (Production Example 43b) and 4-acetamidobenzenesulfonyl chloride in the same method as in Synthetic Example 1b.

$^1$H-NMR(DMSO-d$_6$) δ (ppm): 2.01 (3H, s), 3.96 (3H, s), 7.23 (1H, d, J=6.0 Hz), 7.32 (1H, d, J=9.2 Hz), 7.47 (1H, s), 7.67 (2H, d, J=8.8 Hz), 7.76 (2H, d, J=8.8 Hz). 7.88 (1H, d, J=6.0 Hz), 8.00 (1H, d, J=9.2 Hz), 10.26 (1H, s), 10.75 (1H, s).

ESI MS: 372.1.

SYNTHETIC EXAMPLE 72b

6-(4-Methanesulfonylaminobenzenesulfonylamino)-1-methoxyisoquinoline

The compound synthesized using 6-amino-1-methoxyisoquinoline (Production Example 43b) and 4-nitrobenzenesulfonyl chloride in the same manner as in Synthetic Example 1b was processed in the same manner as in Production Example 170b, to reduce the nitro group thereof. The resulting compound was dissolved in pyridine and methanesulfonyl chloride was added thereto under ice-cooling, followed by stirring for 4 hours as it was. Brine was added thereto, followed by extracting with ethyl acetate. The extract was washed with brine and dried over anhydrous magnesium sulfate. After evaporating the solvent, the residue was purified by silica gel column and the resulting crystals were recrystallized from ethanol, to give the title compound.

$^1$H-NMR(DMSO-d$_6$) δ (ppm): 3.06 (3H, s), 3.97 (3H, s), 7.24 (3H, m), 7.33 (1H, d, J=9.0 Hz), 7.49 (1H, s), 7.79 (2H, d, J=8.8 Hz), 7.89 (1H, d, J=6.0 Hz), 8.01 (1H, d, J=9.0 Hz), 10.39 (1H, s), 10.80 (1H, s).

ESI MS: 372.1.

SYNTHETIC EXAMPLE 73b

6-(2-Chloropyridine-5-ylsulfonylamino)-1-methoxyisoquinoline

The title compound was obtained using 6-amino-1-methoxyisoquinoline (Production Example 43b) and 6-chloro-3-pyridinesulfonyl chloride in the same method as in Synthetic Example 1b.

$^1$H-NMR(DMSO-d$_6$) δ (ppm): 3.31 (3H, s), 3.99 (3H, s), 7.30 (1H, d, J=6.0 Hz), 7.34 (1H, d, J=8.8 Hz), 7.56 (1H, s), 7.71 (1H, d, J=8.8 Hz), 7.92 (1H, d, J=6.0 Hz), 8.06 (1H, d, J=8.8 Hz), 8.19 (1H, d, J=8.8 Hz), 11.13 (1H, s).

ESI MS: 350.1.

SYNTHETIC EXAMPLE 74b

1-Methoxy-6-(3-methylbenzenesulfonylamino)isoquinoline

The title compound was obtained using 6-amino-1-methoxyisoquinoline (Production Example 43b) and 3-toluenesulfonyl chloride in the same method as in Synthetic Example 1b.

$^1$H-NMR(DMSO-d$_6$) δ (ppm): 2.31 (3H, s), 3.96 (3H, s), 7.22 (1H, d, J=6.0 Hz), 7.32 (1H, dd, J=2.0, 8.8 Hz), 7.39 (2H, m), 7.47 (1H, d, J=2.0 Hz), 7.62 (1H, m), 7.67 (1H, s), 7.87 (1H, d, J=6.0 Hz), 8.00 (1H, d, J=8.8 Hz), 10.84 (1H, s).

SYNTHETIC EXAMPLE 75b

6-Benzylsulfonylamino-1-methoxyisoquinoline

The title compound was obtained using 6-amino-1-methoxyisoquinoline (Production Example 43b) and benzylsulfonyl chloride in the same method as in Synthetic Example 1b.

$^1$H-NMR(CDCl$_3$) δ (ppm): 4.13 (3H, s), 4.42 (2H, s), 6.69 (1H, br s), 7.13 (2H, m), 7.22 (2H, m), 7.30-7.37 (3H, m), 7.50 (1H, d, J=2.4 Hz), 7.99 (1H, d, J=6.0 Hz), 8.20 (1H, d, J=8.8 Hz).

SYNTHETIC EXAMPLE 76b

6-(3-Cyanobenzenesulfonylamino)-1-methoxyisoquinoline

The title compound was obtained using 6-amino-1-methoxyisoquinoline (Production Example 43b) and 3-cyanobenzenesulfonyl chloride in the same method as in Synthetic Example 1b.

$^1$H-NMR(DMSO-d$_6$) δ (ppm): 3.98 (3H, s), 7.28 (1H, d, J=6.0 Hz), 7.34 (1H, dd, J=2.0, 8.8 Hz), 7.53 (1H, d, J=2.0 Hz), 7.75 (1H, dd, J=8.0, 8.0 Hz), 7.91 (1H, d, J=6.0 Hz), 8.04 (1H, d, J=8.8 Hz), 8.09 (2H, m), 9.29 (1H, m), 11.05 (1H, s).

SYNTHETIC EXAMPLE 77b

1-Methoxy-6-(4-thiazole-2-ylbenzenesulfonylamino)isoquinoline

The compound (40 mg) obtained using 6-amino-1-methoxyisoquinoline (Production Example 43b) and 4-iodobenzenesulfonyl chloride in the same method as in Synthetic Example 1b, 2-tri-n-butylstannylthiazole (136 mg) and tetrakis(triphenylphosphine)palladium (0) (11 mg) were heated under reflux for one hour in toluene in a nitrogen atmosphere. After evaporating the solvent, the residue was purified by silica gel column. The resulting crystals were recrystallized from methanol, to give the title compound (20 mg).

$^1$H-NMR(CDCl$_3$) δ (ppm): 4.08 (3H, s), 6.94 (1H, br s), 7.09 (1H, d, J=6.0 Hz), 7.23 (1H, dd, J=2.0, 8.8 Hz), 7.41 (1H, d, J=3.6 Hz), 7.45 (1H, d, J=2.0 Hz), 7.89 (2H, d, J=8.4 Hz), 7.90 (1H, d, J=8.6 Hz), 7.95 (1H, d, J=6.0 Hz), 7 82 (2H, d, J=8.4 Hz), 8.13 (1H, d, J=8.8 Hz).

SYNTHETIC EXAMPLE 78b

6-(4-Chlorobenzenesulfonylamino)-1-methoxyisoquinoline

The title compound was obtained using 6-amino-1-methoxyisoquinoline (Production Example 43b) and 4-chlorobenzenesulfonyl chloride in the same method as in Synthetic Example 1b.

$^1$H-NMR(DMSO-d$_6$) δ (ppm): 4.00 (3H, s), 7.27 (1H, d, J=5.6 Hz), 7.45 (1H, dd, J=2.0, 8.8 Hz), 7.53 (1H, d, J=2.0 Hz), 7.63 (2H, d, J=8.8 Hz), 7.85 (1H, d, J=8.8 Hz), 7.92 (1H, d, J=5.6 Hz), 8.06, (1H, J=8.8 Hz), 10.97 (1H, s).

SYNTHETIC EXAMPLE 79b 6-(4-Chlorobenzenesulfonylamino)-1-methylisoquinoline

The title compound was obtained using 6-amino-1-methylisoquinoline (Production Example 33b) and 4-chlorobenzenesulfonyl chloride in the same method as in Synthetic Example 1b.

$^1$H-NMR(DMSO-$d_6$) δ (ppm): 2.76 (3H, s), 7.56 (1H, d, J=6.0 Hz), 7.52 (2H, m), 7.60 (2H, d, J=8.8 Hz), 7.82 (2H, d, J=8.8 Hz), 8.08 (1H, d, J=9.2 Hz), 8.20 (1H, d, J=6.0 Hz).
ESI-MS: 333.0.

SYNTHETIC EXAMPLE 80b 6-(4-Chlorobenzenesulfonylamino)-1-ethylisoquinoline

The title compound was obtained using 6-amino-1-ethylisoquinoline (Production Example 48b) and 4-chlorobenzenesulfonyl chloride in the same manner as in Synthetic Example 1b.

$^1$H-NMR(DMSO-$d_6$) δ (ppm): 1.39 (3H, t, J=7.6 Hz), 3.25 (2H, q, J=7.6 Hz), 7.35 (1H, dd, J=2.4, 9.2 Hz), 7.38 (1H, d, J=5.6 Hz), 7.41 (2H, d, J=8.8 Hz), 7.53 (1H, d, J=2.4 Hz), 7.81 (2H, d, J=8.8 Hz), 8.05 (1H, d, J=9.2 Hz), 8.37 (1H, d, J=5.6 Hz).
ESI-MS: 347.0.

SYNTHETIC EXAMPLE 81b 6-(4-Chlorobenzenesulfonylamino)-4-ethylisoquinoline

The title compound was obtained using 6-amino-4-ethylisoquinoline (Production Example 66b) and 4-chlorobenzenesulfonyl chloride in the same method as in Synthetic Example 1b.

$^1$H-NMR(DMSO-$d_6$) δ (ppm): 1.18 (3H, t, J=7.2 Hz), 2.85 (2H, q, J=7.2 Hz), 7.38 (1H, d, J=8.8 Hz), 7.60 (1H, s), 7.62 (2H, d, J=8.0 Hz), 7.82 (2H, d, J=8.0 Hz), 8.00 (1H, d, J=8.8 Hz), 8.26 (1H, s), 8.99 (1H, s).

SYNTHETIC EXAMPLE 82b 6-(4-Chlorobenzenesulfonylamino)-4-methylisoquinoline

The title compound was obtained using 6-amino-4-methylisoquinoline (Production Example 58b) and 4-chlorobenzenesulfonyl chloride in the same method as in Synthetic Example 1b.

$^1$H-NMR(DMSO-$d_6$) δ (ppm): 2.43 (3H, s), 7.41 (1H, d, J=8.8 Hz), 7.56 (1H, s), 7.62 (2H, d, J=8.8 Hz), 7.85 (2H, d, J=8.8 Hz), 7.99 (1H, d, J=8.8 Hz), 8.26 (1H, s), 8.98 (1H, s), 11.09 (1H, br s).

SYNTHETIC EXAMPLE 83b 6-(4-Chlorobenzenesulfonylamino)-3-methylisoquinoline

The title compound was obtained using 6-amino-3-methylisoquinolinne (Production Example 76b) and 4-chlorobenzenesulfonyl chloride in the same method as in Synthetic Example 1b.

$^1$H-NMR(DMSO-$d_6$) δ (ppm): 2.53 (3H, s), 7.30 (1H, d, J=8.8 Hz), 7.45 (1H, s), 7.50 (1H, s), 7.62 (2H, d, J=8.4 Hz), 7.84 (2H, d, J=8.4 Hz), 7.93 (1H, d, J=8.8 Hz), 9.03 (1H, s).

SYNTHETIC EXAMPLE 84b 6-(4-Chlorobenzenesulfonylamino)-1-cyanoisoquinoline

The compound obtained using 6-aminoisoquinoline (0.5 g, Synthesis, 733 (1975)) and 4-chlorobenzenesulfonyl chloride (0.88 g) in the same method as in Synthetic Example 1b was dissolved in chloroform (150 ml). Under ice-cooling, m-chloroperbenzoic acid (0.9 g) was added thereto, followed by stirring at room temperature overnight. The solvent was evaporated, and the resulting crystals were washed with diethyl ether, collected by filtration and dried, to give 6-(4-chlorobenzenesulfonylamino) isoquinoline-N-oxide (1.072 g) In acetonitrile (1.5 ml) was dissolved 50 mg in the amount of the product, to which were then added trimethyl cyanide (0.08 ml) and triethylamine (0.04 ml), followed by heating under reflux for 3.5 hours. After evaporating the solvent, the residue was purified by silica gel column, to give the title compound (23 mg, 64%) as yellow crystals.

$^1$H-NMR(DMSO-$d_6$) δ (ppm): 7.66 (2H, d, J=8.8 Hz), 7.67 (1H, dd, J=2.0, 9.2 Hz), 7.80 (1H, d, J=2.0 Hz), 7.93 (2H, d, J=8.8 Hz), 8.17 (1H, d, J=9.2 Hz), 8.18 (1H, d, J=5.6 Hz), 8.59 (1H, d, J=5.6 Hz).
ESI-MS: 344.1

SYNTHETIC EXAMPLE 85b

1-Carbamoyl-6-(4-chlorobenzenesulfonylamino)isoquinoline

Crystals obtained from 6-(4-chlorobenzenesulfonylamino)-1-cyanoisoquinoline (30 mg, Synthetic Example 83b) according to the method described in Synthesis, 949 (1989) were washed with diethyl ether, to give the title compound (26 mg, 82%) as colorless crystals.

$^1$H-NMR(CDCl$_3$) δ (ppm): 6.25 (1H, br s), 7.35 (2H, d, J=8.8 Hz), 7.43 (1H, dd, J=2.0, 9.2 Hz), 7.62 (1H, d, J=2.0 Hz), 7.66 (1H, d, J=6.8 Hz), 7.81 (2H, d, J=8.8 Hz), 8.04 (1H, br s), 8.37 (1H, br s), 9.32 (1H, d, J=9.2 Hz), 9.76 (1H, br s).

SYNTHETIC EXAMPLE 86b 6-(4-Chlorobenzenesulfonylamino)-1-methylaminoisoquinoline 1-Chloro-6-(4-chlorobenzenesulfonylamino)isoquinoline (50 mg, Synthetic Example 61b) and a 40% methylamine methanol solution (5.0 ml) were heated at 130° C. in a sealed tube for 18 hours. After cooling as it was, an aqueous saturated sodium bicarbonate was added thereto, and the mixture was extracted with ethyl acetate. The extract was washed with brine and dried over anhydrous magnesium sulfate. After evaporating the solvent, the residue was purified by silica gel column, to give the title compound (28 mg, 52%) as a pale yellow solid.

$^1$H-NMR(CDCl$_3$) δ (ppm): 3.14 (3H, s), 5.22 (1H, br s), 6.89 (1H, d, J=6.0 Hz), 7.19 (1H, dd, J=2.4 Hz, 9.2 Hz), 7.31 (1H, d, J 2.4 Hz), 7.40 (2H, d, J=8.8 Hz), 7.64 (1H, d, J=9.2 Hz), 7.73 (2H, d, J=8.8 Hz), 7.98 (1H, d, J=6.0 Hz).

SYNTHETIC EXAMPLE 87b

1-Amino-6-(4-chlorobenzenesulfonylamino)iso-quinoline

Crystals obtained using 6-(4-chlorobenzenesulfony-lamino)isoquinoline-N-oxide (intermediate in Synthetic Example 83b, 50 mg) according to the method described in J. Medicine 84,35 (1964) were washed with diethyl ether and dried, to give the title compound (2 mg) as pale brownish crystals.
$^1$H-NMR(DMSO-$d_6$) δ (ppm): 7.76 (1H, d, J=6.0 Hz), 6.93 (2H, br s), 7.15 (1H, dd, J=2.0, 8.8 Hz), 7.27 (1H, d, J=2.0 Hz), 7.59 (2H, d, J=8.8 Hz), 7.63 (1H, d, J=6.0 Hz), 7.80 (2H, d, J=8.8 Hz), 9.05 (1H, d, J=6.0 Hz).
ESI-MS: 334.1.

SYNTHETIC EXAMPLE 88b 6-(4-Chlorobenzenesulfonylamino)-1-dimethylami-noisoquinoline 1-Chloro-6-(4-chlorobenzenesulfonylamino)isoquinoline (Synthetic Example 61b, 60 mg) was dissolved in dimethyl sulfoxide (1 ml), to which was then added a 50% dimethy-laminemethanol solution (0.04 ml), followed by heating under stirring at 80° C. for 10 hours. After cooling as it was, water was added thereto, followed by extracting with ethyl acetate. The extract was washed with brine and dried over anhydrous magnesium sulfate. After evaporating the solvent, the residue was purified by preparative TLC and solidified using isopropyl ether, to give the title compound (17 mg).
$^1$H-NMR(DMSO-$d_6$) δ (ppm): 2.96 (6H, s), 7.12 (1H, d, J=6.0 Hz), 7.27 (1H, dd, J=2.0, 9.2 Hz), 7.45 (1H, d, J=2.0 Hz), 7.64 (2H, d, J=8.8 Hz), 7.85 (2H, d, J=8.8 Hz), 7.93 (1H, d, J=6.0 Hz), 8.01 (1H, d, J=9.2 Hz), 10.91 (1H, br s).

SYNTHETIC EXAMPLE 89b 6-(4-Chlorobenzenesulfonylamino)-1-hydroxyiso-quinoline 6-(4-Chlorobenzenesulfonylamino)isoquinoline-N-oxide (intermediate in Synthetic Example 83b, 50 mg) was dissolved in acetic acid anhydride (0.75 ml), followed by heating under stirring at 80° C. for 16 hours. Then, the mixture was refluxed under heating for 2 hours. After cooling as it was, an aqueous saturated sodium bicarbonate was added thereto, followed by extracting with ethyl acetate. The extract was washed with brine and dried over anhydrous magnesium sulfate. After evaporating the solvent, the residue was dissolved in ethanol (2.0 ml) and water (0.5 ml), followed by heating under reflux for 0.5 hours. After evaporating the solvent, the residue was purified by silica gel column, to give the title compound (20 mg) as a pale red solid.
$^1$H-NMR(CDCl$_3$) δ (ppm): 6.58 (1H, d, J=7.2 Hz), 7.22 (1H, d, J=7.2 Hz), 7.31 (1H, dd, J=2.0, 8.4 Hz), 7.54 (1H, d, J=2.0 Hz), 7.56 (2H, d, J=8.8 Hz), 8.01 (2H, d, J=8.8 Hz), 8.53 (1H, d, J=8.4 Hz), 10.36 (1H, br s)
ESI-MS: 335.1.

SYNTHETIC EXAMPLE 90b 6-(4-Chlorobenzenesulfonylamino)-1-ethoxyiso-quinoline 1-Chloro-6-(4-chlorobenzenesulfonylamino)isoquinoline (Synthetic Example 61b, 57 mg) was dissolved in dimethyl sulfoxide (1 ml). Ethanol (0.1 ml) and 60% sodium hydride (14 mg) were added thereto, followed by heating under stirring at 80° C. for 9 hours. After cooling as it was, water was added thereto, followed by extracting with ethyl acetate. The extract was washed with brine and dried over anhydrous magnesium sulfate. After evaporating the solvent, the residue was purified by preparative TLC and solidified using isopropyl ether, to give the title compound (21 mg).
$^1$H-NMR(DMSO-$d_6$) δ (ppm): 1.38 (3H, t, J=7.2 Hz), 4.46 (2H, q, J=7.2 Hz), 7.24 (1H, d, J=6.0 Hz), 7.35 (1H, dd, J=2.0, 9.2 Hz), 7.50 (1H, d, J=2.0 Hz), 7.63 (2H, d, J=8.8 Hz), 7.90 (1H, d, J=6.0 Hz), 8.04 (1H, d, J=9.2 Hz), 10.94 (1H, br s)

SYNTHETIC EXAMPLE 91b

N-(5-Vinylquinoline-2-yl)-3-pyridinesulfonamide

A solution containing 2-amino-5-bromoquinoline (510 mg, Production Example 1b), vinyltributyltin (0.94 ml), toluene (4 ml), tetrakistriphenylphosphinepalladium (0 valence) (20 mg) and 2,6-ditertiarybutyl/p-cresol (about 0.1 mg) was stirred at 120° C. for 4 hours. After the reaction mixture was returned to room temperature, water was added thereto, followed by extracting with ethyl acetate. The ethyl acetate layer was dried over sodium sulfate and concentrated. Then, the resulting solid was washed with hexane, to give 282 mg of a solid including a vinyl material. The solid was dissolved in 2 ml of pyridine and 412 mg of 3-pyridinesulfonyl chloride was added thereto, followed by stirring at room temperature overnight. Water was added thereto, followed by extracting with ethyl acetate. The ethyl acetate layer was dried over sodium sulfate and concentrated. Then, the resulting solid was washed with methanol, to give the title compound (235 mg).
$^1$H-NMR(CDCl$_3$) δ (ppm): 5.59 (1H, dd, J=10.8 Hz, 1.5 Hz), 5.82 (1H, dd, J=16.9 Hz, 1.5 Hz), 6.95 (1H, d, J=10.3 Hz), 7.20 (1H, dd, J=10.8 Hz, 16.9 Hz), 7.36 (1H, d, J=8.5 Hz), 7.43 (1H, m), 7.50 (1H, d, J=8.5 Hz), 7.62 (1H, t, J=8.5 Hz), 8.24 (1H, d, J=10.3 Hz), 8.29 (1H, m), 8.74 (1H, m), 9.22 (1H, m).

SYNTHETIC EXAMPLE 92b

N-(4-Trifluoromethylcumarin-7-yl)-4-chlorobenze-nesulfonamide 203 mg (0.96 mmol) of 4-chlorobenzenesulfonyl chloride was added to a pyridine solution (3 ml) containing 200 mg (0.87 mmol) of 7-amino-4-trifluoromethylcumarin and 1 mg of 4-dimethylaminopyridine, followed by stirring at 70° C. for 50 minutes. An aqueous 2 N hydrochloric acid was added thereto, followed by extracting with ethyl acetate. The organic layer was washed with water and brine, dried over magnesium sulfate and evaporated. The resulting residue was crystallized from ethyl acetate-diisopropyl ether, to give 253 mg of the title compound as a pale yellow solid.
$^1$H-NMR(DMSO-$d_6$) δ (ppm): 6.87 (1H, s), 7.12 (1H, d, J=2.4 Hz), 7.17 (1H, dd, J=2.6, 8.4 Hz), 7.60 (1H, d, J=8.4 Hz), 7.67 (2H, d, J=6.8 Hz), 7.87 (2H, d, J=6.8 Hz), 11.29 (1H, s).

The invention claimed is:
1. A method for treating or improving a disease against which an integrin expression inhibition is effective, wherein said disease is at least one selected from the group consisting of arterial sclerosis and retinal angiogenesis, said method comprising:

administering a pharmacologically effective amount of an integrin expression inhibitor of a sulfonamide compound represented by formula (I$^a$), a pharmacologically acceptable salt thereof or a hydrate thereof, to a patient in need thereof for treating or improving said disease:

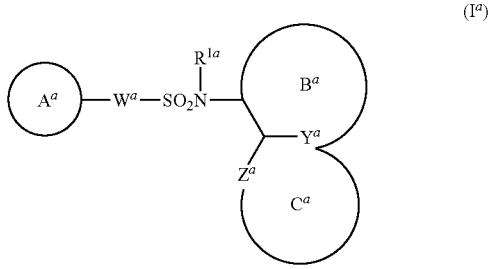

(I$^a$)

wherein in formula (I$^a$):

the A$^a$ ring represents a monocyclic or bicyclic aromatic ring optionally having a substituent;

the B$^a$ ring represents an optionally substituted 6-membered cyclic unsaturated hydrocarbon or unsaturated 6-membered heterocycle containing one nitrogen atom as a heteroatom;

the C$^a$ ring represents an optionally substituted 5-membered heterocycle containing 1 or 2 nitrogen atoms;

R$^{1a}$ represents a hydrogen atom or a C$_1$-C$_6$ alkyl group;

W$^a$ represents a single bond or —CH=CH—;

Y$^a$ represents a carbon atom or nitrogen atom; and

Z$^a$ represents a nitrogen atom or —N(R$^{2a}$)—, wherein R$^{2a}$ is a hydrogen atom or a lower alkyl group.

2. The method of claim 1, wherein the ring of formula (I$^a$) formed by the B$^a$ ring and C$^a$ ring is a N-substituted indole, quinoline or isoquinoline.

3. The method of claim 1, wherein said sulfonamide compound is N-(3-cyano-4-methyl-1H-indole-7-yl)-3-cyanobenzene-sulfonamide or N-(5-bromo-3-chloro-1H-indole-7-yl)-6-amino-3-pyridinesulfonamide.

4. The method of claim 1, wherein said disease is a disease against which an antiangiogenic effect is effective.

* * * * *